US011028416B2

(12) United States Patent
Siddiqui et al.

(10) Patent No.: US 11,028,416 B2
(45) Date of Patent: Jun. 8, 2021

(54) ENGINEERED BIOSYNTHETIC PATHWAYS FOR PRODUCTION OF TYRAMINE BY FERMENTATION

(71) Applicant: Zymergen Inc., Emeryville, CA (US)

(72) Inventors: Michael Shareef Siddiqui, San Mateo, CA (US); Stefan de Kok, Emeryville, CA (US); Alexander Glennon Shearer, San Francisco, CA (US); Franklin Lu, Emeryville, CA (US); Cara Ann Tracewell, Walnut Creek, CA (US); Steven M. Edgar, Albany, CA (US)

(73) Assignee: ZYMERGEN INC., Emeryville, CA (US)

( * ) Notice: Subject to any disclaimer, the term of this patent is extended or adjusted under 35 U.S.C. 154(b) by 0 days.

(21) Appl. No.: 16/453,648

(22) Filed: Jun. 26, 2019

(65) Prior Publication Data

US 2019/0390236 A1 Dec. 26, 2019

Related U.S. Application Data

(63) Continuation of application No. PCT/US2018/017127, filed on Feb. 6, 2018.

(60) Provisional application No. 62/455,428, filed on Feb. 6, 2017.

(51) Int. Cl.

| | |
|---|---|
| ***C12P 13/00*** | (2006.01) |
| ***C12N 1/15*** | (2006.01) |
| ***C12N 1/21*** | (2006.01) |
| ***C12N 9/02*** | (2006.01) |
| ***C12N 9/10*** | (2006.01) |
| ***C12N 9/12*** | (2006.01) |
| ***C12N 9/88*** | (2006.01) |
| ***C12N 9/90*** | (2006.01) |

(52) U.S. Cl.

CPC ............ *C12P 13/001* (2013.01); *C12N 9/001* (2013.01); *C12N 9/1022* (2013.01); *C12N 9/1085* (2013.01); *C12N 9/1205* (2013.01); *C12N 9/88* (2013.01); *C12N 9/90* (2013.01); *C12Y 103/01012* (2013.01); *C12Y 202/01002* (2013.01); *C12Y 205/01054* (2013.01); *C12Y 207/01071* (2013.01); *C12Y 401/01025* (2013.01); *C12Y 504/99005* (2013.01)

(58) Field of Classification Search

CPC ..................................................... C12P 13/001

See application file for complete search history.

(56) References Cited

U.S. PATENT DOCUMENTS

| | | | |
|---|---|---|---|
| 4,681,852 A | 7/1987 | Tribe | |
| 5,756,347 A | 5/1998 | Sugimoto et al. | |
| 6,210,937 B1 | 4/2001 | Ward et al. | |
| 7,642,083 B2 | 1/2010 | Frost et al. | |
| 9,234,203 B2 | 1/2016 | Pang et al. | |
| 9,322,039 B2 | 4/2016 | Smolke et al. | |
| 2002/0009801 A1 | 1/2002 | Falco et al. | |
| 2004/0091891 A1 | 5/2004 | Iomantas et al. | |
| 2005/0089974 A1 | 4/2005 | Townsend et al. | |
| 2008/0102499 A1 | 5/2008 | Templeton et al. | |
| 2008/0118958 A1 | 5/2008 | Gatenby et al. | |
| 2008/0176754 A1 | 7/2008 | Smolke et al. | |
| 2009/0139134 A1 | 6/2009 | Yoshikuni et al. | |
| 2011/0097767 A1 | 4/2011 | Pharkya et al. | |
| 2014/0134689 A1 | 5/2014 | Lee et al. | |
| 2015/0044755 A1 | 2/2015 | Yocum et al. | |
| 2016/0251688 A1 | 9/2016 | Siddiqui et al. | |
| 2017/0130250 A1* | 5/2017 | Facchini | C12P 13/001 |
| 2018/0163241 A1* | 6/2018 | Smolke | C12Y 101/01247 |

FOREIGN PATENT DOCUMENTS

| | | |
|---|---|---|
| EP | 0077196 A2 | 4/1983 |
| EP | 1187930 B1 | 8/2006 |
| EP | 2302067 B1 | 3/2014 |
| EP | 2147972 B1 | 11/2015 |
| WO | WO 96/008567 | 3/1996 |
| WO | WO 2008/064835 A1 | 6/2008 |
| WO | WO 2015/066642 A1 | 5/2015 |
| WO | WO 2015/192233 A1 | 12/2015 |
| WO | WO 2016/027870 A1 | 2/2016 |
| WO | WO 2018/203947 A2 | 11/2018 |

OTHER PUBLICATIONS

F. Liu et al. "Heterologous Expression and Characterization of Tyrosine Decarboxylase from Enterococcus faecalis R612Z1 and Enterococcus faecium R615Z1", Journal of Food Protection 77(4):592-598. (Year: 2014).*

A. Rao et al. "Cloning and expression of a tyrosinase from Aspergillus oryzae in Yarrowia lipolytica: application in L-DOPA biotransformation", Appl. Microbiol. Biotechnol. 92: 951-959. (Year: 2011).*

PCT International Search Report and Written Opinion dated Dec. 20, 2018 issued in PCT/US2018/017127.

PCT International Preliminary Report on Patentability and Written Opinion dated Aug. 6, 2019 issued in PCT/US2018/017127.

Database Protein [Online] (Feb. 15, 2014) "probable tyrosine decarboxylase [Zygosaccharomyces bailii ISA1307]", XP002786815, retrieved from NCBI Database accession No. CDH10044 (2 pages).

Database Protein [Online] (Jan. 16, 2015) "3-dehydroquinate synthase [*Escherichia coli* ]", XP002786811, retrieved from GenBank accession No. KIH37536.1 (2 pages).

Database Protein [Online] (Apr. 22, 1996) "tyrosine decarboxylase [Papaver somniferum]", XP0002786812, retrieved from GenBank accession No. AAA97535.1 (2 pages).

Database Protein [Online] (Sep. 25, 2013) "tyrosine decarboxylase [Enterococcus faecium]", XP002786813, retrieved from GenBank accession No. AGW24520.1 (2 pages).

(Continued)

*Primary Examiner* — Rebecca E Prouty

(74) *Attorney, Agent, or Firm* — Emily M. Haliday; Weaver Austin Villeneuve & Sampson LLP

(57) ABSTRACT

The present disclosure describes the engineering of microbial cells for fermentative production of tyramine and provides novel engineered microbial cells and cultures, as well as related tyramine production methods.

9 Claims, 10 Drawing Sheets

Specification includes a Sequence Listing.

(56) References Cited

OTHER PUBLICATIONS

Database Protein [Online] (Jul. 26, 2016) "Lactobacillus brevis drug transport protein (dtp) gene, partial cds; acetyl coA synthetase (act), transposase (tra), tyrosyl-tRNA synthetase (tyrS), tyrosine decarboxylase (tyrdc), tyrosine permease(tyrP), Na+/H+ antiporter (nhaC), and ornithine transcarbamyl . . . ", XP0002786814, retrieved from GenBank accession No. EU195891.1 (8 pages).
Database Protein [Online] (Nov. 30, 2016) "RecName: Full= Pentafunctional AROM polypeptide; Includes: RecName: Full=3-dehydroquinate synthase; Short=DHQS; Includes: RecName: Full= 3-phosphoshikimate1-carboxyvinyltransferase; AltName: Full= 5-enolpyruvylshikimate-3-phosphate synthase; Short=EPSP synthase; . . . ", XP002786810, retrieved from UniProt accession No. P08566 (11 pages).
Dewick et al. (1993) "The Biosynthesis of Shikimate Metabolites", *Natural Product Reports*, 10:233 (31 pages).
Gold et al. (2015) "Metabolic engineering of a tyrosine-overproducing yeast platform using targeted metabolomics", *Microbial Cell Factories*, 14:73 (16 pages).
Hawkins, Kristy (2009) "Metabolic Engineering of *Saccharomyces cerevisiae* for the Production of Benzylisoquinoline Alkaloids" *California Institute of Technology, Pasadena, California*, 168 pages.
Ikeda (2006) "Towards bacterial strains overproducing L-tryptophan and other aromatics by metabolic engineering", *Appl Microbiol Biotechnol*, 69: 615-626.
Jossek et al. (2001) "Characterization of a new feedback-resistant 3-deoxy-D-arabino-heptulosonate 7-phosphate synthase AroF of *Escherichia coli*", *FEMS Microbiol Lett*, 202: 145-148.
Koma et al. (2012) "A convenient method for multiple insertions of desired genes into target loci on the *Escherichia coli* chromosome", *Appl Microbiol Biotechnol*, 93:815-829.
Koma et al. (2012) "Production of Aromatic Compounds by Metabolically Engineered *Escherichia coli* with an Expanded Shikimate Pathway", *Applied and Environmental Microbiology*, 78(17):6203-6216.
Liao et al. (2001) "Serine 187 is a crucial residue for allosteric regulation of Corynebacterium glutamicum 3-deoxy-D-arabino-heptulosonate-7-phosphate synthase", *FEMS Microbiol Lett*, 194: 59-64.
Liu et al. (2008) "Corynebacterium glutamicum Contains 3-Deoxy-D-Arabino-Heptulosonate 7-Phosphate Synthases That Display Novel Biochemical Features", *Applied and Environmental Microbiology*, 74(17): 5497-5503.
Meuris et al. (1974) "Feedback-Insensitive Mutants of the Gene for the Tyrosine-Inhibited Dahp* Synthetase in Yeast", *Genetics*, 16: 735-744.
Noda et al. (2015) "Evaluation of Brachypodium distachyon L-Tyrosine Decarboxylase Using L-Tyrosine Over-Producing *Saccharomyces cerevisiae*", *PLOS ONE*, 10(5): E0125488 (12 pages).
Romboli et al. (2015) "Effect of *Saccharomyces cerevisiae* and Candida zemplinina on quercetin, vitisin A and hydroxytyrosol contents in Sangiovese wines", *World J Microbiol Biotechnol*, 31:1137-1145.
Webby et al. (2005) "Characterization of a recombinant type II 3-deoxy-D-arabino-heptulosonate-7-phosphate synthase from Helicobacter pylori", *Biochem. J.*, 390: 223-230.
Zhang et al. (2014) "Construction and application of novel feedback-resistant 3-deoxy-D-arabino-heptulosonate-7-phosphate synthases by engineering the N-terminal domain for L-phenylalanine synthesis", *FEMS Microbiol Lett*, 353: 11-18.
Zhang et al. (2016) "Three-step biocatalytic reaction using whole cells for efficient production of tyramine from keratin acid hydrolysis wastewater", *Appl Microbiol Biotechnol*, 100: 1691-1700.

* cited by examiner

High Constant Feed
3mL/min at 20 hour, 6 mL/min at 24 hour, 12mL/min at 44 hr, 16 mL/min at 55 hr

Low Constant Feed
3mL/min at 24 hour, 6 mL/min at 44 hour, 12mL/min at 49 hr pH-triggered
pH > 4.7, 30mL/min for 4 minutes

Tank Desc
——— High constant feed
– – – Low constant feed
·········· pH-triggered, medium 1
-—-— pH-triggered, medium 2

High Constant Feed
3mL/min at 20 hour, 6 mL/min at 24 hour, 12mL/min at 44 hr, 16 mL/min at 55 hr

Low Constant Feed
3mL/min at 24 hour, 6 mL/min at 44 hour, 12mL/min at 49 hr pH-triggered
pH > 4.7, 30mL/min for 4 minutes

ENGINEERED BIOSYNTHETIC PATHWAYS FOR PRODUCTION OF TYRAMINE BY FERMENTATION

CROSS-REFERENCE TO RELATED APPLICATIONS

This application is a continuation application of international application no. PCT/US2018/17127, filed Feb. 6, 2018, which claims the benefit of U.S. provisional application No. 62/455,428, filed Feb. 6, 2017, both of which are hereby incorporated by reference in their entireties.

STATEMENT AS TO RIGHTS TO INVENTIONS MADE UNDER FEDERALLY SPONSORED RESEARCH AND DEVELOPMENT

This invention was made with Government support under Agreement No. HR0011-15-9-0014, awarded by DARPA. The Government has certain rights in the invention.

INCORPORATION BY REFERENCE OF THE SEQUENCE LISTING

This application includes a sequence listing which has been submitted electronically in ASCII format and is hereby incorporated by reference in its entirety. This ASCII copy, created on Jun. 23, 2019, is named 2019-06-23_ZMGNP001US_seqlist.txt and is 331,410 bytes in size.

FIELD OF THE DISCLOSURE

The present disclosure relates generally to the area of engineering microbes for overproduction of tyramine by fermentation.

BACKGROUND

Tyramine is known to exist in nature as the decarboxylation product of tyrosine. Often tyramine is produced in environments or processes where protein-rich materials have rotted or decayed. Tyramine is present in foods produced from fermentation of protein-rich substances such as animal milk or legumes. These processes rely on an external source of proteins containing aromatic amino acids and microbes expressing tyrosine decarboxylases.

SUMMARY

Various embodiments contemplated herein may include, but need not be limited to, one or more of the following:

Embodiment 1: An engineered microbial cell, wherein the engineered microbial cell expresses: (a) a heterologous tyrosine decarboxylase (TYDC); and (b) the engineered microbial cell includes increased activity of one or more upstream enzyme(s) in the tyramine biosynthesis pathway, said increased activity being increased relative to a control cell.

Embodiment 2: The engineered microbial cell of embodiment 1, wherein the one or more upstream enzyme(s) includes 3-deoxy-D-arabino-heptulosonate-7-phosphate (DAHP) synthase.

Embodiment 3: An engineered microbial cell, wherein the engineered microbial cell expresses: (a) a heterologous tyrosine decarboxylase (TYDC); and (b) the engineered microbial cell includes increased activity of one or more enzyme(s) selected from the group consisting of a dehydroquinate synthase, a dehydroquinate dehydratase, a shikimate dehydrogenase, a shikimate kinase, EPSP synthase, aromatic pentafunctional enzyme, a chorismate synthase, a chorismate mutase, a prephenate dehydratase, a phenyalananine aminotransferase, a prephenate dehydrogenase, a prephenate aminotransferase, an arogenate dehydrogenase, a phenylalanine hydroxylase, and a tyrosine aminotransferase, said increased activity being increased relative to a control cell; wherein the engineered microbial cell produces tyramine.

Embodiment 4: The engineered microbial cell of embodiment 3, wherein the engineered microbial cell additionally expresses: (c) a feedback-disregulated 3-deoxy-D-arabino-heptulosonate-7-phosphate (DAHP) synthase or a feedback-disregulated chorismate mutase.

Embodiment 5: An engineered microbial cell, wherein the engineered microbial cell includes: (a) means for expressing a heterologous tyrosine decarboxylase (TYDC); and (b) means for increasing the activity of one or more upstream enzyme(s) in the tyramine biosynthesis pathway.

Embodiment 6: The engineered microbial cell of embodiment 5, wherein the one or more upstream enzyme(s) includes 3-deoxy-D-arabino-heptulosonate-7-phosphate (DAHP) synthase.

Embodiment 7: An engineered microbial cell, wherein the engineered microbial cell includes: (a) means for expressing a heterologous tyrosine decarboxylase (TYDC); and (b) means for increasing the activity of one or more enzyme(s) selected from the group consisting of a dehydroquinate synthase, a dehydroquinate dehydratase, a shikimate dehydrogenase, a shikimate kinase, EPSP synthase, aromatic pentafunctional enzyme, a chorismate synthase, a chorismate mutase, a prephenate dehydratase, a prephenate aminotransferase, an arogenate dehydrogenase, a phenylalanine hydroxylase, a phenylalananine aminotransferase, a prephenate dehydrogenase, and a tyrosine aminotransferase, said increased activity being increased relative to a control cell; wherein the engineered microbial cell produces tyramine.

Embodiment 8: The engineered microbial cell of embodiment 7, wherein the engineered microbial cell additionally expresses: (c) means for expressing a feedback-disregulated DAHP synthase or a feedback-disregulated chorismate mutase.

Embodiment 9: The engineered microbial cell of any one of embodiments 1-8, wherein the engineered microbial cell produces tyramine by fermentation of a substrate, wherein at least 50% of the substrate is not derived from protein or amino acid sources.

Embodiment 10: The engineered microbial cell of any one of embodiments 4, 8, or 9, wherein the engineered microbial cell includes: (a) a heterologous TYDC; and (b) a feedback-disregulated DAHP synthase.

Embodiment 11: The engineered microbial cell of any one of embodiments 3-10, wherein the engineered microbial cell includes a fungal cell.

Embodiment 12: The engineered microbial cell of any one of embodiments 3-11, wherein the engineered microbial cell includes a yeast cell.

Embodiment 13: The engineered microbial cell of embodiment 8, wherein the yeast cell includes a cell of the genus *Saccharomyces.*

Embodiment 14: The engineered microbial cell of embodiment 13, wherein the yeast cell is a cell of the species *cerevisiae.*

Embodiment 15: The engineered microbial cell of any one of embodiments 4, 8, or 9-14, wherein the DAHP synthase is a variant of a *S. cerevisiae* DAHP synthase.

Embodiment 16: The engineered microbial cell of any one of embodiments 3-15, wherein the heterologous TYDC includes a TYDC having at least 70% amino acid sequence identity with a TYDC from *Papaver somniferum.*

Embodiment 17: The engineered microbial cell of any one of embodiments 4, 8, or 9-16, wherein the: (a) heterologous TYDC includes a *P. somniferum* Tyrosine/DOPA decarboxylase 2; and the (b) feedback-disregulated DAHP synthase is a *S. cerevisiae* DAHP synthase encoded by the Aro4 gene that additionally includes a K229L mutation.

Embodiment 18: The engineered microbial cell of any one of embodiments 3-17, wherein the engineered microbial cell includes increased activity of a prephenate dehydrogenase relative to the control cell.

Embodiment 19: The engineered microbial cell of embodiment 18, wherein the engineered microbial cell expresses an extra copy of a wild-type *S. cerevisiae* prephenate dehydrogenase gene.

Embodiment 20: The engineered microbial cell of embodiment 18, wherein the engineered microbial cell expresses an extra copy of a wild-type *S. cerevisiae* transaldolase gene.

Embodiment 21: The engineered microbial cell of embodiment 2 or embodiment 6, wherein the engineered microbial cell includes a yeast cell.

Embodiment 22: The engineered microbial cell of embodiment 21, wherein the yeast cell includes a cell of the genus *Yarrowia.*

Embodiment 23: The engineered microbial cell of embodiment 22, wherein the yeast cell is a cell of the species *lipolytica.*

Embodiment 24: The engineered microbial cell of embodiment 22 or embodiment 23, wherein the heterologous TYDC includes a TYDC having at least 70% amino acid sequence identity with a TYDC from *Enterococcus faecium.*

Embodiment 25: The engineered microbial cell of any one of embodiments 22-24, wherein the DAHP synthase includes a DAHP synthase having at least 70% amino acid sequence identity with a DAHP synthase from *S. cerevisiae.*

Embodiment 26: The engineered microbial cell of embodiment 25, wherein the: (a) heterologous TYDC includes a pyridoxal-dependent decarboxylase (TYDC) from *E. faecium* Com15; and (b) DAHP synthase includes a phospho-2-dehydro-3-deoxyheptonate aldolase (DAHP synthase) from *S. cerevisiae* S288c.

Embodiment 27: An engineered microbial cell which is a yeast cell including a heterologous tyrosine decarboxylase (TYDC) having at least 70% amino acid sequence identity to a TYDC from *Papaver somniferum*, wherein the engineered yeast cell produces tyramine.

Embodiment 28: The engineered microbial cell of embodiment 27, wherein the engineered yeast cell is a cell of the genus *Saccharomyces.*

Embodiment 29: The engineered microbial cell of embodiment 28, wherein the engineered yeast cell is a cell of the species *cerevisiae.*

Embodiment 30: The engineered microbial cell of any one of embodiments 3-10, wherein the engineered microbial cell is a bacterial cell.

Embodiment 31: The engineered microbial cell of embodiment 30, wherein the bacterial cell is a cell of the genus *Corynebacteria.*

Embodiment 32: The engineered microbial cell of embodiment 31, wherein the bacterial cell is a cell of the species *glutamicum.*

Embodiment 33: The engineered microbial cell of any one of embodiments 30-32, wherein the bacterial cell includes a feedback-disregulated DAHP synthase that is a variant of an *S. cerevisiae* DAHP synthase.

Embodiment 34: The engineered microbial cell of any one of embodiments 30-33, wherein the heterologous TYDC includes a TYDC having at least 70% amino acid sequence identity with a TYDC from *Enterococcus faecium* or having at least 70% amino acid sequence identity with a TYDC from *Zygosaccharomyces bailii.*

Embodiment 35: The engineered microbial cell of embodiment 33 or embodiment 34, wherein the: (a) heterologous TYDC includes an *E. faecium* TYDC; and the (b) feedback-disregulated DAHP synthase is a *S. cerevisiae* DAHP synthase encoded by the Aro4 gene that additionally includes a K229L mutation.

Embodiment 36: The engineered microbial cell of embodiment 33 or embodiment 34, wherein the: (a) heterologous TYDC includes an *Z. bailii* TYDC; and the (b) feedback-disregulated DAHP synthase is a *S. cerevisiae* DAHP synthase encoded by the Aro4 gene that additionally includes a K229L mutation.

Embodiment 37: The engineered microbial cell of embodiment 34, additionally including increased activity of chorismate synthase or prephrenate dehydrogenase, relative to a control cell.

Embodiment 38: The engineered microbial cell of embodiment 37, wherein the engineered microbial cell includes increased activity of chorismate synthase and expresses a heterologous chorismate synthase.

Embodiment 39: The engineered microbial cell of embodiment 38, wherein the heterologous chorismate synthase includes a chorismate synthase having at least 70% amino acid sequence identity to a *S. cerevisiae* chorismate synthase.

Embodiment 40: The engineered microbial cell of embodiment 39, wherein the heterologous chorismate synthase includes a *S. cerevisiae* chorismate synthase.

Embodiment 41: The engineered microbial cell of embodiment 37, wherein the engineered microbial cell includes increased activity of prephenate dehydrogenase and expresses an additional copy of a prephenate dehydrogenase gene.

Embodiment 42: The engineered microbial cell of embodiment 41, wherein the additional copy of the prephenate dehydrogenase gene encodes a prephenate dehydrogenase having at least 70% amino acid sequence identity to a prephenate dehydrogenase from *S. cerevisiae.*

Embodiment 43: The engineered microbial cell of embodiment 42, wherein the additional copy of the prephenate dehydrogenase gene encodes a prephenate dehydrogenase from *S. cerevisiae.*

Embodiment 44: The engineered microbial cell of embodiment 2 or embodiment 6, wherein the engineered microbial cell includes a bacterial cell.

Embodiment 45: The engineered microbial cell of embodiment 44, wherein the bacterial cell includes a cell of the genus *Corynebacterium* or *Bacillus.*

Embodiment 46: The engineered microbial cell of embodiment 45, wherein the bacterial cell is a cell of the species *glutamicum* or *subtilis*, respectively.

Embodiment 47: The engineered microbial cell of embodiment 45 or embodiment 46, wherein the heterologous TYDC includes a TYDC having at least 70% amino acid sequence identity with a TYDC from *Enterococcus faecium.*

Embodiment 48: The engineered microbial cell of any one of embodiments 45-47, wherein the DAHP synthase includes a DAHP synthase having at least 70% amino acid sequence identity with a DAHP synthase from *S. cerevisiae.*

Embodiment 49: The engineered microbial cell of any one of embodiments 45-48, wherein the engineered microbial cell includes increased activity of a shikimate kinase relative to a control cell.

Embodiment 50: The engineered microbial cell of embodiment 49, wherein the shikimate kinase includes a shikimate kinase having at least 70% amino acid sequence identity with a shikimate kinase from *Escherichia coli.*

Embodiment 51: The engineered microbial cell of embodiment 50, wherein the: (a) heterologous TYDC includes a pyridoxal-dependent decarboxylase (TYDC) from *E. faecium* Com15; (b) DAHP synthase includes a phospho-2-dehydro-3-deoxyheptonate aldolase (DAHP synthase) from *S. cerevisiae* S288c; and (c) shikimate kinase includes a shikimate kinase from *E. coli* K12.

Embodiment 52: The engineered microbial cell of any one of embodiments 13-43, wherein, when cultured, the engineered microbial cell produces tyramine at a level greater than 100 mg/L of culture medium.

Embodiment 53: The engineered microbial cell of embodiment 52, wherein the engineered microbial cell produces tyramine at a level of at least 2.5 g/L of culture medium.

Embodiment 54: An engineered microbial cell which is a bacterial cell including a heterologous tyrosine decarboxylase (TYDC) having at least 70% amino acid sequence identity with a TYDC from *Enterococcus faecium*, wherein the engineered bacterial cell produces tyramine.

Embodiment 55: The engineered microbial cell of embodiment 54, wherein the bacterial cell is of the genus *Corynebacteria.*

Embodiment 56: The engineered microbial cell of embodiment 55, wherein the bacterial cell is of the species *glutamicum.*

Embodiment 57: An engineered microbial cell which is a bacterial cell including a heterologous tyrosine decarboxylase (TYDC) having at least 70% amino acid sequence identity with a TYDC from *Zygosaccharomyces bailii*, wherein the engineered bacterial cell produces tyramine.

Embodiment 58: The engineered microbial cell of embodiment 57, wherein the bacterial cell is of the genus *Corynebacteria.*

Embodiment 59: The engineered microbial cell of embodiment 58, wherein the bacterial cell is of the species *glutamicum.*

Embodiment 60: A culture of engineered microbial cells according to any one of embodiments 13-59.

Embodiment 61: The culture of embodiment 60, wherein the tyramine is produced from fermentation of a substrate wherein at least 50% of the substrate is not derived from protein or amino acid sources.

Embodiment 62: The culture of embodiment 61, wherein the substrate includes a carbon source and a nitrogen source selected from the group consisting of urea, an ammonium salt, ammonia, and any combination thereof.

Embodiment 63: The culture of any one of embodiments 60-62, wherein the engineered microbial cells are present in a concentration such that the culture has an optical density at 600 nm of 10-500.

Embodiment 64: The culture of any one of embodiments 60-63, wherein the culture includes tyramine.

Embodiment 65: The culture of any one of embodiments 60-64, wherein the culture includes tyramine at a level greater than 100 mg/L of culture medium.

Embodiment 66: The culture of any one of embodiments 60-65, wherein the culture includes tyramine at a level of at least 2.5 g/L of culture medium.

Embodiment 67: A method of culturing engineered microbial cells according to any one of embodiments 1-59, the method including culturing the cells in the presence of a fermentation substrate including a non-protein carbon and a non-protein nitrogen source, wherein the engineered microbial cells produce tyramine.

Embodiment 68: The method of embodiment 67, wherein the method includes fed-batch culture, with an initial glucose level in the range of 1-100 g/L, followed controlled sugar feeding.

Embodiment 69: The method of embodiment 67 or embodiment 68, wherein the fermentation substrate includes glucose and a nitrogen source selected from the group consisting of urea, an ammonium salt, ammonia, and any combination thereof.

Embodiment 70: The method of any one of embodiments 67-69, wherein the culture is pH-controlled during culturing.

Embodiment 71: The method of any one of embodiments 67-70, wherein the culture is aerated during culturing.

Embodiment 72: The method of any one of embodiments 67-71, wherein the engineered microbial cells produce tyramine at a level greater than 100 mg/L of culture medium.

Embodiment 73: The method of any one of embodiments 67-72, wherein the engineered microbial cells produce tyramine at a level of at least 2.5 g/L of culture medium.

Embodiment 74: The method of any one of embodiments 67-73, wherein the method additionally includes recovering tyramine from the culture.

BRIEF DESCRIPTION OF THE DRAWINGS

FIG. 4A shows a graph of biomass as a function of culture time under different process conditions for a culture of *S. cerevisiae* engineered to produce tyramine. The data come from a study described in Example 2. FIG. 4B shows the tyramine titer for the same culture. FIG. 4C shows the glucose concentration in this culture as a function of culture time.

DETAILED DESCRIPTION

Figure 1:
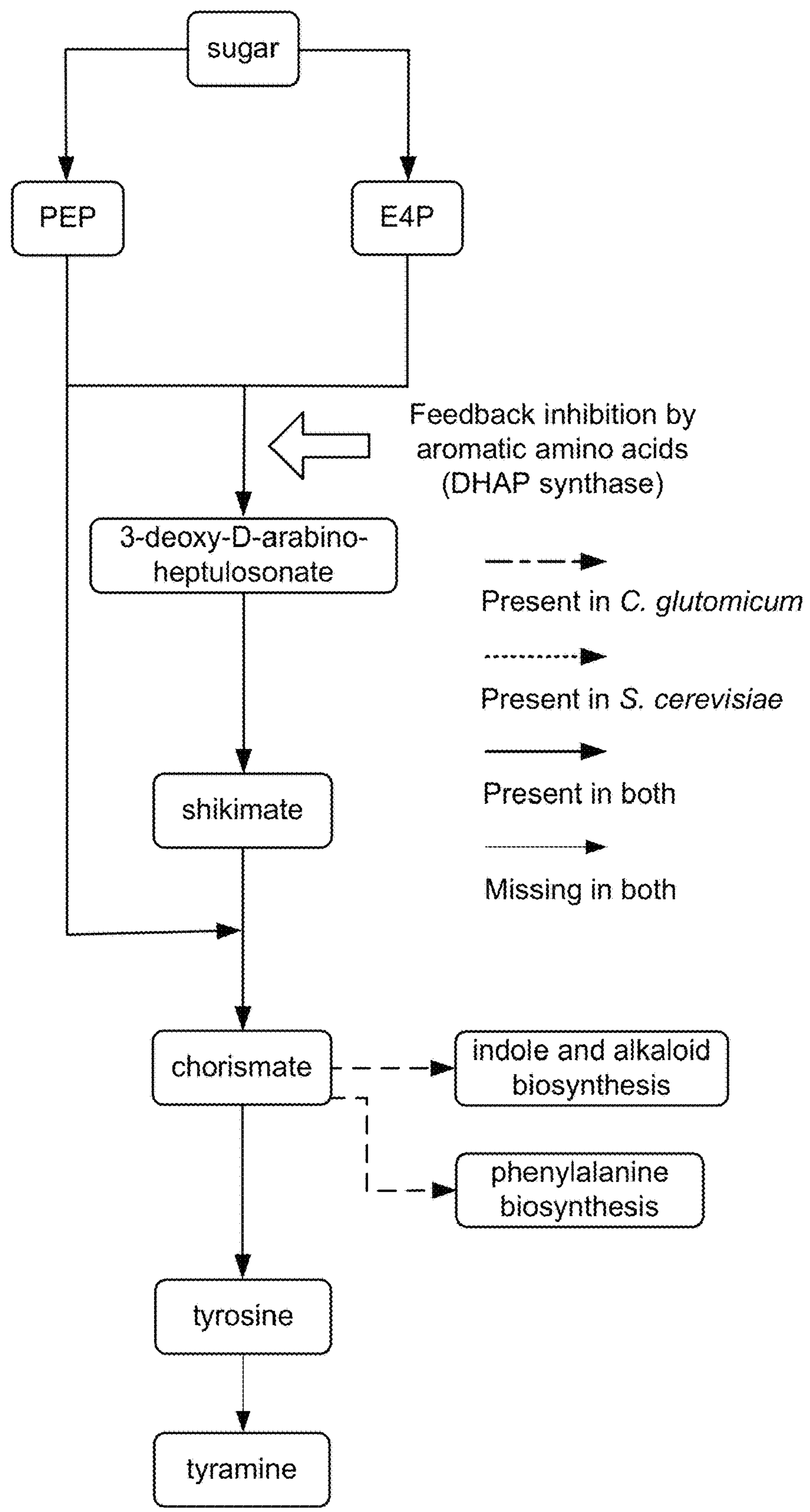
FIG. 1: Pathway for production of tyramine by fermentation.

The present disclosure describes the engineering of microbial cells for fermentative production of tyramine and provides novel engineered microbial cells and cultures, as well as related tyramine production methods.

Definitions

Terms used in the claims and specification are defined as set forth below unless otherwise specified.

The term "fermentation" is used herein to refer to a process whereby a microbial cell converts one or more substrate(s) into a desired product (such as tyramine) by means of one or more biological conversion steps, without the need for any chemical conversion step.

The term "engineered" is used herein, with reference to a cell, to indicate that the cell contains at least one targeted genetic alteration introduced by man that distinguishes the engineered cell from the naturally occurring cell.

The term "endogenous" is used herein to refer to a cellular component, such as a polynucleotide or polypeptide, that is naturally present in a particular cell.

The term "heterologous" is used herein, with reference to a polynucleotide or polypeptide introduced into a host cell, to refer to a polynucleotide or polypeptide, respectively, derived from a different organism, species, or strain than that of the host cell. A heterologous polynucleotide or polypeptide has a sequence that is different from any sequence(s) found in the same host cell.

As used with reference to polypeptides, the term "wild-type" refers to any polypeptide having an amino acid sequence present in a polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized. The term wild-type is also used to denote naturally occurring cells.

A "control cell" is a cell that is otherwise identical to an engineered cell being tested, including being of the same genus and species as the engineered cell, but lacks the specific genetic modification(s) being tested for in the engineered cell.

Enzymes are identified herein by the reactions they catalyze and, unless otherwise indicated, refer to any polypeptide capable of catalyzing the identified reaction. Unless otherwise indicated, enzymes may be derived from any organism and may have a naturally occurring or mutated amino acid sequence. As is well known, enzymes may have multiple functions and/or multiple names, sometimes depending on the source organism from which they derive. The enzyme names used herein encompass orthologs, including enzymes that may have one or more additional functions or a different name.

The term "feedback-disregulated" is used herein with reference to an enzyme that is normally negatively regulated by a downstream product of the enzymatic pathway (i.e., feedback-inhibition) in a particular cell. In this context, a "feedback-disregulated" enzyme is a form of the enzyme that is less sensitive to feedback-inhibition than the wild-type enzyme endogenous to the cell. A feedback-disregulated enzyme may be produced by introducing one or more mutations into a wild-type enzyme. Alternatively, a feedback-disregulated enzyme may simply be a heterologous, wild-type enzyme that, when introduced into a particular microbial cell, is not as sensitive to feedback-inhibition as the endogenous, wild-type enzyme. In some embodiments, the feedback-disregulated enzyme shows no feedback-inhibition in the microbial cell.

The term "tyramine" refers to 4-(2-aminoethyl)phenol (CAS #51-67-2).

The term "sequence identity," in the context of two or more amino acid or nucleotide sequences, refers to two or more sequences that are the same or have a specified percentage of amino acid residues or nucleotides that are the same, when compared and aligned for maximum correspondence, as measured using a sequence comparison algorithm or by visual inspection.

For sequence comparison to determine percent nucleotide or amino acid sequence identity, typically one sequence acts as a "reference sequence," to which a "test" sequence is compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence relative to the reference sequence, based on the designated program parameters. Alignment of sequences for comparison can be conducted using BLAST set to default parameters.

The term "titer," as used herein, refers to the mass of a product (e.g., tyramine) produced by a culture of microbial cells divided by the culture volume.

As used herein with respect to recovering tyramine from a cell culture, "recovering" refers to separating the tyramine from at least one other component of the cell culture medium.

Engineering Microbes for Tyramine Production

Tyramine Biosynthesis Pathway

Tyramine is derived from the aromatic branch of amino acid biosynthesis, based on the precursors phosphoenolpyruvate (PEP) and erythrose-4-phosphate (E4P). This pathway is illustrated in FIG. 1. The first step of the amino acid biosynthesis pathway, catalyzed by 3-deoxy-D-arabino-heptulosonate-7-phosphate (DAHP) synthase, is subject to feedback inhibition by the aromatic amino acids tyrosine, tryptophan and phenylalanine. Many microbes lack the enzyme that catalyzes the final step in this pathway, namely tyrosine decarboxylase (TYDC). Production of tyramine in such microbial hosts requires the addition of at least one heterologous TYDC enzyme.

Engineering for Microbial Tyramine Production

Any TYDC that is active in the microbial cell being engineered may be introduced into the cell, typically by introducing and expressing the gene encoding the enzyme using standard genetic engineering techniques. Suitable TYDCs may be derived from any source, including plant, archaeal, fungal, gram-positive bacterial, and gram-negative bacterial sources. Exemplary sources include, but are not limited to: *Papaver somniferum, Petroselinum crispum, Oryza sativa, Methanosphaerula palustris Methanocaldococcus jannaschii, Zygosaccharomyces bailii, Penicillium marneffei, Talaromyces stipitatus, Trichophyton equinum, Propionibacterium* sp. *oral, Enterococcus faecium, Streptomyces hygroscopicus, Streptomyces sviceus, Modestobacter marinus, Pseudomonas putida, Sinorhizobium fredii*. Some sources, such as *P. somniferum*, may include more than one form of TYDC, and any of these can be used in the methods described herein.

One or more copies of a TYDC can be introduced into a selected microbial host cell. If more than one copy of a TYDC gene is introduced, the copies can be copies of the same or different TYDC gene. In some embodiments, the heterologous TYDC gene(s) is/are expressed from a strong, constitutive promoter. In some embodiments, the heterologous TYDC gene(s) is/are expressed from inducible promoters. The heterologous genes can optionally be codon-optimized to enhance expression in the selected microbial host cell. Codon-optimization tables are available for common microbial host cells. The codon-optimization tables used in the Examples are as follows: *Bacillus subtilis* Kazusa codon table: www.kazusa.or.jp/codon/cgi-bin/showcodon.cgi?species=1423&aa=1&style=N; *Yarrowia lipolytica* Kazusa codon table: www.kazusa.or.jp/codon/cgi-bin/showcodon.cgi?species=4952&aa=1&style=N; *Corynebacteria glutamicum* Kazusa codon table: www.kazusa.or.jp/codon/cgi-bin/showcodon.cgi?species=340322&aa=1&style=N; *Saccharomyces cerevisiae* Kazusa codon table: http://www.kazusa.or.jp/codon/cgi-bin/showcodon.cgi?species=4932&aa=1&style=N. Also used, was a modified, combined codon usage scheme for *S. cereviae* and *C. glutamicum*, which is reproduced below.

| Amino Acid | Codon | Fraction |
|---|---|---|
| A | GCG | 0.22 |
| A | GCA | 0.29 |
| A | GCT | 0.24 |
| A | GCC | 0.25 |
| C | TGT | 0.36 |
| C | TGC | 0.64 |
| D | GAT | 0.56 |
| D | GAC | 0.44 |
| E | GAG | 0.44 |
| E | GAA | 0.56 |
| F | TTT | 0.37 |
| F | TTC | 0.63 |
| G | GGG | 0.08 |
| G | GGA | 0.19 |
| G | GGT | 0.3 |
| G | GGC | 0.43 |
| H | CAT | 0.32 |
| H | CAC | 0.68 |
| I | ATA | 0.03 |
| I | ATT | 0.38 |
| I | ATC | 0.59 |
| K | AAG | 0.6 |
| K | AAA | 0.4 |
| L | TTG | 0.29 |
| L | TTA | 0.05 |
| L | CTG | 0.29 |
| L | CTA | 0.06 |
| L | CTT | 0.17 |
| L | CTC | 0.14 |
| M | ATG | 1 |
| N | AAT | 0.33 |
| N | AAC | 0.67 |
| P | CCG | 0.22 |
| P | CCA | 0.35 |
| P | CCT | 0.23 |
| P | CCC | 0.2 |
| Q | CAG | 0.61 |
| Q | CAA | 0.39 |
| R | AGG | 0.11 |
| R | AGA | 0.12 |
| R | CGG | 0.09 |
| R | CGA | 0.17 |
| R | CGT | 0.34 |
| R | CGC | 0.18 |
| S | AGT | 0.08 |
| S | AGC | 0.16 |
| S | TCG | 0.12 |
| S | TCA | 0.13 |
| S | TCT | 0.17 |
| S | TCC | 0.34 |
| T | ACG | 0.14 |
| T | ACA | 0.12 |
| T | ACT | 0.2 |
| T | ACC | 0.53 |
| V | GTG | 0.36 |
| V | GTA | 0.1 |
| V | GTT | 0.26 |
| V | GTC | 0.28 |
| W | TGG | 1 |
| Y | TAT | 0.34 |
| Y | TAC | 0.66 |

In Example 1, *C. glutamicum* was engineered to express a TYDC from *E. faecium* (SEQ ID NO:1), which yielded a tyramine titer of 80 μg/L.

Engineering for Increased Tyramine Production

Increasing the Activity of Endogenous Upstream Enzymes

One approach to increasing tyramine production in a microbial cell which expresses a heterologous TYDC is to increase the activity of one or more upstream enzymes in the tyramine biosynthesis pathway. Upstream pathway enzymes include all enzymes involved in the conversions from a feedstock all the way to tyrosine. In certain embodiments, the upstream pathway enzymes refer specifically to the enzymes involved in the conversion of key precursors (i.e., E4P and PEP) into the last native metabolite (i.e. tyrosine) in the pathway leading to tyramine. In some embodiments, the activity of one or more upstream pathway enzymes is increased by modulating the expression or activity of the endogenous enzyme(s). In some embodiments, the activity of one or more upstream pathway enzymes is supplemented by introducing one or more of the corresponding genes into the TYDC-expressing microbial host cell. Such genes include those encoding a dehydroquinate synthase, a dehydroquinate dehydratase, a shikimate dehydrogenase, a shikimate kinase, EPSP synthase, aromatic pentafunctional enzyme, a chorismate synthase, a chorismate mutase, a prephenate dehydratase, a phenylalanine aminotransferase, a prephenate dehydrogenase, a prephenate aminotransferase, an arogenate dehydrogenase, a phenylalanine hydroxylase, an aromatic amino acid transferase such as a tyrosine aminotransferase, a glyceraldehyde-3-phosphate dehydrogenase, a transaldolase, a transketolase, a DAHP synthase, a phosphoenolpyruvate synthase, a glutamate synthase. Suitable upstream pathway genes may be derived from any source, including, for example, those discussed above as sources for a heterologous TYDC gene.

Example 1 describes the successful engineering of a microbial host cell to express a heterologous TYDC, along with an introduced gene encoding an upstream gene; either a chorismate synthase or a prephenate dehydrogenase. In particular, *S. cerevisiae* was engineered to express a TYDC from *P. somniferum* (SEQ ID NO:2) and an additional copy of the *S. cerevisiae* gene encoding either chorismate synthase (SEQ ID NO:3) or prephenate dehydrogenase (SEQ ID NO:4). The results are provided in Example 1, below.

An introduced upstream pathway gene may be heterologous or may simply be an additional copy of an endogenous gene. In some embodiments, one or more such genes are introduced into the TYDC-expressing microbial host cell and expressed from a strong constitutive promoter and/or can optionally be codon-optimized to enhance expression in the selected microbial host cell. A TYDC-expressing microbial cell can, for example, be engineered to express one or more copies of one or more upstream pathway genes.

In various embodiments, the engineering of a TYDC-expressing microbial cell to increase the activity of one or more upstream pathway enzymes increases the tyramine titer by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold. In various embodiments, the increase in tyramine titer is in the range of 10 percent to 100-fold, 2-fold to 50-fold, 5-fold to 40-fold, 10-fold to 30-fold, or any range bounded by any of the values listed above. (Ranges herein include their endpoints.) These increases are determined relative to the tyramine titer observed in a tyramine-producing microbial cell that lacks any increase in activity of upstream pathway enzymes. This reference cell may have one or more other genetic alterations aimed at increasing tyramine production, e.g., the cell may express a feedback-disregulated enzyme.

In various embodiments, the tyramine titers achieved by increasing the activity of one or more upstream pathway genes are at least 10, 50, 75, 100, 200, 300, 400, 500, 600, 700, 800, or 900 mg/L or at least 1, 1.5, 2, 2.5, 3, 3.5, 4, 4.5, 5, or 10 gm/L. In various embodiments, the titer is in the range of 10 mg/L to 10 gm/L, 100 mg/L to 5 gm/L, 200 mg/L to 4 gm/L, 300 mg/L to 3 gm/L, or any range bounded by any of the values listed above.

Introduction of Feedback-Disregulated Enzymes

Since aromatic amino acid biosynthesis is subject to feedback inhibition, another approach to increasing tyramine production in a microbial cell engineered to express a heterologous TYDC is to introduce feedback-disregulated forms of one or more enzymes that are normally subject to feedback inhibition in the TYDC-expressing microbial cell. Examples of such enzymes include DAHP synthase and chorismate mutase. A feedback-disregulated form can be a heterologous, wild-type enzyme that is less sensitive to feedback inhibition than the endogenous enzyme in the particular microbial host cell. Alternatively, a feedback-disregulated form can be a variant of an endogenous or heterologous enzyme that has one or more mutations rendering it less sensitive to feedback inhibition than the corresponding wild-type enzyme. Examples of the latter include variant DAHP synthases (two from *S. cerevisiae*, one from *E. coli*) that have known point mutations rendering them resistant to feedback inhibition, e.g., *S. cerevisiae* ARO4Q166K (SEQ ID NO:5), *S. cerevisiae* ARO4K229L (SEQ ID NO:6), and *E. coli* AroGD146N (SEQ ID NO:7). The last 5 characters of these designations indicate amino acid substitutions, using the standard one-letter code for amino acids, with the first letter referring to the wild-type residue and the last letter referring to the replacement reside; the numbers indicate the position of the amino acid substitution in the translated protein.

Example 1 describes the successful engineering of a fungal and bacterial host cells to express a heterologous TYDC, along with an introduced gene encoding a feedback-disregulated DAHP synthase. In particular, *S. cerevisiae* was engineered to express a TYDC 2 from *P. somniferum* (SEQ ID NO:2) and *S. cerevisiae* ARO4K229L (SEQ ID NO:6), which gave a tyramine titer of 387 μg/L.

In various embodiments, the engineering of a TYDC-expressing microbial cell to express a feedback-disregulated enzymes increases the tyramine titer by at least 10, 20, 30, 40, 50, 60, 70, 80, or 90 percent or by at least 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 8.5-fold, 9-fold, 9.5-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold. In various embodiments, the increase in tyramine titer is in the range of 10 percent to 100-fold, 2-fold to 50-fold, 5-fold to 40-fold, 10-fold to 30-fold, or any range bounded by any of the values listed above. These increases are determined relative to the tyramine titer observed in a tyramine-producing microbial cell that does not express a feedback-disregulated enzyme. This reference cell may (but need not) have other genetic alterations aimed at increasing tyramine production, i.e., the cell may have increased activity of an upstream pathway enzyme resulting from some means other than feedback-insensitivity.

In various embodiments, the tyramine titers achieved by using a feedback-disregulated enzyme to increase flux though the tyramine biosynthetic pathway are at least 50, 75, 100, 200, 300, 400, 500, 600, 700, 800, or 900 mg/L or at least 1, 1.5, 2, 2.5, 3, 3.5, 4, 4.5, or 5 gm/L. In various embodiments, the titer is in the range of 100 mg/L to 5 gm/L, 200 mg/L to 4 gm/L, 300 mg/L to 3 gm/L, or any range bounded by any of the values listed above.

The approaches of supplementing the activity of one or more endogenous enzymes and/or introducing one or more feedback-disregulated enzymes can be combined in TYDC-expressing microbial cells to achieve even higher tyramine production levels.

Microbial Host Cells

Any microbe that can be used to express introduced genes can be engineered for fermentative production of tyramine as described above. In certain embodiments, the microbe is one that is naturally incapable of fermentative production of tyramine. In some embodiments, the microbe is one that is readily cultured, such as, for example, a microbe known to be useful as a host cell in fermentative production of compounds of interest. Bacteria cells, including gram positive or gram negative bacteria can be engineered as described above. Examples include, in addition to *C. glutamicum* cells, *P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *P. alcaligenes, Lactobacilis* spp. (such as *L. lactis, L. plantarum*), *L. grayi, E. coli, E. faecium, E. gallinarum, E. casseliflavus*, and/or *E. faecalis* cells.

There are numerous types of anaerobic cells that can be used as microbial host cells in the methods described herein. In some embodiments, the microbial cells are obligate anaerobic cells. Obligate anaerobes typically do not grow well, if at all, in conditions where oxygen is present. It is to be understood that a small amount of oxygen may be present, that is, there is some level of tolerance level that obligate anaerobes have for a low level of oxygen. Obligate anaerobes engineered as described above can be grown under substantially oxygen-free conditions, wherein the amount of oxygen present is not harmful to the growth, maintenance, and/or fermentation of the anaerobes.

Alternatively, the microbial host cells used in the methods described herein can be facultative anaerobic cells. Facultative anaerobes can generate cellular ATP by aerobic respiration (e.g., utilization of the TCA cycle) if oxygen is present. However, facultative anaerobes can also grow in the absence of oxygen. Facultative anaerobes engineered as described above can be grown under substantially oxygen-free conditions, wherein the amount of oxygen present is not harmful to the growth, maintenance, and/or fermentation of the anaerobes, or can be alternatively grown in the presence of greater amounts of oxygen.

In some embodiments, the microbial host cells used in the methods described herein are filamentous fungal cells. (See, e.g., Berka & Barnett, Biotechnology Advances, (1989), 7(2):127-154). Examples include *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp. (such as *A. oryzae, A. niger, A. sojae, A. japonicus, A. nidulans*, or *A. awamori*), *Fusarium* sp. (such as *F. roseum, F. graminum F. cerealis, F. oxysporuim*, or *F. venenatum*), *Neurospora* sp. (such as *N. crassa* or *Hypocrea* sp.), *Mucor* sp. (such as *M. miehei*), *Rhizopus* sp., and *Emericella* sp. cells. In particular embodiments, the fungal cell engineered as described above is *A. nidulans, A. awamori, A. oryzae, A. aculeatus, A. niger, A. japonicus, T. reesei, T. viride, F. oxysporum*, or *F. solani*. Illustrative plasmids or plasmid components for use with such hosts include those described in U.S. Patent Pub. No. 2011/0045563.

Yeasts can also be used as the microbial host cell in the methods described herein. Examples include: *Saccharomyces* sp., *Schizosaccharomyces* sp., *Pichia* sp., *Hansenula polymorpha, Pichia stipites, Kluyveromyces marxianus, Kluyveromyces* spp., *Yarrowia lipolytica* and *Candida* sp. In some embodiments, the *Saccharomyces* sp. is *S. cerevisiae* (See, e.g., Romanos et al., Yeast, (1992), 8(6):423-488). Illustrative plasmids or plasmid components for use with such hosts include those described in U.S. Pat. No. 7,659,097 and U.S. Patent Pub. No. 2011/0045563.

In some embodiments, the host cell can be an algal cell derived, e.g., from a green algae, red algae, a glaucophyte, a chlorarachniophyte, a euglenid, a chromista, or a dinoflagellate. (See, e.g., Saunders & Warmbrodt, "Gene Expression in Algae and Fungi, Including Yeast," (1993), National Agricultural Library, Beltsville, Md.). Illustrative plasmids or plasmid components for use in algal cells include those described in U.S. Patent Pub. No. 2011/0045563.

In other embodiments, the host cell is a cyanobacterium, such as cyanobacterium classified into any of the following groups based on morphology: *Chlorococcales, Pleurocapsales, Oscillatoriales, Nostocales, Synechosystic* or *Stigonematales* (See, e.g., Lindberg et al., Metab. Eng., (2010) 12(1):70-79). Illustrative plasmids or plasmid components for use in cyanobacterial cells include those described in U.S. Patent Pub. Nos. 2010/0297749 and 2009/0282545 and in Intl. Pat. Pub. No. WO 2011/034863.

Genetic Engineering Methods

Microbial cells can be engineered for fermentative tyramine production using conventional techniques of molecular biology (including recombinant techniques), microbiology, cell biology, and biochemistry, which are within the skill of the art. Such techniques are explained fully in the literature, see e.g., "Molecular Cloning: A Laboratory Manual," fourth edition (Sambrook et al., 2012); "Oligonucleotide Synthesis" (M. J. Gait, ed., 1984); "Culture of Animal Cells: A Manual of Basic Technique and Specialized Applications" (R. I. Freshney, ed., 6th Edition, 2010); "Methods in Enzymology" (Academic Press, Inc.); "Current Protocols in Molecular Biology" (F. M. Ausubel et al., eds., 1987, and periodic updates); "PCR: The Polymerase Chain Reaction," (Mullis et al., eds., 1994); Singleton et al., Dictionary of Microbiology and Molecular Biology 2nd ed., J. Wiley & Sons (New York, N.Y. 1994).

Vectors are polynucleotide vehicles used to introduce genetic material into a cell. Vectors useful in the methods described herein can be linear or circular. Vectors can integrate into a target genome of a host cell or replicate independently in a host cell. For many applications, integrating vectors that produced stable transformants are preferred. Vectors can include, for example, an origin of replication, a multiple cloning site (MCS), and/or a selectable marker. An expression vector typically includes an expression cassette containing regulatory elements that facilitate expression of a polynucleotide sequence (often a coding sequence) in a particular host cell. Vectors include, but are not limited to, integrating vectors, prokaryotic plasmids, episomes, viral vectors, cosmids, and artificial chromosomes.

Illustrative regulatory elements that may be used in expression cassettes include promoters, enhancers, internal ribosomal entry sites (IRES), and other expression control elements (e.g., transcription termination signals, such as polyadenylation signals and poly-U sequences). Such regulatory elements are described, for example, in Goeddel, Gene Expression Technology: Methods In Enzymology 185, Academic Press, San Diego, Calif. (1990).

In some embodiments, vectors may be used to introduce systems that can carry out genome editing, such as CRISPR systems. See U.S. Patent Pub. No. 2014/0068797, published 6 Mar. 2014; see also Jinek M., et al., "A programmable dual-RNA-guided DNA endonuclease in adaptive bacterial immunity," Science 337:816-21, 2012). In Type II CRISPR-Cas9 systems, Cas9 is a site-directed endonuclease, namely an enzyme that is, or can be, directed to cleave a polynucleotide at a particular target sequence using two distinct endonuclease domains (HNH and RuvC/RNase H-like domains). Cas9 can be engineered to cleave DNA at any desired site because Cas9 is directed to its cleavage site by RNA. Cas9 is therefore also described as an "RNA-guided nuclease." More specifically, Cas9 becomes associated with one or more RNA molecules, which guide Cas9 to a specific polynucleotide target based on hybridization of at least a portion of the RNA molecule(s) to a specific sequence in the target polynucleotide. Ran, F. A., et al., ("In vivo genome editing using *Staphylococcus aureus* Cas9," Nature 520 (7546):186-91, 2015 Apr. 9], including all extended data) present the crRNA/tracrRNA sequences and secondary structures of eight Type II CRISPR-Cas9 systems. Cas9-like synthetic proteins are also known in the art (see U.S. Published Patent Application No. 2014-0315985, published 23 Oct. 2014).

Example 1 describes two illustrative integration approaches for introducing polynucleotides into the genomes of *S. cerevisiae* and *C. glutamicum* cells.

Vectors or other polynucleotides can be introduced into microbial cells by any of a variety of standard methods, such as transformation, conjugation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. Transformants can be selected by any method known in the art. Suitable methods for selecting transformants are described in U.S. Patent Pub. Nos. 2009/0203102, 2010/0048964, and 2010/0003716, and International Publication Nos. WO 2009/076676, WO 2010/003007, and WO 2009/132220.

Engineered Microbial Cells

The above-described methods can be used to produce engineered microbial cells that produce, and in certain embodiments, overproduce, tyramine. Engineered microbial cells can have at least 1, 2, 3, 4, 5, 6, 7, 8, 9, 10, or more genetic alterations, such as 30-40 alterations, as compared to a wild-type microbial cell, such as any of the microbial host cells described herein. Engineered microbial cells described in the Example below have one, two, or three genetic alterations, but those of skill in the art can, following the guidance set forth herein, design microbial cells with additional alterations. In some embodiments, the engineered microbial cells have not more than 15, 14, 13, 12, 11, 10, 9, 8, 7, 6, 5, or 4 genetic alterations, as compared to a wild-type microbial cell. In various embodiments, microbial cells engineered for tyramine production can have a number of genetic alterations falling within the any of the following illustrative ranges: 1-10, 1-9, 1-8, 2-7, 2-6, 2-5, 2-4, 2-3, 3-7, 3-6, 3-5, 3-4, etc.

In some embodiments, an engineered microbial cell expresses at least one heterologous tyrosine decarboxylase (TYDC). This is necessary in the case of a microbial host cell that does not naturally produce tyramine. In various embodiments, the microbial cell can include and express, for example: (1) a single heterologous TYDC gene, (2) two or more heterologous TYDC genes, which can be the same or different (in other words, multiple copies of the same heterologous TYDC genes can be introduced or multiple, different heterologous TYDC genes can be introduced), (3) a single heterologous TYDC gene and one or more additional copies of an endogenous TYDC gene, or (4) two or more heterologous TYDC genes, which can be the same or different, and one or more additional copies of an endogenous TYDC gene.

This engineered host cell can include at least one additional genetic alteration that increases flux through the pathway leading to the production of tyrosine (the immediate precursor of tyramine). These "upstream" enzymes in the pathway include: dehydroquinate synthase, dehydroquinate dehydratase, shikimate dehydrogenase, shikimate kinase, EPSP synthase, aromatic pentafunctional enzyme, chorismate synthase, chorismate mutase, prephenate dehydratase, phenyalananine aminotransferase, prephenate dehydrogenase, prephenate aminotransferase, arogenate dehydrogenase, phenylalanine hydroxylase, and tyrosine aminotransferase, including any isoforms, paralogs, or orthologs having these enzymatic activities (which as those of skill in the art readily appreciate may be known by different names). The at least one additional alteration can increase the activity of the upstream pathway enzyme(s) by any available means, e.g., by: (1) modulating the expression or activity of the endogenous enzyme(s), (2) expressing one or more additional copies of the genes for the endogenous enzymes, or (3) expressing one or more copies of the genes for one or more heterologous enzymes.

In some embodiments, increased flux through the pathway can be achieved by expressing one or more genes encoding a feedback-disregulated enzyme, as discussed above. For example, the engineered host cell can include and express: (1) one or more feedback-disregulated DAHP synthase genes, (2) one or more feedback-disregulated chorismate mutase genes, or (3) one or more feedback-disregulated DAHP synthase genes and one or more feedback-disregulated chorismate mutase genes. Thus, an engineered microbial cell having any of these genetic alterations can also include at least one heterologous TYDC and, optionally, one more genetic alterations that increase the activity of one or more upstream pathway enzymes.

The engineered microbial cells can contain introduced genes that have a wild-type nucleotide sequence or that differ from wild-type. For example, the wild-type nucleotide sequence can be codon-optimized for expression in a particular host cell. The amino acid sequences encoded by any of these introduced genes can be wild-type or can differ from wild-type. In various embodiments, the amino acid sequences have at least 0 percent, 70 percent, 75 percent, 80 percent, 85 percent, 90 percent, 95 percent or 100 percent amino acid sequence identity with a wild-type amino acid sequence.

The engineered microbial cells can, in various embodiments, be capable of producing tyramine at high titer, as described above. In some embodiments, the engineered microbial cell can produce tyramine by fermentation of a substrate, wherein at least 20 percent of the substrate is not derived from protein or amino acid sources. In various embodiments, at least 25 percent, 30 percent, 35 percent, 40 percent, 45 percent, 50 percent, 55 percent, 60 percent, 65 percent, 70 percent, 75 percent, 80 percent, 85 percent, 90 percent, 95 percent or 100 percent of the substrate is not derived from protein or amino acid sources. In some embodiments, the percentage of the fermentation substrate that is not derived from protein or amino acid sources falls within any of the following illustrative ranges: 40-100 percent, 40-90 percent, 40-80 percent, 50-100 percent, 50-90 percent, 50-80 percent, 60-100 percent, 60-90 percent, 60-80 percent, etc.

The approach described herein has been carried out in fungal cells, namely the yeast *S. cerevisiae* (a eukaryote), and in bacterial cells, namely *C. glutamicum* (a prokaryote). (See Example 1.)

Illustrative Engineered Fungal Cells

Illustrative Engineered *Saccharomyces cerevisiae* Cells

In certain embodiments the engineered yeast (e.g., *S. cerevisiae*) cell expresses a heterologous tyrosine decarboxylase (TYDC) having at least 70 percent, 75 percent, 80 percent, 85 percent, 90 percent, 95 percent or 100 percent amino acid sequence identity to a TYDC from *Papaver somniferum*. In various embodiments, the *P. somniferum* TYDC can include SEQ ID NO:2. This may be the only genetic alteration of the engineered yeast cell, or the yeast cell can include one or more additional genetic alterations, as discussed more generally above.

In particular embodiments, the engineered yeast (e.g., *S. cerevisiae*) cell additionally expresses a variant of a *S. cerevisiae* DAHP synthase, which typically has at least 70 percent, 75 percent, 80 percent, 85 percent, 90 percent, or 95 percent amino acid sequence identity to the wild-type *S. cerevisiae* DAHP synthase. In an illustrative embodiment, the engineered yeast (e.g., *S. cerevisiae*) cell expresses a *P. somniferum* Tyrosine/DOPA decarboxylase 2 (SEQ ID NO:2) and a feedback-disregulated *S. cerevisiae* DAHP synthase encoded by the Aro4 gene that additionally comprises a K229L mutation (SEQ ID NO:6) to yield a tyramine titer of about 387 μg/L (see Table 1—First-Round Results).

An illustrative yeast (e.g., *S. cerevisiae*) cell having a third genetic alteration can additionally have increased activity of an upstream pathway enzyme, such as prephenate dehydrogenase, relative to the control cell, e.g., produced by introducing an additional copy of a wild-type *S. cereviseae* prephenate dehydrogenase (SEQ ID NO:4) gene into the cell or a gene encoding a prephenate dehydrogenase having at least 70 percent, 75 percent, 80 percent, 85 percent, 90 percent, or 95 percent amino acid sequence identity to the wild-type *S. cereviseae* prephenate dehydrogenase. This alteration increased the tyramine titer to about 346 mg/L (see Table 1—Second-Round Results).

An illustrative yeast (e.g., *S. cerevisiae*) cell having a fourth genetic alteration can additionally have increased activity of an upstream pathway enzyme, such as transaldolase, relative to the control cell, e.g., produced by introducing an additional copy of a wild-type *S. cereviseae* transaldolase (SEQ ID NO:8) gene into the cell or a gene encoding a transaldolase having at least 70 percent, 75 percent, 80 percent, 85 percent, 90 percent, or 95 percent amino acid sequence identity to the wild-type *S. cereviseae* transaldolase. This alteration gave a tyramine titer of about 299 mg/L (see Table 7—Improvement-Round Results for *Saccharomyces cerevisiae* Strains Engineered to Produce Tyramine; note that this was better than the control strain, which contained the three alterations described in the preceding paragraphs; the titer for the control strain, in this experiment, was about 266 mg/L). In an illustrative embodiment, an engineered *S. cereviseae* cell expresses versions of these genes that are codon-optimized using a using a modified combined codon table for *Corynebacterium glutamicum* and *S. cereviseae.*

Illustrative Engineered *Yarrowia lipolytica* Cells

In certain embodiments the engineered yeast (e.g., *Yarrowia lipolytica*) cell expresses a heterologous tyrosine decarboxylase (TYDC) having at least 70 percent, 75 percent, 80 percent, 85 percent, 90 percent, 95 percent or 100 percent amino acid sequence identity to a pyridoxal-dependent decarboxylase (TYDC) from *Enterococcus faecium* (e.g., Com15). In various embodiments, the *E. faecium* TYDC can include SEQ ID NO:1. This may be the only genetic alteration of the engineered yeast cell, or the yeast cell can include one or more additional genetic alterations, as discussed more generally above.

In particular embodiments, the engineered yeast (e.g., *Y. lipolytica*) cell additionally expresses a *S. cerevisiae* DAHP synthase, which typically has at least 70 percent, 75 percent, 80 percent, 85 percent, 90 percent, or 95 percent amino acid sequence identity to the wild-type *S. cerevisiae* (e.g., S288c) phospho-2-dehydro-3-deoxyheptonate aldolase (DAHP synthase)(SEQ ID NO:9). This additional genetic alteration yielded a tyramine titer of 55 mg/L (see Table 3—Host Evaluation Results for *Yarrowia lipolytica* Strains Engineered to Produce Tyramine.) In an illustrative embodiment, an engineered *Y. lipolytica* cell expresses versions of these genes that are codon-optimized for *Y. lipolytica* (SEQ ID NO:10).

Illustrative Engineered Bacterial Cells

Illustrative Engineered *Corynebacterium glutamicum* Cells

In certain embodiments the engineered bacterial (e.g., *C. glutamicum*) cell expresses a heterologous tyrosine decarboxylase (TYDC) having at least 70 percent, 75 percent, 80 percent, 85 percent, 90 percent, 95 percent or 100 percent amino acid sequence identity to a TYDC from *Enterococcus faecium* (e.g., Com15) or from *Zygosaccharomyces bailii*. For example, the *E. faecium* TYDC can include SEQ ID NO:1, and the *Z. bailii* TYDC can include SEQ ID NO:11. Expression of a heterologous TYDC may be the only genetic alteration of the engineered bacterial cell, or the bacterial cell can include one or more additional genetic alterations, as discussed more generally above.

In particular embodiments, the engineered bacterial (e.g., *C. glutamicum*) cell additionally expresses a *S. cerevisiae* DAHP synthase (e.g., phospho-2-dehydro-3-deoxyheptonate aldolase from strain 288c) or a variant thereof, which typically has at least 70 percent, 75 percent, 80 percent, 85 percent, 90 percent, or 95 percent amino acid sequence identity to the wild-type *S. cerevisiae* DAHP synthase (SEQ ID NO:9). Both genes can be codon-optimized, for example, for *S. cerevisiae*. In illustrative embodiments, the engineered bacterial (e.g., *C. glutamicum*) cell expresses either (or both) an *E. faecium* TYDC (SEQ ID NO:1) or a *Z. bailii* TYDC (SEQ ID NO:11) in combination with a feedback-disregulated *S. cerevisiae* DAHP synthase encoded by the Aro4 gene that additionally comprises a K229L mutation (SEQ ID NO:6).

Alternatively, or in addition to expressing a DAHP synthase variant, a TYDC-expressing bacterial (e.g., *C. glutamicum*) cell can have increased activity of an upstream pathway enzyme, such as chorismate synthase and/or prephrenate dehydrogenase relative to the control cell. In an illustrative embodiment, the engineered bacterial (e.g., *C. glutamicum*) cell expresses an *E. faecium* TYDC (SEQ ID NO:1) in combination with a copy of a wild-type *S. cereviseae* chorismate synthase (SEQ ID NO:12) gene or a gene encoding a chorismate synthase having at least 70 percent, 75 percent, 80 percent, 85 percent, 90 percent, or 95 percent amino acid sequence identity to the wild-type *S. cereviseae* chorismate synthase (SEQ ID NO:3). In another illustrative embodiment, the engineered bacterial (e.g., *C. glutamicum*) cell expresses an *E. faecium* TYDC (SEQ ID NO:1) in combination with a copy of a wild-type *S. cereviseae* prephenate dehydrogenase (SEQ ID NO:13) gene or a gene encoding a prephenate dehydrogenase having at least 70 percent, 75 percent, 80 percent, 85 percent, 90 percent, or 95 percent amino acid sequence identity to the wild-type *S. cereviseae* prephenate dehydrogenase (SEQ ID NO:4).

Figure 8:
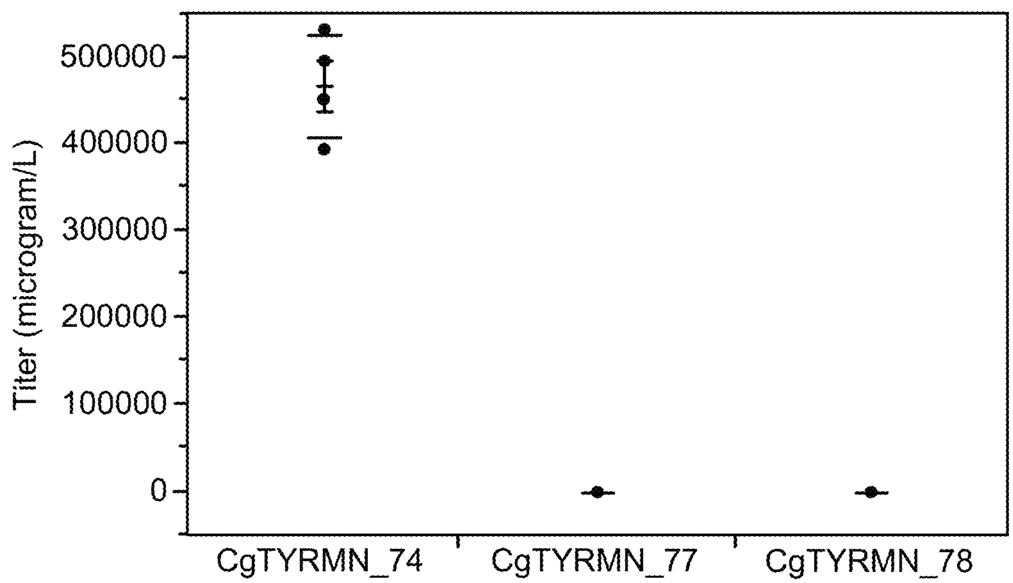
FIG. 8: Tyramine titers measured in extracellular broth following fermentation by the host *C. glutamicum* engineered to express the host evaluation designs for production of tyramine.

An illustrative *C. glutamicum* strain from Example 2B produced 467 mg/L tyramine and expressed pyridoxal-dependent decarboxylase (TYDC) from *E. faecium* Com15 (UniProt ID C9ASN2) (SEQ ID NO:1), phospho-2-dehydro-3-deoxyheptonate aldolase from (DAHP synthase) *S. cerevisiae* S288c (UniProt ID P32449) (SEQ ID NO:9), where the DNA sequences for both enzymes was codon-optimized for *S. cerevisiae*. (Table 6, FIG. 8.) (SEQ ID NOs: 43, 42).

Illustrative Engineered *Bacillus subtilus* Cells

In certain embodiments the engineered bacterial (e.g., *Bacillus subtilus*) cell expresses a heterologous tyrosine decarboxylase (TYDC) having at least 70 percent, 75 percent, 80 percent, 85 percent, 90 percent, 95 percent or 100 percent amino acid sequence identity to a TYDC from *Enterococcus faecium* (e.g., Com15). For example, the *E. faecium* TYDC can include SEQ ID NO:1. Expression of a heterologous TYDC may be the only genetic alteration of the engineered bacterial cell, or the bacterial cell can include one or more additional genetic alterations, as discussed more generally above.

In particular embodiments, the engineered bacterial (e.g., *B. subtilus*) cell additionally expresses a variant of a *S. cerevisiae* DAHP synthase (e.g., phospho-2-dehydro-3-deoxyheptonate aldolase from strain 288c), which typically has at least 70 percent, 75 percent, 80 percent, 85 percent, 90 percent, or 95 percent amino acid sequence identity to the wild-type *S. cerevisiae* DAHP synthase (SEQ ID NO:9).

An illustrative bacterial (e.g., *B. subtilus*) cell having a third genetic alteration can additionally have increased activity of an upstream pathway enzyme, such as shikimate kinase, relative to the control cell, e.g., produced by introducing an additional copy of a wild-type *E. coli* (e.g., K12) shikimate kinase 2 (SEQ ID NO:14) gene into the cell or a gene encoding a shikimate kinase having at least 70 percent, 75 percent, 80 percent, 85 percent, 90 percent, or 95 percent amino acid sequence identity to the wild-type *E. coli* shikimate kinase 2 (SEQ ID NO:15). In an illustrative embodiment, an engineered *B. subtilus* cell expresses versions of these genes that are codon-optimized for *S. cerevisiae.*

Culturing of Engineered Microbial Cells

Any of the microbial cells described herein can be cultured, e.g., for maintenance, growth, and/or tyramine production. Generally, tyramine is produced from fermentation of a substrate wherein at least 20% of the substrate is not derived from protein or amino acid sources. Accordingly, cultures of the engineered microbial cells described herein include a fermentation substrate, wherein at least 20 percent of the substrate is not derived from protein or amino acid sources. In various embodiments, at least 25 percent, 30 percent, 35 percent, 40 percent, 45 percent, 50 percent, 55 percent, 60 percent, 65 percent, 70 percent, 75 percent, 80 percent, 85 percent, 90 percent, 95 percent or 100 percent of the substrate is not derived from protein or amino acid sources. In some embodiments, the percentage of the fermentation substrate that is not derived from protein or amino acid sources falls within any of the following illustrative ranges: 40-100 percent, 40-90 percent, 40-80 percent, 50-100 percent, 50-90 percent, 50-80 percent, 60-100 percent, 60-90 percent, 60-80 percent, etc.

In some embodiments, the cultures are grown to an optical density at 600 nm of 10-500, such as an optical density of 50-150.

In various embodiments, the cultures include produced tyramine at titers of at least 10, 50, 75, 100, 200, 300, 400, 500, 600, 700, 800, or 900 mg/L or at least 1, 1.5, 2, 2.5, 3, 3.5, 4, 4.5, 5, or 10 gm/L. In various embodiments, the titer is in the range of 10 mg/L to 10 gm/L, 100 mg/L to 5 gm/L, 200 mg/L to 4 gm/L, 300 mg/L to 3 gm/L, or any range bounded by any of the values listed above.

Culture Media

Microbial cells can be cultured in any suitable medium including, but not limited to, a minimal medium, i.e., one containing the minimum nutrients possible for cell growth. Minimal medium typically contains: (1) a carbon source for microbial growth; (2) salts, which may depend on the particular microbial cell and growing conditions; and (3) water. Suitable media can also include any combination of the following: a nitrogen source for growth and product formation, a sulfur source for growth, a phosphate source for growth, metal salts for growth, vitamins for growth, and other cofactors for growth.

Any suitable carbon source can be used to cultivate the host cells. The term “carbon source” refers to one or more carbon-containing compounds capable of being metabolized by a microbial cell. In various embodiments, the carbon source is a carbohydrate (such as a monosaccharide, a disaccharide, an oligosaccharide, or a polysaccharide), or an invert sugar (e.g., enzymatically treated sucrose syrup). Illustrative monosaccharides include glucose (dextrose), fructose (levulose), and galactose; illustrative oligosaccharides include dextran or glucan, and illustrative polysaccharides include starch and cellulose. Suitable sugars include C6 sugars (e.g., fructose, mannose, galactose, or glucose) and C5 sugars (e.g., xylose or arabinose). Other, less expensive carbon sources include sugar cane juice, beet juice, sorghum juice, and the like, any of which may, but need not be, fully or partially deionized.

The salts in a culture medium generally provide essential elements, such as magnesium, nitrogen, phosphorus, and sulfur to allow the cells to synthesize proteins and nucleic acids.

Minimal medium can be supplemented with one or more selective agents, such as antibiotics.

To produce tyramine, the culture medium can include, and/or is supplemented during culture with, glucose and/or a nitrogen source such as urea, an ammonium salt, ammonia, or any combination thereof.

Culture Conditions

Materials and methods suitable for the maintenance and growth of microbial cells are well known in the art. See, for example, U.S. Pub. Nos. 2009/0203102, 2010/0003716, and 2010/0048964, and International Pub. Nos. WO 2004/033646, WO 2009/076676, WO 2009/132220, and WO 2010/003007, Manual of Methods for General Bacteriology Gerhardt et al., eds), American Society for Microbiology, Washington, D.C. (1994) or Brock in Biotechnology: A Textbook of Industrial Microbiology, Second Edition (1989) Sinauer Associates, Inc., Sunderland, Mass.

In general, cells are grown and maintained at an appropriate temperature, gas mixture, and pH (such as about 20° C. to about 37° C., about 6% to about 84% $CO_2$, and a pH between about 5 to about 9). In some aspects, cells are grown at 35° C. In certain embodiments, such as where thermophilic bacteria are used as the host cells, higher temperatures (e.g., 50° C.-75° C.) may be used. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the particular cell.

Standard culture conditions and modes of fermentation, such as batch, fed-batch, or continuous fermentation that can be used are described in U.S. Publ. Nos. 2009/0203102, 2010/0003716, and 2010/0048964, and International Pub. Nos. WO 2009/076676, WO 2009/132220, and WO 2010/003007. Batch and Fed-Batch fermentations are common and well known in the art, and examples can be found in Brock, Biotechnology: A Textbook of Industrial Microbiology, Second Edition (1989) Sinauer Associates, Inc.

In some embodiments, the cells are cultured under limited sugar (e.g., glucose) conditions. In various embodiments, the amount of sugar that is added is less than or about 105% (such as about 100%, 90%, 80%, 70%, 60%, 50%, 40%, 30%, 20%, or 10%) of the amount of sugar that can be consumed by the cells. In particular embodiments, the amount of sugar that is added to the culture medium is approximately the same as the amount of sugar that is consumed by the cells during a specific period of time. In some embodiments, the rate of cell growth is controlled by limiting the amount of added sugar such that the cells grow at the rate that can be supported by the amount of sugar in the cell medium. In some embodiments, sugar does not accumulate during the time the cells are cultured. In various embodiments, the cells are cultured under limited sugar conditions for times greater than or about 1, 2, 3, 5, 10, 15, 20, 25, 30, 35, 40, 50, 60, or 70 hours or even up to about 5-10 days. In various embodiments, the cells are cultured under limited sugar conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited sugar conditions can allow more favorable regulation of the cells.

In some aspects, the cells are grown in batch culture. The cells can also be grown in fed-batch culture or in continuous culture. Additionally, the cells can be cultured in minimal medium, including, but not limited to, any of the minimal media described above. The minimal medium can be further supplemented with 1.0% (w/v) glucose (or any other six-carbon sugar) or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. In some cultures, significantly higher levels of sugar (e.g., glucose) are used, e.g., at least 10% (w/v), 20% (w/v), 30% (w/v), 40% (w/v), 50% (w/v), 60% (w/v), 70% (w/v), or up to the solubility limit for the sugar in the medium. In some embodiments, the sugar levels falls within a range of any two of the above values, e.g.: 0.1-10% (w/v), 1.0-20% (w/v), 10-70% (w/v), 20-60% (w/v), or 30-50% (w/v). Furthermore, different sugar levels can be used for different phases of culturing. For fed-batch culture (e.g., of *S. cerevisiae* or *C. glutamicum*), the sugar level can be about 100-200 g/L (10-20% (w/v)) in the batch phase and then up to about 500-700 g/L (50-70% in the feed).

Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), or 0.02% (w/v) yeast extract. In some cultures, significantly higher levels of yeast extract can be used, e.g., at least 1.5% (w/v), 2.0% (w/v), 2.5% (w/v), or 3% (w/v). In some cultures (e.g., of *S. cerevisiae* or *C. glutamicum*), the yeast extract level falls within a range of any two of the above values, e.g.: 0.5-3.0% (w/v), 1.0-2.5% (w/v), or 1.5-2.0% (w/v).

Illustrative materials and methods suitable for the maintenance and growth of the engineered microbial cells described herein can be found below in Example 1.

Tyramine Production and Recovery

Any of the methods described herein may further include a step of recovering tyramine. In some embodiments, the produced tyramine contained in a so-called harvest stream is recovered/harvested from the production vessel. The harvest stream may include, for instance, cell-free or cell-containing aqueous solution coming from the production vessel, which contains tyramine as a result of the conversion of production substrate by the resting cells in the production vessel. Cells still present in the harvest stream may be separated from the tyramine by any operations known in the art, such as for instance filtration, centrifugation, decantation, membrane crossflow ultrafiltration or microfiltration, tangential flow ultrafiltration or microfiltration or dead end filtration. After this cell separation operation, the harvest stream is essentially free of cells.

Further steps of separation and/or purification of the produced tyramine from other components contained in the harvest stream, i.e., so-called downstream processing steps may optionally be carried out. These steps may include any means known to a skilled person, such as, for instance, concentration, extraction, crystallization, precipitation, adsorption, ion exchange, chromatography, distillation, electrodialysis, bipolar membrane electrodialysis and/or reverse osmosis. Any of these procedures can be used alone or in combination to purify tyramine. Further purification steps can include one or more of, e.g., concentration, crystallization, precipitation, washing and drying, treatment with activated carbon, ion exchange and/or re-crystallization. The design of a suitable purification protocol may depend on the cells, the culture medium, the size of the culture, the production vessel, etc. and is within the level of skill in the art.

The following example is given for the purpose of illustrating various embodiments of the disclosure and is not meant to limit the present disclosure in any fashion. Changes therein and other uses which are encompassed within the spirit of the disclosure, as defined by the scope of the claims, will be identifiable to those skilled in the art.

Example 1—Construction and Selection of Strains of *Saccharomyces cerevisiae* and *Corynebacterium glutamicum* Engineered to Produce Tyramine Plasmid/DNA Design All strains tested for this work were transformed with plasmid DNA designed using proprietary software. Plasmid designs were specific to one of the two host organisms engineered in this work. The plasmid DNA was physically constructed by a standard DNA assembly method. This plasmid DNA was then used to integrate metabolic pathway inserts by one of two host-specific methods, each described below.

*S. cerevisiae* Pathway Integration

Figure 2:
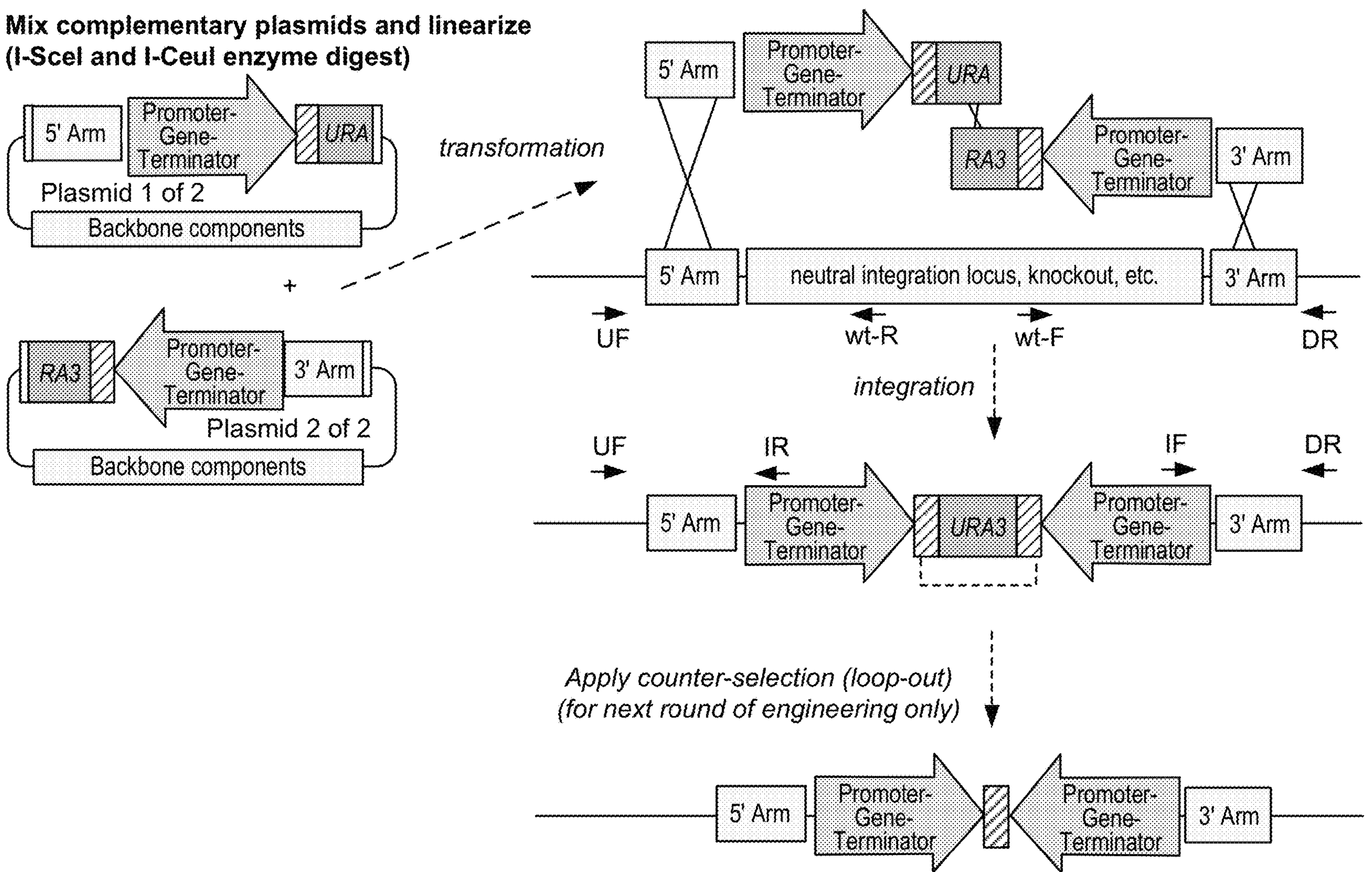
FIG. 2: A "split-marker, double-crossover" genomic integration strategy, which was developed to engineer *S. cerevisiae* strains. Two plasmids with complementary 5' and 3' homology arms and overlapping halves of a URA3 selectable marker (direct repeats shown by the hashed bars) were digested with meganucleases and transformed as linear fragments. A triple-crossover event integrated the desired heterologous genes into the targeted locus and re-constituted the full URA3 gene. Colonies derived from this integration event were assayed using two 3-primer reactions to confirm both the 5' and 3' junctions (UF/IF/wt-R and DR/IF/wt-F). See Example 1.

A "split-marker, double-crossover" genomic integration strategy has been developed to engineer *S. cerevisiae* strains. FIG. 2 illustrates genomic integration of complementary, split-marker plasmids and verification of correct genomic integration via colony PCR in *S. cerevisiae*. Two plasmids with complementary 5' and 3' homology arms and overlapping halves of a URA3 selectable marker (direct repeats shown by the hashed bars) were digested with meganucleases and transformed as linear fragments. A triple-crossover event integrated the desired heterologous genes into the targeted locus and re-constituted the full URA3 gene. Colonies derived from this integration event were assayed using two 3-primer reactions to confirm both the 5' and 3' junctions (UF/IF/wt-R and DR/IF/wt-F). For strains in which further engineering is desired, the strains can be plated on 5-FOA plates to select for the removal of URA3, leaving behind a small single copy of the original direct repeat. This genomic integration strategy can be used for gene knock-out, gene knock-in, and promoter titration in the same workflow.

*C. glutamicum* Pathway Integration

Figure 3:
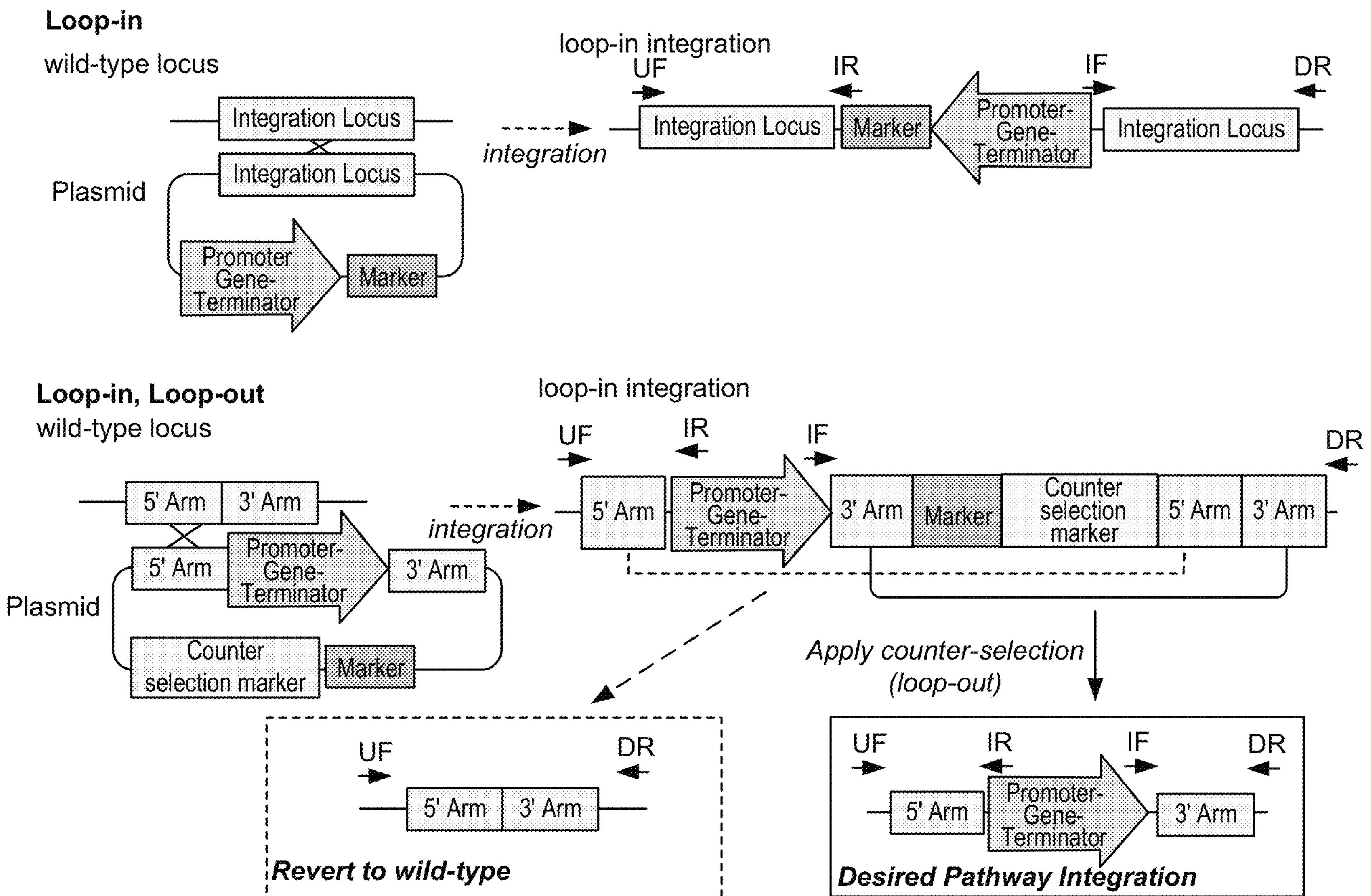
FIG. 3: A "loop-in, single-crossover" genomic integration strategy, which was developed to engineer *C. glutamicum* strains. Loop-in only constructs (shown under the heading "Loop-in") contained a single 2-kb homology arm (denoted as "integration locus"), a positive selection marker (denoted as "Marker")), and gene(s) of interest (denoted as "promoter-gene-terminator"). A single crossover event integrated the plasmid into the *C. glutamicum* chromosome. Integration events are stably maintained in the genome by growth in the presence of antibiotic (e.g., 25 μg/ml kanamycin). Correct genomic integration in colonies derived from loop-in integration were confirmed by colony PCR with UF/IR and DR/IF PCR primers. Loop-in, loop-out constructs (shown under the heading "Loop-in, loop-out) contained two 2-kb homology arms (5' and 3' arms), gene(s) of interest (arrows), a positive selection marker (denoted "Marker"), and a counter-selection marker. Similar to "loop-in" only constructs, a single crossover event integrated the plasmid into the chromosome of *C. glutamicum*. Note: only one of two possible integrations is shown here. Correct genomic integration was confirmed by colony PCR and counter-selection was applied so that the plasmid backbone and counter-selection marker could be excised. This results in one of two possibilities: reversion to wild-type or the desired pathway integration. Again, correct genomic loop-out is confirmed by colony PCR. (Abbreviations: Primers: UF=upstream forward, DR=downstream reverse, IR=internal reverse, IF=internal forward.) See Example 1.
Figure 4A:
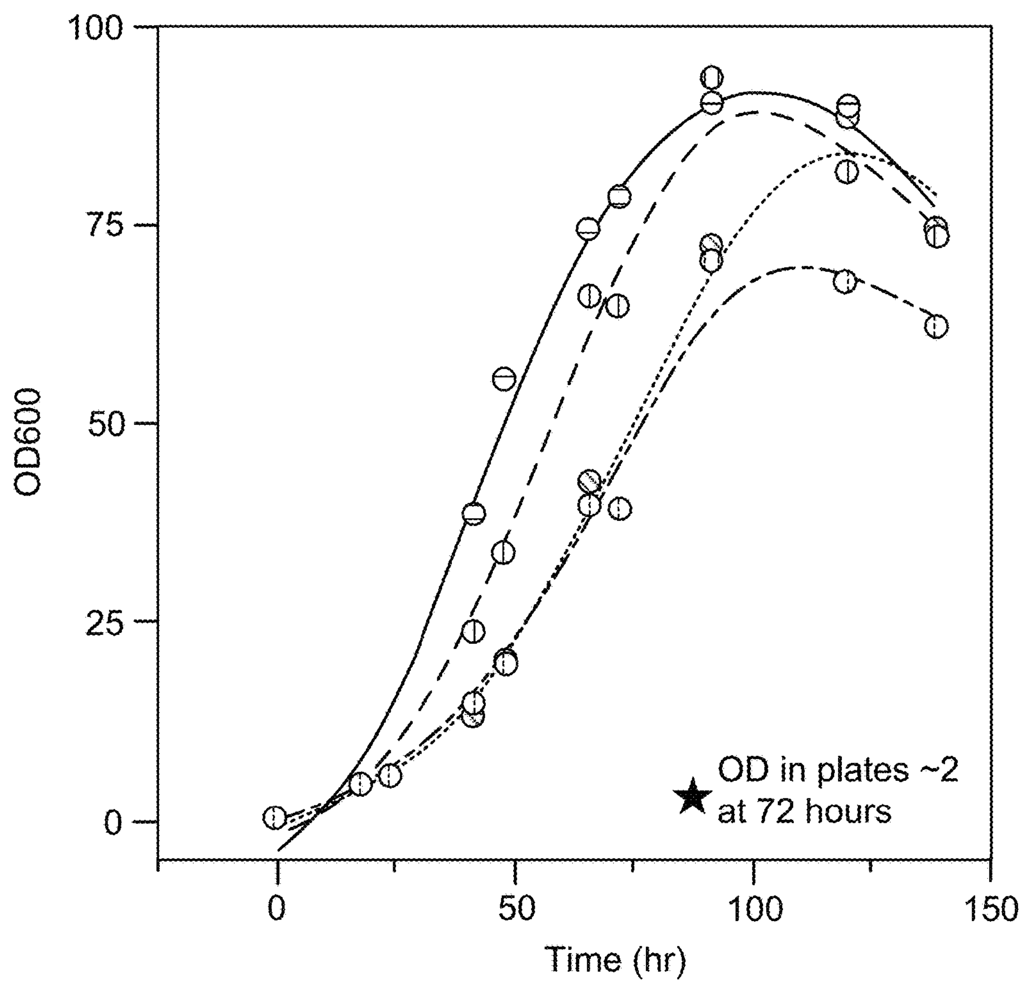
FIG. 4A-4C.
Figure 4B:
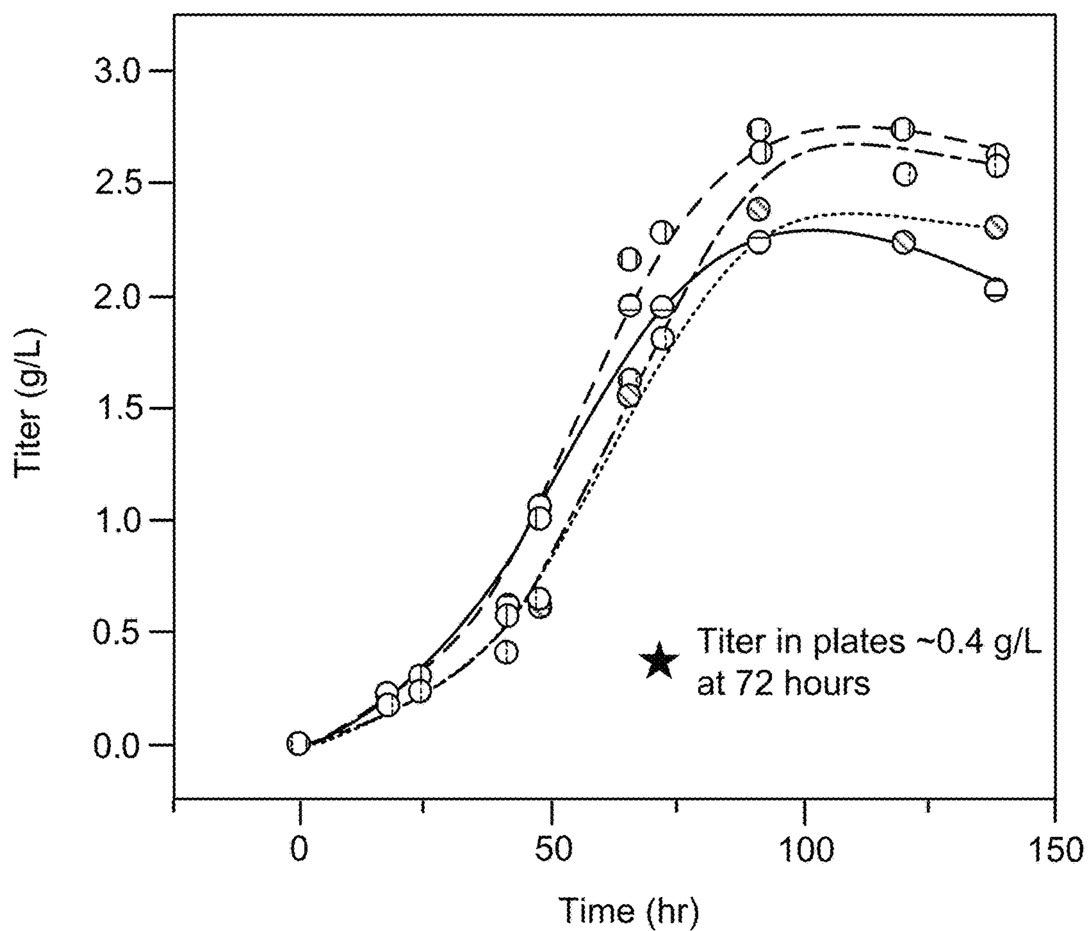
Figure 4C:
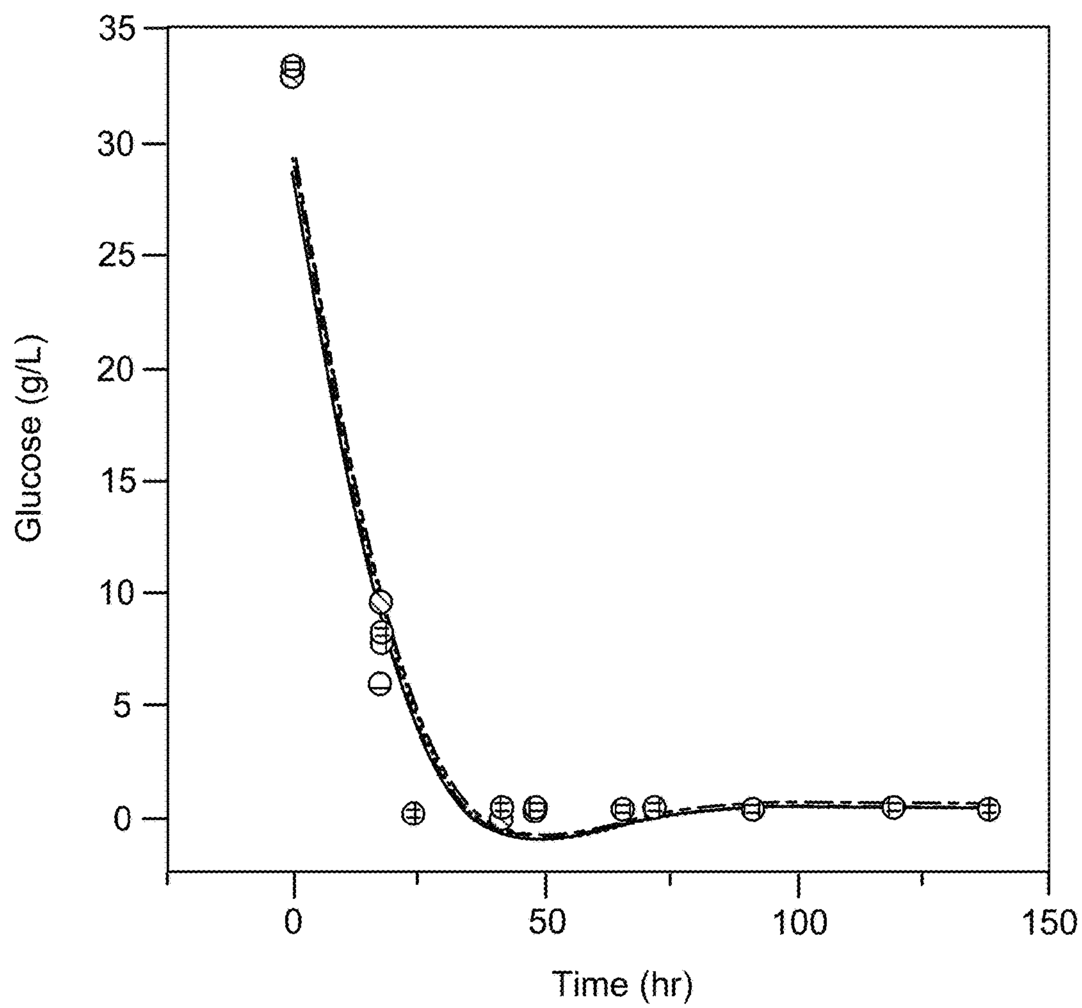

A "loop-in, single-crossover" genomic integration strategy has been developed to engineer *C. glutamicum* strains. FIG. 3 illustrates genomic integration of loop-in only and loop-in/loop-out constructs and verification of correct integration via colony PCR. Loop-in only constructs (shown under the heading "Loop-in") contained a single 2-kb homology arm (denoted as "integration locus"), a positive selection marker (denoted as "Marker")), and gene(s) of interest (denoted as "promoter-gene-terminator"). A single crossover event integrated the plasmid into the *C. glutamicum* chromosome. Integration events are stably maintained in the genome by growth in the presence of antibiotic (25 μg/ml kanamycin). Correct genomic integration in colonies derived from loop-in integration were confirmed by colony PCR with UF/IR and DR/IF PCR primers.

Loop-in, loop-out constructs (shown under the heading "Loop-in, loop-out) contained two 2-kb homology arms (5' and 3' arms), gene(s) of interest (arrows), a positive selection marker (denoted "Marker"), and a counter-selection marker. Similar to "loop-in" only constructs, a single crossover event integrated the plasmid into the chromosome of *C. glutamicum*. Note: only one of two possible integrations is shown here. Correct genomic integration was confirmed by colony PCR and counter-selection was applied so that the plasmid backbone and counter-selection marker could be excised. This results in one of two possibilities: reversion to wild-type (lower left box) or the desired pathway integration (lower right box). Again, correct genomic loop-out is confirmed by colony PCR. (Abbreviations: Primers: UF=upstream forward, DR=downstream reverse, IR=internal reverse, IF=internal forward.)

Cell Culture

Separate workflows were established for *C. glutamicum* and *S. cerevisiae* due to differences in media requirements and growth. Both processes involved a hit-picking step that consolidated successfully built strains using an automated workflow that randomized strains across the plate. For each strain that was successfully built, up to four replicates were tested from distinct colonies to test colony-to-colony variation and other process variation. If fewer than four colonies were obtained, the existing colonies were replicated so that at least four wells were tested from each desired genotype.

The colonies were consolidated into 96-well plates with selective medium (BHI for *C. glutamicum*, SD-ura for *S. cerevisiae*) and cultivated for two days until saturation and then frozen with 16.6% glycerol at −80° C. for storage. The frozen glycerol stocks were then used to inoculate a seed stage in minimal media with a low level of amino acids to help with growth and recovery from freezing. The seed plates were grown at 30° C. for 1-2 days. The seed plates were then used to inoculate a main cultivation plate with minimal medium and grown for 48-88 hours. Plates were removed at the desired time points and tested for cell density (OD600), viability and glucose, supernatant samples stored for LC-MS analysis for product of interest.

Cell Density

Cell density was measured using a spectrophotometric assay detecting absorbance of each well at 600 nm. Robotics were used to transfer fixed amounts of culture from each cultivation plate into an assay plate, followed by mixing with 175 mM sodium phosphate (pH 7.0) to generate a 10-fold dilution. The assay plates were measured using a Tecan M1000 spectrophotometer and assay data uploaded to a LIMS database. A non-inoculated control was used to subtract background absorbance. Cell growth was monitored by inoculating multiple plates at each stage, and then sacrificing an entire plate at each time point.

To minimize settling of cells while handling large number of plates (which could result in a non-representative sample during measurement) each plate was shaken for 10-15 seconds before each read. Wide variations in cell density within a plate may also lead to absorbance measurements outside of the linear range of detection, resulting in underestimate of higher OD cultures. In general, the tested strains so far have not varied significantly enough for this be a concern.

Cell Viability

Two methods were used to measure cell viability. The first assay utilized a single stain, propidium iodide, to assess cell viability. Propidium iodide binds to DNA and is permeable to cells with compromised cell membranes. Cells that take up the propidium iodide are considered non-viable. A dead cell control was used to normalize to total number of cells, by incubating a cell sample of control culture at 95° C. for 10 minutes. These control samples and test samples were incubated with the propidium iodide stain for 5 minutes, washed twice with 175 mM phosphate buffer, and fluorescence measured in black solid-bottom 96-well plates at 617 nm.

Glucose

Glucose is measured using an enzymatic assay with 16 U/mL glucose oxidase (Sigma) with 0.2 U/mL horseradish peroxidase (Sigma) and 0.2 mM Amplex red in 175 mM sodium phosphate buffer, pH 7. Oxidation of glucose generates hydrogen peroxide, which is then oxidized to reduce Amplex red, which changes absorbance at 560 nm. The change is absorbance is correlated to the glucose concentration in the sample using standards of known concentration.

Liquid-Solid Separation

To harvest extracellular samples for analysis by LC-MS, liquid and solid phases were separated via centrifugation. Cultivation plates were centrifuged at 2000 rpm for 4 minutes, and the supernatant was transferred to destination plates using robotics. 75 µL of supernatant was transferred to each plate, with one stored at 4° C., and the second stored at 80° C. for long-term storage.

A first round of genetic engineering and screening was carried out using *C. glutamicum* and *S. cerevisiae* as host cells. A heterologous TYDC was expressed in the host cells, in some cases, along with a feedback-disregulated DAHP synthase. In some cases, the TYDC nucleotide sequence was codon-optimized for either *C. glutamicum* or *S. cerevisiae*. The strains were produced and cultured as described above, and the tyramine titer in the culture media was measured by LC-MS. The strains and results are shown in Table 1. The best-performing strain was an *S. cerevisiae* strain expressing a *P. somniferum* TYDC (SEQ ID NO:2), along with an *S. cerevisiae* DAHP synthase with a K229L amino acid substitution (SEQ ID NO:6), which gave a tyramine titer of almost 387 µg/L of culture medium. This strain was selected for a second round of genetic engineering and screening.

TABLE 1

First-Round Results

| Titer µg/L | E1 activity name | E1 source organism | E1 taxonomic region | E1 codon opt | E2 activity name | E2 source organism | E2 taxonomic region | E2 modifications |
|---|---|---|---|---|---|---|---|---|
| | | | | *C. glutamicum* | | | | |
| 80.20 | TYDC* | *E. faecium* (*S. faecium*) | Bacteria | Cg | | | | |
| 54.6927 | TYDC | *Z. bailii* ISA1307 | Fungi | Cg | | | | |
| 14.3711 | TYDC | *E. faecium* (*S. faecium*) | Bacteria | Cg | DAHP synthase** | *S. cerevisiae**** | Fungi | Q166K, reduces pathway feedback inhibition |
| 4.8087 | TYDC | *M. palustris* (strain ATCC BAA-1556/ DSM 19958/ E1-9c) | Archaea | Cg | | | | |
| 2.2345 | TYDC | *Propionibacterium* sp. oral taxon 192 str. F0372 | Bacteria | Cg | | | | |
| 0.9617 | TYDC | *P. crispum* | Viridi-plantae | Cg | DAHP synthase | *E. coli***** | Bacteria | D146N, reduces pathway feedback inhibition |
| 0.5946 | TYDC | *T. equinum* (strain ATCC MYA-4606/ CBS 127.97) (Horse ringworm fungus) | Fungi | Cg | DAHP synthase | *E. coli* | Bacteria | D146N, reduces pathway feedback inhibition |
| 0.1045 | TYDC | *S. sviceus* ATCC 29083 | Bacteria | Cg | | | | |
| 0.0825 | TYDC | *P. putida* (strain KT2440) | Bacteria | Cg | DAHP synthase | *E. coli* | Bacteria | D146N, reduces pathway feedback inhibition |
| 0.0269 | TYDC | *M. marinus* (strain BC501) | Bacteria | Cg | | | | |
| 0.0024 | TYDC | *P. somniferum* | Viridi-plantae | Cg | DAHP synthase | *S. cerevisiae* | Fungi | Q166K, reduces pathway feedback inhibition |

TABLE 1-continued

| First-Round Results | | | | | | | | |
|---|---|---|---|---|---|---|---|---|
| Titer μg/L | E1 activity name | E1 source organism | E1 taxonomic region | E1 codon opt | E2 activity name | E2 source organism | E2 taxonomic region | E2 modifications |
| 0.0018 | TYDC | *T. equinum* (strain ATCC MYA-4606/ CBS 127.97) (Horse ringworm fungus) | Fungi | Cg | | | | |
| 0.0008 | TYDC | *S. fredii* USDA 257 | Bacteria | Cg | | | | |
| 0 | TYDC | *P. somniferum*) | Viridi-plantae | Sc | DAHP synthase | *S. cerevisiae* | Fungi | K229L, reduces pathway feedback inhibition |
| *S. cerevisiae* | | | | | | | | |
| 386.7658 | TYDC | *P. somniferum* | Viridi-plantae | Sc | DAHP synthase | *S. cerevisiae* | Fungi | K229L, reduces pathway feedback inhibition |
| 162.2137 | TYDC | *P. somniferum* | Viridi-plantae | Cg | DAHP synthase | *E. coli* | Bacteria | D146N, reduces pathway feedback inhibition |
| 115.9018 | TYDC | *P. somniferum* | Viridi-plantae | Sc | | | | |
| 4.7859 | TYDC | *O. sativa* subsp. *Japonica* | Viridi-plantae | Cg | DAHP synthase | *E. coli* | Bacteria | D146N, reduces pathway feedback inhibition |
| 3.2748 | TYDC | *S. fredii* USDA 257 | Bacteria | Sc | | | | |
| 1.1297 | TYDC | *P. putida* (strain KT2440) | Bacteria | Sc | | | | |
| 1.0391 | TYDC | *M. palustris* (strain ATCC BAA-1556/ DSM 19958/ E1-9c) | Archaea | Sc | | | | |
| 0.6421 | TYDC | *M. jannaschii* | Archaea | Sc | | | | |
| 0.4238 | TYDC | *O. sativa* subsp. *Japonica* | Viridi-plantae | Cg | DAHP synthase | *E. coli* | Bacteria | D146N, reduces pathway feedback inhibition |
| 0.1481 | TYDC | *M. marinus* (strain BC501) | Bacteria | Sc | | | | |

*TYDC GO ID: GO:0004837
**DAHP Synthase: GO ID: GO:0003849
****S. cerevisiae* DAHP synthase taxon ID: Sc; Uniprot ID: P32449
*****E. coli* DAHP synthase taxon ID: 83333; Uniprot ID: P0AB91
Codon optimization was for *C. glutamicum* (Cg) or *S. cerevisiae* (Sc)

In the second round of engineering/screening, a third enzyme was expressed in the *S. cerevisiae* strain expressing a *P. somniferum* TYDC, along with an *S. cerevisiae* DAHP synthase with a K229L amino acid substitution from the first round. In some cases, the nucleotide sequence encoding the third enzymes was codon-optimized. Table 2 shows the third enzymes tested and the resultant tyramine titers. The higher titer was about 346 mg/L, an almost 1000-fold improvement, which was achieved by the strain expressing native *S. cerevisiae* prephenate dehydrogenase as the third enzyme.

TABLE 2

| Second-Round Results | | | | |
|---|---|---|---|---|
| Titer (μg/L) | Enzyme3-activity name | Enzyme3-source organism | E3 UniProt id | E3 codon opt |
| 238453.9398 | DAHP synthase (D146N) | *Escherichia coli* | P0AB91 | Sc |
| 288361.4515 | DAHP synthase (Q166K) | *Saccharomyces cerevisiae* | P32449 | Cg |
| 228876.649 | DAHP synthase (D146N) | *Escherichia coli* | P0AB91 | Sc |
| 285231.8609 | DAHP synthase (Q166K) | *Saccharomyces cerevisiae* | P32449 | Cg |
| 283175.3481 | DAHP synthase (wild type) | *Saccharomyces cerevisiae* CEN.PK2 | N1P8J9 | native |

TABLE 2-continued

| Second-Round Results | | | | |
|---|---|---|---|---|
| Titer (μg/L) | Enzyme3-activity name | Enzyme3-source organism | E3 UniProt id | E3 codon opt |
| 253015.743 | phospho-2-dehydro-3-deoxyheptonate aldolase | *Saccharomyces cerevisiae* (strain ATCC 204508/S288c) (Baker's yeast) | P14843 | native |
| 243755.6441 | phospho-2-dehydro-3-deoxyheptonate aldolase | *Saccharomyces cerevisiae* (strain ATCC 204508/S288c) (Baker's yeast) | P32449 | native |
| 249195.9423 | chorismate synthase | *Saccharomyces cerevisiae* (strain ATCC 204508/S288c) (Baker's yeast) | P28777 | native |
| 345546.6876 | prephenate dehydrogenase | *Saccharomyces cerevisiae* (strain ATCC 204508/S288c) (Baker's yeast) | P20049 | native |
| 300138.6771 | aromatic/aminoadipate aminotransferase 1; 2-aminoadipate transaminase, L-phenylalanine:2-oxoglutarate aminotransferase | *Saccharomyces cerevisiae* (strain ATCC 204508/S288c) (Baker's yeast) | P53090 | native |
| 284884.7302 | aromatic amino acid aminotransferase 2; 2-aminoadipate transaminase, L-phenylalanine:2-oxoglutarate aminotransferase, kynurenine-oxoglutarate transaminase | *Saccharomyces cerevisiae* (strain ATCC 204508/S288c) (Baker's yeast) | P38840 | native |
| 334432.6849 | prephenate dehydrogenase | *Saccharomyces cerevisiae* (strain ATCC 204508/S288c) (Baker's yeast) | P20049 | native |
| 245114.4577 | phospho-2-dehydro-3-deoxyheptonate aldolase | *Saccharomyces cerevisiae* (strain ATCC 204508/S288c) (Baker's yeast) | P14843 | native |
| 271440.4966 | phospho-2-dehydro-3-deoxyheptonate aldolase | *Saccharomyces cerevisiae* (strain ATCC 204508/S288c) (Baker's yeast) | P32449 | native |

Example 2A—Improvement-Round (Third-Round) Results in *S. cerevisiae* Constructions and Evaluation of Different Microbial Host Cells for Production of Tyramine

Summary

The best-performing strain of Example 1 was selected as the control strain to in which to test a third round of genetic engineering in an effort to improve tyramine in *Saccharomyces cerevisiae* ("Improvement Round"). The control strain expressed prephenate dehydrogenase from *S. cerevisiae* (UniProt ID P20049)(SEQ ID NO:4), DAHP synthase from *S. cerevisiae* S288c (UniProt ID P32449)(SEQ ID NO:6) harboring the amino acid substitution K229L and tyrosine/DOPA decarboxylase 2 from *Papaver somniferum* (UniProt ID P54769)(SEQ ID NO:2). Tyramine production was improved in *S. cerevisiae* for eight strains relative to the control, and of these strains the strain giving the highest titer (299 mg/L vs. 266 mg/L for the control) expressed transaldolase from *S. cerevisiae* (UniProt ID P15019)(SEQ ID NO:8).

Strain Designs Tested

Tyramine production was improved by expression of each of the following heterologous enzymes or combinations of heterologous enzymes relative to the control:

1) Aromatic amino acid aminotransferase (SEQ ID NO:28)
2) Phosphoenolpyruvate synthase (UniProt ID P23538) from *Escherichia coli* K12 (SEQ ID NO:29)
3) Transketolase (UniProt ID P23254) from *S. cerevisiae* (SEQ ID NO:30)
4) Transaldolase (UniProt ID P15019) from *S. cerevisiae* (SEQ ID NO:8)
5) Transketolase (UniProt ID P23254) from *S. cerevisiae* (SEQ ID NO:30) AND transaldolase (UniProt ID P15019) from *S. cerevisiae* (SEQ ID NO:8)
6) Transketolase (UniProt ID P23254) from *S. cerevisiae* (SEQ ID NO:30) AND phosphoenolpyruvate synthase (UniProt ID P23538) from *E. coli* K12 (SEQ ID NO:29).
7) Transaldolase (UniProt ID P15019) from *S. cerevisiae* (SEQ ID NO:8) AND DAHP synthase (UniProt ID P32449) from *S. cerevisiae* harboring amino acid substitution K299L (SEQ ID NO:6).
8) Glyceraldehyde-3-phosphate dehydrogenase (UniProt ID P30724) from *Gracilaria gracilis* (SEQ ID NO:31)

Results

Figure 9:
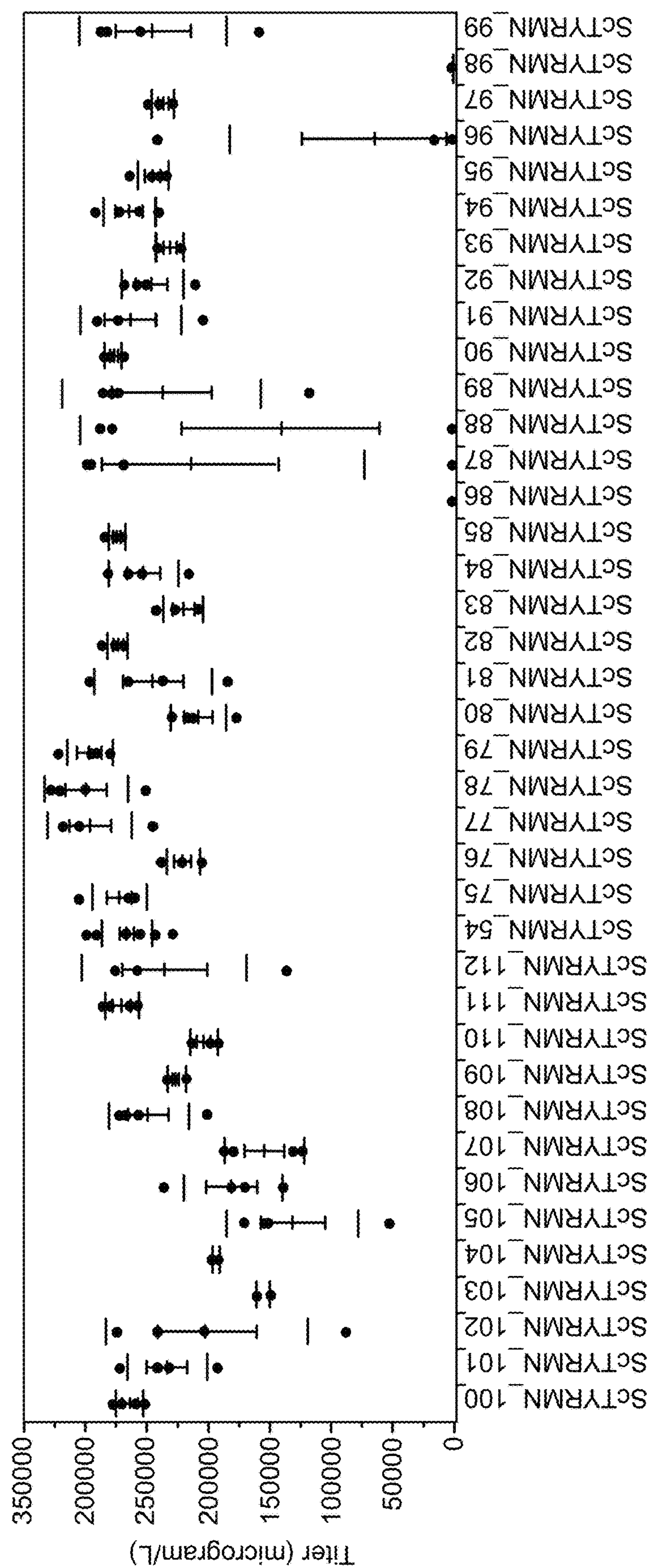
FIG. 9: Tyramine titers measured in extracellular broth following fermentation by the (third round) engineered host *S. cerevisiae*. Strain designs tested the expression of additional heterologous enzymes.
Figure 10:
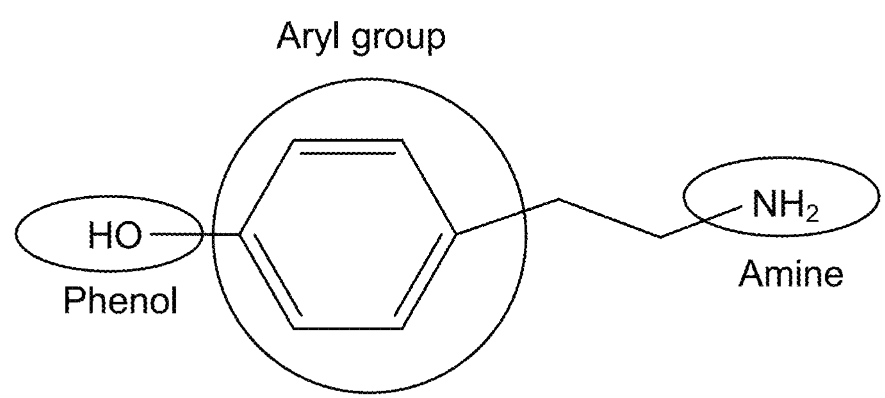
FIG. 10: Structure of tyramine.

The results are shown in Table 7 (below) and FIG. 9.

In further designs, production of tyramine can be tested for improvement in strains containing the addition of the following heterologous enzymes or combinations of heterologous enzymes to the best-performing strain from this Example:

1) 2-dehydro-3-deoxyphosphoheptonate aldolase (SEQ ID NO:32)
2) Chorismate mutase (SEQ ID NO:33)
3) Chorismate mutase (SEQ ID NO:33) and Prephenate dehydrogenase (SEQ ID NO:4)
4) Shikimate kinase1 (SEQ ID NO:34)

5) shikimate dehydrogenase (SEQ ID NO:35)
6) prephenate dehydrogenase (SEQ ID NO:4)
7) Tyrosine aminotransferase (SEQ ID NO:36)
8) Prephenate dehydrogenase (SEQ ID NO:4)
9) Glutamate synthase (GOGAT) large subunit (SEQ ID NO:37)
10) Glutamine synthetase (GS) (SEQ ID NO:39)
11) Glutamate synthase small subunit (SEQ ID NO:38)
12) Shikimate dehydrogenase (SEQ ID NO:35)
13) Shikimate kinase2 (SEQ ID NO:15)

Example 2B—Evaluation of Different Microbial Host Cells for Production of Tyramine

Summary

Host evaluation designs were tested in *Yarrowia lipolytica, Bacillus subtilus, S. cerevisiae* and *Corynebacteria glutamicum*. Tyramine production was demonstrated in all strains tested. The best-performing *Y. lipolytica* strain on average produced 54.5 mg/L tyramine. The best-performing *B. subtilus* strain produced 19.9 mg/L tyramine. The best-performing *S. cerevisiae* strain from the host evaluation produced 189 mg/L tyramine. The best-performing *C. glutamicum* strain produced 467 mg/L tyramine.

Results

Figure 5:
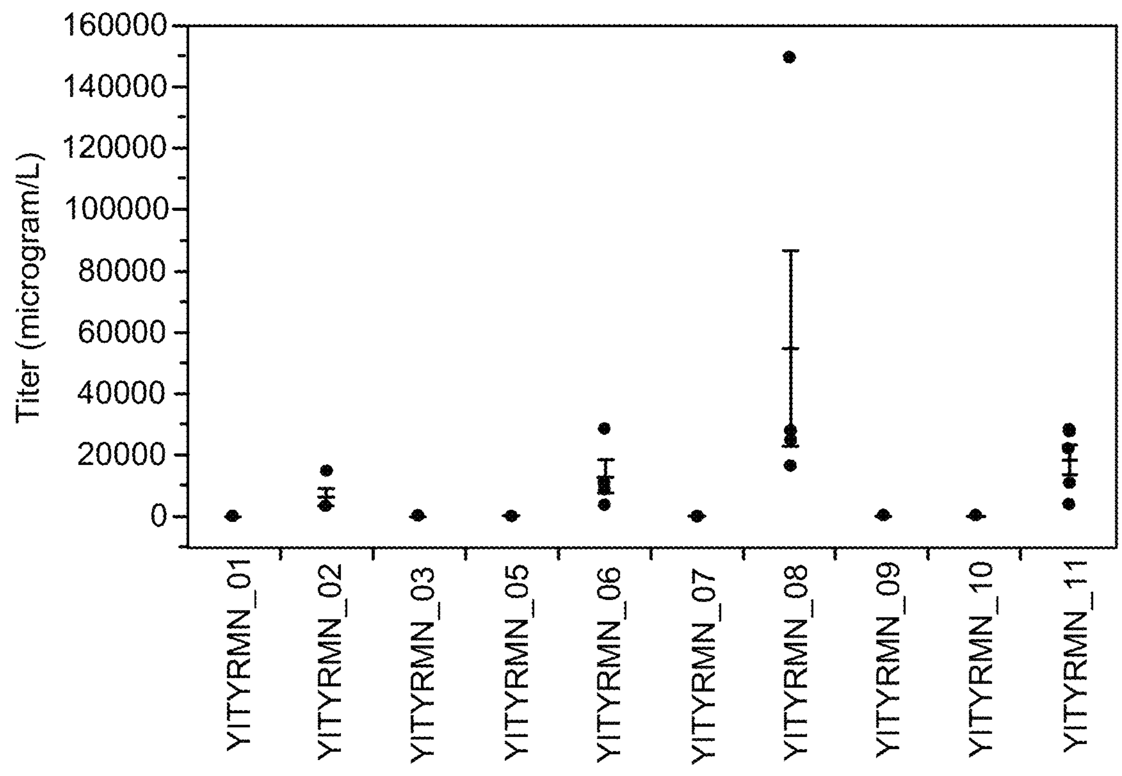
FIG. 5: Tyramine titers measured in extracellular broth following fermentation by the first-round engineered host *Yarrowia lipolytica*. Strain designs tested the expression of additional heterologous enzymes.

The best performing *Y. lipolytica* strain on average produced 54.5 mg/L tyramine and expressed the pyridoxal-dependent decarboxylase (TYDC) from *Enterococcus faecium* Com15 (UniProt ID C9ASN2) (SEQ ID NO:1), phospho-2-dehydro-3-deoxyheptonate aldolase (DAHP synthase) from *S. cerevisiae* S288c (UniProt ID P32449) (SEQ ID NO:9), where the DNA sequences for both enzymes were codon-optimized for *Y. lipolytica*. (Table 3, FIG. 5.) (SEQ ID Nos: 40 and 10, respectively).

Figure 6:
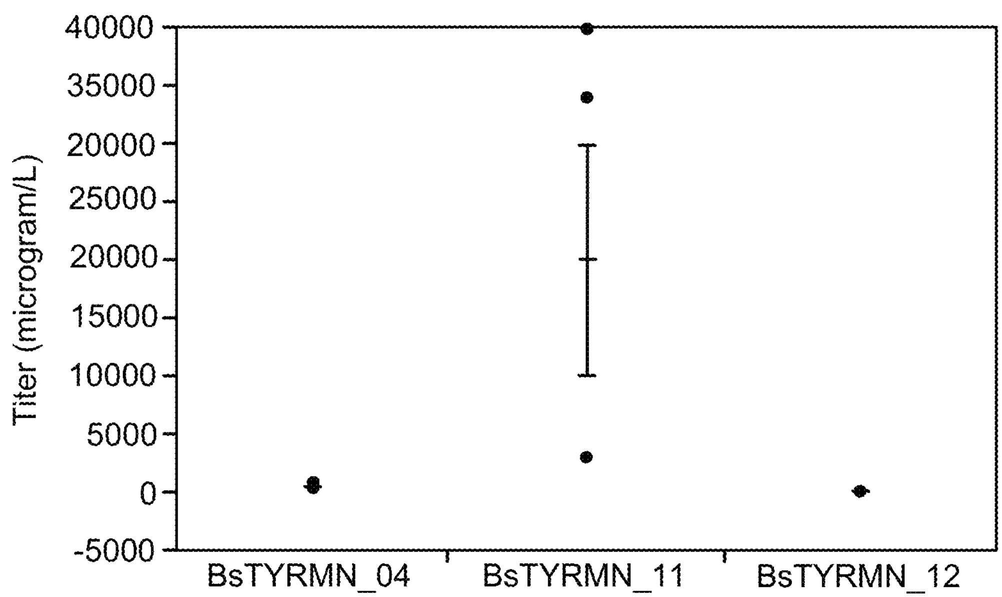
FIG. 6: Tyramine titers measured in extracellular broth following fermentation by the first round engineered host *Bacillus subtilis*. Strain designs tested the expression of additional heterologous enzymes.

The best-performing *B. subtilis* strain produced 19.9 mg/L tyramine and expressed the tyrosine/DOPA decarboxylase 2 (TYDC) from *Papaver somniferum* (SEQ ID NO:2), phospho-2-dehydro-3-deoxyheptonate aldolase (DAHP synthase) from *Saccharomyces cerevisiae* S288c (UniProt ID P32449) (SEQ ID NO: 9), and shikimate kinase 2 from *Escherichia coli* K12 (UniProt ID P0A6E1) (SEQ ID NO: 15), where the DNA sequences for all three enzymes were codon-optimized for *S. cerevisiae*. (Table 4, FIG. 6.) (SEQ ID NOs: 43, 42, 41.)

Figure 7:
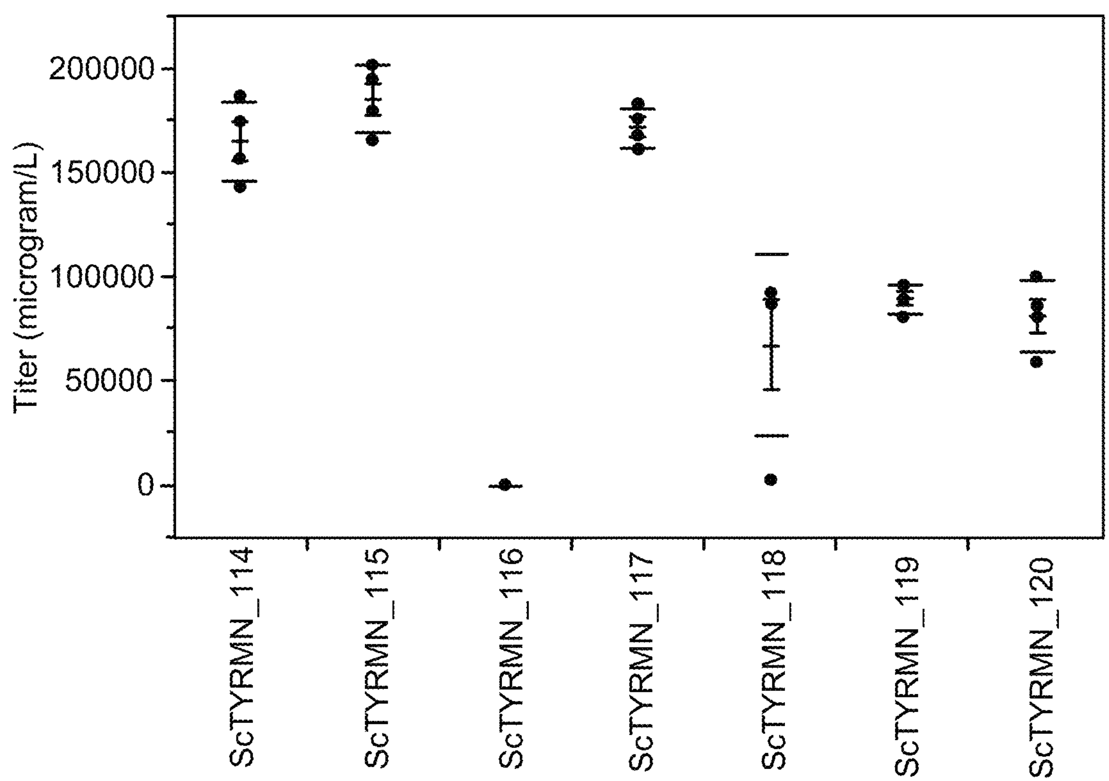
FIG. 7: Tyramine titers measured in extracellular broth following fermentation by the host *S. cerevisiae* engineered to express the host evaluation designs for production of tyramine.

The best-performing *S. cerevisiae* strain from the host evaluation produced 189 mg/L tyramine and expressed pyridoxal-dependent decarboxylase (TYDC) from *E. faecium* Com15 (UniProt ID C9ASN2) (SEQ ID NO:1), phospho-2-dehydro-3-deoxyheptonate aldolase (DAHP synthase) from *S. cerevisiae* S288c (UniProt ID P32449) harboring the amino acid substitution K229L (SEQ ID NO:6), where the DNA sequences for both enzymes were codon-optimized using a modified combined codon table for *C. glutamicum* and *S. cerevisiae*. (Table 5, FIG. 7.) (SEQ ID NOs: 45, 44).

The best-performing *C. glutamicum* strain produced 467 mg/L tyramine and expressed pyridoxal-dependent decarboxylase (TYDC) from *E. faecium* Com15 (UniProt ID C9ASN2) (SEQ ID NO:1), phospho-2-dehydro-3-deoxyheptonate aldolase from (DAHP synthase) *S. cerevisiae* S288c (UniProt ID P32449) (SEQ ID NO:9), where the DNA sequences for both enzymes was codon-optimized for *S. cerevisiae*. (Table 6, FIG. 8.) (SEQ ID NOs: 43, 42).

To improve a platform *C. glutamicum* strain for production of stilbenes and (2S)-flavanones Kallscheuer et al. (see References below) deleted genes and operons that degrade aromatic rings including polypropanoid degradation operon (phdBCDE, cg0344-47); 4-hydroxybenzoate-3-hydrolase (pobA (cg1226); the gene cluster harboring cat, ben, pca (cg2625-40), which is essential for degradation of 4-hydroxybenzoate, catechol, benzoate, and protocatechuate; and qsuE (cg0502), which is part of an operon comprised of essential genes of the anabolic shikimate pathway. Production of tyramine in *C. glutamicum* can also be tested for further improvement by deleting or lowering expression of these enzymes which degrade aromatics, since tyramine contains an aromatic ring.

TABLE 3

Host Evaluation Results for *Yarrowia lipolytica* Strains Engineered to Produce Tyramine

| Strain name | Titer (microgram/L) | E1 Uniprot ID | E1 - activity name | E1 - source organism | E1 CO | E2 Uniprot ID | E2 - activity name |
|---|---|---|---|---|---|---|---|
| YITYRMN_01 | 22.7 | P54769 | Tyrosine/DOPA decarboxylase 2 | *Papaver somniferum* | Bs | P32449 | Phospho-2-dehydro-3-deoxyheptonate aldolase |
| YITYRMN_02 | 6069.1 | P54769 | Tyrosine/DOPA decarboxylase 2 | *Papaver somniferum* | Mod | P32449 | Phospho-2-dehydro-3-deoxyheptonate aldolase |
| YITYRMN_03 | 13.9 | P54769 | Tyrosine/DOPA decarboxylase 2 | *Papaver somniferum* | Sc | P32449 | Phospho-2-dehydro-3-deoxyheptonate aldolase |
| YITYRMN_04 | | P54769 | Tyrosine/DOPA decarboxylase 2 | *Papaver somniferum* | Yl | P32449 | Phospho-2-dehydro-3-deoxyheptonate aldolase |
| YITYRMN_05 | 16.8 | C9ASN2 | Pyridoxal-dependent decarboxylase | *Enterococcus faecium* Com15 | Bs | P32449 | Phospho-2-dehydro-3-deoxyheptonate aldolase |

TABLE 3-continued

| Host Evaluation Results for *Yarrowia lipolytica* Strains Engineered to Produce Tyramine | | | | | | | |
|---|---|---|---|---|---|---|---|
| YITYRMN_06 | 12804.6 | C9ASN2 | Pyridoxal-dependent decarboxylase | *Enterococcus faecium* Com15 | Mod | P32449 | Phospho-2-dehydro-3-deoxy-heptonate aldolase |
| YITYRMN_07 | 7.5 | C9ASN2 | Pyridoxal-dependent decarboxylase | *Enterococcus faecium* Com15 | Sc | P32449 | Phospho-2-dehydro-3-deoxy-heptonate aldolase |
| YITYRMN_08 | 54503.8 | C9ASN2 | Pyridoxal-dependent decarboxylase | *Enterococcus faecium* Com15 | Yl | P32449 | Phospho-2-dehydro-3-deoxy-heptonate aldolase |
| YITYRMN_09 | 14.6 | P54769 | Tyrosine/DOPA decarboxylase 2 | *Papaver somniferum* | Bs | P32449 | Phospho-2-dehydro-3-deoxy-heptonate aldolase |
| YITYRMN_10 | 15 | P54769 | Tyrosine/DOPA decarboxylase 2 | *Papaver somniferum* | Sc | P32449 | Phospho-2-dehydro-3-deoxy-heptonate aldolase |
| YITYRMN_11 | 18461.8 | P54769 | Tyrosine/DOPA decarboxylase 2 | *Papaver somniferum* | Yl | P32449 | Phospho-2-dehydro-3-deoxy-heptonate aldolase |

| Strain name | E2 Modifications | E2 - source organism | E2 CO | E3 Uniprot ID | E3 - activity name | E3 - source organism | E3 CO |
|---|---|---|---|---|---|---|---|
| YITYRMN_01 | K229L | *S. cerevisiae* S288c | Bs | | | | |
| YITYRMN_02 | K229L | *S. cerevisiae* S288c | Mod | | | | |
| YITYRMN_03 | K229L | *S. cerevisiae* S288c | Sc | | | | |
| YITYRMN_04 | K229L | *S. cerevisiae* S288c | Yl | | | | |
| YITYRMN_05 | | *S. cerevisiae* S288c | Bs | | | | |
| YITYRMN_06 | | *S. cerevisiae* S288c | Mod | | | | |
| YITYRMN_07 | | *S. cerevisiae* S288c | Sc | | | | |
| YITYRMN_08 | | *S. cerevisiae* S288c | Yl | | | | |
| YITYRMN_09 | | *S. cerevisiae* S288c | Bs | P0A 6E1 | Shikimate kinase 2 | *Escherichia coli* K12 | Bs |
| YITYRMN_10 | | *S. cerevisiae* S288c | Sc | P0A 6E1 | Shikimate kinase 2 | *Escherichia coli* K12 | Sc |
| YITYRMN_11 | | *S. cerevisiae* S288c | Yl | P0A 6E1 | Shikimate kinase 2 | *Escherichia coli* K12 | Yl |

CO = Codon Optimization; Bs = *Bacillus subtilus*; Mod = codon usage for Cg and Sc; Sc = *Saccharomyces cerevisiae* Yl = *Yarrowia lipolytica*.

TABLE 4

Host Evaluation Results for *Bacillus subtilus* Strains Engineered to Produce Tyramine

| Strain name | Titer (microgram/L) | E1 Uniprot ID | E1 - activity name | E1 - source organism | E1 CO | E2 Uniprot ID | Enzyme 2 - activity name |
|---|---|---|---|---|---|---|---|
| BsTYRMN_01 | | P54769 | Tyrosine/DOPA decarboxylase 2 | *Papaver somniferum* | Yl | P32449 | Phospho-2-dehydro-3-deoxy-heptonate aldolase |

TABLE 4-continued

Host Evaluation Results for *Bacillus subtilus* Strains Engineered to Produce Tyramine

| | | | | | | | |
|---|---|---|---|---|---|---|---|
| BsTYRMN_02 | | C9ASN2 | Pyridoxal-dependent decarboxylase | *Enterococcus faecium* Com15 | Yl | P32449 | Phospho-2-dehydro-3-deoxy-heptonate aldolase |
| BsTYRMN_03 | | P54769 | Tyrosine/DOPA decarboxylase 2 | *Papaver somniferum* | Bs | P32449 | Phospho-2-dehydro-3-deoxy-heptonate aldolase |
| BsTYRMN_04 | 564.7 | P54769 | Tyrosine/DOPA decarboxylase 2 | *Papaver somniferum* | Mod | P32449 | Phospho-2-dehydro-3-deoxy-heptonate aldolase |
| BsTYRMN_05 | | P54769 | Tyrosine/DOPA decarboxylase 2 | *Papaver somniferum* | Sc | P32449 | Phospho-2-dehydro-3-deoxy-heptonate aldolase |
| BsTYRMN_06 | | C9ASN2 | Pyridoxal-dependent decarboxylase | *Enterococcus faecium* Com15 | Bs | P32449 | Phospho-2-dehydro-3-deoxy-heptonate aldolase |
| BsTYRMN_07 | | C9ASN2 | Pyridoxal-dependent decarboxylase | *Enterococcus faecium* Com15 | Mod | P32449 | Phospho-2-dehydro-3-deoxy-heptonate aldolase |
| BsTYRMN_08 | | C9ASN2 | Pyridoxal-dependent decarboxylase | *Enterococcus faecium* Com15 | Sc | P32449 | Phospho-2-dehydro-3-deoxy-heptonate aldolase |
| BsTYRMN_09 | | P54769 | Tyrosine/DOPA decarboxylase 2 | *Papaver somniferum* | Bs | P32449 | Phospho-2-dehydro-3-deoxy-heptonate aldolase |
| BsTYRMN_10 | | P54769 | Tyrosine/DOPA decarboxylase 2 | *Papaver somniferum* | Mod | P32449 | Phospho-2-dehydro-3-deoxy-heptonate aldolase |
| BsTYRMN_11 | 19873.2 | P54769 | Tyrosine/DOPA decarboxylase 2 | *Papaver somniferum* | Sc | P32449 | Phospho-2-dehydro-3-deoxy-heptonate aldolase |
| BsTYRMN_12 | 124.7 | P54769 | Tyrosine/DOPA decarboxylase 2 | *Papaver somniferum* | Yl | P32449 | Phospho-2-dehydro-3-eoxy-heptonate aldolase |
| BsTYRMN_13 | | P54769 | Tyrosine/DOPA decarboxylase 2 | *Papaver somniferum* | Mod | P32449 | Phospho-2-dehydro-3-deoxy-heptonate aldolase |

| Strain name | E2 Modifications | E2 - source organism | E2 CO | E3 Uniprot ID | Enzyme 3 - activity name | E3 - source organism | E3 CO |
|---|---|---|---|---|---|---|---|
| BsTYRMN_01 | K229L | *S. cerevisiae* S288c | Yl | | | | |
| BsTYRMN_02 | | *S. cerevisiae* S288c | Yl | | | | |
| BsTYRMN_03 | K229L | *S. cerevisiae* S288c | Bs | | | | |
| BsTYRMN_04 | K229L | *S. cerevisiae* S288c | Mod | | | | |
| BsTYRMN_05 | K229L | *S. cerevisiae* S288c | Sc | | | | |
| BsTYRMN_06 | | *S. cerevisiae* S288c | Bs | | | | |

TABLE 4-continued

Host Evaluation Results for *Bacillus subtilus* Strains Engineered to Produce Tyramine

| | | | | | | | |
|---|---|---|---|---|---|---|---|
| BsTYRMN_07 | | *S. cerevisiae* S288c | Mod | | | | |
| BsTYRMN_08 | | *S. cerevisiae* S288c | Sc | | | | |
| BsTYRMN_09 | | *S. cerevisiae* S288c | Bs | P0A6E1 | Shikimate kinase 2 | *Escherichia coli* (strain K12) | Bs |
| BsTYRMN_10 | | *S. cerevisiae* S288c | Mod | P0A6E1 | Shikimate kinase 2 | *Escherichia coli* (strain K12) | Mod |
| BsTYRMN_11 | | *S. cerevisiae* S288c | Sc | P0A6E1 | Shikimate kinase 2 | *Escherichia coli* (strain K12) | Sc |
| BsTYRMN_12 | | *S. cerevisiae* S288c | Yl | P0A6E1 | Shikimate kinase 2 | *Escherichia coli* (strain K12) | Yl |
| BsTYRMN_13 | | *S. cerevisiae* S288c | Mod | P20049 | Prephenate dehydro-genase | *Saccharomyces cerevisiae* S288c | Mod |

CO = Codon Optimization; Bs =*Bacillus subtilus*; Mod = codon usage for Cg and Sc; Sc = *Saccharomyces cerevisiae* Yl = *Yarrowia lipolytica*.

TABLE 5

Host Evaluation Results for *Saccharomyces cerevisiae* Strains Engineered to Produce Tyramine

| Strain name | Titer (microgram/L) | E1 Uniprot ID | E1 - activity name | E1 - source organism | E1 CO | E2 Uniprot ID | E2 - activity name |
|---|---|---|---|---|---|---|---|
| ScTYRMN_114 | 164602 | P54769 | Tyrosine/DOPA decarbox-ylase 2 | *Papaver somniferum* | Bs | P32449 | Phospho-2-dehydro-3-deoxy-heptonate aldolase |
| ScTYRMN_115 | 184762 | P54769 | Tyrosine/DOPA decarbox-ylase 2 | *Papaver somniferum* | Mod | P32449 | Phospho-2-dehydro-3-deoxy-heptonate aldolase |
| ScTYRMN_116 | 188 | P54769 | Tyrosine/DOPA decarbox-ylase 2 | *Papaver somniferum* | Sc | P32449 | Phospho-2-dehydro-3-deoxy-heptonate aldolase |
| ScTYRMN_117 | 171171 | P54769 | Tyrosine/DOPA decarbox-ylase 2 | *Papaver somniferum* | Yl | P32449 | Phospho-2-dehydro-3-deoxy-heptonate aldolase |
| ScTYRMN_118 | 66972 | P54769 | Tyrosine/DOPA decarbox-ylase 2 | *Papaver somniferum* | Bs | P32449 | Phospho-2-dehydro-3-deoxy-heptonate aldolase |
| ScTYRMN_119 | 89422 | P54769 | Tyrosine/DOPA decarbox-ylase 2 | *Papaver somniferum* | Sc | P32449 | Phospho-2-dehydro-3-deoxy-heptonate aldolase |
| ScTYRMN_120 | 81170 | P54769 | Tyrosine/DOPA decarbox-ylase 2 | *Papaver somniferum* | Yl | P32449 | Phospho-2-dehydro-3-deoxy-heptonate aldolase |

| Strain name | E2 Modifications | E2 - source organism | E2 CO | E3 Uniprot ID | E3 - activity name | E3 - source organism | E3 CO |
|---|---|---|---|---|---|---|---|
| ScTYRMN_114 | K229L | *S. cerevisiae* S288c | Bs | | | | |
| ScTYRMN_115 | K229L | *S. cerevisiae* S288c | Mod | | | | |
| ScTYRMN_116 | K229L | *S. cerevisiae* S288c | Sc | | | | |

TABLE 5-continued

Host Evaluation Results for *Saccharomyces cerevisiae* Strains Engineered to Produce Tyramine

| | | | | | | | |
|---|---|---|---|---|---|---|---|
| ScTYRMN_117 | K229L | *S. cerevisiae* S288c | Yl | | | | |
| ScTYRMN_118 | | *S. cerevisiae* S288c | Bs | P0A6E1 | Shikimate kinase 2 | *Escherichia coli* (strain K12) | Bs |
| ScTYRMN_119 | | *S. cerevisiae* S288c | Sc | P0A6E1 | Shikimate kinase 2 | *Escherichia coli* (strain K12) | Sc |
| ScTYRMN_120 | | *S. cerevisiae* S288c | Yl | P0A6E1 | Shikimate kinase 2 | *Escherichia coli* (strain K12) | Yl |

CO = Codon Optimization; Bs = *Bacillus subtilus*; Mod = codon usage for Cg and Sc; Sc = *Saccharomyces cerevisiae* Yl = *Yarrowia lipolytica*.

TABLE 6

Host Evaluation Results for *Corynebacteria glutamicum* Strains Engineered to Produce Tyramine

| Strain name | Titer (microgram/L) | E1 Uniprot ID | E1 - activity name | E1 - source organism | E1 CO | E2 Uniprot ID | E2 - activity name |
|---|---|---|---|---|---|---|---|
| CgTYRMN_69 | | P54769 | Tyrosine/DOPA decarboxylase 2 | *Papaver somniferum* | Bs | P32449 | Phospho-2-dehydro-3-deoxyheptonate aldolase |
| CgTYRMN_70 | | P54769 | Tyrosine/DOPA decarboxylase 2 | *Papaver somniferum* | Mod | P32449 | Phospho-2-dehydro-3-deoxyheptonate aldolase |
| CgTYRMN_71 | | P54769 | Tyrosine/DOPA decarboxylase 2 | *Papaver somniferum* | Sc | P32449 | Phospho-2-dehydro-3-deoxyheptonate aldolase |
| CgTYRMN_72 | | P54769 | Tyrosine/DOPA decarboxylase 2 | *Papaver somniferum* | Yl | P32449 | Phospho-2-dehydro-3-deoxyheptonate aldolase |
| CgTYRMN_73 | | C9ASN2 | Pyridoxal-dependent decarboxylase | *Enterococcus faecium* Com15 | Bs | P32449 | Phospho-2-dehydro-3-deoxyheptonate aldolase |
| CgTYRMN_74 | 466779 | C9ASN2 | Pyridoxal-dependent decarboxylase | *Enterococcus faceium* Com15 | Sc | P32449 | Phospho-2-dehydro-3-deoxyheptonate aldolase |
| CgTYRMN_75 | | C9ASN2 | Pyridoxal-dependent decarboxylase | *Enterococcus faecium* Com15 | Yl | P32449 | Phospho-2-dehydro-3-deoxyheptonate aldolase |
| CgTYRMN_76 | | P54769 | Tyrosine/DOPA decarboxylase 2 | *Papaver somniferum* | Bs | P32449 | Phospho-2-dehydro-3-deoxyheptonate aldolase |
| CgTYRMN_77 | 14 | P54769 | Tyrosine/DOPA decarboxylase 2 | *Papaver somniferum* | Sc | P32449 | Phospho-2-dehydro-3-deoxyheptonate aldolase |
| CgTYRMN_78 | 49 | P54769 | Tyrosine/DOPA decarboxylase 2 | *Papaver somniferum* | Yl | P32449 | Phospho-2-dehydro-3-deoxyheptonate aldolase |

TABLE 6-continued

Host Evaluation Results for *Corynebacteria glutamicum* Strains Engineered to Produce Tyramine

| Strain name | E2 Modifications | E2 - source organism | E2 CO | E3 Uniprot ID | E3 - activity name | E3 - source organism | E3 CO |
|---|---|---|---|---|---|---|---|
| CgTYRMN_69 | K229L | *S. cerevisiae* S288c | Bs | | | | |
| CgTYRMN_70 | K229L | *S. cerevisiae* S288c | Mod | | | | |
| CgTYRMN_71 | K229L | *S. cerevisiae* S288c | Sc | | | | |
| CgTYRMN_72 | K229L | *S. cerevisiae* S288c | Yl | | | | |
| CgTYRMN_73 | | *S. cerevisiae* S288c | Bs | | | | |
| CgTYRMN_74 | | *S. cerevisiae* S288c | Sc | | | | |
| CgTYRMN_75 | | *S. cerevisiae* S288c | Yl | | | | |
| CgTYRMN_76 | | *S. cerevisiae* S288c | Bs | P0A6E1 | Shikimate kinase 2 | *Escherichia coli* (strain K12) | Bs |
| CgTYRMN_77 | | *S. cerevisiae* S288c | Sc | P0A6E1 | Shikimate kinase 2 | *Escherichia coli* (strain K12) | Sc |
| CgTYRMN_78 | | *S. cerevisiae* S288c | Yl | P0A6E1 | Shikimate kinase 2 | *Escherichia coli* (strain K12) | Yl |

CO = Codon Optimization; Bs = *Bacillus subtilus*; Mod = codon usage for Cg and Sc; Sc = *Saccharomyces cerevisiae* Yl = *Yarrowia lipolytica*.

TABLE 7

Improvement-Round Results for *Saccharomyces cerevisiae* Strains Engineered to Produce Tyramine

| | Titer (microgram/L) | E1 Uniprot ID | E1 - activity name | E1 Modifications | E1 - source organism | E1 CO | E2 Uniiprot ID | E2 - activity name |
|---|---|---|---|---|---|---|---|---|
| ScTYRMN_100 | 263842 | Q8U0A9 | 2-dehydro-3-deoxy-phospho-heptonate aldolase | | *Pyrococcus furiosus* ATCC 43587 | Mod | P23538 | Phospho-enolpyruvate synthase |
| ScTYRMN_101 | 233752 | A5DB21 | Chorismate mutase | | *Meyerozyma guilliermondii* ATCC 6260 | Mod | P22259 | Phospho-enolpyruvate carboxy-kinase |
| ScTYRMN_102 | 200881 | P07023 | Chorismate mutase and Prephenate dehydro-genase | M53I, A354V | *Escherichia coli* K12 | Mod | P32449 | Phospho-2-dehydro-3-deoxy-heptonate aldolase |
| ScTYRMN_103 | 155522 | P0A6E1 | Shikimate kinase | | *Escherichia coli* K12 | Mod | P32449 | Phospho-2-dehydro-3-deoxy-heptonate aldolase |
| ScTYRMN_104 | 193051 | P0A6D7 | Shikimate kinase | | *Escherichia coli* K12 | Mod | | |
| ScTYRMN_105 | 131046 | P10880 | Shikimate kinase | C162S | *Dickeya chrysanthemi* | Mod | | |
| ScTYRMN_106 | 180373 | P08566 | shikimate dehydro-genase | Error | *S. cerevisiae* S288c | Mod | | |
| ScTYRMN_107 | 154577 | P0A6E1 | Shikimate kinase | | *Escherichia coli* K12 | Mod | | |
| ScTYRMN_108 | 248412 | P0A6E1 | Shikimate kinase | | *Escherichia coli* K12 | Mod | | |
| ScTYRMN_109 | 226394 | P20049 | prephenate dehydro-genase | | *S. cerevisiae* S288c | Mod | P09831 | Glutamate synthase |
| ScTYRMN_110 | 203759 | P32449 | Phospho-2-dehydro-3-deoxy-heptonate aldolase | K229L | *S. cerevisiae* S288c | Mod | | |

TABLE 7-continued

| Improvement-Round Results for *Saccharomyces cerevisiae* Strains Engineered to Produce Tyramine | | | | | | | |
|---|---|---|---|---|---|---|---|
| ScTYRMN_111 | 270601 | P38840 | Aromatic amino acid amino-transferase | *S. cerevisiae* S288c | Mod | | |
| ScTYRMN_112 | 235307 | P17735 | Tyrosine amino-transferase | *Homo sapiens* | Mod | | |
| ScTYRMN_54 | 265899 | P20049 | Prephenate dehydro-genase | *S. cerevisiae* S288c | Mod | | |
| ScTYRMN_75 | 271983 | P23538 | Phospho-enolpyruvate synthase | *Escherichia coli* K12 | Mod | | |
| ScTYRMN_76 | 220715 | P23538 | Phospho-enolpyruvate synthase | *Escherichia coli* K12 | Mod | | |
| ScTYRMN_77 | 296242 | P23254 | Transketolase | *S. cerevisiae* S288c | Mod | | |
| ScTYRMN_78 | 299143 | P15019 | Transaldolase | *S. cerevisiae* S288c | Mod | | |
| ScTYRMN_79 | 296289 | P23254 | Transketolase | *S. cerevisiae* S288c | Mod | P15019 | Transaldolase |
| ScTYRMN_80 | 208329 | P23254 | Transketolase | *S. cerevisiae* S288c | Mod | P08566 | shikimate dehydro-genase |
| ScTYRMN_81 | 244921 | P23254 | Transketolase | *S. cerevisiae* S288c | Mod | P08566 | shikimate dehydro-genase |
| ScTYRMN_82 | 274335 | P23254 | Transketolase | *S. cerevisiae* S288c | Mod | P23538 | Phospho-enolpyruvate synthase |
| ScTYRMN_83 | 220523 | P23254 | Transketolase | *S. cerevisiae* S288c | Mod | | |
| ScTYRMN_84 | 252995 | P23254 | Transketolase | *S. cerevisiae* S288c | Mod | | |
| ScTYRMN_85 | 274284 | P15019 | Transaldolase | *S. cerevisiae* S288c | Mod | P32449 | Phospho-2-dehydro-3-deoxy-heptonate aldolase, tyrosine-inhibited (EC 2.5.1.54) (3-deoxy-D-arabino-heptulosonate 7-phosphate synthase) (DAHP synthase) (Phospho-2-keto-3-deoxy-heptonate aldolase) |
| ScTYRMN_86 | 199 | O52631 | Glycer-aldehyde-3-phosphate dehydro-genase | *Clostridium acetobutylicum* ATCC 824 | Mod | P08566 | shikimate dehydro-genase |
| ScTYRMN_87 | 215006 | P25856 | Glycer-aldehyde-3-phosphate dehydro-genase | *Arabidopsis thaliana* | Mod | P08566 | shikimate dehydro-genase |
| ScTYRMN_88 | 141184 | P50362 | Glycer-aldehyde-3-phosphate dehydro-genase | *Chlamy-domonas reinhardtii* | Mod | P08566 | shikimate dehydro-genase |
| ScTYRMN_89 | 238075 | Q5HQV4 | Glycer-aldehyde-3-phosphate dehydro-genase | *Staphylo-coccus epidermidis* ATCC 35984 | Mod | P08566 | shikimate dehydro-genase |

TABLE 7-continued

Improvement-Round Results for *Saccharomyces cerevisiae* Strains Engineered to Produce Tyramine

| | | | | | | |
|---|---|---|---|---|---|---|
| ScTYRMN_90 | 277029 | P30724 | Glycer-aldehyde-3-phosphate dehydro-genase | | *Gracilaria gracilis* (Red alga) | Mod |
| ScTYRMN_91 | 263562 | P09832 | Glutamate synthase | | *Escherichia coli* K12 | Mod |
| ScTYRMN_92 | 245798 | P32288 | Glutamine synthetase | | *S cerevisiae* S288c | Mod |
| ScTYRMN_93 | 231297 | P32449 | Phospho-2-dehydro-3-deoxy-heptonate aldolase | Q166K | *S cerevisiae* S288c | Mod |
| ScTYRMN_94 | 264041 | P32449 | Phospho-2-dehydro-3-deoxy-heptonate aldolase | K229L | *S cerevisiae* S288c | Mod |
| ScTYRMN_95 | 245229 | P0AB91 | Phospho-2-dehydro-3-deoxy-heptonate aldolase | D146N | *Escherichia coli* K12 | Mod |
| ScTYRMN_96 | 64088 | P0AB91 | Phospho-2-dehydro-3-deoxy-heptonate aldolase | P150L | *Escherichia coli* K12 | Mod |
| ScTYRMN_97 | 236618 | P00888 | Phospho-2-dehydro-3-deoxy-heptonate aldolase | N8K | *Escherichia coli* K12 | Mod |
| ScTYRMN_98 | 140 | Q9ZMU5 | Phospho-2-dehydro-3-deoxy-heptonate aldolase | | *Helicobacter pylori* ATCC 700824 | Mod |
| ScTYRMN_99 | 244825 | Q9YEJ7 | Phospho-2-dehydro-3-deoxy-heptonate aldolase | | *Aero-pyrum pernix* ATCC 700893 | Mod |

| | E2 Modifications | E2 - source organism | E2 CO | E3 Uniprot ID | E3 - activity name | E3 Modifications | E3 - source organism | E3 CO |
|---|---|---|---|---|---|---|---|---|
| ScTYRMN_100 | | *Escherichia coli* (strain K12) | Mod | | | | | |
| ScTYRMN_101 | | *Escherichia coli* (strain K12) | Mod | | | | | |
| ScTYRMN_102 | K229L | *S. cerevisiae* S288c | Mod | | | | | |
| ScTYRMN_103 | K229L | *S. cerevisiae* S288c | Mod | | | | | |
| ScTYRMN_104 | | | | | | | | |
| ScTYRMN_105 | | | | | | | | |
| ScTYRMN_106 | | | | | | | | |
| ScTYRMN_107 | | | | | | | | |
| ScTYRMN_108 | | | | | | | | |
| ScTYRMN_109 | | *Escherichia coli* (strain K12) | Mod | | | | | |
| ScTYRMN_110 | | | | | | | | |
| ScTYRMN_111 | | | | | | | | |
| ScTYRMN_112 | | | | | | | | |
| ScTYRMN_54 | | | | | | | | |
| ScTYRMN_75 | | | | | | | | |
| ScTYRMN_76 | | | | | | | | |
| ScTYRMN_77 | | | | | | | | |
| ScTYRMN_78 | | | | | | | | |

TABLE 7-continued

Improvement-Round Results for *Saccharomyces cerevisiae* Strains Engineered to Produce Tyramine

| | | | | | | | | |
|---|---|---|---|---|---|---|---|---|
| ScTYRMN_79 | | *S. cerevisiae* (strain ATCC 204508/ S288c) (Baker's yeast) | Mod | | | | | |
| ScTYRMN_80 | | *S. cerevisiae* S288c | Mod | P0A6E1 | Shikimate kinase | | *E. coli* K12 | Mod |
| ScTYRMN_81 | | *S. cerevisiae* S288c | Mod | P0A6E1 | Shikimate kinase | | *E. coli* K12 | Mod |
| ScTYRMN_82 | | *Escherichia coli* K12 | Mod | | | | | |
| ScTYRMN_83 | | | | | | | | |
| ScTYRMN_84 | | | | | | | | |
| ScTYRMN_85 | K229L | Fungi | Mod | | | | | |
| ScTYRMN_86 | | *S. cerevisiae* S288c | Mod | | | | | |
| ScTYRMN_87 | | *S. cerevisiae* S288c | Mod | P07023 | Chorismate mutase and Prephenate dehydro-genase | M53I, A354V | *E. coli* K12 | Mod |
| ScTYRMN_88 | | *S. cerevisiae* S288c | Mod | P07023 | Chorismate mutase and Prephenate dehydro-genase | M53I, A354V | *E. coli* K12 | Mod |
| ScTYRMN_89 | | *S. cerevisiae* S288c | Mod | P07023 | Chorismate mutase and Prephenate dehydro-genase | M53I, A354V | *E. coli* K12 | Mod |
| ScTYRMN_90 | | | | | | | | |
| ScTYRMN_91 | | | | | | | | |
| ScTYRMN_92 | | | | | | | | |
| ScTYRMN_93 | | | | | | | | |
| ScTYRMN_94 | | | | | | | | |
| ScTYRMN_95 | | | | | | | | |
| ScTYRMN_96 | | | | | | | | |
| ScTYRMN_97 | | | | | | | | |
| ScTYRMN_98 | | | | | | | | |
| ScTYRMN_99 | | | | | | | | |

TABLE 8

SEQ ID NO Cross-Reference Table

| SEQ ID NO | SEQ ID NO from Provisional | Sequence Type with Modifications | Uniprot ID | Activity name |
|---|---|---|---|---|
| 1 | 2 | AA seq for enzyme C9ASN2 | C9ASN2 | Pyridoxal-dependent decarboxylase |
| 2 | 20 | AA seq for enzyme P54769 | P54769 | Tyrosine/DOPA decarboxylase 2 [Includes: DOPA decarboxylase |
| 3 | 45 | AA seq | P28777 | chorismate synthase |
| 4 | 47 | AA seq for enzyme P20049 | P20049 | Prephenate dehydrogenase [NADP |
| 5 | 31 | AA seq for enzyme P32449 with substitution Q166K | P32449 | Phospho-2-dehydro-3-deoxyheptonate aldolase, tyrosine-inhibited (EC 2.5.1.54) (3-deoxy-D-arabino-heptulosonate 7-phosphate synthase) (DAHP synthase) (Phospho-2-keto-3-deoxy heptonate aldolase) |
| 6 | 37 + 39 (seqs were duplicates) | AA seq for enzyme P32449 with substitution K229L | P32449 | Phospho-2-dehydro-3-deoxyheptonate aldolase, tyrosine-inhibited |
| 7 | 33 + 35 (seqs were duplicates) | AA seq for enzyme P0AB91 with substitution D146N | P0AB91 | Phospho-2-dehydro-3-deoxyheptonate aldolase, Phe-sensitive (EC 2.5.1.54) (3-deoxy-D-arabino-heptulosonate 7-phosphate synthase) (DAHP synthase) (Phospho-2-keto-3-deoxy heptonate aldolase) |
| 8 | | AA seq for enzyme P15019 | P15019 | Transaldolase (EC 2.2.1.2) |
| 9 | 43 | AA seq for enzyme P32449 | P32449 | Phospho-2-dehydro-3-deoxyheptonate aldolase, tyrosine-inhibited |
| 10 | | DNA seq4 for enzyme P32449 | P32449 | Phospho-2-dehydro-3-deoxyheptonate aldolase, tyrosine-inhibited |

TABLE 8-continued

SEQ ID NO Cross-Reference Table

| | | | | |
|---|---|---|---|---|
| 11 | 4 | AA | W0VJZ5 | TYDC |
| 12 | 44 | DNA | P28777 | chorismate synthase |
| 13 | 46 | DNA seq3 for enzyme P20049 | P20049 | Prephenate dehydrogenase [NADP(+)[ |
| 14 | | DNA seq1 for enzyme P0A6E1 | P0A6E1 | Shikimate kinase 2 |
| 15 | | AA seq for enzyme P0A6E1 | P0A6E1 | Shikimate kinase 2 |
| 16 | 6 | AA | B8GDM7 | TYDC |
| 17 | 8 | AA | S3X9X3 | TYDC |
| 18 | 10 | AA | Q06085 | TYDC |
| 19 | 12 + 22 (seqs were duplicates) | AA | F2PNN9 | TYDC |
| 20 | 14 | AA | B5HRY3 | TYDC |
| 21 | 16 | AA | Q88JU5 | TYDC |
| 22 | 18 | AA | I4EZJ8 | TYDC |
| 23 | 24 | AA | I3X3G3 | TYDC |
| 24 | 27 | AA | Q7XHL3 | TYDC |
| 25 | 29 | AA | Q60358 | TYDC |
| 26 | 41 | AA | P14843 | Phospho-2-dehydro-3-deoxyheptonate aldolase, tyrosine-inhibited (EC 2.5.1.54) (3-deoxy-D-arabino-heptulosonate 7-phosphate synthase) (DAHP synthase) (Phospho-2-keto-3-deoxy heptonate aldolase) |
| 27 | 49 | AA | P53090 | aromatic amino acid aminotransferase 2__2-aminoadipate transaminase, L-phenylalanine: 2-oxoglutarate aminotransferase, kynurenine-oxoglutarate transaminase |
| 28 | 51 | AA seq for enzyme P38840 | P38840 | Aromatic amino acid aminotransferase 2 (EC 2.6.1.57) (Aromatic amino acid aminotransferase II) (Aromatic amino acid-requiring protein 9) (Kynurenine aminotransferase I) (KAT I) (EC 2.6.1.7) |
| 29 | | AA seq for enzyme P23538 | P23538 | Phosphoenolpyruvate synthase (PEP synthase) (EC 2.7.9.2) (Pyruvate, water dikinase) |
| 30 | | AA seq for enzyme P23254 | P23254 | Transketolase |
| 31 | | AA seq for enzyme P30724 | P30724 | Glyceraldehyde-3-phosphate dehydrogenase, chloroplastic (EC 1.2.1.13) (NADP-dependent glyceraldehydephosphate dehydrogenase) |
| 32 | | AA seq for enzyme Q8U0A9 | Q8U0A9 | 2-dehydro-3-deoxyphosphoheptonate aldolase (EC 2.5.1.54) |
| 33 | | AA seq for enzyme A5DB21 | A5DB21 | Chorismate mutase (EC 5.4.99.5) |
| 34 | | AA seq for enzyme P0A6D7 | P0A6D7 | Shikimate kinase 1 (SK 1) (EC 2.7.1.71) (Shikimate kinase I) (SKI) |
| 35 | | AA seq for enzyme P08566 | P08566 | shikimate dehydrogenase |
| 36 | | AA seq for enzyme P17735 | P17735 | Tyrosine aminotransferase (TAT) (EC 2.6.1.5) (L-tyrosine: 2-oxoglutarate aminotransferase) |
| 37 | | AA seq for enzyme P09831 | P09831 | Glutamate synthase [NADPH] large chain (EC 1.4.1.13) (Glutamate synthase subunit alpha) (GLTS alpha chain) (NADPH-GOGAT) |
| 38 | | AA seq for enzyme P09832 | P09832 | Glutamate synthase [NADPH] small chain (EC 1.4.1.13) (Glutamate synthase subunit beta) (GLTS beta chain) (NADPH-GOGAT) |
| 39 | | AA seq for enzyme P32288 | P32288 | Glutamine synthetase (GS) (EC 6.3.1.2) (Glutamate-ammonia ligase) |
| 40 | | DNA seq4 for enzyme C9ASN2 | C9ASN2 | Pyridoxal-dependent decarboxylase |
| 41 | | DNA seq2 for enzyme P0A6E1 | P0A6E1 | Shikimate kinase 2 |
| 42 | | DNA seq3 for enzyme P32449 | P32449 | Phospho-2-dehydro-3-deoxyheptonate aldolase, tyrosine-inhibited |
| 43 | | DNA seq3 for enzyme C9ASN2 | C9ASN2 | Pyridoxal-dependent decarboxylase |
| 44 | | DNA seq2 for enzyme P32449 with substitution K229L | P32449 | Phospho-2-dehydro-3-deoxyheptonate aldolase, tyrosine-inhibited |
| 45 | | DNA seq2 for enzyme C9ASN2 | C9ASN2 | Pyridoxal-dependent decarboxylase |
| 46 | | AA seq for enzyme P22259 | P22259 | Phosphoenolpyruvate carboxykinase (ATP) (PCK) (PEP carboxykinase) (PEPCK) (EC 4.1.1.49) |
| 47 | | AA seq for enzyme P07023 with substitution M53I, A354V | P07023 | T-protein [Includes: Chorismate mutase (CM) (EC 5.4.99.5); Prephenate dehydrogenase (PDH) (EC 1.3.1.12)] |
| 48 | | AA seq for enzyme P10880 with substitution C162S | P10880 | Shikimate kinase 2 (SK 2) (EC 2.7.1.71) (Shikimate kinase II) (SKII) |
| 49 | | AA seq for enzyme O52631 | O52631 | Glyceraldehyde-3-phosphate dehydrogenase (GAPDH) (EC 1.2.1.12) (NAD-dependent glyceraldehyde-3-phosphate dehydrogenase) |
| 50 | | AA seq for enzyme P25856 | P25856 | Glyceraldehyde-3-phosphate dehydrogenase GAPA1, chloroplastic (EC 1.2.1.13) (NADP-dependent glyceraldehydephosphate dehydrogenase A subunit 1) |

TABLE 8-continued

| SEQ ID NO Cross-Reference Table | | | | |
|---|---|---|---|---|
| 51 | | AA seq for enzyme P50362 | P50362 | Glyceraldehyde-3-phosphate dehydrogenase A, chloroplastic (EC 1.2.1.13) (NADP-dependent glyceraldehydephosphate dehydrogenase subunit A) |
| 52 | | AA seq for enzyme Q5HQV4 | Q5HQV4 | Glyceraldehyde-3-phosphate dehydrogenase 1 (GAPDH 1) (EC 1.2.1.12) (NAD-dependent glyceraldehyde-3-phosphate dehydrogenase) |
| 53 | | AA seq for enzyme P00888 with substitution N8K | P00888 | Phospho-2-dehydro-3-deoxyheptonate aldolase, Tyr-sensitive (EC 2.5.1.54) (3-deoxy-D-arabino-heptulosonate 7-phosphate synthase) (DAHP synthase) (Phospho-2-keto-3-deoxy heptonate aldolase) |
| 54 | | AA seq for enzyme Q9ZMU5 | Q9ZMU5 | Phospho-2-dehydro-3-deoxyheptonate aldolase (EC 2.5.1.54) |
| 55 | | AA seq for enzyme Q9YEJ7 | Q9YEJ7 | Phospho-2-dehydro-3-deoxyheptonate aldolase (EC 2.5.1.54) |
| 56 | | AA seq for enzyme P0AB91 with substitution P150L | P0AB91 | Phospho-2-dehydro-3-deoxyheptonate aldolase, Phe-sensitive (EC 2.5.1.54) (3-deoxy-D-arabino-heptulosonate 7-phosphate synthase) (DAHP synthase) (Phospho-2-keto-3-deoxy heptonate aldolase) |
| 57 | | DNA seq1 for enzyme P54769 | P54769 | Tyrosine/DOPA decarboxylase 2 [Includes: DOPA decarboxylase |
| 58 | | DNA seq1 for enzyme P32449 with substitution K229L | P32449 | Phospho-2-dehydro-3-deoxyheptonate aldolase, tyrosine-inhibited |
| 59 | | DNA seq2 for enzyme P54769 | P54769 | Tyrosine/DOPA decarboxylase 2 [Includes: DOPA decarboxylase |
| 60 | | DNA seq3 for enzyme P54769 | P54769 | Tyrosine/DOPA decarboxylase 2 [Includes: DOPA decarboxylase |
| 61 | | DNA seq3 for enzyme P32449 with substitution K229L | P32449 | Phospho-2-dehydro-3-deoxyheptonate aldolase, tyrosine-inhibited |
| 62 | | DNA seq4 for enzyme P54769 | P54769 | Tyrosine/DOPA decarboxylase 2 [Includes: DOPA decarboxylase |
| 63 | | DNA seq4 for enzyme P32449 with substitution K229L | P32449 | Phospho-2-dehydro-3-deoxyheptonate aldolase, tyrosine-inhibited |
| 64 | | DNA seq1 for enzyme C9ASN2 | C9ASN2 | Pyridoxal-dependent decarboxylase |
| 65 | | DNA seq1 for enzyme P32449 | P32449 | Phospho-2-dehydro-3-deoxyheptonate aldolase, tyrosine-inhibited |
| 66 | | DNA seq2 for enzyme P32449 | P32449 | Phospho-2-dehydro-3-deoxyheptonate aldolase |
| 67 | | DNA seq3 for enzyme P0A6E1 | P0A6E1 | Shikimate kinase 2 |
| 68 | | DNA seq4 for enzyme P0A6E1 | P0A6E1 | Shikimate kinase 2 |
| 69 | | DNA seq5 for enzyme P54769 | P54769 | Tyrosine/DOPA decarboxylase 2 [Includes: DOPA decarboxylase |
| 70 | 36 | DNA seq5 for enzyme P32449 with substitution K229L | P32449 | Phospho-2-dehydro-3-deoxyheptonate aldolase, tyrosine-inhibited |
| 71 | | DNA seq1 for enzyme P20049 | P20049 | Prephenate dehydrogenase [NADP |
| 72 | | DNA seq1 for enzyme Q8U0A9 | Q8U0A9 | 2-dehydro-3-deoxyphosphoheptonate aldolase (EC 2.5.1.54) |
| 73 | | DNA seq1 for enzyme P23538 | P23538 | Phosphoenolpyruvate synthase (PEP synthase) (EC 2.7.9.2) (Pyruvate, water dikinase) |
| 74 | | DNA seq1 for enzyme A5DB21 | A5DB21 | Chorismate mutase (EC 5.4.99.5) |
| 75 | | DNA seq1 for enzyme P22259 | P22259 | Phosphoenolpyruvate carboxykinase (ATP) (PCK) (PEP carboxykinase) (PEPCK) (EC 4.1.1.49) |
| 76 | | DNA seq1 for enzyme P07023 with substitution M53I, A354V | P07023 | T-protein [Includes: Chorismate mutase (CM) (EC 5.4.99.5); Prephenate dehydrogenase (PDH) (EC 1.3.1.12)] |
| 77 | | DNA seq6 for enzyme P32449 with substitution K229L | P32449 | Phospho-2-dehydro-3-deoxyheptonate aldolase, tyrosine-inhibited (EC 2.5.1.54) (3-deoxy-D-arabino-heptulosonate 7-phosphate synthase) (DAHP synthase) (Phospho-2-keto-3-deoxy heptonate aldolase) |
| 78 | | DNA seq5 for enzyme P0A6E1 | P0A6E1 | Shikimate kinase 2 (SK 2) (EC 2.7.1.71) (Shikimate kinase II) (SKII) |
| 79 | | DNA seq1 for enzyme P0A6D7 | P0A6D7 | Shikimate kinase 1 (SK 1) (EC 2.7.1.71) (Shikimate kinase I) (SKI) |
| 80 | | DNA seq1 for enzyme P10880 with substitution C162S | P10880 | Shikimate kinase 2 (SK 2) (EC 2.7.1.71) (Shikimate kinase II) (SKII) |
| 81 | | DNA seq1 for enzyme P08566 | P08566 | shikimate dehydrogenase |
| 82 | | DNA seq2 for enzyme P20049 | P20049 | prephenate dehydrogenase |
| 83 | | DNA seq1 for enzyme P09831 | P09831 | Glutamate synthase [NADPH] large chain (EC 1.4.1.13) (Glutamate synthase subunit alpha) (GLTS alpha chain) (NADPH-GOGAT) |
| 84 | | DNA seq1 for enzyme P38840 | P38840 | Aromatic amino acid aminotransferase 2 (EC 2.6.1.57) (Aromatic amino acid aminotransferase II) (Aromatic amino acid-requiring protein 9) (Kynurenine aminotransferase I) (KAT I) (EC 2.6.1.7) |

TABLE 8-continued

| SEQ ID NO Cross-Reference Table | | | | |
|---|---|---|---|---|
| 85 | | DNA seq1 for enzyme P17735 | P17735 | Tyrosine aminotransferase (TAT) (EC 2.6.1.5) (L-tyrosine: 2-oxoglutarate aminotransferase) |
| 86 | | DNA seq1 for enzyme P23254 | P23254 | Transketolase |
| 87 | | DNA seq1 for enzyme P15019 | P15019 | Transaldolase (EC 2.2.1.2) |
| 88 | | DNA seq1 for enzyme O52631 | O52631 | Glyceraldehyde-3-phosphate dehydrogenase (GAPDH) (EC 1.2.1.12) (NAD-dependent glyceraldehyde-3-phosphate dehydrogenase) |
| 89 | | DNA seq1 for enzyme P25856 | P25856 | Glyceraldehyde-3-phosphate dehydrogenase GAPA1, chloroplastic (EC 1.2.1.13) (NADP-dependent glyceraldehydephosphate dehydrogenase A subunit 1) |
| 90 | | DNA seq1 for enzyme P50362 | P50362 | Glyceraldehyde-3-phosphate dehydrogenase A, chloroplastic (EC 1.2.1.13) (NADP-dependent glyceraldehydephosphate dehydrogenase subunit A) |
| 91 | | DNA seq1 for enzyme Q5HQV4 | Q5HQV4 | Glyceraldehyde-3-phosphate dehydrogenase 1 (GAPDH 1) (EC 1.2.1.12) (NAD-dependent glyceraldehyde-3-phosphate dehydrogenase) |
| 92 | | DNA seq1 for enzyme P30724 | P30724 | Glyceraldehyde-3-phosphate dehydrogenase, chloroplastic (EC 1.2.1.13) (NADP-dependent glyceraldehydephosphate dehydrogenase) |
| 93 | | DNA seq1 for enzyme P09832 | P09832 | Glutamate synthase [NADPH] small chain (EC 1.4.1.13) (Glutamate synthase subunit beta) (GLTS beta chain) (NADPH-GOGAT) |
| 94 | | DNA seq1 for enzyme P32288 | P32288 | Glutamine synthetase (GS) (EC 6.3.1.2) (Glutamate-ammonia ligase) |
| 95 | | DNA seq1 for enzyme P32449 with substitution Q166K | P32449 | Phospho-2-dehydro-3-deoxyheptonate aldolase, tyrosine-inhibited (EC 2.5.1.54) (3-deoxy-D-arabino-heptulosonate 7-phosphate synthase) (DAHP synthase) (Phospho-2-keto-3-deoxy heptonate aldolase) |
| 96 | | DNA seq1 for enzyme P0AB91 with substitution D146N | P0AB91 | Phospho-2-dehydro-3-deoxyheptonate aldolase, Phe-sensitive (EC 2.5.1.54) (3-deoxy-D-arabino-heptulosonate 7-phosphate synthase) (DAHP synthase) (Phospho-2-keto-3-deoxy heptonate aldolase) |
| 97 | | DNA seq1 for enzyme P0AB91 with substitution P150L | P0AB91 | Phospho-2-dehydro-3-deoxyheptonate aldolase, Phe-sensitive (EC 2.5.1.54) (3-deoxy-D-arabino-heptulosonate 7-phosphate synthase) (DAHP synthase) (Phospho-2-keto-3-deoxy heptonate aldolase) |
| 98 | | DNA seq1 for enzyme P00888 with substitution N8K | P00888 | Phospho-2-dehydro-3-deoxyheptonate aldolase, Tyr-sensitive (EC 2.5.1.54) (3-deoxy-D-arabino-heptulosonate 7-phosphate synthase) (DAHP synthase) (Phospho-2-keto-3-deoxy heptonate aldolase) |
| 99 | | DNA seq1 for enzyme Q9ZMU5 | Q9ZMU5 | Phospho-2-dehydro-3-deoxyheptonate aldolase (EC 2.5.1.54) |
| 100 | | DNA seq1 for enzyme Q9YEJ7 | Q9YEJ7 | Phospho-2-dehydro-3-deoxyheptonate aldolase (EC 2.5.1.54) |
| 101 | 1 | DNA | C5IXK9 | TYDC |
| 102 | 3 | DNA | W0VJZ5 | TYDC |
| 103 | 5 | DNA | B8GDM7 | TYDC |
| 104 | 7 | DNA | S3X9X3 | TYDC |
| 105 | 9 | DNA | Q06085 | TYDC |
| 106 | 11 + 21 (seqs were duplicates) | DNA | F2PNN9 | TYDC |
| 107 | 13 | DNA | B5HRY3 | TYDC |
| 108 | 15 | DNA | Q88JU5 | TYDC |
| 109 | 17 | DNA | I4EZJ8 | TYDC |
| 110 | 19 | DNA | P54769 | TYDC |
| 111 | 23 | DNA | I3X3G3 | TYDC |
| 112 | 25 | DNA | P54769 | TYDC |
| 113 | 26 | DNA | Q7XHL3 | TYDC |
| 114 | 28 | DNA | Q60358 | TYDC |
| 115 | 30 | DNA with substitution Q166K | P32449 | Phospho-2-dehydro-3-deoxyheptonate aldolase, tyrosine-inhibited (EC 2.5.1.54) (3-deoxy-D-arabino-heptulosonate 7-phosphate synthase) (DAHP synthase) (Phospho-2-keto-3-deoxy heptonate aldolase) |
| 116 | 32 | DNA with substitution D146N | P0AB91 | Phospho-2-dehydro-3-deoxyheptonate aldolase, tyrosine-inhibited (EC 2.5.1.54) (3-deoxy-D-arabino-heptulosonate 7-phosphate synthase) (DAHP synthase) (Phospho-2-keto-3-deoxy heptonate aldolase) |

TABLE 8-continued

SEQ ID NO Cross-Reference Table

| | | | | |
|---|---|---|---|---|
| 117 | 34 | DNA with substitution D146N | P0AB91 | Phospho-2-dehydro-3-deoxyheptonate aldolase, tyrosine-inhibited (EC 2.5.1.54) (3-deoxy-D-arabino-heptulosonate 7-phosphate synthase) (DAHP synthase) (Phospho-2-keto-3-deoxy heptonate aldolase) |
| 118 | 38 | DNA | N1P8J9 | Phospho-2-dehydro-3-deoxyheptonate aldolase, tyrosine-inhibited (EC 2.5.1.54) (3-deoxy-D-arabino-heptulosonate 7-phosphate synthase) (DAHP synthase) (Phospho-2-keto-3-deoxy heptonate aldolase) |
| 119 | 40 | DNA | P14843 | phospho-2-dehydro-3-deoxyheptonate aldolase 02 |
| 120 | 42 | DNA | P32449 | phospho-2-dehydro-3-deoxyheptonate aldolase 03 |
| 121 | 48 | DNA | P53090 | aromatic/aminoadipate aminotransferase 1__2-aminoadipate transaminase, L-phenylalanine: 2-oxoglutarate aminotransferase |
| 122 | 50 | DNA | P38840 | aromatic amino acid aminotransferase 2__2-aminoadipate transaminase, L-phenylalanine: 2-oxoglutarate aminotransferase, kynurenine-oxoglutarate transaminase |

| SEQ ID NO | Source organism | Codon Optimization Abbrev. |
|---|---|---|
| 1 | *Enterococcus faecium* Com15 | |
| 2 | *Papaver somniferum* (Opium poppy) | |
| 3 | *S cerevisiae* | |
| 4 | *Saccharomyces cerevisiae* (strain ATCC 204508/S288c) (Baker's yeast) | |
| 5 | *Saccharomyces cerevisiae* (strain ATCC 204508/S288c) (Baker's yeast) | |
| 6 | *Saccharomyces cerevisiae* (strain ATCC 204508/S288c) (Baker's yeast) | |
| 7 | *Escherichia coli* (strain K12) | |
| 8 | *Saccharomyces cerevisiae* (strain ATCC 204508/S288c) (Baker's yeast) | |
| 9 | *Saccharomyces cerevisiae* (strain ATCC 204508/S288c) (Baker's yeast) | |
| 10 | *Saccharomyces cerevisiae* (strain ATCC 204508/S288c) (Baker's yeast) | *Yarrowia lipolytica* |
| 11 | *Zygosaccharomyces bailii* | |
| 12 | *S cerevisiae* | |
| 13 | *Saccharomyces cerevisiae* S288c | modified codon usage for *Corynebacterium glutamicum* and *Saccharomyces cerevisiae* |
| 14 | *Escherichia coli* (strain K12) | *Bacillus subtillus* |
| 15 | *Escherichia coli* (strain K12) | |
| 16 | *Methanosphaerula palustris* (strain ATCC BAA-1556/DSM 19958/E1-9c) | |
| 17 | *Propionibacterium* sp. oral taxon 192 str. F0372 | |
| 18 | *Petroselinum crispum* | |
| 19 | *Trichophyton equinum* (strain ATCC MYA-4606 CBS 127.97) (Horse ringworm fungus) | |
| 20 | *Streptomyces sviceus* ATCC 29083 | |
| 21 | *Pseudomonas putida* (strain KT2440) | |
| 22 | *Modestobacter marinus* (strain BC501) | |
| 23 | *Sinorhizobium fredii* USDA 257 | |
| 24 | *Oryza sativa* subsp. *Japonica* | |
| 25 | *Methanocaldococcus jannaschii* | |
| 26 | *Saccharomyces cerevisiae* (strain ATCC 204508/S288c) (Baker's yeast) | |
| 27 | *Saccharomyces cerevisiae*(strain ATCC 204508/S288c) (Baker's yeast) | |
| 28 | *Saccharomyces cerevisiae* (strain ATCC 204508/S288c) (Baker's yeast) | |
| 29 | *Escherichia coli* (strain K12) | |
| 30 | *Saccharomyces cerevisiae* (strain ATCC 204508/S288c) (Baker's yeast) | |
| 31 | *Gracilaria gracilis* (Red alga) | |
| 32 | *Pyrococcus furiosus* (strain ATCC 43587/DSM 3638/JCM 8422/Vc1) | |

TABLE 8-continued

SEQ ID NO Cross-Reference Table

| | | |
|---|---|---|
| 33 | *Meyerozyma guilliermondii* (strain ATCC 6260/CBS 566/DSM 6381/JCM 1539/NBRC 10279/RRL Y-324) (Yeast) (*Candida guilliermondii*) | |
| 34 | *Escherichia coli* (strain K12) | |
| 35 | *Saccharomyces cerevisiae* (strain ATCC 204508/S288c) (Baker's yeast) | |
| 36 | *Homo sapiens* (Human) | |
| 37 | *Escherichia coli* (strain K12) | |
| 38 | *Escherichia coli* (strain K12) | |
| 39 | *Saccharomyces cerevisiae* (strain ATCC 204508/S288c) (Baker's yeast) | |
| 40 | *Enterococcus faecium* Com15 | *Yarrowia lipolytica* |
| 41 | *Escherichia coli* (strain K12) | *Saccharomyces cerevisiae* |
| 42 | *Saccharomyces cerevisiae* (strain ATCC 204508/S288c) (Baker's yeast) | *Saccharomyces cerevisiae* |
| 43 | *Enterococcus faecium* Com15 | *Saccharomyces cerevisiae* |
| 44 | *Saccharomyces cerevisiae* (strain ATCC 204508/S288c) (Baker's yeast) | modified codon usage for *Corynebacterium glutamicum* and *Saccharomyces cerevisiae* |
| 45 | *Enterococcus faecium* Com15 | modified codon usage for *Corynebacterium glutamicum* and *Saccharomyces cerevisiae* |
| 46 | *Escherichia coli* (strain K12) | |
| 47 | *Escherichia coli* (strain K12) | |
| 48 | *Dickeya chrysanthemi* (*Pectobacterium chrysanthemi*) (*Erwinia chrysanthemi*) | |
| 49 | *Clostridium acetobutylicum* (strain ATCC 824/DSM 792/JCM 1419/LMG5710/VKM B-1787) | |
| 50 | *Arabidopsis thaliana* (Mouse-ear cress) | |
| 51 | *Chlamydomonas reinhardtii* (*Chlamydomonas smithii*) | |
| 52 | *Staphylococcus epidermidis* (strain ATCC 35984/RP62A) | |
| 53 | *Escherichia coli* (strain K12) | |
| 54 | *Helicobacter pylori* (strain J99/ATCC 700824) (*Campylobacter pylori* J99) | |
| 55 | *Aeropyrum pernix* (strain ATCC 700893/DSM 11879/JCM 9820/NBRC 100138/K1) | |
| 56 | *Escherichia coli* (strain K12) | |
| 57 | *Papaver somniferum* (Opium poppy) | *Bacillus subtillus* |
| 58 | *Saccharomyces cerevisiae* (strain ATCC 204508/S288c) (Baker's yeast) | *Bacillus subtillus* |
| 59 | *Papaver somniferum* (Opium poppy) | modified codon usage for *Corynebacterium glutamicum* and *Saccharomyces cerevisiae* |
| 60 | *Papaver somniferum* (Opium poppy) | *Saccharomyces cerevisiae* |
| 61 | *Saccharomyces cerevisiae* (strain ATCC 204508/S288c) (Baker's yeast) | *Saccharomyces cerevisiae* |
| 62 | *Papaver somniferum* (Opium poppy) | *Yarrowia lipolytica* |
| 63 | *Saccharomyces cerevisiae* (strain ATCC 204508/S288c) (Baker's yeast) | *Yarrowia lipolytica* |
| 64 | *Enterococcus faecium* Com15 | *Bacillus subtillus* |
| 65 | *Saccharomyces cerevisiae* (strain ATCC 204508/S288c) (Baker's yeast) | *Bacillus subtillus* |
| 66 | *Saccharomyces cerevisiae* (strain ATCC 204508/S288c) (Baker's yeast) | modified codon usage for *Corynebacterium glutamicum* and *Saccharomyces cerevisiae* |
| 67 | *Escherichia coli* (strain K12) | *Yarrowia lipolytica* |

TABLE 8-continued

| SEQ ID NO Cross-Reference Table | | |
|---|---|---|
| 68 | *Escherichia coli* (strain K12) | modified codon usage for *Corynebacterium glutamicum* and *Saccharomyces cerevisiae* |
| 69 | *Papaver somniferum* (Opium poppy) | modified codon usage for *Corynebacterium glutamicum* and *Saccharomyces cerevisiae* |
| 70 | *Saccharomyces cerevisiae* (strain ATCC 204508/S288c) (Baker's yeast) | modified codon usage for *Corynebacterium glutamicum* and *Saccharomyces cerevisiae* |
| 71 | *Saccharomyces cerevisiae* (strain ATCC 204508/S288c) (Baker's yeast) | modified codon usage for *Corynebacterium glutamicum* and *Saccharomyces cerevisiae* |
| 72 | *Pyrococcus furiosus* (strain ATCC 43587/DSM 3638/JCM 8422/Vc1) | modified codon usage for *Corynebacterium glutamicum* and *Saccharomyces cerevisiae* |
| 73 | *Escherichia coli* (strain K12) | modified codon usage for *Corynebacterium glutamicum* and *Saccharomyces cerevisiae* |
| 74 | *Meyerozyma guilliermondii* (strain ATCC 6260/CBS 566/DSM 6381/ JCM 1539/NBRC 10279/NRRL Y-324) (Yeast) (*Candida guilliermondii*) | modified codon usage for *Corynebacterium glutamicum* and *Saccharomyces cerevisiae* |
| 75 | *Escherichia coli* (strain K12) | modified codon usage for *Corynebacterium glutamicum* and *Saccharomyces cerevisiae* |
| 76 | *Escherichia coli* (strain K12) | modified codon usage for *Corynebacterium glutamicum* and *Saccharomyces cerevisiae* |
| 77 | *Saccharomyces cerevisiae* (strain ATCC 204508/S288c) (Baker's yeast) | modified codon usage for *Corynebacterium glutamicum* and *Saccharomyces cerevisiae* |
| 78 | *Escherichia coli* (strain K12) | modified codon usage for *Corynebacterium glutamicum* and *Saccharomyces cerevisiae* |
| 79 | *Escherichia coli* (strain K12) | modified codon usage for *Corynebacterium glutamicum* and *Saccharomyces cerevisiae* |
| 80 | *Dickeya chrysanthemi* (*Pectobacterium chrysanthemi*) (*Erwinia chrysanthemi*) | modified codon usage for *Corynebacterium glutamicum* and *Saccharomyces cerevisiae* |
| 81 | *Saccharomyces cerevisiae* (strain ATCC 204508/S288c) (Baker's yeast) | modified *Corynebacterium glutamicum* codon usage |
| 82 | *Saccharomyces cerevisiae* (strain ATCC 204508/S288c) (Baker's yeast) | modified codon usage for *Corynebacterium glutamicum* and *Saccharomyces cerevisiae* |
| 83 | *Escherichia coli* (strain K12) | modified codon usage for *Corynebacterium glutamicum* and *Saccharomyces* |

TABLE 8-continued

| SEQ ID NO Cross-Reference Table | | |
|---|---|---|
| 84 | *Saccharomyces cerevisiae* (strain ATCC 204508/S288c) (Baker's yeast) | modified codon usage for *Corynebacterium glutamicum* and *Saccharomyces cerevisiae* |
| 85 | *Homo sapiens* (Human) | modified codon usage for *Corynebacterium glutamicum* and *Saccharomyces cerevisiae* |
| 86 | *Saccharomyces cerevisiae* (strain ATCC 204508/S288c) (Baker's yeast) | modified codon usage for *Corynebacterium glutamicum* and *Saccharomyces cerevisiae* |
| 87 | *Saccharomyces cerevisiae* (strain ATCC 204508/S288c) (Baker's yeast) | modified codon usage for *Corynebacterium glutamicum* and *Saccharomyces cerevisiae* |
| 88 | *Clostridium acetobutylicum* (strain ATCC 824/DSM 792/JCM 1419/ LMG 5710/VKM B-1787) | modified codon usage for *Corynebacterium glutamicum* and *Saccharomyces cerevisiae* |
| 89 | *Arabidopsis thaliana* (Mouse-ear cress) | modified codon usage for *Corynebacterium glutamicum* and *Saccharomyces cerevisiae* |
| 90 | *Chlamydomonas reinhardtii* (*Chlamydomonas smithii*) | modified codon usage for *Corynebacterium glutamicum* and *Saccharomyces cerevisiae* |
| 91 | *Staphylococcus epidermidis* (strain ATCC 35984/RP62A) | modified codon usage for *Corynebacterium glutamicum* and *Saccharomyces cerevisiae* |
| 92 | *Gracilaria gracilis* (Red alga) | modified codon usage for *Corynebacterium glutamicum* and *Saccharomyces cerevisiae* |
| 93 | *Escherichia coli* (strain K12) | modified codon usage for *Corynebacterium glutamicum* and *Saccharomyces cerevisiae* |
| 94 | *Saccharomyces cerevisiae* (strain ATCC 204508/S288c) (Baker's yeast) | modified codon usage for *Corynebacterium glutamicum* and *Saccharomyces cerevisiae* |
| 95 | *Saccharomyces cerevisiae* (strain ATCC 204508/S288c) (Baker's yeast) | modified codon usage for *Corynebacterium glutamicum* and *Saccharomyces cerevisiae* |
| 96 | *Escherichia coli* (strain K12) | modified codon usage for *Corynebacterium glutamicum* and *Saccharomyces cerevisiae* |
| 97 | *Escherichia coli* (strain K12) | modified codon usage for *Corynebacterium glutamicum* and *Saccharomyces cerevisiae* |
| 98 | *Escherichia coli* (strain K12) | modified codon usage for *Corynebacterium glutamicum* and *Saccharomyces cerevisiae* |

TABLE 8-continued

SEQ ID NO Cross-Reference Table

| | | |
|---|---|---|
| 99 | *Helicobacter pylori* (strain J99/ATCC 700824) (*Campylobacter pylori* J99) | modified codon usage for *Corynebacterium glutamicum* and *Saccharomyces cerevisiae* |
| 100 | *Aeropyrum pernix* (strain ATCC 700893/DSM 11879/JCM 9820/NBRC 100138/K1) | modified codon usage for *Corynebacterium glutamicum* and *Saccharomyces cerevisiae* |
| 101 | *Enterococcus faecium* (*Streptococcus faecium*) | codon optimized for Cg |
| 102 | *Zygosaccharomyces bailii* ISA 1307 | codon optimized for Cg |
| 103 | *Methanosphaerula palustris* (strain ATCC BAA-1556/DSM 19958/E1-9c) | codon optimized for Cg |
| 104 | *Propionibacterium* sp. oral taxon 192 str. F0372 | codon optimized for Cg |
| 105 | *Petroselinum crispum* | codon optimized for Cg |
| 106 | *Trichophyton equinum* (strain ATCC MYA-4606/CBS 127.97) (Horse ringworm fungus) | codon optimized for Cg |
| 107 | *Streptomyces sviceus* ATCC 29083 | codon optimized for Cg |
| 108 | *Pseudomonas putida* (strain KT2440) | codon optimized for Cg |
| 109 | *Modestobacter marinus* (strain BC501) | codon optimized for Cg |
| 110 | *Papaver somniferum* | codon optimized for Cg |
| 111 | *Sinorhizobium fredii* USDA 257 | codon optimized for Cg |
| 112 | *Papaver somniferum* | codon optimized for Sc |
| 113 | *Oryza sativa* subsp. *Japonica* | codon optimized for Cg |
| 114 | *Methanocaldococcus jannaschii* | codon optimized for Sc |
| 115 | *Saccharomyces cerevisiae* | codon optimized for Cg |
| 116 | *Escherichia coli* | codon optimized for Sc |
| 117 | *Escherichia coli* | codon optimized for Cg |
| 118 | *Saccharomyces cerevisiae* CEN.PK2 | |
| 119 | *Saccharomyces cerevisiae* (strain ATCC 204508/S288c) (Baker's yeast) | |
| 120 | *Saccharomyces cerevisiae* (strain ATCC 204508/S288c) (Baker's yeast) | |
| 121 | *Saccharomyces cerevisiae* (strain ATCC 204508/S288c) (Baker's yeast) | |
| 122 | *Saccharomyces cerevisiae* (strain ATCC 204508/S288c) (Baker's yeast) | |

REFERENCES

Noda, S. et al., PLoS One, DOI:10.1371/journal-.pone.0125488 May 21, 2015.

Koma, D. et al., Appl Microbiol Biotechnol (2012) 93:815-829, DOI 10.1007/s00253-011-3735-z, November, 2011.

WO 2008/064835, filed Nov. 27, 2007, priority date Nov. 27, 2006, assigned to DSM IP ASSETS B.V.

Zhang, C. et al., FEMS Microbiol Lett 353 (2014) 11-18, 0.1111/1574-6968.12397, 2014.

Kallscheuer, N., et al., Construction of a *Corynebacterium glutamicum* platform strain for the production of stilbenes and (2S)-flavanones. Metab Eng, 2016. 38: p. 47-55.

What is claimed is:

1. An engineered *Yarrowia lipolytica* or *Corynebacterium glutamicum* cell, wherein the engineered cell expresses:

(a) a heterologous tyrosine decarboxylase (TYDC) having at least 95% amino acid sequence identity to a pyridoxal-dependent decarboxylase (TYDC) from *Enterococcus faecium* Com15 comprising SEQ ID NO:1; and (b) a heterologous, 3-deoxy-D-arabino-heptulosonate-7-phosphate (DAHP) synthase having at least 95% amino acid sequence identity to a wild-type phospho-2-dehydro-3-deoxyheptonate aldolase (DAHP synthase) from *Saccharomyces cerevisiae* S288c comprising SEQ ID NO:9;

wherein, when cultured, the engineered *Yarrowia lipolytica* or *Corynebacterium glutamicum* cell produces tyramine at a level greater than 50 mg/L of culture medium.

2. The engineered *Yarrowia lipolytica* or *Corynebacterium glutamicum* cell of claim 1, wherein the engineered cell comprises a *Yarrowia lipolytica* cell.

3. The engineered *Yarrowia lipolytica* cell of claim 2, wherein the:

(a) heterologous TYDC comprises SEQ ID NO:1; and (b) the heterologous DAHP synthase comprises SEQ ID NO:9.

4. The engineered *Yarrowia lipolytica* or *Corynebacterium glutamicum* cell of claim 1, wherein the engineered cell comprises a *Corynebacterium glutamicum* cell.

5. The engineered *Corynebacterium glutamicum* cell of claim 4, wherein the:

(a) heterologous TYDC comprises SEQ ID NO:1; and (b) the heterologous DAHP synthase comprises SEQ ID NO:9.

6. The engineered *Corynebacterium glutamicum* cell of claim 4, wherein, when cultured, the engineered cell produces tyramine at a level greater than 400 mg/L of culture medium.

7. A culture of engineered *Yarrowia lipolytica* or *Corynebacterium glutamicum* cells according to claim 1, wherein the culture comprises tyramine at a level greater than 50 mg/L of culture medium.

8. A method of culturing engineered *Yarrowia lipolytica* or *Corynebacterium glutamicum* cells according to claim 1, the method comprising culturing the cells in the presence of a fermentation substrate comprising a non-protein carbon and a non-protein nitrogen source, wherein the engineered *Yarrowia lipolytica* or *Corynebacterium glutamicum* cells produce tyramine.

9. The method of claim 8, wherein the method additionally comprises recovering tyramine from the culture.

* * * * *

```
                         SEQUENCE LISTING


<160> NUMBER OF SEQ ID NOS: 122

<210> SEQ ID NO 1
<211> LENGTH: 625
<212> TYPE: PRT
<213> ORGANISM: Enterococcus faecium Com15

<400> SEQUENCE: 1

Met Ser Glu Ser Leu Ser Lys Asp Leu Asn Leu Asn Ala Leu Phe Ile
1               5                   10                  15

Gly Asp Lys Ala Glu Asn Gly Gln Ile Tyr Lys Ala Leu Leu Asn Glu
            20                  25                  30

Leu Val Asp Glu His Leu Gly Trp Arg Gln Asn Tyr Met Pro Gln Asp
        35                  40                  45

Met Pro Ile Ile Thr Pro Glu Glu Lys Ser Ser Ala Ser Phe Glu His
    50                  55                  60
```

```
Thr Val Asn Lys Thr Lys Asp Val Leu Ser Glu Ile Ser Ala Arg Met
65                  70                  75                  80

Arg Thr His Ser Val Pro Trp His Asn Ala Gly Arg Tyr Trp Gly His
                85                  90                  95

Met Asn Ser Glu Thr Leu Met Pro Ser Leu Leu Ala Tyr Asn Phe Ala
            100                 105                 110

Met Leu Trp Asn Gly Asn Asn Val Ala Tyr Glu Ser Ser Pro Ala Thr
        115                 120                 125

Ser Gln Met Glu Glu Glu Val Gly Met Glu Phe Ala Lys Leu Met Ser
    130                 135                 140

Tyr Lys Asp Gly Trp Gly His Ile Val Ala Asp Gly Ser Leu Ala Asn
145                 150                 155                 160

Leu Glu Gly Leu Trp Tyr Ala Arg Asn Ile Lys Ser Leu Pro Leu Ala
                165                 170                 175

Met Lys Glu Val Thr Pro Glu Leu Val Ala Gly Lys Ser Asp Trp Glu
            180                 185                 190

Leu Met Asn Leu Ser Thr Glu Glu Ile Met Asn Leu Leu Asp Ser Val
        195                 200                 205

Pro Glu Lys Ile Asp Glu Ile Lys Ala His Ser Ala Arg Ser Gly Lys
    210                 215                 220

His Leu Glu Lys Leu Gly Lys Trp Leu Val Pro Gln Thr Lys His Tyr
225                 230                 235                 240

Ser Trp Leu Lys Ala Ala Asp Ile Ile Gly Ile Gly Leu Asp Gln Val
                245                 250                 255

Ile Pro Val Pro Val Asp His Asn Tyr Arg Met Asp Ile Asn Glu Leu
            260                 265                 270

Glu Lys Ile Val Arg Gly Leu Ala Ala Glu Lys Thr Pro Ile Leu Gly
        275                 280                 285

Val Val Gly Val Val Gly Ser Thr Glu Glu Gly Ala Ile Asp Gly Ile
    290                 295                 300

Asp Lys Ile Val Ala Leu Arg Arg Val Leu Glu Lys Asp Gly Ile Tyr
305                 310                 315                 320

Phe Tyr Leu His Val Asp Ala Ala Tyr Gly Gly Tyr Gly Arg Ala Ile
                325                 330                 335

Phe Leu Asp Glu Asp Asn Asn Phe Ile Pro Phe Glu Asp Leu Lys Asp
            340                 345                 350

Val His Tyr Lys Tyr Asn Val Phe Thr Glu Asn Lys Asp Tyr Ile Leu
        355                 360                 365

Glu Glu Val His Ser Ala Tyr Lys Ala Ile Glu Glu Ala Glu Ser Val
    370                 375                 380

Thr Ile Asp Pro His Lys Met Gly Tyr Val Pro Tyr Ser Ala Gly Gly
385                 390                 395                 400

Ile Val Ile Lys Asp Ile Arg Met Arg Asp Val Ile Ser Tyr Phe Ala
                405                 410                 415

Thr Tyr Val Phe Glu Lys Gly Ala Asp Ile Pro Ala Leu Leu Gly Ala
            420                 425                 430

Tyr Ile Leu Glu Gly Ser Lys Ala Gly Ala Thr Ala Ala Ser Val Trp
        435                 440                 445

Ala Ala His His Val Leu Pro Leu Asn Val Thr Gly Tyr Gly Lys Leu
    450                 455                 460

Met Gly Ala Ser Ile Glu Gly Ala His Arg Phe Tyr Asn Phe Leu Asn
465                 470                 475                 480
```

```
Asp Leu Ser Phe Lys Val Gly Asp Lys Glu Ile Glu Val His Pro Leu
                485                 490                 495

Thr Tyr Pro Asp Phe Asn Met Val Asp Tyr Val Phe Lys Glu Lys Gly
            500                 505                 510

Asn Asp Asp Leu Val Ala Met Asn Lys Leu Asn His Asp Val Tyr Asp
        515                 520                 525

Tyr Ser Ser Tyr Val Lys Gly Ser Ile Tyr Gly Asn Glu Phe Leu Thr
    530                 535                 540

Ser His Thr Asp Phe Ala Ile Pro Asp Tyr Gly Asn Ser Pro Leu Gln
545                 550                 555                 560

Phe Val Asn Gln Leu Gly Phe Ser Asp Glu Glu Trp Asn Arg Ala Gly
                565                 570                 575

Lys Val Thr Val Leu Arg Ala Ser Val Met Thr Pro Tyr Met Asn Lys
            580                 585                 590

Glu Glu His Phe Glu Glu Tyr Ala Glu Lys Ile Lys Ala Ala Leu Gln
        595                 600                 605

Glu Lys Leu Glu Lys Ile Tyr Ala Asp Gln Leu Leu Ala Ser Glu Ala
    610                 615                 620

Lys
625


<210> SEQ ID NO 2
<211> LENGTH: 531
<212> TYPE: PRT
<213> ORGANISM: Papaver somniferum (Opium poppy)

<400> SEQUENCE: 2

Met Gly Ser Leu Asn Thr Glu Asp Val Leu Glu Asn Ser Ser Ala Phe
1               5                   10                  15

Gly Val Thr Asn Pro Leu Asp Pro Glu Glu Phe Arg Arg Gln Gly His
            20                  25                  30

Met Ile Ile Asp Phe Leu Ala Asp Tyr Tyr Arg Asp Val Glu Lys Tyr
        35                  40                  45

Pro Val Arg Ser Gln Val Glu Pro Gly Tyr Leu Arg Lys Arg Leu Pro
    50                  55                  60

Glu Thr Ala Pro Tyr Asn Pro Glu Ser Ile Glu Thr Ile Leu Gln Asp
65                  70                  75                  80

Val Thr Thr Glu Ile Ile Pro Gly Leu Thr His Trp Gln Ser Pro Asn
                85                  90                  95

Tyr Tyr Ala Tyr Phe Pro Ser Ser Gly Ser Val Ala Gly Phe Leu Gly
            100                 105                 110

Glu Met Leu Ser Thr Gly Phe Asn Val Val Gly Phe Asn Trp Met Ser
        115                 120                 125

Ser Pro Ala Ala Thr Glu Leu Glu Ser Val Val Met Asp Trp Phe Gly
    130                 135                 140

Lys Met Leu Asn Leu Pro Glu Ser Phe Leu Phe Ser Gly Ser Gly Gly
145                 150                 155                 160

Gly Val Leu Gln Gly Thr Ser Cys Glu Ala Ile Leu Cys Thr Leu Thr
                165                 170                 175

Ala Ala Arg Asp Arg Lys Leu Asn Lys Ile Gly Arg Glu His Ile Gly
            180                 185                 190

Arg Leu Val Val Tyr Gly Ser Asp Gln Thr His Cys Ala Leu Gln Lys
        195                 200                 205

Ala Ala Gln Val Ala Gly Ile Asn Pro Lys Asn Phe Arg Ala Ile Lys
    210                 215                 220
```

```
Thr Phe Lys Glu Asn Ser Phe Gly Leu Ser Ala Ala Thr Leu Arg Glu
225                 230                 235                 240

Val Ile Leu Glu Asp Ile Glu Ala Gly Leu Ile Pro Leu Phe Val Cys
                245                 250                 255

Pro Thr Val Gly Thr Thr Ser Ser Thr Ala Val Asp Pro Ile Ser Pro
            260                 265                 270

Ile Cys Glu Val Ala Lys Glu Tyr Glu Met Trp Val His Val Asp Ala
        275                 280                 285

Ala Tyr Ala Gly Ser Ala Cys Ile Cys Pro Glu Phe Arg His Phe Ile
    290                 295                 300

Asp Gly Val Glu Glu Ala Asp Ser Phe Ser Leu Asn Ala His Lys Trp
305                 310                 315                 320

Phe Phe Thr Thr Leu Asp Cys Cys Cys Leu Trp Val Lys Asp Pro Ser
                325                 330                 335

Ala Leu Val Lys Ala Leu Ser Thr Asn Pro Glu Tyr Leu Arg Asn Lys
            340                 345                 350

Ala Thr Glu Ser Arg Gln Val Val Asp Tyr Lys Asp Trp Gln Ile Ala
        355                 360                 365

Leu Ser Arg Arg Phe Arg Ser Leu Lys Leu Trp Met Val Leu Arg Ser
    370                 375                 380

Tyr Gly Val Thr Asn Leu Arg Asn Phe Leu Arg Ser His Val Lys Met
385                 390                 395                 400

Ala Lys Thr Phe Glu Gly Leu Ile Cys Met Asp Gly Arg Phe Glu Ile
                405                 410                 415

Thr Val Pro Arg Thr Phe Ala Met Val Cys Phe Arg Leu Leu Pro Pro
            420                 425                 430

Lys Thr Ile Lys Val Tyr Asp Asn Gly Val His Gln Asn Gly Asn Gly
        435                 440                 445

Val Val Pro Leu Arg Asp Glu Asn Glu Asn Leu Val Leu Ala Asn Lys
    450                 455                 460

Leu Asn Gln Val Tyr Leu Glu Thr Val Asn Ala Thr Gly Ser Val Tyr
465                 470                 475                 480

Met Thr His Ala Val Val Gly Gly Val Tyr Met Ile Arg Phe Ala Val
                485                 490                 495

Gly Ser Thr Leu Thr Glu Glu Arg His Val Ile Tyr Ala Trp Lys Ile
            500                 505                 510

Leu Gln Glu His Ala Asp Leu Ile Leu Gly Lys Phe Ser Glu Ala Asp
        515                 520                 525

Phe Ser Ser
    530


<210> SEQ ID NO 3
<211> LENGTH: 376
<212> TYPE: PRT
<213> ORGANISM: Saccharomyces cerevisiae (strain ATCC 204508  S288c)
      (Baker's yeast)

<400> SEQUENCE: 3

Met Ser Thr Phe Gly Lys Leu Phe Arg Val Thr Thr Tyr Gly Glu Ser
1               5                   10                  15

His Cys Lys Ser Val Gly Cys Ile Val Asp Gly Val Pro Pro Gly Met
            20                  25                  30

Ser Leu Thr Glu Ala Asp Ile Gln Pro Gln Leu Thr Arg Arg Arg Pro
        35                  40                  45
```

```
Gly Gln Ser Lys Leu Ser Thr Pro Arg Asp Glu Lys Asp Arg Val Glu
    50                  55                  60

Ile Gln Ser Gly Thr Glu Phe Gly Lys Thr Leu Gly Thr Pro Ile Ala
65                  70                  75                  80

Met Met Ile Lys Asn Glu Asp Gln Arg Pro His Asp Tyr Ser Asp Met
                85                  90                  95

Asp Lys Phe Pro Arg Pro Ser His Ala Asp Phe Thr Tyr Ser Glu Lys
            100                 105                 110

Tyr Gly Ile Lys Ala Ser Ser Gly Gly Gly Arg Ala Ser Ala Arg Glu
        115                 120                 125

Thr Ile Gly Arg Val Ala Ser Gly Ala Ile Ala Glu Lys Phe Leu Ala
    130                 135                 140

Gln Asn Ser Asn Val Glu Ile Val Ala Phe Val Thr Gln Ile Gly Glu
145                 150                 155                 160

Ile Lys Met Asn Arg Asp Ser Phe Asp Pro Glu Phe Gln His Leu Leu
                165                 170                 175

Asn Thr Ile Thr Arg Glu Lys Val Asp Ser Met Gly Pro Ile Arg Cys
            180                 185                 190

Pro Asp Ala Ser Val Ala Gly Leu Met Val Lys Glu Ile Glu Lys Tyr
        195                 200                 205

Arg Gly Asn Lys Asp Ser Ile Gly Gly Val Val Thr Cys Val Val Arg
    210                 215                 220

Asn Leu Pro Thr Gly Leu Gly Glu Pro Cys Phe Asp Lys Leu Glu Ala
225                 230                 235                 240

Met Leu Ala His Ala Met Leu Ser Ile Pro Ala Ser Lys Gly Phe Glu
                245                 250                 255

Ile Gly Ser Gly Phe Gln Gly Val Ser Val Pro Gly Ser Lys His Asn
            260                 265                 270

Asp Pro Phe Tyr Phe Glu Lys Glu Thr Asn Arg Leu Arg Thr Lys Thr
        275                 280                 285

Asn Asn Ser Gly Gly Val Gln Gly Gly Ile Ser Asn Gly Glu Asn Ile
    290                 295                 300

Tyr Phe Ser Val Pro Phe Lys Ser Val Ala Thr Ile Ser Gln Glu Gln
305                 310                 315                 320

Lys Thr Ala Thr Tyr Asp Gly Glu Glu Gly Ile Leu Ala Ala Lys Gly
                325                 330                 335

Arg His Asp Pro Ala Val Thr Pro Arg Ala Ile Pro Ile Val Glu Ala
            340                 345                 350

Met Thr Ala Leu Val Leu Ala Asp Ala Leu Leu Ile Gln Lys Ala Arg
        355                 360                 365

Asp Phe Ser Arg Ser Val Val His
    370                 375


<210> SEQ ID NO 4
<211> LENGTH: 452
<212> TYPE: PRT
<213> ORGANISM: Saccharomyces cerevisiae (strain ATCC 204508 S288c)
      (Baker's yeast)

<400> SEQUENCE: 4

Met Val Ser Glu Asp Lys Ile Glu Gln Trp Lys Ala Thr Lys Val Ile
1               5                   10                  15

Gly Ile Ile Gly Leu Gly Asp Met Gly Leu Leu Tyr Ala Asn Lys Phe
            20                  25                  30

Thr Asp Ala Gly Trp Gly Val Ile Cys Cys Asp Arg Glu Glu Tyr Tyr
```

```
        35                  40                  45

Asp Glu Leu Lys Glu Lys Tyr Ala Ser Ala Lys Phe Glu Leu Val Lys
    50                  55                  60

Asn Gly His Leu Val Ser Arg Gln Ser Asp Tyr Ile Ile Tyr Ser Val
65                  70                  75                  80

Glu Ala Ser Asn Ile Ser Lys Ile Val Ala Thr Tyr Gly Pro Ser Ser
                85                  90                  95

Lys Val Gly Thr Ile Val Gly Gly Gln Thr Ser Cys Lys Leu Pro Glu
            100                 105                 110

Ile Glu Ala Phe Glu Lys Tyr Leu Pro Lys Asp Cys Asp Ile Ile Thr
        115                 120                 125

Val His Ser Leu His Gly Pro Lys Val Asn Thr Glu Gly Gln Pro Leu
    130                 135                 140

Val Ile Ile Asn His Arg Ser Gln Tyr Pro Glu Ser Phe Glu Phe Val
145                 150                 155                 160

Asn Ser Val Met Ala Cys Leu Lys Ser Lys Gln Val Tyr Leu Thr Tyr
                165                 170                 175

Glu Glu His Asp Lys Ile Thr Ala Asp Thr Gln Ala Val Thr His Ala
            180                 185                 190

Ala Phe Leu Ser Met Gly Ser Ala Trp Ala Lys Ile Lys Ile Tyr Pro
        195                 200                 205

Trp Thr Leu Gly Val Asn Lys Trp Tyr Gly Gly Leu Glu Asn Val Lys
    210                 215                 220

Val Asn Ile Ser Leu Arg Ile Tyr Ser Asn Lys Trp His Val Tyr Ala
225                 230                 235                 240

Gly Leu Ala Ile Thr Asn Pro Ser Ala His Gln Gln Ile Leu Gln Tyr
                245                 250                 255

Ala Thr Ser Ala Thr Glu Leu Phe Ser Leu Met Ile Asp Asn Lys Glu
            260                 265                 270

Gln Glu Leu Thr Asp Arg Leu Leu Lys Ala Lys Gln Phe Val Phe Gly
        275                 280                 285

Lys His Thr Gly Leu Leu Leu Leu Asp Asp Thr Ile Leu Glu Lys Tyr
    290                 295                 300

Ser Leu Ser Lys Ser Ser Ile Gly Asn Ser Asn Asn Cys Lys Pro Val
305                 310                 315                 320

Pro Asn Ser His Leu Ser Leu Leu Ala Ile Val Asp Ser Trp Phe Gln
                325                 330                 335

Leu Gly Ile Asp Pro Tyr Asp His Met Ile Cys Ser Thr Pro Leu Phe
            340                 345                 350

Arg Ile Phe Leu Gly Val Ser Glu Tyr Leu Phe Leu Lys Pro Gly Leu
        355                 360                 365

Leu Glu Gln Thr Ile Asp Ala Ala Ile His Asp Lys Ser Phe Ile Lys
    370                 375                 380

Asp Asp Leu Glu Phe Val Ile Ser Ala Arg Glu Trp Ser Ser Val Val
385                 390                 395                 400

Ser Phe Ala Asn Phe Asp Ile Tyr Lys Lys Gln Phe Gln Ser Val Gln
                405                 410                 415

Lys Phe Phe Glu Pro Met Leu Pro Glu Ala Asn Leu Ile Gly Asn Glu
            420                 425                 430

Met Ile Lys Thr Ile Leu Ser His Ser Ser Asp Arg Ser Ala Ala Glu
        435                 440                 445

Lys Arg Asn Thr
    450
```

<210> SEQ ID NO 5
<211> LENGTH: 370
<212> TYPE: PRT
<213> ORGANISM: Saccharomyces cerevisiae (strain ATCC 204508 S288c)
(Baker's yeast)

<400> SEQUENCE: 5

```
Met Ser Glu Ser Pro Met Phe Ala Ala Asn Gly Met Pro Lys Val Asn
1               5                   10                  15

Gln Gly Ala Glu Glu Asp Val Arg Ile Leu Gly Tyr Asp Pro Leu Ala
            20                  25                  30

Ser Pro Ala Leu Leu Gln Val Gln Ile Pro Ala Thr Pro Thr Ser Leu
        35                  40                  45

Glu Thr Ala Lys Arg Gly Arg Arg Glu Ala Ile Asp Ile Ile Thr Gly
    50                  55                  60

Lys Asp Asp Arg Val Leu Val Ile Val Gly Pro Cys Ser Ile His Asp
65                  70                  75                  80

Leu Glu Ala Ala Gln Glu Tyr Ala Leu Arg Leu Lys Lys Leu Ser Asp
                85                  90                  95

Glu Leu Lys Gly Asp Leu Ser Ile Ile Met Arg Ala Tyr Leu Glu Lys
            100                 105                 110

Pro Arg Thr Thr Val Gly Trp Lys Gly Leu Ile Asn Asp Pro Asp Val
        115                 120                 125

Asn Asn Thr Phe Asn Ile Asn Lys Gly Leu Gln Ser Ala Arg Gln Leu
    130                 135                 140

Phe Val Asn Leu Thr Asn Ile Gly Leu Pro Ile Gly Ser Glu Met Leu
145                 150                 155                 160

Asp Thr Ile Ser Pro Lys Tyr Leu Ala Asp Leu Val Ser Phe Gly Ala
                165                 170                 175

Ile Gly Ala Arg Thr Thr Glu Ser Gln Leu His Arg Glu Leu Ala Ser
            180                 185                 190

Gly Leu Ser Phe Pro Val Gly Phe Lys Asn Gly Thr Asp Gly Thr Leu
        195                 200                 205

Asn Val Ala Val Asp Ala Cys Gln Ala Ala Ala His Ser His His Phe
    210                 215                 220

Met Gly Val Thr Lys His Gly Val Ala Ala Ile Thr Thr Thr Lys Gly
225                 230                 235                 240

Asn Glu His Cys Phe Val Ile Leu Arg Gly Gly Lys Lys Gly Thr Asn
                245                 250                 255

Tyr Asp Ala Lys Ser Val Ala Glu Ala Lys Ala Gln Leu Pro Ala Gly
            260                 265                 270

Ser Asn Gly Leu Met Ile Asp Tyr Ser His Gly Asn Ser Asn Lys Asp
        275                 280                 285

Phe Arg Asn Gln Pro Lys Val Asn Asp Val Val Cys Glu Gln Ile Ala
    290                 295                 300

Asn Gly Glu Asn Ala Ile Thr Gly Val Met Ile Glu Ser Asn Ile Asn
305                 310                 315                 320

Glu Gly Asn Gln Gly Ile Pro Ala Glu Gly Lys Ala Gly Leu Lys Tyr
                325                 330                 335

Gly Val Ser Ile Thr Asp Ala Cys Ile Gly Trp Glu Thr Thr Glu Asp
            340                 345                 350

Val Leu Arg Lys Leu Ala Ala Ala Val Arg Gln Arg Arg Glu Val Asn
        355                 360                 365
```

```
Lys Lys
    370


<210> SEQ ID NO 6
<211> LENGTH: 370
<212> TYPE: PRT
<213> ORGANISM: Saccharomyces cerevisiae (strain ATCC 204508 S288c)
      (Baker's yeast)

<400> SEQUENCE: 6

Met Ser Glu Ser Pro Met Phe Ala Ala Asn Gly Met Pro Lys Val Asn
1               5                   10                  15

Gln Gly Ala Glu Glu Asp Val Arg Ile Leu Gly Tyr Asp Pro Leu Ala
            20                  25                  30

Ser Pro Ala Leu Leu Gln Val Gln Ile Pro Ala Thr Pro Thr Ser Leu
        35                  40                  45

Glu Thr Ala Lys Arg Gly Arg Arg Glu Ala Ile Asp Ile Ile Thr Gly
    50                  55                  60

Lys Asp Asp Arg Val Leu Val Ile Val Gly Pro Cys Ser Ile His Asp
65                  70                  75                  80

Leu Glu Ala Ala Gln Glu Tyr Ala Leu Arg Leu Lys Lys Leu Ser Asp
                85                  90                  95

Glu Leu Lys Gly Asp Leu Ser Ile Ile Met Arg Ala Tyr Leu Glu Lys
            100                 105                 110

Pro Arg Thr Thr Val Gly Trp Lys Gly Leu Ile Asn Asp Pro Asp Val
        115                 120                 125

Asn Asn Thr Phe Asn Ile Asn Lys Gly Leu Gln Ser Ala Arg Gln Leu
    130                 135                 140

Phe Val Asn Leu Thr Asn Ile Gly Leu Pro Ile Gly Ser Glu Met Leu
145                 150                 155                 160

Asp Thr Ile Ser Pro Gln Tyr Leu Ala Asp Leu Val Ser Phe Gly Ala
                165                 170                 175

Ile Gly Ala Arg Thr Thr Glu Ser Gln Leu His Arg Glu Leu Ala Ser
            180                 185                 190

Gly Leu Ser Phe Pro Val Gly Phe Lys Asn Gly Thr Asp Gly Thr Leu
        195                 200                 205

Asn Val Ala Val Asp Ala Cys Gln Ala Ala Ala His Ser His His Phe
    210                 215                 220

Met Gly Val Thr Leu His Gly Val Ala Ala Ile Thr Thr Thr Lys Gly
225                 230                 235                 240

Asn Glu His Cys Phe Val Ile Leu Arg Gly Gly Lys Lys Gly Thr Asn
                245                 250                 255

Tyr Asp Ala Lys Ser Val Ala Glu Ala Lys Ala Gln Leu Pro Ala Gly
            260                 265                 270

Ser Asn Gly Leu Met Ile Asp Tyr Ser His Gly Asn Ser Asn Lys Asp
        275                 280                 285

Phe Arg Asn Gln Pro Lys Val Asn Asp Val Val Cys Glu Gln Ile Ala
    290                 295                 300

Asn Gly Glu Asn Ala Ile Thr Gly Val Met Ile Glu Ser Asn Ile Asn
305                 310                 315                 320

Glu Gly Asn Gln Gly Ile Pro Ala Glu Gly Lys Ala Gly Leu Lys Tyr
                325                 330                 335

Gly Val Ser Ile Thr Asp Ala Cys Ile Gly Trp Glu Thr Thr Glu Asp
            340                 345                 350

Val Leu Arg Lys Leu Ala Ala Ala Val Arg Gln Arg Arg Glu Val Asn
```

```
        355                 360                 365

Lys Lys
    370


<210> SEQ ID NO 7
<211> LENGTH: 350
<212> TYPE: PRT
<213> ORGANISM: Escherichia coli (strain K12)

<400> SEQUENCE: 7

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
    130                 135                 140

Leu Asn Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
    210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
    290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350
```

```
<210> SEQ ID NO 8
<211> LENGTH: 335
<212> TYPE: PRT
<213> ORGANISM: Saccharomyces cerevisiae (strain ATCC 204508 S288c)
      (Baker's yeast)

<400> SEQUENCE: 8

Met Ser Glu Pro Ala Gln Lys Lys Gln Lys Val Ala Asn Asn Ser Leu
1               5                   10                  15

Glu Gln Leu Lys Ala Ser Gly Thr Val Val Val Ala Asp Thr Gly Asp
            20                  25                  30

Phe Gly Ser Ile Ala Lys Phe Gln Pro Gln Asp Ser Thr Thr Asn Pro
        35                  40                  45

Ser Leu Ile Leu Ala Ala Ala Lys Gln Pro Thr Tyr Ala Lys Leu Ile
    50                  55                  60

Asp Val Ala Val Glu Tyr Gly Lys Lys His Gly Lys Thr Thr Glu Glu
65                  70                  75                  80

Gln Val Glu Asn Ala Val Asp Arg Leu Leu Val Glu Phe Gly Lys Glu
                85                  90                  95

Ile Leu Lys Ile Val Pro Gly Arg Val Ser Thr Glu Val Asp Ala Arg
            100                 105                 110

Leu Ser Phe Asp Thr Gln Ala Thr Ile Glu Lys Ala Arg His Ile Ile
        115                 120                 125

Lys Leu Phe Glu Gln Glu Gly Val Ser Lys Glu Arg Val Leu Ile Lys
    130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
                165                 170                 175

Ala Val Ala Cys Ala Glu Ala Gln Val Thr Leu Ile Ser Pro Phe Val
            180                 185                 190

Gly Arg Ile Leu Asp Trp Tyr Lys Ser Ser Thr Gly Lys Asp Tyr Lys
        195                 200                 205

Gly Glu Ala Asp Pro Gly Val Ile Ser Val Lys Lys Ile Tyr Asn Tyr
    210                 215                 220

Tyr Lys Lys Tyr Gly Tyr Lys Thr Ile Val Met Gly Ala Ser Phe Arg
225                 230                 235                 240

Ser Thr Asp Glu Ile Lys Asn Leu Ala Gly Val Asp Tyr Leu Thr Ile
                245                 250                 255

Ser Pro Ala Leu Leu Asp Lys Leu Met Asn Ser Thr Glu Pro Phe Pro
            260                 265                 270

Arg Val Leu Asp Pro Val Ser Ala Lys Lys Glu Ala Gly Asp Lys Ile
        275                 280                 285

Ser Tyr Ile Ser Asp Glu Ser Lys Phe Arg Phe Asp Leu Asn Glu Asp
    290                 295                 300

Ala Met Ala Thr Glu Lys Leu Ser Glu Gly Ile Arg Lys Phe Ser Ala
305                 310                 315                 320

Asp Ile Val Thr Leu Phe Asp Leu Ile Glu Lys Lys Val Thr Ala
                325                 330                 335


<210> SEQ ID NO 9
<211> LENGTH: 370
<212> TYPE: PRT
<213> ORGANISM: Saccharomyces cerevisiae (strain ATCC 204508 S288c)
      (Baker's yeast)
```

<400> SEQUENCE: 9

```
Met Ser Glu Ser Pro Met Phe Ala Ala Asn Gly Met Pro Lys Val Asn
1               5                   10                  15

Gln Gly Ala Glu Glu Asp Val Arg Ile Leu Gly Tyr Asp Pro Leu Ala
            20                  25                  30

Ser Pro Ala Leu Leu Gln Val Gln Ile Pro Ala Thr Pro Thr Ser Leu
        35                  40                  45

Glu Thr Ala Lys Arg Gly Arg Arg Glu Ala Ile Asp Ile Ile Thr Gly
    50                  55                  60

Lys Asp Asp Arg Val Leu Val Ile Val Gly Pro Cys Ser Ile His Asp
65                  70                  75                  80

Leu Glu Ala Ala Gln Glu Tyr Ala Leu Arg Leu Lys Lys Leu Ser Asp
                85                  90                  95

Glu Leu Lys Gly Asp Leu Ser Ile Ile Met Arg Ala Tyr Leu Glu Lys
            100                 105                 110

Pro Arg Thr Thr Val Gly Trp Lys Gly Leu Ile Asn Asp Pro Asp Val
        115                 120                 125

Asn Asn Thr Phe Asn Ile Asn Lys Gly Leu Gln Ser Ala Arg Gln Leu
    130                 135                 140

Phe Val Asn Leu Thr Asn Ile Gly Leu Pro Ile Gly Ser Glu Met Leu
145                 150                 155                 160

Asp Thr Ile Ser Pro Gln Tyr Leu Ala Asp Leu Val Ser Phe Gly Ala
                165                 170                 175

Ile Gly Ala Arg Thr Thr Glu Ser Gln Leu His Arg Glu Leu Ala Ser
            180                 185                 190

Gly Leu Ser Phe Pro Val Gly Phe Lys Asn Gly Thr Asp Gly Thr Leu
        195                 200                 205

Asn Val Ala Val Asp Ala Cys Gln Ala Ala Ala His Ser His His Phe
    210                 215                 220

Met Gly Val Thr Lys His Gly Val Ala Ala Ile Thr Thr Thr Lys Gly
225                 230                 235                 240

Asn Glu His Cys Phe Val Ile Leu Arg Gly Gly Lys Lys Gly Thr Asn
                245                 250                 255

Tyr Asp Ala Lys Ser Val Ala Glu Ala Lys Ala Gln Leu Pro Ala Gly
            260                 265                 270

Ser Asn Gly Leu Met Ile Asp Tyr Ser His Gly Asn Ser Asn Lys Asp
        275                 280                 285

Phe Arg Asn Gln Pro Lys Val Asn Asp Val Val Cys Glu Gln Ile Ala
    290                 295                 300

Asn Gly Glu Asn Ala Ile Thr Gly Val Met Ile Glu Ser Asn Ile Asn
305                 310                 315                 320

Glu Gly Asn Gln Gly Ile Pro Ala Glu Gly Lys Ala Gly Leu Lys Tyr
                325                 330                 335

Gly Val Ser Ile Thr Asp Ala Cys Ile Gly Trp Glu Thr Thr Glu Asp
            340                 345                 350

Val Leu Arg Lys Leu Ala Ala Ala Val Arg Gln Arg Arg Glu Val Asn
        355                 360                 365

Lys Lys
    370
```

<210> SEQ ID NO 10
<211> LENGTH: 1110
<212> TYPE: DNA
<213> ORGANISM: Artificial

```
<220> FEATURE:
<223> OTHER INFORMATION: Codon-optimized and/or mutated sequence

<400> SEQUENCE: 10

atgtctgagt ccccaatgtt cgccgcaaac ggtatgccta aagtcaacca gggagcagag     60

gaggacgtgc ggatcctggg ttacgatccc cttgcctcgc ctgcactgct ccaggttcag    120

attccagcca cgcccacctc tctggagacc gccaaacgag gtcgacgaga agcaattgac    180

atcattactg gcaaggatga ccgagtcctg gtgattgttg gcccctgttc tatccacgac    240

ctcgaggccg cacaggagta cgcccttcga cttaaaaagc tttccgatga gcttaagggc    300

gatctgtcga tcatcatgcg tgcttacctg gagaagcccc gtacgactgt cggatggaag    360

ggactgatta acgatcccga cgtcaataac acatttaaca ttaacaaggg cctgcagtcc    420

gctagacagc ttttcgttaa cctcaccaac attggcctcc ccattggctc cgagatgctc    480

gacactattt cgccccagta tctcgccgat ctcgtgtcct ttggtgctat cggtgctcga    540

acaaccgagt cccagctgca tcgagagctg gcatctggcc tctctttccc cgtcggcttc    600

aagaacggaa ccgatggtac cctcaacgtt gccgtggacg cctgtcaggc cgctgcccac    660

tctcaccact tcatgggagt gaccaagcac ggtgtcgctg ctattactac caccaaggga    720

aacgagcact gcttcgttat tctccgaggt ggcaagaagg gtactaacta cgatgccaag    780

tccgtggctg aagccaaggc ccagctgccc gccggctcta acggcctgat gattgattac    840

agccatggta attccaacaa ggatttccga aaccagccta aggtcaacga tgtggtctgc    900

gagcaaatcg ctaacggaga aaatgccatc accggcgtca tgattgagtc taacatcaac    960

gagggcaatc agggtatccc tgctgaggga aaggccggcc tgaagtacgg agtttccatt   1020

acagacgcct gcatcggatg ggagactaca gaggatgtcc tccgaaagct ggctgccgct   1080

gtgcgacagc gtcgggaggt gaacaagaag                                    1110


<210> SEQ ID NO 11
<211> LENGTH: 510
<212> TYPE: PRT
<213> ORGANISM: Zygosaccharomyces bailii ISA1307

<400> SEQUENCE: 11

Met Asp Ala Thr Asn Ile Ser Ala Ser Glu Gln Glu Lys Ile Leu Gly
1               5                   10                  15

Asn Leu Trp Lys Ala Ala Gln Gly Pro Gly Glu Gly His Val Leu Pro
            20                  25                  30

Thr Val Asp Gln Leu Asn Arg Ala Arg Ala Ser Leu Tyr Asn Ser Leu
        35                  40                  45

Pro Glu Glu Gly Val Gly Tyr Gln Ser Val Gln Arg His Ile Leu Asp
    50                  55                  60

Asp Ile Val Pro Ala Phe Asn Gly Gly Ser Ile Asn Pro Asn Tyr Tyr
65                  70                  75                  80

Gly Phe Val Thr Gly Gly Val Thr Pro Ala Ala Leu Phe Ala Asp Ala
                85                  90                  95

Val Val Ser Ala Tyr Asp Gln Asn Val Gln Val His Leu Gln Ser His
            100                 105                 110

Ser Ile Val Thr Asp Val Glu Phe Lys Thr Leu Gly Leu Leu Leu Gln
        115                 120                 125

Leu Leu Lys Leu Asp Val Pro Ser Trp Leu Asn Gly Thr Phe Thr Thr
    130                 135                 140

Gly Ala Thr Ala Ser Asn Ile Ile Gly Leu Ala Cys Gly Arg Glu Phe
```

```
145                 150                 155                 160

Val Ile Gln Lys Ala Ala Gln Arg Lys Gly Ser Pro Ile Lys Ser Thr
                165                 170                 175

Ala Asp Ala Gly Leu His Glu Val Leu Gln Ser Ile Gly Ala Ser Gly
            180                 185                 190

Ile Gln Val Leu Ser Thr Leu Pro His Ser Ser Leu Val Lys Ala Ala
        195                 200                 205

Gly Val Leu Gly Ile Gly Arg Met Asn Val Arg Asp Ile Ser Thr Glu
    210                 215                 220

Ala Asn Pro Leu Asp Ile Asp Leu Lys Lys Leu Gln Thr Glu Leu Ser
225                 230                 235                 240

Arg Val Asp Val Val Ser Ile Val Ala Ile Ser Cys Gly Glu Val Asn
                245                 250                 255

Ser Gly Arg Phe Ala Ser Ala Gly Leu His Glu Leu Arg Lys Ile Arg
            260                 265                 270

Gln Leu Cys Asp Arg His Gly Ala Trp Leu His Val Asp Gly Ala Phe
        275                 280                 285

Gly Ile Phe Gly Arg Leu Val Gly Asp Asp Thr Glu Phe Met Ala Ile
    290                 295                 300

Lys Glu Gly Cys Asp Gly Ile Glu Leu Ala Asp Ser Ile Thr Gly Asp
305                 310                 315                 320

Ala His Lys Leu Leu Asn Val Pro Tyr Asp Cys Gly Phe Phe Phe Cys
                325                 330                 335

Arg His Ala Ser Ile Ala Arg Glu Val Phe Gln Asn Ala Asn Ala Ala
            340                 345                 350

Tyr Leu Ala Ser Val Asp Gly Arg Asp Ser Phe Ile Pro Ser Pro Leu
        355                 360                 365

Asn Ile Gly Ile Glu Asn Ser Arg Arg Phe Arg Ala Leu Pro Val Tyr
    370                 375                 380

Ala Ser Leu Leu Ala Tyr Gly Glu Val Glu Tyr Arg Lys Met Leu His
385                 390                 395                 400

Arg Gln Ile Arg Leu Ala Arg Met Ile Tyr Gly Trp Ile Phe Asp His
                405                 410                 415

Pro Gly Tyr Thr Ala Leu Pro Glu Thr Thr Ser Arg Glu Glu Leu Leu
            420                 425                 430

Asp Leu Thr Tyr Met Val Val Leu Phe Arg Ala Lys Asp Gly Gly Leu
        435                 440                 445

Asn Arg Thr Leu Glu Ala Lys Ile Asn Ala Thr Ser Arg Met Phe Val
    450                 455                 460

Ser Gly Thr Ser Trp Ala Asp Ala Pro Ala Cys Arg Ile Ala Ile Ser
465                 470                 475                 480

Asn Trp Arg Val Asp Glu Lys Arg Asp Phe Ala Leu Val Thr Gly Val
                485                 490                 495

Leu Glu Ser Ala Leu Arg Ser Ser Gly Ser Ala Val Ser Cys
            500                 505                 510


<210> SEQ ID NO 12
<211> LENGTH: 1128
<212> TYPE: DNA
<213> ORGANISM: Saccharomyces cerevisiae (strain ATCC 204508  S288c)
      (Baker's yeast)

<400> SEQUENCE: 12

atgtcaacgt ttgggaaact gttccgcgtc accacatatg gtgaatcgca ttgtaagtct     60
```

```
gtcggttgca ttgtcgacgg tgttcctcca ggaatgtcat taaccgaagc tgacattcag    120

ccacaattga ccagaagaag accgggtcaa tctaagctat cgacccctag agacgaaaag    180

gatagagtgg aaatccagtc cggtaccgag ttcggcaaga ctctaggtac acccatcgcc    240

atgatgatca aaaacgagga ccaaagacct cacgactact ccgacatgga caagttccct    300

agaccttccc atgcggactt cacgtactcg gaaaagtacg gtatcaaggc ctcctctggt    360

ggtggcagag cttctgctag agaaacgatt ggccgtgtcg cttcaggtgc cattgctgag    420

aagttcttag ctcagaactc taatgtcgag atcgtagcct ttgtgacaca aatcggggaa    480

atcaagatga acagagactc tttcgatcct gaatttcagc atctgttgaa caccatcacc    540

agggaaaaag tggactcaat gggtcctatc agatgtccag acgcctccgt tgctggtttg    600

atggtcaagg aaatcgaaaa gtacagaggc aacaaggact ctatcggtgg tgtcgtcact    660

tgtgtcgtga gaaacttgcc taccggtctc ggtgagccat gctttgacaa gttggaagcc    720

atgttggctc atgctatgtt gtccattcca gcatccaagg gtttcgaaat tggctcaggt    780

tttcagggtg tctctgttcc agggtccaag cacaatgacc cattttactt tgaaaaagaa    840

acaaacagat taagaacaaa gaccaacaat tcaggtggtg tacaaggtgg tatctctaat    900

ggtgagaaca tctatttctc tgtcccattc aagtcagtgg ccactatctc tcaagaacaa    960

aaaaccgcca cttacgatgg tgaagaaggt atcttagccg ctaagggtag acatgaccct   1020

gctgtcactc caagagctat tcctattgtg gaagccatga ccgctctggt gttggctgac   1080

gcgcttttga tccaaaaggc aagagatttc tccagatccg tggttcat                1128
```

<210> SEQ ID NO 13
<211> LENGTH: 1356
<212> TYPE: DNA
<213> ORGANISM: Artificial
<220> FEATURE:
<223> OTHER INFORMATION: Codon-optimized and/or mutated sequence

<400> SEQUENCE: 13

```
atggtatcag aggataagat tgagcaatgg aaagccacaa aagtcattgg tataattggt     60

ctgggtgata tgggcctatt atacgctaat aaatttacag atgctggatg gggtgttata    120

tgttgtgata gggaagaata ttatgatgaa ctgaaagaaa aatatgcctc agctaaattc    180

gaactggtga aaaatggtca tttggtatcc aggcaaagcg actatattat ctatagtgtt    240

gaagcatcca atattagtaa gatcgtcgca acgtatggac catcttctaa ggttggaaca    300

attgttgggg gtcaaacgag ttgtaagctg ccggaaatcg aggctttcga aaagtattta    360

cccaaggact gcgacatcat taccgtgcat tcccttcatg ggcctaaagt taatactgaa    420

ggccaaccac tagttattat caatcacaga tcacagtacc cagaatcttt tgagttcgtt    480

aattctgtta tggcatgttt gaaaagtaag caagtttatt tgacatatga agagcatgac    540

aagattaccg ctgatacaca agctgtgaca catgctgctt tcttaagtat gggatctgcg    600

tgggcaaaga taaagattta tccttggact ctgggtgtaa acaaatggta cggtggccta    660

gaaaatgtga aagttaatat atcactaaga atctattcga acaagtggca tgtttacgca    720

ggattagcca taacaaaccc aagtgcacat cagcaaattc ttcaatatgc aaccagtgca    780

acagaactat ttagtttaat gatagataac aaagaacaag aacttactga tagactatta    840

aaagctaagc aatttgtatt tggaaagcat actggtctct tactattgga tgacacgatt    900

ttagagaaat attcgctatc aaaaagcagc attggtaaca gcaacaattg caagccagtg    960

ccgaattcac atttatcatt gttggcgatt gttgattcgt ggtttcaact tggtattgat   1020
```

```
ccatatgatc atatgatttg ttcgacgcca ttattcagaa tattcctggg tgtgtccgaa   1080

tatctttttt taaaacctgg cttattagaa cagacaattg atgcagctat ccatgataaa   1140

tcattcataa aagatgattt agaatttgtt atttcggcta gagaatggag ctcggttgtt   1200

tcttttgcca attttgatat atacaaaaag caatttcaga gtgttcaaaa gttctttgag   1260

ccaatgcttc cagaggctaa tctcattggc aacgagatga taaaaaccat tctgagtcat   1320

tctagtgacc gttcggccgc tgaaaaaaga aataca                              1356
```

```
<210> SEQ ID NO 14
<211> LENGTH: 522
<212> TYPE: DNA
<213> ORGANISM: Artificial
<220> FEATURE:
<223> OTHER INFORMATION: Codon-optimized and/or mutated sequence

<400> SEQUENCE: 14

atgacacaac cgttattctt gataggcccg cgcggctgtg gcaagactac agtaggaatg     60

gcgttggcag actcactgaa ccgacggttc gtggatacag accagtggct tcaatcgcaa    120

ttaaatatga cggtcgccga aatcgtagaa cgggaggagt gggcggggtt tagagcgcgg    180

gagactgctg cgctggaagc ggtcacagca ccgtcaaccg tgattgcgac aggggggggt    240

atcatcctta cggagtttaa tagacacttt atgcagaata atggaatcgt agtgtatctt    300

tgcgcaccgg tgagcgtctt ggtgaataga ctgcaagcag ccccggaaga agatttgaga    360

ccaaccctga ccggcaagcc gttgagcgaa gaggtccagg aggtgttgga agaacgggac    420

gcgctgtatc gggaggtggc acacatcatt attgatgcta cgaatgaacc gtctcaagtc    480

ataagcgaga ttcgtagcgc gttagcccaa acgattaatt gc                       522
```

```
<210> SEQ ID NO 15
<211> LENGTH: 174
<212> TYPE: PRT
<213> ORGANISM: Escherichia coli (strain K12)

<400> SEQUENCE: 15

Met Thr Gln Pro Leu Phe Leu Ile Gly Pro Arg Gly Cys Gly Lys Thr
1               5                   10                  15

Thr Val Gly Met Ala Leu Ala Asp Ser Leu Asn Arg Arg Phe Val Asp
            20                  25                  30

Thr Asp Gln Trp Leu Gln Ser Gln Leu Asn Met Thr Val Ala Glu Ile
        35                  40                  45

Val Glu Arg Glu Glu Trp Ala Gly Phe Arg Ala Arg Glu Thr Ala Ala
    50                  55                  60

Leu Glu Ala Val Thr Ala Pro Ser Thr Val Ile Ala Thr Gly Gly Gly
65                  70                  75                  80

Ile Ile Leu Thr Glu Phe Asn Arg His Phe Met Gln Asn Asn Gly Ile
                85                  90                  95

Val Val Tyr Leu Cys Ala Pro Val Ser Val Leu Val Asn Arg Leu Gln
            100                 105                 110

Ala Ala Pro Glu Glu Asp Leu Arg Pro Thr Leu Thr Gly Lys Pro Leu
        115                 120                 125

Ser Glu Glu Val Gln Glu Val Leu Glu Glu Arg Asp Ala Leu Tyr Arg
    130                 135                 140

Glu Val Ala His Ile Ile Ile Asp Ala Thr Asn Glu Pro Ser Gln Val
145                 150                 155                 160
```

```
Ile Ser Glu Ile Arg Ser Ala Leu Ala Gln Thr Ile Asn Cys
                165                 170


<210> SEQ ID NO 16
<211> LENGTH: 363
<212> TYPE: PRT
<213> ORGANISM: Escherichia coli (D146N) DAHP synthase

<400> SEQUENCE: 16

Met Leu Asn Lys Gly Leu Ala Glu Glu Glu Leu Phe Ser Phe Leu Ser
1               5                   10                  15

Lys Lys Arg Glu Glu Asp Leu Cys His Ser His Ile Leu Ser Ser Met
            20                  25                  30

Cys Thr Val Pro His Pro Ile Ala Val Lys Ala His Leu Met Phe Met
        35                  40                  45

Glu Thr Asn Leu Gly Asp Pro Gly Leu Phe Pro Gly Thr Ala Ser Leu
    50                  55                  60

Glu Arg Leu Leu Ile Glu Arg Leu Gly Asp Leu Phe His His Arg Glu
65                  70                  75                  80

Ala Gly Gly Tyr Ala Thr Ser Gly Gly Thr Glu Ser Asn Ile Gln Ala
                85                  90                  95

Leu Arg Ile Ala Lys Ala Gln Lys Lys Val Asp Lys Pro Asn Val Val
            100                 105                 110

Ile Pro Glu Thr Ser His Phe Ser Phe Lys Lys Ala Cys Asp Ile Leu
        115                 120                 125

Gly Ile Gln Met Lys Thr Val Pro Ala Asp Arg Ser Met Arg Thr Asp
    130                 135                 140

Ile Ser Glu Val Ser Asp Ala Ile Asp Lys Asn Thr Ile Ala Leu Val
145                 150                 155                 160

Gly Ile Ala Gly Ser Thr Glu Tyr Gly Met Val Asp Asp Ile Gly Ala
                165                 170                 175

Leu Ala Thr Ile Ala Glu Glu Glu Asp Leu Tyr Leu His Val Asp Ala
            180                 185                 190

Ala Phe Gly Gly Leu Val Ile Pro Phe Leu Pro Asn Pro Pro Ala Phe
        195                 200                 205

Asp Phe Ala Leu Pro Gly Val Ser Ser Ile Ala Val Asp Pro His Lys
    210                 215                 220

Met Gly Met Ser Thr Leu Pro Ala Gly Ala Leu Leu Val Arg Glu Pro
225                 230                 235                 240

Gln Met Leu Gly Leu Leu Asn Ile Asp Thr Pro Tyr Leu Thr Val Lys
                245                 250                 255

Gln Glu Tyr Thr Leu Ala Gly Thr Arg Pro Gly Ala Ser Val Ala Gly
            260                 265                 270

Ala Leu Ala Val Leu Asp Tyr Met Gly Arg Asp Gly Met Glu Ala Val
        275                 280                 285

Val Ala Gly Cys Met Lys Asn Thr Ser Arg Leu Ile Arg Gly Met Glu
    290                 295                 300

Thr Leu Gly Phe Pro Arg Ala Val Thr Pro Asp Val Asn Val Ala Thr
305                 310                 315                 320

Phe Ile Thr Asn His Pro Ala Pro Lys Asn Trp Val Val Ser Gln Thr
                325                 330                 335

Arg Arg Gly His Met Arg Ile Ile Cys Met Pro His Val Thr Ala Asp
            340                 345                 350

Met Ile Glu Gln Phe Leu Ile Asp Ile Gly Glu
        355                 360
```

<210> SEQ ID NO 17
<211> LENGTH: 384
<212> TYPE: PRT
<213> ORGANISM: Propionibacterium sp. oral taxon 192 str. F0372

<400> SEQUENCE: 17

```
Met Gly Met Asp Ile Ser Ser Arg Pro Val Glu Trp Ala Ser Leu Ser
1               5                   10                  15

Glu Ile Thr Ala Ser Asp Val Ser Phe Glu Gly Gly Ala Ile Phe Asn
            20                  25                  30

Ser Ile Cys Thr Arg Pro His Pro Leu Ala Ala Gln Val Met Ala Asp
        35                  40                  45

Asn Leu His Leu Asn Ala Gly Asp Gly Arg Leu Phe Pro Ser Val Ala
    50                  55                  60

Arg Cys Glu Ser Glu Ile Thr Asn Phe Leu Gly Gly Leu Met Gly Leu
65                  70                  75                  80

Pro Arg Ala Val Gly Met Cys Thr Ser Gly Ala Thr Glu Ala Asn Leu
                85                  90                  95

Ile Ala Val His Ser Ala Ile Glu Asn Trp Arg Arg Lys Gly Gly Gln
            100                 105                 110

Gly Arg Pro Gln Val Ile Leu Gly Arg Gly Gly His Phe Ser Phe Asp
        115                 120                 125

Lys Ile Ser Val Leu Leu Gly Val Glu Leu Val Leu Ala Trp Ser Asp
    130                 135                 140

Ile Asp Thr Leu Lys Val Asp Pro Glu Ser Val Ser Glu Leu Ile Ser
145                 150                 155                 160

Pro Arg Thr Ala Leu Ile Val Ala Thr Ala Gly Ser Ser Glu Thr Gly
                165                 170                 175

Ala Val Asp Asp Val Glu Trp Leu Ser Arg Val Ala Leu Ser Lys Gly
            180                 185                 190

Val Pro Leu His Val Asp Ala Ala Ser Gly Gly Leu Leu Ile Pro Phe
        195                 200                 205

Leu Arg Asp Leu Gly Gly Ala Leu Pro Asp Ile Gly Phe Arg Asn Asp
    210                 215                 220

Gly Val Thr Thr Ile Ala Ile Asp Pro His Lys Phe Gly Ser Ala Pro
225                 230                 235                 240

Ile Pro Ser Gly His Leu Val Ala Arg Glu Trp Thr Trp Ile Glu Gly
                245                 250                 255

Leu Arg Thr Glu Ser His Tyr Gln Gly Thr Ala Arg His Leu Thr Phe
            260                 265                 270

Leu Gly Thr Arg Ser Gly Gly Ser Ile Leu Ala Thr Tyr Ala Leu Phe
        275                 280                 285

Gly His Leu Gly Glu Lys Gly Leu Arg Gly Met Ala Glu Gln Leu Lys
    290                 295                 300

Ala Leu Arg Ser His Leu Val Asp Arg Leu Arg Lys Ala Gly Ala Thr
305                 310                 315                 320

Leu Ala Tyr Val Pro Glu Leu Met Val Val Ala Leu Lys Ala Asp Ser
                325                 330                 335

Asp Ala Val Lys Val Leu Glu Arg Arg Gly Ile Phe Thr Ser Tyr Ala
            340                 345                 350

Lys Arg Leu Gly Tyr Leu Arg Ile Val Val Gln Leu His Met Ser Glu
        355                 360                 365

Gly Gln Val Asp Gly Leu Val Asp Ala Leu Leu Met Glu Gly Ile Val
```

370 375 380

<210> SEQ ID NO 18
<211> LENGTH: 514
<212> TYPE: PRT
<213> ORGANISM: Petroselinum crispum

<400> SEQUENCE: 18

```
Met Gly Ser Ile Asp Asn Leu Thr Glu Lys Leu Ala Ser Gln Phe Pro
1               5                   10                  15

Met Asn Thr Leu Glu Pro Glu Glu Phe Arg Arg Gln Gly His Met Met
            20                  25                  30

Ile Asp Phe Leu Ala Asp Tyr Tyr Arg Lys Val Glu Asn Tyr Pro Val
        35                  40                  45

Arg Ser Gln Val Ser Pro Gly Tyr Leu Arg Glu Ile Leu Pro Glu Ser
    50                  55                  60

Ala Pro Tyr Asn Pro Glu Ser Leu Glu Thr Ile Leu Gln Asp Val Gln
65                  70                  75                  80

Thr Lys Ile Ile Pro Gly Ile Thr His Trp Gln Ser Pro Asn Phe Phe
                85                  90                  95

Ala Tyr Phe Pro Ser Ser Gly Ser Thr Ala Gly Phe Leu Gly Glu Met
            100                 105                 110

Leu Ser Thr Gly Phe Asn Val Val Gly Phe Asn Trp Met Val Ser Pro
        115                 120                 125

Ala Ala Thr Glu Leu Glu Asn Val Val Thr Asp Trp Phe Gly Lys Met
    130                 135                 140

Leu Gln Leu Pro Lys Ser Phe Leu Phe Ser Gly Gly Gly Gly Gly Val
145                 150                 155                 160

Leu Gln Gly Thr Thr Cys Glu Ala Ile Leu Cys Thr Leu Val Ala Ala
                165                 170                 175

Arg Asp Lys Asn Leu Arg Gln His Gly Met Asp Asn Ile Gly Lys Leu
            180                 185                 190

Val Val Tyr Cys Ser Asp Gln Thr His Ser Ala Leu Gln Lys Ala Ala
        195                 200                 205

Lys Ile Ala Gly Ile Asp Pro Lys Asn Phe Arg Ala Ile Glu Thr Thr
    210                 215                 220

Lys Ser Ser Asn Phe Gln Leu Cys Pro Lys Arg Leu Glu Ser Ala Ile
225                 230                 235                 240

Leu His Asp Leu Gln Asn Gly Leu Ile Pro Leu Tyr Leu Cys Ala Thr
                245                 250                 255

Val Gly Thr Thr Ser Ser Thr Thr Val Asp Pro Leu Pro Ala Leu Thr
            260                 265                 270

Glu Val Ala Lys Lys Tyr Asp Leu Trp Val His Val Asp Ala Ala Tyr
        275                 280                 285

Ala Gly Ser Ala Cys Ile Cys Pro Glu Phe Arg Gln Tyr Leu Asp Gly
    290                 295                 300

Val Glu Asn Ala Asp Ser Phe Ser Leu Asn Ala His Lys Trp Phe Leu
305                 310                 315                 320

Thr Thr Leu Asp Cys Cys Cys Leu Trp Val Arg Asn Pro Ser Ala Leu
                325                 330                 335

Ile Lys Ser Leu Ser Thr Tyr Pro Glu Phe Leu Lys Asn Asn Ala Ser
            340                 345                 350

Glu Thr Asn Lys Val Val Asp Tyr Lys Asp Trp Gln Ile Met Leu Ser
        355                 360                 365
```

```
Arg Arg Phe Arg Ala Leu Lys Leu Trp Phe Val Leu Arg Ser Tyr Gly
    370                 375                 380

Val Gly Gln Leu Arg Glu Phe Ile Arg Gly His Val Gly Met Ala Lys
385                 390                 395                 400

Tyr Phe Glu Gly Leu Val Asn Met Asp Lys Arg Phe Glu Val Val Ala
                405                 410                 415

Pro Arg Leu Phe Ser Met Val Cys Phe Arg Ile Lys Pro Ser Ala Met
            420                 425                 430

Ile Gly Lys Asn Asp Glu Asp Glu Val Asn Glu Ile Asn Arg Lys Leu
        435                 440                 445

Leu Glu Ser Val Asn Asp Ser Gly Arg Ile Tyr Val Ser His Thr Val
    450                 455                 460

Leu Gly Gly Ile Tyr Val Ile Arg Phe Ala Ile Gly Gly Thr Leu Thr
465                 470                 475                 480

Asp Ile Asn His Val Ser Ala Ala Trp Lys Val Leu Gln Asp His Ala
                485                 490                 495

Gly Ala Leu Leu Asp Asp Thr Phe Thr Ser Asn Lys Leu Val Glu Val
            500                 505                 510

Leu Ser


<210> SEQ ID NO 19
<211> LENGTH: 517
<212> TYPE: PRT
<213> ORGANISM: Trichophyton equinum (strain ATCC MYA-4606  CBS 127.97)
      (Horse ringworm fungus)

<400> SEQUENCE: 19

Met Glu Arg Asn His Leu Lys Asp Ser Val Gly Val Gln Val Asp Asp
1               5                   10                  15

Gly His Ser Lys Glu Leu Trp Glu Thr Ala Leu Asn Pro Pro Arg Arg
            20                  25                  30

Ser Val Leu Pro Pro Ala Ala Ser Leu Ala His Ser Arg Ser Ser Ile
        35                  40                  45

Ile Thr Glu Leu Pro His Ala Gly Gln Gly Tyr Thr Gln Thr Lys Val
    50                  55                  60

His Leu Phe Asn Asp Ile Ile Pro Gly Leu Asn Asp Cys Ala Ile Asn
65                  70                  75                  80

Ala Asn Tyr Tyr Gly Phe Val Thr Gly Gly Val Thr Pro Ala Ala Leu
                85                  90                  95

Leu Ala Asp Asn Val Val Ser Val Tyr Asp Gln Asn Val Cys Val His
            100                 105                 110

Leu Val Asp His Ser Val Ala Thr Asp Val Asp Tyr Ala Ala Leu Cys
        115                 120                 125

Leu Leu Lys Asp Leu Phe Gly Leu Lys Arg Asp Glu Trp Pro His Gly
    130                 135                 140

Ile Phe Thr Thr Gly Ala Thr Ala Ser Asn Leu Val Gly Leu Ala Cys
145                 150                 155                 160

Gly Arg Glu Tyr Val Leu Arg Lys Ala Ala Gln Lys Arg Gly Leu Ser
                165                 170                 175

Gly Asn Ile Ala Ser Gly Asn Ile Thr Asp Ser Val Gly Glu Tyr Gly
            180                 185                 190

Met Pro Ala Val Leu Glu Ala Ala Gly Leu Lys Gly Leu Gln Val Leu
        195                 200                 205

Ser Thr Met Pro His Ser Ser Val Gly Lys Val Ala Gly Ile Leu Gly
    210                 215                 220
```

```
Ile Gly Arg Ala Asn Val Lys Ser Ile Val Ser Lys Thr Gly Glu Ser
225                 230                 235                 240

His Gly Gln Pro Leu Glu Phe Asp Phe Glu Leu Phe Glu Lys Glu Leu
                245                 250                 255

Ala Arg Ala Gly Phe Ala Ser Ile Val Ser Ile Ser Cys Gly Glu Val
            260                 265                 270

Asn Thr Gly Arg Phe Ala Thr Lys Gly Val Asp Glu Phe Arg Arg Val
        275                 280                 285

Arg Ala Leu Cys Asp Lys Tyr Asn Ala Trp Leu His Val Asp Ala Ala
    290                 295                 300

Phe Gly Met Phe Gly Arg Val Leu Asp Asp Ser Pro Glu Phe Glu Thr
305                 310                 315                 320

Ile Lys Lys Gly Ser Glu Gly Ile Glu Leu Ala Asp Ser Ile Thr Gly
                325                 330                 335

Asp Gly His Lys Leu Leu Asn Val Pro Tyr Asp Cys Gly Phe Phe Phe
            340                 345                 350

Ser Arg His Gly Asp Ile Ala Glu Glu Val Phe Arg Asn Pro Asn Ala
        355                 360                 365

Val Tyr Leu Ser Ser Ser Ala Gly Glu His Ile Pro Thr Pro Leu Asn
    370                 375                 380

Ile Gly Val Glu Asn Ser Arg Arg Phe Arg Ala Leu Pro Val Tyr Ser
385                 390                 395                 400

Thr Leu Val Ala Tyr Gly Lys Asp Gly Tyr Arg Ala Met Val Glu Arg
                405                 410                 415

Gln Ile Arg Leu Ala Arg Leu Ile Thr Gly Trp Leu His Glu His Pro
            420                 425                 430

Lys Tyr Thr Val Leu Gly Gly Gly Ala Ser Lys Glu Asp Leu Ile Ala
        435                 440                 445

Ala Thr Tyr Val Ile Val Leu Phe Arg Ala Lys Asp Glu Ala Leu Asn
    450                 455                 460

Ala Arg Leu Ala Ser Ala Ile Asn Gly Thr Gly Lys Met Phe Val Ser
465                 470                 475                 480

Gly Thr Lys Trp Ala Gly Glu Pro Ala Cys Arg Val Ala Ile Ser Asn
                485                 490                 495

Trp Lys Val Gln Val Glu Arg Asp Phe Thr Leu Val Lys Glu Val Leu
            500                 505                 510

Asp Glu Val Ser Arg
        515


<210> SEQ ID NO 20
<211> LENGTH: 481
<212> TYPE: PRT
<213> ORGANISM: Streptomyces sviceus ATCC 29083

<400> SEQUENCE: 20

Met Pro Asp Leu Glu Pro Asp Glu Phe Arg Arg Gln Gly His Gln Leu
1               5                   10                  15

Val Asp Trp Val Ala Arg Tyr Arg Thr Ser Leu Pro Ser Leu His Val
            20                  25                  30

Arg Pro Lys Val Val Pro Gly Ser Val Lys Ala Gln Leu Pro Arg Glu
        35                  40                  45

Leu Pro Glu Gln Pro Ser Gln Ala Leu Gly Asp Asp Leu Ile Ala Leu
    50                  55                  60

Leu Asn Asp Val Val Val Pro Ser Ser Leu His Trp Gln His Pro Gly
```

-continued

```
65                  70                  75                  80

Phe Phe Gly Tyr Phe Pro Ala Asn Ala Ser Leu Leu Ser Leu Leu Gly
                85                  90                  95

Asp Ile Ala Ser Gly Gly Ile Gly Ala Gln Gly Met Leu Trp Ser Thr
            100                 105                 110

Ser Pro Ala Gly Thr Glu Ile Glu Gln Val Leu Leu Asp Gly Leu Ala
        115                 120                 125

Asp Ala Leu Gly Leu Gly Arg Glu Phe Thr Phe Ala Gly Gly Gly Gly
    130                 135                 140

Gly Ser Leu Gln Asp Ser Ala Ser Ser Ala Ser Leu Ala Ala Leu Leu
145                 150                 155                 160

Ala Ala Leu Gln Arg Ser Asn Pro Asp Trp Arg Glu His Gly Val Asp
                165                 170                 175

Gly Thr Glu Thr Val Tyr Val Thr Ala Glu Thr His Ser Ser Leu Ala
            180                 185                 190

Lys Ala Val Arg Val Ala Gly Leu Gly Ala Arg Ala Leu Arg Ile Val
        195                 200                 205

Pro Phe Thr Gln Gly Thr Leu Ser Met Ser Ala Asp Ala Leu Ala Asp
    210                 215                 220

Met Leu Ala Lys Asp Thr Ala Ala Gly Lys Arg Pro Val Met Val Cys
225                 230                 235                 240

Pro Thr Val Gly Thr Thr Gly Thr Gly Ala Ile Asp Pro Val Arg Glu
                245                 250                 255

Val Ala Leu Ala Ala Arg Thr Tyr Glu Ala Trp Val His Val Asp Ala
            260                 265                 270

Ala Trp Ala Gly Val Ala Ala Leu Cys Pro Glu Phe Arg Trp Leu Leu
        275                 280                 285

Asp Gly Val Asn Leu Val Asp Ser Phe Cys Thr Asp Ala His Lys Trp
    290                 295                 300

Phe Tyr Thr Ala Phe Asp Ala Ser Phe Met Trp Val Arg Asp Ala Arg
305                 310                 315                 320

Ala Leu Pro Thr Ala Leu Ser Ile Thr Pro Glu Tyr Leu Arg Asn Ala
                325                 330                 335

Ala Thr Glu Ser Gly Glu Val Ile Asp Tyr Arg Asp Trp Gln Val Pro
            340                 345                 350

Leu Gly Arg Arg Met Arg Ala Leu Lys Ile Trp Ser Val Val His Gly
        355                 360                 365

Ala Gly Leu Glu Gly Leu Arg Glu Ser Ile Arg Gly His Val Ala Met
    370                 375                 380

Ala Asn Ser Leu Ala Gly Arg Ile Glu Ser Glu Ser Gly Phe Ala Leu
385                 390                 395                 400

Ala Thr Pro Pro Ser Leu Ala Leu Val Cys Leu Tyr Leu Val Asp Gln
                405                 410                 415

Glu Gly Arg Pro Asp Asp Ala Ala Thr Lys Ala Ala Met Glu Ala Val
            420                 425                 430

Asn Ala Glu Gly His Ser Phe Leu Thr His Thr Ser Val Asn Gly His
        435                 440                 445

Phe Ala Ile Arg Val Ala Ile Gly Ala Thr Thr Thr Leu Pro Asp His
    450                 455                 460

Ile Asp Thr Leu Trp Asp Ser Leu Cys Lys Ala Ala Arg Gln Ser Gly
465                 470                 475                 480

Gly
```

<210> SEQ ID NO 21
<211> LENGTH: 470
<212> TYPE: PRT
<213> ORGANISM: Pseudomonas putida (strain KT2440)

<400> SEQUENCE: 21

```
Met Thr Pro Glu Gln Phe Arg Gln Tyr Gly His Gln Leu Ile Asp Leu
1               5                   10                  15

Ile Ala Asp Tyr Arg Gln Thr Val Gly Glu Arg Pro Val Met Ala Gln
            20                  25                  30

Val Glu Pro Gly Tyr Leu Lys Ala Ala Leu Pro Ala Thr Ala Pro Gln
        35                  40                  45

Gln Gly Glu Pro Phe Ala Ala Ile Leu Asp Asp Val Asn Asn Leu Val
    50                  55                  60

Met Pro Gly Leu Ser His Trp Gln His Pro Asp Phe Tyr Gly Tyr Phe
65                  70                  75                  80

Pro Ser Asn Gly Thr Leu Ser Ser Val Leu Gly Asp Phe Leu Ser Thr
                85                  90                  95

Gly Leu Gly Val Leu Gly Leu Ser Trp Gln Ser Ser Pro Ala Leu Ser
            100                 105                 110

Glu Leu Glu Glu Thr Thr Leu Asp Trp Leu Arg Gln Leu Leu Gly Leu
        115                 120                 125

Ser Gly Gln Trp Ser Gly Val Ile Gln Asp Thr Ala Ser Thr Ser Thr
    130                 135                 140

Leu Val Ala Leu Ile Ser Ala Arg Glu Arg Ala Thr Asp Tyr Ala Leu
145                 150                 155                 160

Val Arg Gly Gly Leu Gln Ala Glu Pro Lys Pro Leu Ile Val Tyr Val
                165                 170                 175

Ser Ala His Ala His Ser Ser Val Asp Lys Ala Ala Leu Leu Ala Gly
            180                 185                 190

Phe Gly Arg Asp Asn Ile Arg Leu Ile Pro Thr Asp Glu Arg Tyr Ala
        195                 200                 205

Leu Arg Pro Glu Ala Leu Gln Ala Ala Ile Glu Gln Asp Leu Ala Ala
    210                 215                 220

Gly Asn Gln Pro Cys Ala Val Val Ala Thr Thr Gly Thr Thr Thr Thr
225                 230                 235                 240

Thr Ala Leu Asp Pro Leu Arg Pro Val Gly Glu Ile Ala Gln Ala Asn
                245                 250                 255

Gly Leu Trp Leu His Val Asp Ser Ala Met Ala Gly Ser Ala Met Ile
            260                 265                 270

Leu Pro Glu Cys Arg Trp Met Trp Asp Gly Ile Glu Leu Ala Asp Ser
        275                 280                 285

Val Val Val Asn Ala His Lys Trp Leu Gly Val Ala Phe Asp Cys Ser
    290                 295                 300

Ile Tyr Tyr Val Arg Asp Pro Gln His Leu Ile Arg Val Met Ser Thr
305                 310                 315                 320

Asn Pro Ser Tyr Leu Gln Ser Ala Val Asp Gly Glu Val Lys Asn Leu
                325                 330                 335

Arg Asp Trp Gly Ile Pro Leu Gly Arg Arg Phe Arg Ala Leu Lys Leu
            340                 345                 350

Trp Phe Met Leu Arg Ser Glu Gly Val Asp Ala Leu Gln Ala Arg Leu
        355                 360                 365

Arg Arg Asp Leu Asp Asn Ala Gln Trp Leu Ala Gly Gln Val Glu Ala
    370                 375                 380
```

```
Ala Ala Glu Trp Glu Val Leu Ala Pro Val Gln Leu Gln Thr Leu Cys
385                 390                 395                 400

Ile Arg His Arg Pro Ala Gly Leu Glu Gly Glu Ala Leu Asp Ala His
                405                 410                 415

Thr Lys Gly Trp Ala Glu Arg Leu Asn Ala Ser Gly Ala Ala Tyr Val
            420                 425                 430

Thr Pro Ala Thr Leu Asp Gly Arg Trp Met Val Arg Val Ser Ile Gly
        435                 440                 445

Ala Leu Pro Thr Glu Arg Gly Asp Val Gln Arg Leu Trp Ala Arg Leu
    450                 455                 460

Gln Asp Val Ile Lys Gly
465                 470


<210> SEQ ID NO 22
<211> LENGTH: 575
<212> TYPE: PRT
<213> ORGANISM: Modestobacter marinus (strain BC501)

<400> SEQUENCE: 22

Met Thr Gly His Met Thr Pro Glu Gln Phe Arg Gln His Gly His Glu
1               5                   10                  15

Val Val Asp Trp Ile Ala Asp Tyr Trp Glu Arg Ile Gly Ser Phe Pro
            20                  25                  30

Val Arg Ser Gln Val Ser Pro Gly Asp Val Arg Ala Ser Leu Pro Pro
        35                  40                  45

Thr Ala Pro Glu Gln Gly Glu Pro Phe Ser Ala Val Leu Ala Asp Leu
    50                  55                  60

Asp Arg Val Val Leu Pro Gly Val Thr His Trp Gln His Pro Gly Phe
65                  70                  75                  80

Phe Gly Tyr Phe Pro Ala Asn Thr Ser Gly Pro Ser Val Leu Gly Asp
                85                  90                  95

Leu Val Ser Ala Gly Leu Gly Val Gln Gly Met Ser Trp Val Thr Ser
            100                 105                 110

Pro Ala Ala Thr Glu Leu Glu Gln His Val Met Asp Trp Phe Ala Asp
        115                 120                 125

Leu Leu Gly Leu Pro Glu Ser Phe Arg Ser Thr Gly Ser Gly Gly Gly
    130                 135                 140

Val Val Gln Asp Ser Ser Ser Gly Ala Asn Leu Val Ala Leu Leu Ala
145                 150                 155                 160

Ala Leu His Arg Ala Ser Lys Gly Ala Thr Leu Arg His Gly Val Arg
                165                 170                 175

Pro Glu Asp His Thr Val Tyr Val Ser Ala Glu Thr His Ser Ser Met
            180                 185                 190

Glu Lys Ala Ala Arg Ile Ala Gly Leu Gly Thr Asp Ala Ile Arg Ile
        195                 200                 205

Val Glu Val Gly Pro Asp Leu Ala Met Asn Pro Arg Ala Leu Ala Gln
    210                 215                 220

Arg Leu Glu Arg Asp Val Ala Arg Gly Tyr Thr Pro Val Leu Val Cys
225                 230                 235                 240

Ala Thr Val Gly Thr Thr Ser Thr Thr Ala Ile Asp Pro Leu Ala Glu
                245                 250                 255

Leu Gly Pro Ile Cys Gln Gln His Gly Val Trp Leu His Val Asp Ala
            260                 265                 270

Ala Tyr Ala Gly Val Ser Ala Val Ala Pro Glu Leu Arg Ala Leu Gln
```

```
        275                 280                 285

Ala Gly Val Glu Trp Ala Asp Ser Tyr Thr Thr Asp Ala His Lys Trp
    290                 295                 300

Leu Leu Thr Gly Phe Asp Ala Thr Leu Phe Trp Val Ala Asp Arg Ala
305                 310                 315                 320

Ala Leu Thr Gly Ala Leu Ser Ile Leu Pro Glu Tyr Leu Arg Asn Ala
                325                 330                 335

Ala Thr Asp Thr Gly Ala Val Val Asp Tyr Arg Asp Trp Gln Ile Glu
            340                 345                 350

Leu Gly Arg Arg Phe Arg Ala Leu Lys Leu Trp Phe Val Val Arg Trp
        355                 360                 365

Tyr Gly Ala Glu Gly Leu Arg Glu His Val Arg Ser His Val Ala Leu
    370                 375                 380

Ala Gln Glu Leu Ala Gly Trp Ala Asp Ala Asp Glu Arg Phe Asp Val
385                 390                 395                 400

Ala Ala Pro His Pro Phe Ser Leu Val Cys Leu Arg Pro Arg Trp Ala
                405                 410                 415

Pro Gly Ile Asp Ala Asp Val Ala Thr Met Thr Leu Leu Asp Arg Leu
            420                 425                 430

Asn Asp Gly Gly Glu Val Phe Leu Thr His Thr Thr Val Asp Gly Ala
        435                 440                 445

Ala Val Leu Arg Val Ala Ile Gly Ala Pro Ala Thr Thr Arg Glu His
    450                 455                 460

Val Glu Arg Val Trp Ala Leu Leu Gly Glu Ala His Asp Trp Leu Ala
465                 470                 475                 480

Arg Asp Phe Glu Glu Gln Ala Ala Glu Arg Arg Ala Ala Glu Leu Arg
                485                 490                 495

Glu Arg Glu Ala Ala Glu Glu Gln Leu Arg Ala Arg Arg Glu Ala Glu
            500                 505                 510

Ala Ala Ala Ala Ala Ala Thr Glu Ala Pro Val Glu Pro Ala Ala Glu
        515                 520                 525

Glu Pro Glu Gln Leu Val Val Pro Pro Val Glu Val Pro Ala Val Glu
    530                 535                 540

Thr Pro Ala Ala Trp Asp Glu Ser Ala Thr Gln Val Ala Ala Gln Thr
545                 550                 555                 560

Asp Leu His Ala Asp Pro Ala Pro Gln Pro Ala Asp Gly Gln Gly
                565                 570                 575


<210> SEQ ID NO 23
<211> LENGTH: 418
<212> TYPE: PRT
<213> ORGANISM: Sinorhizobium fredii USDA 257

<400> SEQUENCE: 23

Met Lys Gln Ile Pro Ala Lys Gly Leu Glu Arg Asp Val Ile Met Gln
1               5                   10                  15

Glu Leu Arg Gln Met Lys Ser Leu Asp Phe Asp Trp Arg Ala Gly Arg
            20                  25                  30

Val Pro Ser Tyr Thr Tyr Phe Val Asp Asp Glu Thr Leu Asp Val Gln
        35                  40                  45

Arg Glu Ala Tyr Gly Glu Tyr Ile Ala Glu Asn Gly Leu Gly Ala Gly
    50                  55                  60

Arg Ala Phe Lys Ser Leu Glu Leu Met Thr Asp Asp Ile Lys Ser Met
65                  70                  75                  80
```

```
Ala Ile Ser Leu Phe Asn Ala Pro Ala Ala Ala Gly Ala Ser Phe Thr
                85                  90                  95

Ser Gly Gly Thr Glu Ser Ile Phe Met Ala Val Lys Thr Ala Arg Asp
            100                 105                 110

Leu Thr Arg His Arg Arg Gly Glu Pro Asp Gly Arg Tyr Asn Ile Val
        115                 120                 125

Ala Cys Glu Thr Ala His Pro Cys Leu Asp Lys Ala Gly Gln Leu Leu
    130                 135                 140

Gly Val Asp Ile Arg Arg Thr Pro His Thr Ala Glu Phe Arg Ala Asp
145                 150                 155                 160

Pro Ala Leu Leu Arg Thr Ser Ile Asp Gln Lys Thr Met Met Leu Phe
                165                 170                 175

Ala Ser Ala Pro Asn Tyr Pro Phe Gly Thr Phe Asp Pro Ile Ser Lys
            180                 185                 190

Ile Gly Arg Leu Ala Gln Glu Arg Asp Leu Arg Leu His Val Asp Gly
        195                 200                 205

Cys Trp Gly Gly Phe Leu Ser Pro Phe Ala Glu Arg Leu Gly Tyr Pro
    210                 215                 220

Ile Pro Glu Trp Asp Phe Arg Val Pro Gly Val Ser Ser Leu Ser Ala
225                 230                 235                 240

Asp Ile His Lys Phe Gly Tyr Ala Ala Lys Gly Ala Ser Val Val Leu
                245                 250                 255

Tyr Arg Asp Val Glu Asp Gln Glu His Glu Arg Phe Ser Phe Ser Gly
            260                 265                 270

Trp Pro Arg Gly Thr Tyr Ser Thr Pro Thr Phe Leu Gly Thr Lys Ala
        275                 280                 285

Gly Gly Ala Ile Ala Ser Ala Trp Ala Val Met His Phe Leu Gly Val
    290                 295                 300

Glu Gly Tyr Leu Arg Ala Ala Lys Leu Thr Met Asp Ala Thr Met Gln
305                 310                 315                 320

Leu Ile Glu Gly Leu Asn Ala Ile Pro Asp Ile Tyr Cys Leu Thr Pro
                325                 330                 335

Asn Gly Glu Ser Asn Leu Ile Ser Phe Ala Thr Ser Asp Pro Lys Leu
            340                 345                 350

Asp Ile Tyr Ala Val Ala Asp Arg Leu Glu Glu Cys Gly Trp Leu Arg
        355                 360                 365

Gly Arg Met Arg Glu Pro Lys Ala Ile Gln Gln Gly Val Asn Pro Ala
    370                 375                 380

His Leu Ala Thr Val Thr Glu Tyr Leu Ala Glu Val Arg Lys Ala Ile
385                 390                 395                 400

Asp His Val Arg Gly Asn Val Ala Ala Pro Val Ala Tyr Asp Glu His
                405                 410                 415

Ser Tyr


<210> SEQ ID NO 24
<211> LENGTH: 497
<212> TYPE: PRT
<213> ORGANISM: Oryza sativa subsp. Japonica

<400> SEQUENCE: 24

Met Glu Gly Val Gly Gly Gly Gly Gly Gly Glu Glu Trp Leu Arg Pro
1               5                   10                  15

Met Asp Ala Glu Gln Leu Arg Glu Cys Gly His Arg Met Val Asp Phe
            20                  25                  30
```

```
Val Ala Asp Tyr Tyr Lys Ser Ile Glu Ala Phe Pro Val Leu Ser Gln
        35                  40                  45

Val Gln Pro Gly Tyr Leu Lys Glu Val Leu Pro Asp Ser Ala Pro Arg
    50                  55                  60

Gln Pro Asp Thr Leu Asp Ser Leu Phe Asp Asp Ile Gln Gln Lys Ile
65                  70                  75                  80

Ile Pro Gly Val Thr His Trp Gln Ser Pro Asn Tyr Phe Ala Tyr Tyr
                85                  90                  95

Pro Ser Asn Ser Ser Thr Ala Gly Phe Leu Gly Glu Met Leu Ser Ala
            100                 105                 110

Ala Phe Asn Ile Val Gly Phe Ser Trp Ile Thr Ser Pro Ala Ala Thr
        115                 120                 125

Glu Leu Glu Val Ile Val Leu Asp Trp Phe Ala Lys Met Leu Gln Leu
    130                 135                 140

Pro Ser Gln Phe Leu Ser Thr Ala Leu Gly Gly Gly Val Ile Gln Gly
145                 150                 155                 160

Thr Ala Ser Glu Ala Val Leu Val Ala Leu Leu Ala Ala Arg Asp Arg
                165                 170                 175

Ala Leu Lys Lys His Gly Lys His Ser Leu Glu Lys Leu Val Val Tyr
            180                 185                 190

Ala Ser Asp Gln Thr His Ser Ala Leu Gln Lys Ala Cys Gln Ile Ala
        195                 200                 205

Gly Ile Phe Ser Glu Asn Val Arg Val Val Ile Ala Asp Cys Asn Lys
    210                 215                 220

Asn Tyr Ala Val Ala Pro Glu Ala Val Ser Glu Ala Leu Ser Ile Asp
225                 230                 235                 240

Leu Ser Ser Gly Leu Ile Pro Phe Phe Ile Cys Ala Thr Val Gly Thr
                245                 250                 255

Thr Ser Ser Ser Ala Val Asp Pro Leu Pro Glu Leu Gly Gln Ile Ala
            260                 265                 270

Lys Ser Asn Asp Met Trp Phe His Ile Asp Ala Ala Tyr Ala Gly Ser
        275                 280                 285

Ala Cys Ile Cys Pro Glu Tyr Arg His His Leu Asn Gly Val Glu Glu
    290                 295                 300

Ala Asp Ser Phe Asn Met Asn Ala His Lys Trp Phe Leu Thr Asn Phe
305                 310                 315                 320

Asp Cys Ser Leu Leu Trp Val Lys Asp Arg Ser Phe Leu Ile Gln Ser
                325                 330                 335

Leu Ser Thr Asn Pro Glu Phe Leu Lys Asn Lys Ala Ser Gln Ala Asn
            340                 345                 350

Ser Val Val Asp Phe Lys Asp Trp Gln Ile Pro Leu Gly Arg Arg Phe
        355                 360                 365

Arg Ser Leu Lys Leu Trp Met Val Leu Arg Leu Tyr Gly Val Asp Asn
    370                 375                 380

Leu Gln Ser Tyr Ile Arg Lys His Ile His Leu Ala Glu His Phe Glu
385                 390                 395                 400

Gln Leu Leu Leu Ser Asp Ser Arg Phe Glu Val Val Thr Pro Arg Thr
                405                 410                 415

Phe Ser Leu Val Cys Phe Arg Leu Val Pro Pro Thr Ser Asp His Glu
            420                 425                 430

Asn Gly Arg Lys Leu Asn Tyr Asp Met Met Asp Gly Val Asn Ser Ser
        435                 440                 445

Gly Lys Ile Phe Leu Ser His Thr Val Leu Ser Gly Lys Phe Val Leu
```

```
    450                 455                 460

Arg Phe Ala Val Gly Ala Pro Leu Thr Glu Glu Arg His Val Asp Ala
465                 470                 475                 480

Ala Trp Lys Leu Leu Arg Asp Glu Ala Thr Lys Val Leu Gly Lys Met
                485                 490                 495

Val


<210> SEQ ID NO 25
<211> LENGTH: 396
<212> TYPE: PRT
<213> ORGANISM: Methanocaldococcus jannaschii

<400> SEQUENCE: 25

Met Arg Asn Met Gln Glu Lys Gly Val Ser Glu Lys Glu Ile Leu Glu
1               5                   10                  15

Glu Leu Lys Lys Tyr Arg Ser Leu Asp Leu Lys Tyr Glu Asp Gly Asn
            20                  25                  30

Ile Phe Gly Ser Met Cys Ser Asn Val Leu Pro Ile Thr Arg Lys Ile
        35                  40                  45

Val Asp Ile Phe Leu Glu Thr Asn Leu Gly Asp Pro Gly Leu Phe Lys
    50                  55                  60

Gly Thr Lys Leu Leu Glu Glu Lys Ala Val Ala Leu Leu Gly Ser Leu
65                  70                  75                  80

Leu Asn Asn Lys Asp Ala Tyr Gly His Ile Val Ser Gly Gly Thr Glu
                85                  90                  95

Ala Asn Leu Met Ala Leu Arg Cys Ile Lys Asn Ile Trp Arg Glu Lys
            100                 105                 110

Arg Arg Lys Gly Leu Ser Lys Asn Glu His Pro Lys Ile Ile Val Pro
        115                 120                 125

Ile Thr Ala His Phe Ser Phe Glu Lys Gly Arg Glu Met Met Asp Leu
    130                 135                 140

Glu Tyr Ile Tyr Ala Pro Ile Lys Glu Asp Tyr Thr Ile Asp Glu Lys
145                 150                 155                 160

Phe Val Lys Asp Ala Val Glu Asp Tyr Asp Val Asp Gly Ile Ile Gly
                165                 170                 175

Ile Ala Gly Thr Thr Glu Leu Gly Thr Ile Asp Asn Ile Glu Glu Leu
            180                 185                 190

Ser Lys Ile Ala Lys Glu Asn Asn Ile Tyr Ile His Val Asp Ala Ala
        195                 200                 205

Phe Gly Gly Leu Val Ile Pro Phe Leu Asp Asp Lys Tyr Lys Lys Lys
    210                 215                 220

Gly Val Asn Tyr Lys Phe Asp Phe Ser Leu Gly Val Asp Ser Ile Thr
225                 230                 235                 240

Ile Asp Pro His Lys Met Gly His Cys Pro Ile Pro Ser Gly Gly Ile
                245                 250                 255

Leu Phe Lys Asp Ile Gly Tyr Lys Arg Tyr Leu Asp Val Asp Ala Pro
            260                 265                 270

Tyr Leu Thr Glu Thr Arg Gln Ala Thr Ile Leu Gly Thr Arg Val Gly
        275                 280                 285

Phe Gly Gly Ala Cys Thr Tyr Ala Val Leu Arg Tyr Leu Gly Arg Glu
    290                 295                 300

Gly Gln Arg Lys Ile Val Asn Glu Cys Met Glu Asn Thr Leu Tyr Leu
305                 310                 315                 320

Tyr Lys Lys Leu Lys Glu Asn Asn Phe Lys Pro Val Ile Glu Pro Ile
```

```
                325                 330                 335

Leu Asn Ile Val Ala Ile Glu Asp Glu Asp Tyr Lys Glu Val Cys Lys
            340                 345                 350

Lys Leu Arg Asp Arg Gly Ile Tyr Val Ser Val Cys Asn Cys Val Lys
        355                 360                 365

Ala Leu Arg Ile Val Val Met Pro His Ile Lys Arg Glu His Ile Asp
    370                 375                 380

Asn Phe Ile Glu Ile Leu Asn Ser Ile Lys Arg Asp
385                 390                 395


<210> SEQ ID NO 26
<211> LENGTH: 370
<212> TYPE: PRT
<213> ORGANISM: Saccharomyces cerevisiae (strain ATCC 204508  S288c)
      (Baker's yeast)

<400> SEQUENCE: 26

Met Phe Ile Lys Asn Asp His Ala Gly Asp Arg Lys Arg Leu Glu Asp
1               5                   10                  15

Trp Arg Ile Lys Gly Tyr Asp Pro Leu Thr Pro Pro Asp Leu Leu Gln
            20                  25                  30

His Glu Phe Pro Ile Ser Ala Lys Gly Glu Glu Asn Ile Ile Lys Ala
        35                  40                  45

Arg Asp Ser Val Cys Asp Ile Leu Asn Gly Lys Asp Asp Arg Leu Val
    50                  55                  60

Ile Val Ile Gly Pro Cys Ser Leu His Asp Pro Lys Ala Ala Tyr Asp
65                  70                  75                  80

Tyr Ala Asp Arg Leu Ala Lys Ile Ser Glu Lys Leu Ser Lys Asp Leu
                85                  90                  95

Leu Ile Ile Met Arg Ala Tyr Leu Glu Lys Pro Arg Thr Thr Val Gly
            100                 105                 110

Trp Lys Gly Leu Ile Asn Asp Pro Asp Met Asn Asn Ser Phe Gln Ile
        115                 120                 125

Asn Lys Gly Leu Arg Ile Ser Arg Glu Met Phe Ile Arg Leu Val Glu
    130                 135                 140

Lys Leu Pro Ile Ala Gly Glu Met Leu Asp Thr Ile Ser Pro Gln Phe
145                 150                 155                 160

Leu Ser Asp Cys Phe Ser Leu Gly Ala Ile Gly Ala Arg Thr Thr Glu
                165                 170                 175

Ser Gln Leu His Arg Glu Leu Ala Ser Gly Leu Ser Phe Pro Ile Gly
            180                 185                 190

Phe Lys Asn Gly Thr Asp Gly Gly Leu Gln Val Ala Ile Asp Ala Met
        195                 200                 205

Arg Ala Ala Ala His Asp His Tyr Phe Leu Ser Val Thr Lys Pro Gly
    210                 215                 220

Val Thr Ala Ile Val Gly Thr Glu Gly Asn Lys Asp Thr Phe Leu Ile
225                 230                 235                 240

Leu Arg Gly Gly Lys Asn Gly Thr Asn Phe Asp Lys Glu Ser Val Gln
                245                 250                 255

Asn Thr Lys Lys Gln Leu Glu Lys Ala Gly Leu Thr Asp Asp Ser Gln
            260                 265                 270

Lys Arg Ile Met Ile Asp Cys Ser His Gly Asn Ser Asn Lys Asp Phe
        275                 280                 285

Lys Asn Gln Pro Lys Val Ala Lys Cys Ile Tyr Asp Gln Leu Thr Glu
    290                 295                 300
```

```
Gly Glu Asn Ser Leu Cys Gly Val Met Ile Glu Ser Asn Ile Asn Glu
305                 310                 315                 320

Gly Arg Gln Asp Ile Pro Lys Glu Gly Gly Arg Glu Gly Leu Lys Tyr
                325                 330                 335

Gly Cys Ser Val Thr Asp Ala Cys Ile Gly Trp Glu Thr Thr Glu Gln
            340                 345                 350

Val Leu Glu Leu Leu Ala Glu Gly Val Arg Asn Arg Arg Lys Ala Leu
        355                 360                 365

Lys Lys
    370


<210> SEQ ID NO 27
<211> LENGTH: 500
<212> TYPE: PRT
<213> ORGANISM: Saccharomyces cerevisiae (strain ATCC 204508  S288c)
      (Baker's yeast)

<400> SEQUENCE: 27

Met Thr Leu Pro Glu Ser Arg Asp Phe Ser Tyr Leu Phe Ser Asp Glu
1               5                   10                  15

Thr Asn Ala Arg Lys Pro Ser Pro Leu Lys Thr Cys Ile His Leu Phe
            20                  25                  30

Gln Asp Pro Asn Ile Ile Phe Leu Gly Gly Gly Leu Pro Leu Lys Asp
        35                  40                  45

Tyr Phe Pro Trp Asp Asn Leu Ser Val Asp Ser Pro Lys Pro Pro Phe
    50                  55                  60

Pro Gln Gly Ile Gly Ala Pro Ile Asp Glu Gln Asn Cys Ile Lys Tyr
65                  70                  75                  80

Thr Val Asn Lys Asp Tyr Ala Asp Lys Ser Ala Asn Pro Ser Asn Asp
                85                  90                  95

Ile Pro Leu Ser Arg Ala Leu Gln Tyr Gly Phe Ser Ala Gly Gln Pro
            100                 105                 110

Glu Leu Leu Asn Phe Ile Arg Asp His Thr Lys Ile Ile His Asp Leu
        115                 120                 125

Lys Tyr Lys Asp Trp Asp Val Leu Ala Thr Ala Gly Asn Thr Asn Ala
    130                 135                 140

Trp Glu Ser Thr Leu Arg Val Phe Cys Asn Arg Gly Asp Val Ile Leu
145                 150                 155                 160

Val Glu Ala His Ser Phe Ser Ser Ser Leu Ala Ser Ala Glu Ala Gln
                165                 170                 175

Gly Val Ile Thr Phe Pro Val Pro Ile Asp Ala Asp Gly Ile Ile Pro
            180                 185                 190

Glu Lys Leu Ala Lys Val Met Glu Asn Trp Thr Pro Gly Ala Pro Lys
        195                 200                 205

Pro Lys Leu Leu Tyr Thr Ile Pro Thr Gly Gln Asn Pro Thr Gly Thr
    210                 215                 220

Ser Ile Ala Asp His Arg Lys Glu Ala Ile Tyr Lys Ile Ala Gln Lys
225                 230                 235                 240

Tyr Asp Phe Leu Ile Val Glu Asp Glu Pro Tyr Tyr Phe Leu Gln Met
                245                 250                 255

Asn Pro Tyr Ile Lys Asp Leu Lys Glu Arg Glu Lys Ala Gln Ser Ser
            260                 265                 270

Pro Lys Gln Asp His Asp Glu Phe Leu Lys Ser Leu Ala Asn Thr Phe
        275                 280                 285
```

```
Leu Ser Leu Asp Thr Glu Gly Arg Val Ile Arg Met Asp Ser Phe Ser
    290                 295                 300

Lys Val Leu Ala Pro Gly Thr Arg Leu Gly Trp Ile Thr Gly Ser Ser
305                 310                 315                 320

Lys Ile Leu Lys Pro Tyr Leu Ser Leu His Glu Met Thr Ile Gln Ala
                325                 330                 335

Pro Ala Gly Phe Thr Gln Val Leu Val Asn Ala Thr Leu Ser Arg Trp
            340                 345                 350

Gly Gln Lys Gly Tyr Leu Asp Trp Leu Leu Gly Leu Arg His Glu Tyr
        355                 360                 365

Thr Leu Lys Arg Asp Cys Ala Ile Asp Ala Leu Tyr Lys Tyr Leu Pro
    370                 375                 380

Gln Ser Asp Ala Phe Val Ile Asn Pro Pro Ile Ala Gly Met Phe Phe
385                 390                 395                 400

Thr Val Asn Ile Asp Ala Ser Val His Pro Glu Phe Lys Thr Lys Tyr
                405                 410                 415

Asn Ser Asp Pro Tyr Gln Leu Glu Gln Ser Leu Tyr His Lys Val Val
            420                 425                 430

Glu Arg Gly Val Leu Val Val Pro Gly Ser Trp Phe Lys Ser Glu Gly
        435                 440                 445

Glu Thr Glu Pro Pro Gln Pro Ala Glu Ser Lys Glu Val Ser Asn Pro
    450                 455                 460

Asn Ile Ile Phe Phe Arg Gly Thr Tyr Ala Ala Val Ser Pro Glu Lys
465                 470                 475                 480

Leu Thr Glu Gly Leu Lys Arg Leu Gly Asp Thr Leu Tyr Glu Glu Phe
                485                 490                 495

Gly Ile Ser Lys
            500


<210> SEQ ID NO 28
<211> LENGTH: 513
<212> TYPE: PRT
<213> ORGANISM: Saccharomyces cerevisiae (strain ATCC 204508 S288c)
      (Baker's yeast)

<400> SEQUENCE: 28

Met Thr Ala Gly Ser Ala Pro Pro Val Asp Tyr Thr Ser Leu Lys Lys
1               5                   10                  15

Asn Phe Gln Pro Phe Leu Ser Arg Arg Val Glu Asn Arg Ser Leu Lys
            20                  25                  30

Ser Phe Trp Asp Ala Ser Asp Ile Ser Asp Asp Val Ile Glu Leu Ala
        35                  40                  45

Gly Gly Met Pro Asn Glu Arg Phe Phe Pro Ile Glu Ser Met Asp Leu
    50                  55                  60

Lys Ile Ser Lys Val Pro Phe Asn Asp Asn Pro Lys Trp His Asn Ser
65                  70                  75                  80

Phe Thr Thr Ala His Leu Asp Leu Gly Ser Pro Ser Glu Leu Pro Ile
                85                  90                  95

Ala Arg Ser Phe Gln Tyr Ala Glu Thr Lys Gly Leu Pro Pro Leu Leu
            100                 105                 110

His Phe Val Lys Asp Phe Val Ser Arg Ile Asn Arg Pro Ala Phe Ser
        115                 120                 125

Asp Glu Thr Glu Ser Asn Trp Asp Val Ile Leu Ser Gly Gly Ser Asn
    130                 135                 140

Asp Ser Met Phe Lys Val Phe Glu Thr Ile Cys Asp Glu Ser Thr Thr
```

```
145                 150                 155                 160

Val Met Ile Glu Glu Phe Thr Phe Thr Pro Ala Met Ser Asn Val Glu
                165                 170                 175

Ala Thr Gly Ala Lys Val Ile Pro Ile Lys Met Asn Leu Thr Phe Asp
            180                 185                 190

Arg Glu Ser Gln Gly Ile Asp Val Glu Tyr Leu Thr Gln Leu Leu Asp
        195                 200                 205

Asn Trp Ser Thr Gly Pro Tyr Lys Asp Leu Asn Lys Pro Arg Val Leu
    210                 215                 220

Tyr Thr Ile Ala Thr Gly Gln Asn Pro Thr Gly Met Ser Val Pro Gln
225                 230                 235                 240

Trp Lys Arg Glu Lys Ile Tyr Gln Leu Ala Gln Arg His Asp Phe Leu
                245                 250                 255

Ile Val Glu Asp Asp Pro Tyr Gly Tyr Leu Tyr Phe Pro Ser Tyr Asn
            260                 265                 270

Pro Gln Glu Pro Leu Glu Asn Pro Tyr His Ser Ser Asp Leu Thr Thr
        275                 280                 285

Glu Arg Tyr Leu Asn Asp Phe Leu Met Lys Ser Phe Leu Thr Leu Asp
    290                 295                 300

Thr Asp Ala Arg Val Ile Arg Leu Glu Thr Phe Ser Lys Ile Phe Ala
305                 310                 315                 320

Pro Gly Leu Arg Leu Ser Phe Ile Val Ala Asn Lys Phe Leu Leu Gln
                325                 330                 335

Lys Ile Leu Asp Leu Ala Asp Ile Thr Thr Arg Ala Pro Ser Gly Thr
            340                 345                 350

Ser Gln Ala Ile Val Tyr Ser Thr Ile Lys Ala Met Ala Glu Ser Asn
        355                 360                 365

Leu Ser Ser Ser Leu Ser Met Lys Glu Ala Met Phe Glu Gly Trp Ile
    370                 375                 380

Arg Trp Ile Met Gln Ile Ala Ser Lys Tyr Asn His Arg Lys Asn Leu
385                 390                 395                 400

Thr Leu Lys Ala Leu Tyr Glu Thr Glu Ser Tyr Gln Ala Gly Gln Phe
                405                 410                 415

Thr Val Met Glu Pro Ser Ala Gly Met Phe Ile Ile Ile Lys Ile Asn
            420                 425                 430

Trp Gly Asn Phe Asp Arg Pro Asp Asp Leu Pro Gln Gln Met Asp Ile
        435                 440                 445

Leu Asp Lys Phe Leu Leu Lys Asn Gly Val Lys Val Val Leu Gly Tyr
    450                 455                 460

Lys Met Ala Val Cys Pro Asn Tyr Ser Lys Gln Asn Ser Asp Phe Leu
465                 470                 475                 480

Arg Leu Thr Ile Ala Tyr Ala Arg Asp Asp Asp Gln Leu Ile Glu Ala
                485                 490                 495

Ser Lys Arg Ile Gly Ser Gly Ile Lys Glu Phe Phe Asp Asn Tyr Lys
            500                 505                 510

Ser


<210> SEQ ID NO 29
<211> LENGTH: 792
<212> TYPE: PRT
<213> ORGANISM: Escherichia coli (strain K12)

<400> SEQUENCE: 29

Met Ser Asn Asn Gly Ser Ser Pro Leu Val Leu Trp Tyr Asn Gln Leu
```

-continued

```
1               5                   10                  15

Gly Met Asn Asp Val Asp Arg Val Gly Gly Lys Asn Ala Ser Leu Gly
            20                  25                  30

Glu Met Ile Thr Asn Leu Ser Gly Met Gly Val Ser Val Pro Asn Gly
        35                  40                  45

Phe Ala Thr Thr Ala Asp Ala Phe Asn Gln Phe Leu Asp Gln Ser Gly
    50                  55                  60

Val Asn Gln Arg Ile Tyr Glu Leu Leu Asp Lys Thr Asp Ile Asp Asp
65                  70                  75                  80

Val Thr Gln Leu Ala Lys Ala Gly Ala Gln Ile Arg Gln Trp Ile Ile
                85                  90                  95

Asp Thr Pro Phe Gln Pro Glu Leu Glu Asn Ala Ile Arg Glu Ala Tyr
            100                 105                 110

Ala Gln Leu Ser Ala Asp Asp Glu Asn Ala Ser Phe Ala Val Arg Ser
        115                 120                 125

Ser Ala Thr Ala Glu Asp Met Pro Asp Ala Ser Phe Ala Gly Gln Gln
    130                 135                 140

Glu Thr Phe Leu Asn Val Gln Gly Phe Asp Ala Val Leu Val Ala Val
145                 150                 155                 160

Lys His Val Phe Ala Ser Leu Phe Asn Asp Arg Ala Ile Ser Tyr Arg
                165                 170                 175

Val His Gln Gly Tyr Asp His Arg Gly Val Ala Leu Ser Ala Gly Val
            180                 185                 190

Gln Arg Met Val Arg Ser Asp Leu Ala Ser Ser Gly Val Met Phe Ser
        195                 200                 205

Ile Asp Thr Glu Ser Gly Phe Asp Gln Val Val Phe Ile Thr Ser Ala
    210                 215                 220

Trp Gly Leu Gly Glu Met Val Val Gln Gly Ala Val Asn Pro Asp Glu
225                 230                 235                 240

Phe Tyr Val His Lys Pro Thr Leu Ala Ala Asn Arg Pro Ala Ile Val
                245                 250                 255

Arg Arg Thr Met Gly Ser Lys Lys Ile Arg Met Val Tyr Ala Pro Thr
            260                 265                 270

Gln Glu His Gly Lys Gln Val Lys Ile Glu Asp Val Pro Gln Glu Gln
        275                 280                 285

Arg Asp Ile Phe Ser Leu Thr Asn Glu Glu Val Gln Glu Leu Ala Lys
    290                 295                 300

Gln Ala Val Gln Ile Glu Lys His Tyr Gly Arg Pro Met Asp Ile Glu
305                 310                 315                 320

Trp Ala Lys Asp Gly His Thr Gly Lys Leu Phe Ile Val Gln Ala Arg
                325                 330                 335

Pro Glu Thr Val Arg Ser Arg Gly Gln Val Met Glu Arg Tyr Thr Leu
            340                 345                 350

His Ser Gln Gly Lys Ile Ile Ala Glu Gly Arg Ala Ile Gly His Arg
        355                 360                 365

Ile Gly Ala Gly Pro Val Lys Val Ile His Asp Ile Ser Glu Met Asn
    370                 375                 380

Arg Ile Glu Pro Gly Asp Val Leu Val Thr Asp Met Thr Asp Pro Asp
385                 390                 395                 400

Trp Glu Pro Ile Met Lys Lys Ala Ser Ala Ile Val Thr Asn Arg Gly
                405                 410                 415

Gly Arg Thr Cys His Ala Ala Ile Ile Ala Arg Glu Leu Gly Ile Pro
            420                 425                 430
```

```
Ala Val Val Gly Cys Gly Asp Ala Thr Glu Arg Met Lys Asp Gly Glu
        435                 440                 445

Asn Val Thr Val Ser Cys Ala Glu Gly Asp Thr Gly Tyr Val Tyr Ala
    450                 455                 460

Glu Leu Leu Glu Phe Ser Val Lys Ser Ser Ser Val Glu Thr Met Pro
465                 470                 475                 480

Asp Leu Pro Leu Lys Val Met Met Asn Val Gly Asn Pro Asp Arg Ala
                485                 490                 495

Phe Asp Phe Ala Cys Leu Pro Asn Glu Gly Val Gly Leu Ala Arg Leu
            500                 505                 510

Glu Phe Ile Ile Asn Arg Met Ile Gly Val His Pro Arg Ala Leu Leu
        515                 520                 525

Glu Phe Asp Asp Gln Glu Pro Gln Leu Gln Asn Glu Ile Arg Glu Met
    530                 535                 540

Met Lys Gly Phe Asp Ser Pro Arg Glu Phe Tyr Val Gly Arg Leu Thr
545                 550                 555                 560

Glu Gly Ile Ala Thr Leu Gly Ala Ala Phe Tyr Pro Lys Arg Val Ile
                565                 570                 575

Val Arg Leu Ser Asp Phe Lys Ser Asn Glu Tyr Ala Asn Leu Val Gly
            580                 585                 590

Gly Glu Arg Tyr Glu Pro Asp Glu Glu Asn Pro Met Leu Gly Phe Arg
        595                 600                 605

Gly Ala Gly Arg Tyr Val Ser Asp Ser Phe Arg Asp Cys Phe Ala Leu
    610                 615                 620

Glu Cys Glu Ala Val Lys Arg Val Arg Asn Asp Met Gly Leu Thr Asn
625                 630                 635                 640

Val Glu Ile Met Ile Pro Phe Val Arg Thr Val Asp Gln Ala Lys Ala
                645                 650                 655

Val Val Glu Glu Leu Ala Arg Gln Gly Leu Lys Arg Gly Glu Asn Gly
            660                 665                 670

Leu Lys Ile Ile Met Met Cys Glu Ile Pro Ser Asn Ala Leu Leu Ala
        675                 680                 685

Glu Gln Phe Leu Glu Tyr Phe Asp Gly Phe Ser Ile Gly Ser Asn Asp
    690                 695                 700

Met Thr Gln Leu Ala Leu Gly Leu Asp Arg Asp Ser Gly Val Val Ser
705                 710                 715                 720

Glu Leu Phe Asp Glu Arg Asn Asp Ala Val Lys Ala Leu Leu Ser Met
                725                 730                 735

Ala Ile Arg Ala Ala Lys Lys Gln Gly Lys Tyr Val Gly Ile Cys Gly
            740                 745                 750

Gln Gly Pro Ser Asp His Glu Asp Phe Ala Ala Trp Leu Met Glu Glu
        755                 760                 765

Gly Ile Asp Ser Leu Ser Leu Asn Pro Asp Thr Val Val Gln Thr Trp
    770                 775                 780

Leu Ser Leu Ala Glu Leu Lys Lys
785                 790


<210> SEQ ID NO 30
<211> LENGTH: 680
<212> TYPE: PRT
<213> ORGANISM: Saccharomyces cerevisiae (strain ATCC 204508 S288c)
      (Baker's yeast)

<400> SEQUENCE: 30
```

```
Met Thr Gln Phe Thr Asp Ile Asp Lys Leu Ala Val Ser Thr Ile Arg
1               5                   10                  15

Ile Leu Ala Val Asp Thr Val Ser Lys Ala Asn Ser Gly His Pro Gly
            20                  25                  30

Ala Pro Leu Gly Met Ala Pro Ala Ala His Val Leu Trp Ser Gln Met
        35                  40                  45

Arg Met Asn Pro Thr Asn Pro Asp Trp Ile Asn Arg Asp Arg Phe Val
    50                  55                  60

Leu Ser Asn Gly His Ala Val Ala Leu Leu Tyr Ser Met Leu His Leu
65                  70                  75                  80

Thr Gly Tyr Asp Leu Ser Ile Glu Asp Leu Lys Gln Phe Arg Gln Leu
                85                  90                  95

Gly Ser Arg Thr Pro Gly His Pro Glu Phe Glu Leu Pro Gly Val Glu
            100                 105                 110

Val Thr Thr Gly Pro Leu Gly Gln Gly Ile Ser Asn Ala Val Gly Met
        115                 120                 125

Ala Met Ala Gln Ala Asn Leu Ala Ala Thr Tyr Asn Lys Pro Gly Phe
    130                 135                 140

Thr Leu Ser Asp Asn Tyr Thr Tyr Val Phe Leu Gly Asp Gly Cys Leu
145                 150                 155                 160

Gln Glu Gly Ile Ser Ser Glu Ala Ser Ser Leu Ala Gly His Leu Lys
                165                 170                 175

Leu Gly Asn Leu Ile Ala Ile Tyr Asp Asp Asn Lys Ile Thr Ile Asp
            180                 185                 190

Gly Ala Thr Ser Ile Ser Phe Asp Glu Asp Val Ala Lys Arg Tyr Glu
        195                 200                 205

Ala Tyr Gly Trp Glu Val Leu Tyr Val Glu Asn Gly Asn Glu Asp Leu
    210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Thr Ile Gly Tyr Gly Ser Leu His
                245                 250                 255

Ala Gly Ser His Ser Val His Gly Ala Pro Leu Lys Ala Asp Asp Val
            260                 265                 270

Lys Gln Leu Lys Ser Lys Phe Gly Phe Asn Pro Asp Lys Ser Phe Val
        275                 280                 285

Val Pro Gln Glu Val Tyr Asp His Tyr Gln Lys Thr Ile Leu Lys Pro
    290                 295                 300

Gly Val Glu Ala Asn Asn Lys Trp Asn Lys Leu Phe Ser Glu Tyr Gln
305                 310                 315                 320

Lys Lys Phe Pro Glu Leu Gly Ala Glu Leu Ala Arg Arg Leu Ser Gly
                325                 330                 335

Gln Leu Pro Ala Asn Trp Glu Ser Lys Leu Pro Thr Tyr Thr Ala Lys
            340                 345                 350

Asp Ser Ala Val Ala Thr Arg Lys Leu Ser Glu Thr Val Leu Glu Asp
        355                 360                 365

Val Tyr Asn Gln Leu Pro Glu Leu Ile Gly Gly Ser Ala Asp Leu Thr
    370                 375                 380

Pro Ser Asn Leu Thr Arg Trp Lys Glu Ala Leu Asp Phe Gln Pro Pro
385                 390                 395                 400

Ser Ser Gly Ser Gly Asn Tyr Ser Gly Arg Tyr Ile Arg Tyr Gly Ile
                405                 410                 415

Arg Glu His Ala Met Gly Ala Ile Met Asn Gly Ile Ser Ala Phe Gly
```

```
            420                 425                 430

Ala Asn Tyr Lys Pro Tyr Gly Gly Thr Phe Leu Asn Phe Val Ser Tyr
        435                 440                 445

Ala Ala Gly Ala Val Arg Leu Ser Ala Leu Ser Gly His Pro Val Ile
    450                 455                 460

Trp Val Ala Thr His Asp Ser Ile Gly Val Gly Glu Asp Gly Pro Thr
465                 470                 475                 480

His Gln Pro Ile Glu Thr Leu Ala His Phe Arg Ser Leu Pro Asn Ile
                485                 490                 495

Gln Val Trp Arg Pro Ala Asp Gly Asn Glu Val Ser Ala Ala Tyr Lys
            500                 505                 510

Asn Ser Leu Glu Ser Lys His Thr Pro Ser Ile Ile Ala Leu Ser Arg
        515                 520                 525

Gln Asn Leu Pro Gln Leu Glu Gly Ser Ser Ile Glu Ser Ala Ser Lys
    530                 535                 540

Gly Gly Tyr Val Leu Gln Asp Val Ala Asn Pro Asp Ile Ile Leu Val
545                 550                 555                 560

Ala Thr Gly Ser Glu Val Ser Leu Ser Val Glu Ala Ala Lys Thr Leu
                565                 570                 575

Ala Ala Lys Asn Ile Lys Ala Arg Val Val Ser Leu Pro Asp Phe Phe
            580                 585                 590

Thr Phe Asp Lys Gln Pro Leu Glu Tyr Arg Leu Ser Val Leu Pro Asp
        595                 600                 605

Asn Val Pro Ile Met Ser Val Glu Val Leu Ala Thr Thr Cys Trp Gly
    610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
                645                 650                 655

Ala Glu Arg Ala Gln Lys Thr Ile Ala Phe Tyr Lys Gly Asp Lys Leu
            660                 665                 670

Ile Ser Pro Leu Lys Lys Ala Phe
        675                 680


<210> SEQ ID NO 31
<211> LENGTH: 416
<212> TYPE: PRT
<213> ORGANISM: Gracilaria gracilis (Red alga)

<400> SEQUENCE: 31

Met Ala Phe Val Ala Pro Val Ser Ser Val Phe Ser Thr Ser Ser Lys
1               5                   10                  15

Ser Ala Val Cys Ser Gly Arg Ser Ser Phe Ala Gln Phe Ser Gly Leu
            20                  25                  30

Lys Lys Val Asn Asn Thr Ala Arg Leu Gln Thr Ala Glu Gln Gly Ser
        35                  40                  45

Ala Phe Gly Gly Val Ser Asp Ala Asn Asp Ala Phe Phe Asn Ala Val
    50                  55                  60

Asn Thr Met Gly Ala Pro Ala Arg Thr Ser Asn Ala Pro Ser Met Lys
65                  70                  75                  80

Val Arg Val Ala Ile Asn Gly Phe Gly Arg Ile Gly Arg Asn Phe Ile
                85                  90                  95

Arg Cys Trp Ala Gly Arg Thr Asp Ser Asn Met Asp Val Val Cys Ile
            100                 105                 110
```

```
Asn Asp Thr Ser Gly Val Lys Thr Ala Ser His Leu Leu Lys Tyr Asp
        115                 120                 125

Ser Ile Leu Gly Thr Phe Asp Ser Asp Val Val Ala Gly Glu Asp Ser
    130                 135                 140

Ile Thr Val Asp Gly Lys Thr Ile Lys Val Val Ser Asn Arg Asn Pro
145                 150                 155                 160

Leu Glu Leu Pro Trp Lys Glu Met Glu Ile Asp Ile Val Val Glu Ala
                165                 170                 175

Thr Gly Val Phe Val Asp Ala Val Gly Ala Gly Lys His Ile Gln Ala
            180                 185                 190

Gly Ala Lys Lys Val Leu Ile Thr Ala Pro Gly Lys Gly Glu Gly Val
        195                 200                 205

Gly Thr Phe Val Val Gly Val Asn Asp His Leu Tyr Ser His Asp Lys
    210                 215                 220

Phe Asp Ile Val Ser Asn Ala Ser Cys Thr Thr Asn Cys Met Ala Pro
225                 230                 235                 240

Phe Met Lys Val Leu Asp Asp Glu Phe Gly Val Val Arg Gly Met Met
                245                 250                 255

Thr Thr Thr His Ser Tyr Thr Gly Asp Gln Arg Leu Leu Asp Ala Gly
            260                 265                 270

His Arg Asp Leu Arg Arg Ala Arg Ser Ala Ala Leu Asn Ile Val Pro
        275                 280                 285

Thr Thr Thr Gly Ala Ala Lys Ala Val Ala Leu Val Val Pro Thr Leu
    290                 295                 300

Ala Gly Lys Leu Asn Gly Ile Ala Leu Arg Val Pro Thr Pro Asn Val
305                 310                 315                 320

Ser Val Cys Asp Val Val Met Gln Val Ser Lys Lys Thr Phe Lys Glu
                325                 330                 335

Glu Val Asn Gly Ala Leu Leu Lys Ala Ala Asn Gly Ser Met Lys Gly
            340                 345                 350

Ile Ile Lys Tyr Ser Asp Glu Pro Leu Val Ser Cys Asp Tyr Arg Gly
        355                 360                 365

Thr Asp Glu Ser Thr Ile Ile Asp Ser Ser Leu Thr Met Val Met Gly
    370                 375                 380

Asp Asp Met Leu Lys Val Val Ala Trp Tyr Asp Asn Glu Trp Gly Tyr
385                 390                 395                 400

Ser Gln Arg Val Val Asp Leu Gly Glu Val Met Ala Ser Gln Trp Lys
                405                 410                 415


<210> SEQ ID NO 32
<211> LENGTH: 262
<212> TYPE: PRT
<213> ORGANISM: Pyrococcus furiosus (strain ATCC 43587 DSM 3638 JCM 8422
      Vc1)

<400> SEQUENCE: 32

Met Lys Tyr Ser Lys Glu Tyr Lys Glu Lys Thr Val Val Lys Ile Asn
1               5                   10                  15

Asp Val Lys Phe Gly Glu Gly Phe Thr Ile Ile Ala Gly Pro Cys Ser
            20                  25                  30

Ile Glu Ser Arg Asp Gln Ile Met Lys Val Ala Glu Phe Leu Ala Glu
        35                  40                  45

Val Gly Ile Lys Val Leu Arg Gly Gly Ala Phe Lys Pro Arg Thr Ser
    50                  55                  60

Pro Tyr Ser Phe Gln Gly Tyr Gly Glu Lys Ala Leu Arg Trp Met Arg
```

```
65                  70                  75                  80

Glu Ala Ala Asp Glu Tyr Gly Leu Val Thr Val Thr Glu Val Met Asp
                85                  90                  95

Thr Arg His Val Glu Leu Val Ala Lys Tyr Ser Asp Ile Leu Gln Ile
            100                 105                 110

Gly Ala Arg Asn Ser Gln Asn Phe Glu Leu Leu Lys Glu Val Gly Lys
        115                 120                 125

Val Glu Asn Pro Val Leu Leu Lys Arg Gly Met Gly Asn Thr Ile Gln
    130                 135                 140

Glu Leu Leu Tyr Ser Ala Glu Tyr Ile Met Ala Gln Gly Asn Glu Asn
145                 150                 155                 160

Val Ile Leu Cys Glu Arg Gly Ile Arg Thr Phe Glu Thr Ala Thr Arg
                165                 170                 175

Phe Thr Leu Asp Ile Ser Ala Val Pro Val Val Lys Glu Leu Ser His
            180                 185                 190

Leu Pro Ile Ile Val Asp Pro Ser His Pro Ala Gly Arg Arg Ser Leu
        195                 200                 205

Val Ile Pro Leu Ala Lys Ala Ala Tyr Ala Ile Gly Ala Asp Gly Ile
    210                 215                 220

Met Val Glu Val His Pro Glu Pro Glu Lys Ala Leu Ser Asp Ser Gln
225                 230                 235                 240

Gln Gln Leu Thr Phe Asp Asp Phe Leu Gln Leu Leu Lys Glu Leu Glu
                245                 250                 255

Ala Leu Gly Trp Lys Gly
            260


<210> SEQ ID NO 33
<211> LENGTH: 267
<212> TYPE: PRT
<213> ORGANISM: Meyerozyma guilliermondii (strain ATCC 6260 CBS 566 DSM
      6381 JCM 1539 NBRC 10279 NRRL Y-324) (Yeast) (Candida
guilliermondii)

<400> SEQUENCE: 33

Met Asp Phe Thr Lys Pro Glu Thr Val Leu Asp Leu Gly Asn Ile Arg
1               5                   10                  15

Gln Ala Leu Ile Arg Met Glu Asp Thr Ile Val Phe Phe Leu Ile Glu
            20                  25                  30

Arg Ser Gln Phe Tyr Ser Ser Pro Ser Val Tyr Ile Lys Asn Lys Phe
        35                  40                  45

Pro Ile Pro Asn Phe Asp Gly Ser Phe Leu Asp Trp Ser Leu Gln Gln
    50                  55                  60

Met Glu Arg Thr His Ser Gln Ile Arg Arg Tyr Glu Ala Pro Asp Glu
65                  70                  75                  80

Ile Pro Phe Phe Pro Glu Val Leu Leu Glu Ser Phe Leu Pro Pro Ile
                85                  90                  95

Asn Tyr Pro Asn Ile Leu Ala Ser Tyr His Lys Glu Val Asn His Asn
            100                 105                 110

Gln Thr Val Leu Asn Phe Tyr Val Glu Asn Ile Val Pro Gln Val Ala
        115                 120                 125

Cys Glu Ile Gly Glu Gln Glu Glu Asn Ile Gly Ser Val Ser Val Cys
    130                 135                 140

Asp Ile Asp Cys Leu Gln Ser Leu Ser Arg Arg Ile His Phe Gly Lys
145                 150                 155                 160

Phe Val Ala Glu Ala Lys Tyr Gln Ser Asp Lys Pro Lys Tyr Ile Lys
```

```
                165                 170                 175

Leu Ile Leu Ala Lys Asp Val Lys Gly Ile Glu Asp Ser Ile Thr Asn
            180                 185                 190

Ser Ala Val Glu Glu Lys Ile Leu Glu Arg Leu Gln Lys Lys Gly Gln
        195                 200                 205

Ser Tyr Gly Thr Asp Pro Thr Leu Met Tyr Ser Gln Asn Pro Gln Ser
    210                 215                 220

Lys Val Arg Pro Glu Val Ile Ala Gln Leu Tyr Lys Asp His Val Ile
225                 230                 235                 240

Pro Leu Thr Lys Lys Val Glu Val Asp Tyr Leu Leu Arg Arg Leu Glu
                245                 250                 255

Asp Glu Asp Glu Ala Val Val Ala Lys Tyr Lys
            260                 265


<210> SEQ ID NO 34
<211> LENGTH: 173
<212> TYPE: PRT
<213> ORGANISM: Escherichia coli (strain K12)

<400> SEQUENCE: 34

Met Ala Glu Lys Arg Asn Ile Phe Leu Val Gly Pro Met Gly Ala Gly
1               5                   10                  15

Lys Ser Thr Ile Gly Arg Gln Leu Ala Gln Gln Leu Asn Met Glu Phe
            20                  25                  30

Tyr Asp Ser Asp Gln Glu Ile Glu Lys Arg Thr Gly Ala Asp Val Gly
        35                  40                  45

Trp Val Phe Asp Leu Glu Gly Glu Glu Gly Phe Arg Asp Arg Glu Glu
    50                  55                  60

Lys Val Ile Asn Glu Leu Thr Glu Lys Gln Gly Ile Val Leu Ala Thr
65                  70                  75                  80

Gly Gly Gly Ser Val Lys Ser Arg Glu Thr Arg Asn Arg Leu Ser Ala
                85                  90                  95

Arg Gly Val Val Val Tyr Leu Glu Thr Thr Ile Glu Lys Gln Leu Ala
            100                 105                 110

Arg Thr Gln Arg Asp Lys Lys Arg Pro Leu Leu His Val Glu Thr Pro
        115                 120                 125

Pro Arg Glu Val Leu Glu Ala Leu Ala Asn Glu Arg Asn Pro Leu Tyr
    130                 135                 140

Glu Glu Ile Ala Asp Val Thr Ile Arg Thr Asp Asp Gln Ser Ala Lys
145                 150                 155                 160

Val Val Ala Asn Gln Ile Ile His Met Leu Glu Ser Asn
                165                 170


<210> SEQ ID NO 35
<211> LENGTH: 1588
<212> TYPE: PRT
<213> ORGANISM: Saccharomyces cerevisiae (strain ATCC 204508 S288c)
      (Baker's yeast)

<400> SEQUENCE: 35

Met Val Gln Leu Ala Lys Val Pro Ile Leu Gly Asn Asp Ile Ile His
1               5                   10                  15

Val Gly Tyr Asn Ile His Asp His Leu Val Glu Thr Ile Ile Lys His
            20                  25                  30

Cys Pro Ser Ser Thr Tyr Val Ile Cys Asn Asp Thr Asn Leu Ser Lys
        35                  40                  45
```

-continued

Val Pro Tyr Tyr Gln Gln Leu Val Leu Glu Phe Lys Ala Ser Leu Pro
50 55 60

Glu Gly Ser Arg Leu Leu Thr Tyr Val Val Lys Pro Gly Glu Thr Ser
65 70 75 80

Lys Ser Arg Glu Thr Lys Ala Gln Leu Glu Asp Tyr Leu Leu Val Glu
85 90 95

Gly Cys Thr Arg Asp Thr Val Met Val Ala Ile Gly Gly Gly Val Ile
100 105 110

Gly Asp Met Ile Gly Phe Val Ala Ser Thr Phe Met Arg Gly Val Arg
115 120 125

Val Val Gln Val Pro Thr Ser Leu Leu Ala Met Val Asp Ser Ser Ile
130 135 140

Gly Gly Lys Thr Ala Ile Asp Thr Pro Leu Gly Lys Asn Phe Ile Gly
145 150 155 160

Ala Phe Trp Gln Pro Lys Phe Val Leu Val Asp Ile Lys Trp Leu Glu
165 170 175

Thr Leu Ala Lys Arg Glu Phe Ile Asn Gly Met Ala Glu Val Ile Lys
180 185 190

Thr Ala Cys Ile Trp Asn Ala Asp Glu Phe Thr Arg Leu Glu Ser Asn
195 200 205

Ala Ser Leu Phe Leu Asn Val Val Asn Gly Ala Lys Asn Val Lys Val
210 215 220

Thr Asn Gln Leu Thr Asn Glu Ile Asp Glu Ile Ser Asn Thr Asp Ile
225 230 235 240

Glu Ala Met Leu Asp His Thr Tyr Lys Leu Val Leu Glu Ser Ile Lys
245 250 255

Val Lys Ala Glu Val Val Ser Ser Asp Glu Arg Glu Ser Ser Leu Arg
260 265 270

Asn Leu Leu Asn Phe Gly His Ser Ile Gly His Ala Tyr Glu Ala Ile
275 280 285

Leu Thr Pro Gln Ala Leu His Gly Glu Cys Val Ser Ile Gly Met Val
290 295 300

Lys Glu Ala Glu Leu Ser Arg Tyr Phe Gly Ile Leu Ser Pro Thr Gln
305 310 315 320

Val Ala Arg Leu Ser Lys Ile Leu Val Ala Tyr Gly Leu Pro Val Ser
325 330 335

Pro Asp Glu Lys Trp Phe Lys Glu Leu Thr Leu His Lys Lys Thr Pro
340 345 350

Leu Asp Ile Leu Leu Lys Lys Met Ser Ile Asp Lys Lys Asn Glu Gly
355 360 365

Ser Lys Lys Lys Val Val Ile Leu Glu Ser Ile Gly Lys Cys Tyr Gly
370 375 380

Asp Ser Ala Gln Phe Val Ser Asp Glu Asp Leu Arg Phe Ile Leu Thr
385 390 395 400

Asp Glu Thr Leu Val Tyr Pro Phe Lys Asp Ile Pro Ala Asp Gln Gln
405 410 415

Lys Val Val Ile Pro Pro Gly Ser Lys Ser Ile Ser Asn Arg Ala Leu
420 425 430

Ile Leu Ala Ala Leu Gly Glu Gly Gln Cys Lys Ile Lys Asn Leu Leu
435 440 445

His Ser Asp Asp Thr Lys His Met Leu Thr Ala Val His Glu Leu Lys
450 455 460

Gly Ala Thr Ile Ser Trp Glu Asp Asn Gly Glu Thr Val Val Val Glu

-continued

```
465                 470                 475                 480

Gly His Gly Gly Ser Thr Leu Ser Ala Cys Ala Asp Pro Leu Tyr Leu
                485                 490                 495

Gly Asn Ala Gly Thr Ala Ser Arg Phe Leu Thr Ser Leu Ala Ala Leu
            500                 505                 510

Val Asn Ser Thr Ser Ser Gln Lys Tyr Ile Val Leu Thr Gly Asn Ala
        515                 520                 525

Arg Met Gln Gln Arg Pro Ile Ala Pro Leu Val Asp Ser Leu Arg Ala
    530                 535                 540

Asn Gly Thr Lys Ile Glu Tyr Leu Asn Asn Glu Gly Ser Leu Pro Ile
545                 550                 555                 560

Lys Val Tyr Thr Asp Ser Val Phe Lys Gly Gly Arg Ile Glu Leu Ala
                565                 570                 575

Ala Thr Val Ser Ser Gln Tyr Val Ser Ser Ile Leu Met Cys Ala Pro
            580                 585                 590

Tyr Ala Glu Glu Pro Val Thr Leu Ala Leu Val Gly Gly Lys Pro Ile
        595                 600                 605

Ser Lys Leu Tyr Val Asp Met Thr Ile Lys Met Met Glu Lys Phe Gly
    610                 615                 620

Ile Asn Val Glu Thr Ser Thr Thr Glu Pro Tyr Thr Tyr Tyr Ile Pro
625                 630                 635                 640

Lys Gly His Tyr Ile Asn Pro Ser Glu Tyr Val Ile Glu Ser Asp Ala
                645                 650                 655

Ser Ser Ala Thr Tyr Pro Leu Ala Phe Ala Ala Met Thr Gly Thr Thr
            660                 665                 670

Val Thr Val Pro Asn Ile Gly Phe Glu Ser Leu Gln Gly Asp Ala Arg
        675                 680                 685

Phe Ala Arg Asp Val Leu Lys Pro Met Gly Cys Lys Ile Thr Gln Thr
    690                 695                 700

Ala Thr Ser Thr Thr Val Ser Gly Pro Pro Val Gly Thr Leu Lys Pro
705                 710                 715                 720

Leu Lys His Val Asp Met Glu Pro Met Thr Asp Ala Phe Leu Thr Ala
                725                 730                 735

Cys Val Val Ala Ala Ile Ser His Asp Ser Asp Pro Asn Ser Ala Asn
            740                 745                 750

Thr Thr Thr Ile Glu Gly Ile Ala Asn Gln Arg Val Lys Glu Cys Asn
        755                 760                 765

Arg Ile Leu Ala Met Ala Thr Glu Leu Ala Lys Phe Gly Val Lys Thr
    770                 775                 780

Thr Glu Leu Pro Asp Gly Ile Gln Val His Gly Leu Asn Ser Ile Lys
785                 790                 795                 800

Asp Leu Lys Val Pro Ser Asp Ser Ser Gly Pro Val Gly Val Cys Thr
                805                 810                 815

Tyr Asp Asp His Arg Val Ala Met Ser Phe Ser Leu Leu Ala Gly Met
            820                 825                 830

Val Asn Ser Gln Asn Glu Arg Asp Glu Val Ala Asn Pro Val Arg Ile
        835                 840                 845

Leu Glu Arg His Cys Thr Gly Lys Thr Trp Pro Gly Trp Trp Asp Val
    850                 855                 860

Leu His Ser Glu Leu Gly Ala Lys Leu Asp Gly Ala Glu Pro Leu Glu
865                 870                 875                 880

Cys Thr Ser Lys Lys Asn Ser Lys Lys Ser Val Val Ile Ile Gly Met
                885                 890                 895
```

```
Arg Ala Ala Gly Lys Thr Thr Ile Ser Lys Trp Cys Ala Ser Ala Leu
            900                 905                 910

Gly Tyr Lys Leu Val Asp Leu Asp Glu Leu Phe Glu Gln Gln His Asn
        915                 920                 925

Asn Gln Ser Val Lys Gln Phe Val Val Glu Asn Gly Trp Glu Lys Phe
    930                 935                 940

Arg Glu Glu Glu Thr Arg Ile Phe Lys Glu Val Ile Gln Asn Tyr Gly
945                 950                 955                 960

Asp Asp Gly Tyr Val Phe Ser Thr Gly Gly Gly Ile Val Glu Ser Ala
                965                 970                 975

Glu Ser Arg Lys Ala Leu Lys Asp Phe Ala Ser Ser Gly Gly Tyr Val
            980                 985                 990

Leu His Leu His Arg Asp Ile Glu  Glu Thr Ile Val Phe  Leu Gln Ser
        995                 1000                1005

Asp Pro  Ser Arg Pro Ala Tyr  Val Glu Glu Ile Arg  Glu Val Trp
    1010                 1015                1020

Asn Arg  Arg Glu Gly Trp Tyr  Lys Glu Cys Ser Asn  Phe Ser Phe
    1025                 1030                1035

Phe Ala  Pro His Cys Ser Ala  Glu Ala Glu Phe Gln  Ala Leu Arg
    1040                 1045                1050

Arg Ser  Phe Ser Lys Tyr Ile  Ala Thr Ile Thr Gly  Val Arg Glu
    1055                 1060                1065

Ile Glu  Ile Pro Ser Gly Arg  Ser Ala Phe Val Cys  Leu Thr Phe
    1070                 1075                1080

Asp Asp  Leu Thr Glu Gln Thr  Glu Asn Leu Thr Pro  Ile Cys Tyr
    1085                 1090                1095

Gly Cys  Glu Ala Val Glu Val  Arg Val Asp His Leu  Ala Asn Tyr
    1100                 1105                1110

Ser Ala  Asp Phe Val Ser Lys  Gln Leu Ser Ile Leu  Arg Lys Ala
    1115                 1120                1125

Thr Asp  Ser Ile Pro Ile Ile  Phe Thr Val Arg Thr  Met Lys Gln
    1130                 1135                1140

Gly Gly  Asn Phe Pro Asp Glu  Glu Phe Lys Thr Leu  Arg Glu Leu
    1145                 1150                1155

Tyr Asp  Ile Ala Leu Lys Asn  Gly Val Glu Phe Leu  Asp Leu Glu
    1160                 1165                1170

Leu Thr  Leu Pro Thr Asp Ile  Gln Tyr Glu Val Ile  Asn Lys Arg
    1175                 1180                1185

Gly Asn  Thr Lys Ile Ile Gly  Ser His His Asp Phe  Gln Gly Leu
    1190                 1195                1200

Tyr Ser  Trp Asp Asp Ala Glu  Trp Glu Asn Arg Phe  Asn Gln Ala
    1205                 1210                1215

Leu Thr  Leu Asp Val Asp Val  Val Lys Phe Val Gly  Thr Ala Val
    1220                 1225                1230

Asn Phe  Glu Asp Asn Leu Arg  Leu Glu His Phe Arg  Asp Thr His
    1235                 1240                1245

Lys Asn  Lys Pro Leu Ile Ala  Val Asn Met Thr Ser  Lys Gly Ser
    1250                 1255                1260

Ile Ser  Arg Val Leu Asn Asn  Val Leu Thr Pro Val  Thr Ser Asp
    1265                 1270                1275

Leu Leu  Pro Asn Ser Ala Ala  Pro Gly Gln Leu Thr  Val Ala Gln
    1280                 1285                1290
```

```
Ile Asn  Lys Met Tyr Thr Ser  Met Gly Gly Ile Glu  Pro Lys Glu
    1295                 1300                 1305

Leu Phe  Val Val Gly Lys Pro  Ile Gly His Ser Arg  Ser Pro Ile
    1310                 1315                 1320

Leu His  Asn Thr Gly Tyr Glu  Ile Leu Gly Leu Pro  His Lys Phe
    1325                 1330                 1335

Asp Lys  Phe Glu Thr Glu Ser  Ala Gln Leu Val Lys  Glu Lys Leu
    1340                 1345                 1350

Leu Asp  Gly Asn Lys Asn Phe  Gly Gly Ala Ala Val  Thr Ile Pro
    1355                 1360                 1365

Leu Lys  Leu Asp Ile Met Gln  Tyr Met Asp Glu Leu  Thr Asp Ala
    1370                 1375                 1380

Ala Lys  Val Ile Gly Ala Val  Asn Thr Val Ile Pro  Leu Gly Asn
    1385                 1390                 1395

Lys Lys  Phe Lys Gly Asp Asn  Thr Asp Trp Leu Gly  Ile Arg Asn
    1400                 1405                 1410

Ala Leu  Ile Asn Asn Gly Val  Pro Glu Tyr Val Gly  His Thr Ala
    1415                 1420                 1425

Gly Leu  Val Ile Gly Ala Gly  Gly Thr Ser Arg Ala  Ala Leu Tyr
    1430                 1435                 1440

Ala Leu  His Ser Leu Gly Cys  Lys Lys Ile Phe Ile  Ile Asn Arg
    1445                 1450                 1455

Thr Thr  Ser Lys Leu Lys Pro  Leu Ile Glu Ser Leu  Pro Ser Glu
    1460                 1465                 1470

Phe Asn  Ile Ile Gly Ile Glu  Ser Thr Lys Ser Ile  Glu Glu Ile
    1475                 1480                 1485

Lys Glu  His Val Gly Val Ala  Val Ser Cys Val Pro  Ala Asp Lys
    1490                 1495                 1500

Pro Leu  Asp Asp Glu Leu Leu  Ser Lys Leu Glu Arg  Phe Leu Val
    1505                 1510                 1515

Lys Gly  Ala His Ala Ala Phe  Val Pro Thr Leu Leu  Glu Ala Ala
    1520                 1525                 1530

Tyr Lys  Pro Ser Val Thr Pro  Val Met Thr Ile Ser  Gln Asp Lys
    1535                 1540                 1545

Tyr Gln  Trp His Val Val Pro  Gly Ser Gln Met Leu  Val His Gln
    1550                 1555                 1560

Gly Val  Ala Gln Phe Glu Lys  Trp Thr Gly Phe Lys  Gly Pro Phe
    1565                 1570                 1575

Lys Ala  Ile Phe Asp Ala Val  Thr Lys Glu
    1580                 1585
```

<210> SEQ ID NO 36
<211> LENGTH: 454
<212> TYPE: PRT
<213> ORGANISM: Homo sapiens (Human)

<400> SEQUENCE: 36

```
Met Asp Pro Tyr Met Ile Gln Met Ser Ser Lys Gly Asn Leu Pro Ser
1               5                   10                  15

Ile Leu Asp Val His Val Asn Val Gly Gly Arg Ser Ser Val Pro Gly
            20                  25                  30

Lys Met Lys Gly Arg Lys Ala Arg Trp Ser Val Arg Pro Ser Asp Met
        35                  40                  45

Ala Lys Lys Thr Phe Asn Pro Ile Arg Ala Ile Val Asp Asn Met Lys
    50                  55                  60
```

```
Val Lys Pro Asn Pro Asn Lys Thr Met Ile Ser Leu Ser Ile Gly Asp
65                  70                  75                  80

Pro Thr Val Phe Gly Asn Leu Pro Thr Asp Pro Glu Val Thr Gln Ala
                85                  90                  95

Met Lys Asp Ala Leu Asp Ser Gly Lys Tyr Asn Gly Tyr Ala Pro Ser
            100                 105                 110

Ile Gly Phe Leu Ser Ser Arg Glu Glu Ile Ala Ser Tyr Tyr His Cys
        115                 120                 125

Pro Glu Ala Pro Leu Glu Ala Lys Asp Val Ile Leu Thr Ser Gly Cys
    130                 135                 140

Ser Gln Ala Ile Asp Leu Cys Leu Ala Val Leu Ala Asn Pro Gly Gln
145                 150                 155                 160

Asn Ile Leu Val Pro Arg Pro Gly Phe Ser Leu Tyr Lys Thr Leu Ala
                165                 170                 175

Glu Ser Met Gly Ile Glu Val Lys Leu Tyr Asn Leu Leu Pro Glu Lys
            180                 185                 190

Ser Trp Glu Ile Asp Leu Lys Gln Leu Glu Tyr Leu Ile Asp Glu Lys
        195                 200                 205

Thr Ala Cys Leu Ile Val Asn Asn Pro Ser Asn Pro Cys Gly Ser Val
    210                 215                 220

Phe Ser Lys Arg His Leu Gln Lys Ile Leu Ala Val Ala Ala Arg Gln
225                 230                 235                 240

Cys Val Pro Ile Leu Ala Asp Glu Ile Tyr Gly Asp Met Val Phe Ser
                245                 250                 255

Asp Cys Lys Tyr Glu Pro Leu Ala Thr Leu Ser Thr Asp Val Pro Ile
            260                 265                 270

Leu Ser Cys Gly Gly Leu Ala Lys Arg Trp Leu Val Pro Gly Trp Arg
        275                 280                 285

Leu Gly Trp Ile Leu Ile His Asp Arg Arg Asp Ile Phe Gly Asn Glu
    290                 295                 300

Ile Arg Asp Gly Leu Val Lys Leu Ser Gln Arg Ile Leu Gly Pro Cys
305                 310                 315                 320

Thr Ile Val Gln Gly Ala Leu Lys Ser Ile Leu Cys Arg Thr Pro Gly
                325                 330                 335

Glu Phe Tyr His Asn Thr Leu Ser Phe Leu Lys Ser Asn Ala Asp Leu
            340                 345                 350

Cys Tyr Gly Ala Leu Ala Ala Ile Pro Gly Leu Arg Pro Val Arg Pro
        355                 360                 365

Ser Gly Ala Met Tyr Leu Met Val Gly Ile Glu Met Glu His Phe Pro
    370                 375                 380

Glu Phe Glu Asn Asp Val Glu Phe Thr Glu Arg Leu Val Ala Glu Gln
385                 390                 395                 400

Ser Val His Cys Leu Pro Ala Thr Cys Phe Glu Tyr Pro Asn Phe Ile
                405                 410                 415

Arg Val Val Ile Thr Val Pro Glu Val Met Met Leu Glu Ala Cys Ser
            420                 425                 430

Arg Ile Gln Glu Phe Cys Glu Gln His Tyr His Cys Ala Glu Gly Ser
        435                 440                 445

Gln Glu Glu Cys Asp Lys
    450
```

<210> SEQ ID NO 37
<211> LENGTH: 1486

```
<212> TYPE: PRT
<213> ORGANISM: Escherichia coli (strain K12)

<400> SEQUENCE: 37

Met Leu Tyr Asp Lys Ser Leu Glu Arg Asp Asn Cys Gly Phe Gly Leu
1               5                   10                  15

Ile Ala His Ile Glu Gly Glu Pro Ser His Lys Val Val Arg Thr Ala
            20                  25                  30

Ile His Ala Leu Ala Arg Met Gln His Arg Gly Ala Ile Leu Ala Asp
        35                  40                  45

Gly Lys Thr Gly Asp Gly Cys Gly Leu Leu Leu Gln Lys Pro Asp Arg
    50                  55                  60

Phe Phe Arg Ile Val Ala Gln Glu Arg Gly Trp Arg Leu Ala Lys Asn
65                  70                  75                  80

Tyr Ala Val Gly Met Leu Phe Leu Asn Lys Asp Pro Glu Leu Ala Ala
                85                  90                  95

Ala Ala Arg Arg Ile Val Glu Glu Glu Leu Gln Arg Glu Thr Leu Ser
            100                 105                 110

Ile Val Gly Trp Arg Asp Val Pro Thr Asn Glu Gly Val Leu Gly Glu
        115                 120                 125

Ile Ala Leu Ser Ser Leu Pro Arg Ile Glu Gln Ile Phe Val Asn Ala
    130                 135                 140

Pro Ala Gly Trp Arg Pro Arg Asp Met Glu Arg Arg Leu Phe Ile Ala
145                 150                 155                 160

Arg Arg Arg Ile Glu Lys Arg Leu Glu Ala Asp Lys Asp Phe Tyr Val
                165                 170                 175

Cys Ser Leu Ser Asn Leu Val Asn Ile Tyr Lys Gly Leu Cys Met Pro
            180                 185                 190

Thr Asp Leu Pro Arg Phe Tyr Leu Asp Leu Ala Asp Leu Arg Leu Glu
        195                 200                 205

Ser Ala Ile Cys Leu Phe His Gln Arg Phe Ser Thr Asn Thr Val Pro
    210                 215                 220

Arg Trp Pro Leu Ala Gln Pro Phe Arg Tyr Leu Ala His Asn Gly Glu
225                 230                 235                 240

Ile Asn Thr Ile Thr Gly Asn Arg Gln Trp Ala Arg Ala Arg Thr Tyr
                245                 250                 255

Lys Phe Gln Thr Pro Leu Ile Pro Asp Leu His Asp Ala Ala Pro Phe
            260                 265                 270

Val Asn Glu Thr Gly Ser Asp Ser Ser Ser Met Asp Asn Met Leu Glu
        275                 280                 285

Leu Leu Leu Ala Gly Gly Met Asp Ile Ile Arg Ala Met Arg Leu Leu
    290                 295                 300

Val Pro Pro Ala Trp Gln Asn Asn Pro Asp Met Asp Pro Glu Leu Arg
305                 310                 315                 320

Ala Phe Phe Asp Phe Asn Ser Met His Met Glu Pro Trp Asp Gly Pro
                325                 330                 335

Ala Gly Ile Val Met Ser Asp Gly Arg Phe Ala Ala Cys Asn Leu Asp
            340                 345                 350

Arg Asn Gly Leu Arg Pro Ala Arg Tyr Val Ile Thr Lys Asp Lys Leu
        355                 360                 365

Ile Thr Cys Ala Ser Glu Val Gly Ile Trp Asp Tyr Gln Pro Asp Glu
    370                 375                 380

Val Val Glu Lys Gly Arg Val Gly Pro Gly Glu Leu Met Val Ile Asp
385                 390                 395                 400
```

```
Thr Arg Ser Gly Arg Ile Leu His Ser Ala Glu Thr Asp Asp Asp Leu
                405                 410                 415

Lys Ser Arg His Pro Tyr Lys Glu Trp Met Glu Lys Asn Val Arg Arg
            420                 425                 430

Leu Val Pro Phe Glu Asp Leu Pro Asp Glu Glu Val Gly Ser Arg Glu
        435                 440                 445

Leu Asp Asp Asp Thr Leu Ala Ser Tyr Gln Lys Gln Phe Asn Tyr Ser
    450                 455                 460

Ala Glu Glu Leu Asp Ser Val Ile Arg Val Leu Gly Glu Asn Gly Gln
465                 470                 475                 480

Glu Ala Val Gly Ser Met Gly Asp Asp Thr Pro Phe Ala Val Leu Ser
                485                 490                 495

Ser Gln Pro Arg Ile Ile Tyr Asp Tyr Phe Arg Gln Gln Phe Ala Gln
            500                 505                 510

Val Thr Asn Pro Pro Ile Asp Pro Leu Arg Glu Ala His Val Met Ser
        515                 520                 525

Leu Ala Thr Ser Ile Gly Arg Glu Met Asn Val Phe Cys Glu Ala Glu
    530                 535                 540

Gly Gln Ala His Arg Leu Ser Phe Lys Ser Pro Ile Leu Leu Tyr Ser
545                 550                 555                 560

Asp Phe Lys Gln Leu Thr Thr Met Lys Glu Glu His Tyr Arg Ala Asp
                565                 570                 575

Thr Leu Asp Ile Thr Phe Asp Val Thr Lys Thr Thr Leu Glu Ala Thr
            580                 585                 590

Val Lys Glu Leu Cys Asp Lys Ala Glu Lys Met Val Arg Ser Gly Thr
        595                 600                 605

Val Leu Leu Val Leu Ser Asp Arg Asn Ile Ala Lys Asp Arg Leu Pro
    610                 615                 620

Val Pro Ala Pro Met Ala Val Gly Ala Ile Gln Thr Arg Leu Val Asp
625                 630                 635                 640

Gln Ser Leu Arg Cys Asp Ala Asn Ile Ile Val Glu Thr Ala Ser Ala
                645                 650                 655

Arg Asp Pro His His Phe Ala Val Leu Leu Gly Phe Gly Ala Thr Ala
            660                 665                 670

Ile Tyr Pro Tyr Leu Ala Tyr Glu Thr Leu Gly Arg Leu Val Asp Thr
        675                 680                 685

His Ala Ile Ala Lys Asp Tyr Arg Thr Val Met Leu Asn Tyr Arg Asn
    690                 695                 700

Gly Ile Asn Lys Gly Leu Tyr Lys Ile Met Ser Lys Met Gly Ile Ser
705                 710                 715                 720

Thr Ile Ala Ser Tyr Arg Cys Ser Lys Leu Phe Glu Ala Val Gly Leu
                725                 730                 735

His Asp Asp Val Val Gly Leu Cys Phe Gln Gly Ala Val Ser Arg Ile
            740                 745                 750

Gly Gly Ala Ser Phe Glu Asp Phe Gln Gln Asp Leu Leu Asn Leu Ser
        755                 760                 765

Lys Arg Ala Trp Leu Ala Arg Lys Pro Ile Ser Gln Gly Gly Leu Leu
    770                 775                 780

Lys Tyr Val His Gly Gly Glu Tyr His Ala Tyr Asn Pro Asp Val Val
785                 790                 795                 800

Arg Thr Leu Gln Gln Ala Val Gln Ser Gly Glu Tyr Ser Asp Tyr Gln
                805                 810                 815
```

```
Glu Tyr Ala Lys Leu Val Asn Glu Arg Pro Ala Thr Thr Leu Arg Asp
            820                 825                 830

Leu Leu Ala Ile Thr Pro Gly Glu Asn Ala Val Asn Ile Ala Asp Val
        835                 840                 845

Glu Pro Ala Ser Glu Leu Phe Lys Arg Phe Asp Thr Ala Ala Met Ser
    850                 855                 860

Ile Gly Ala Leu Ser Pro Glu Ala His Glu Ala Leu Ala Glu Ala Met
865                 870                 875                 880

Asn Ser Ile Gly Gly Asn Ser Asn Ser Gly Glu Gly Gly Glu Asp Pro
                885                 890                 895

Ala Arg Tyr Gly Thr Asn Lys Val Ser Arg Ile Lys Gln Val Ala Ser
            900                 905                 910

Gly Arg Phe Gly Val Thr Pro Ala Tyr Leu Val Asn Ala Asp Val Ile
        915                 920                 925

Gln Ile Lys Val Ala Gln Gly Ala Lys Pro Gly Glu Gly Gly Gln Leu
    930                 935                 940

Pro Gly Asp Lys Val Thr Pro Tyr Ile Ala Lys Leu Arg Tyr Ser Val
945                 950                 955                 960

Pro Gly Val Thr Leu Ile Ser Pro Pro Pro His His Asp Ile Tyr Ser
                965                 970                 975

Ile Glu Asp Leu Ala Gln Leu Ile Phe Asp Leu Lys Gln Val Asn Pro
            980                 985                 990

Lys Ala Met Ile Ser Val Lys Leu  Val Ser Glu Pro Gly  Val Gly Thr
        995                 1000                 1005

Ile Ala  Thr Gly Val Ala Lys  Ala Tyr Ala Asp Leu  Ile Thr Ile
    1010                 1015                 1020

Ala Gly  Tyr Asp Gly Gly Thr  Gly Ala Ser Pro Leu  Ser Ser Val
    1025                 1030                 1035

Lys Tyr  Ala Gly Cys Pro Trp  Glu Leu Gly Leu Val  Glu Thr Gln
    1040                 1045                 1050

Gln Ala  Leu Val Ala Asn Gly  Leu Arg His Lys Ile  Arg Leu Gln
    1055                 1060                 1065

Val Asp  Gly Gly Leu Lys Thr  Gly Val Asp Ile Ile  Lys Ala Ala
    1070                 1075                 1080

Ile Leu  Gly Ala Glu Ser Phe  Gly Phe Gly Thr Gly  Pro Met Val
    1085                 1090                 1095

Ala Leu  Gly Cys Lys Tyr Leu  Arg Ile Cys His Leu  Asn Asn Cys
    1100                 1105                 1110

Ala Thr  Gly Val Ala Thr Gln  Asp Asp Lys Leu Arg  Lys Asn His
    1115                 1120                 1125

Tyr His  Gly Leu Pro Phe Lys  Val Thr Asn Tyr Phe  Glu Phe Ile
    1130                 1135                 1140

Ala Arg  Glu Thr Arg Glu Leu  Met Ala Gln Leu Gly  Val Thr Arg
    1145                 1150                 1155

Leu Val  Asp Leu Ile Gly Arg  Thr Asp Leu Leu Lys  Glu Leu Asp
    1160                 1165                 1170

Gly Phe  Thr Ala Lys Gln Gln  Lys Leu Ala Leu Ser  Lys Leu Leu
    1175                 1180                 1185

Glu Thr  Ala Glu Pro His Pro  Gly Lys Ala Leu Tyr  Cys Thr Glu
    1190                 1195                 1200

Asn Asn  Pro Pro Phe Asp Asn  Gly Leu Leu Asn Ala  Gln Leu Leu
    1205                 1210                 1215

Gln Gln  Ala Lys Pro Phe Val  Asp Glu Arg Gln Ser  Lys Thr Phe
```

```
    1220                1225                1230

Trp Phe  Asp Ile Arg Asn Thr  Asp Arg Ser Val Gly  Ala Ser Leu
    1235                1240                1245

Ser Gly  Tyr Ile Ala Gln Thr  His Gly Asp Gln Gly  Leu Ala Ala
    1250                1255                1260

Asp Pro  Ile Lys Ala Tyr Phe  Asn Gly Thr Ala Gly  Gln Ser Phe
    1265                1270                1275

Gly Val  Trp Asn Ala Gly Gly  Val Glu Leu Tyr Leu  Thr Gly Asp
    1280                1285                1290

Ala Asn  Asp Tyr Val Gly Lys  Gly Met Ala Gly Gly  Leu Ile Ala
    1295                1300                1305

Ile Arg  Pro Pro Val Gly Ser  Ala Phe Arg Ser His  Glu Ala Ser
    1310                1315                1320

Ile Ile  Gly Asn Thr Cys Leu  Tyr Gly Ala Thr Gly  Gly Arg Leu
    1325                1330                1335

Tyr Ala  Ala Gly Arg Ala Gly  Glu Arg Phe Gly Val  Arg Asn Ser
    1340                1345                1350

Gly Ala  Ile Thr Val Val Glu  Gly Ile Gly Asp Asn  Gly Cys Glu
    1355                1360                1365

Tyr Met  Thr Gly Gly Ile Val  Cys Ile Leu Gly Lys  Thr Gly Val
    1370                1375                1380

Asn Phe  Gly Ala Gly Met Thr  Gly Gly Phe Ala Tyr  Val Leu Asp
    1385                1390                1395

Glu Ser  Gly Asp Phe Arg Lys  Arg Val Asn Pro Glu  Leu Val Glu
    1400                1405                1410

Val Leu  Ser Val Asp Ala Leu  Ala Ile His Glu Glu  His Leu Arg
    1415                1420                1425

Gly Leu  Ile Thr Glu His Val  Gln His Thr Gly Ser  Gln Arg Gly
    1430                1435                1440

Glu Glu  Ile Leu Ala Asn Trp  Ser Thr Phe Ala Thr  Lys Phe Ala
    1445                1450                1455

Leu Val  Lys Pro Lys Ser Ser  Asp Val Lys Ala Leu  Leu Gly His
    1460                1465                1470

Arg Ser  Arg Ser Ala Ala Glu  Leu Arg Val Gln Ala  Gln
    1475                1480                1485


<210> SEQ ID NO 38
<211> LENGTH: 472
<212> TYPE: PRT
<213> ORGANISM: Escherichia coli (strain K12)

<400> SEQUENCE: 38

Met Ser Gln Asn Val Tyr Gln Phe Ile Asp Leu Gln Arg Val Asp Pro
1               5                   10                  15

Pro Lys Lys Pro Leu Lys Ile Arg Lys Ile Glu Phe Val Glu Ile Tyr
            20                  25                  30

Glu Pro Phe Ser Glu Gly Gln Ala Lys Ala Gln Ala Asp Arg Cys Leu
        35                  40                  45

Ser Cys Gly Asn Pro Tyr Cys Glu Trp Lys Cys Pro Val His Asn Tyr
    50                  55                  60

Ile Pro Asn Trp Leu Lys Leu Ala Asn Glu Gly Arg Ile Phe Glu Ala
65                  70                  75                  80

Ala Glu Leu Ser His Gln Thr Asn Thr Leu Pro Glu Val Cys Gly Arg
                85                  90                  95
```

```
Val Cys Pro Gln Asp Arg Leu Cys Glu Gly Ser Cys Thr Leu Asn Asp
            100                 105                 110

Glu Phe Gly Ala Val Thr Ile Gly Asn Ile Glu Arg Tyr Ile Asn Asp
        115                 120                 125

Lys Ala Phe Glu Met Gly Trp Arg Pro Asp Met Ser Gly Val Lys Gln
    130                 135                 140

Thr Gly Lys Lys Val Ala Ile Ile Gly Ala Gly Pro Ala Gly Leu Ala
145                 150                 155                 160

Cys Ala Asp Val Leu Thr Arg Asn Gly Val Lys Ala Val Val Phe Asp
                165                 170                 175

Arg His Pro Glu Ile Gly Gly Leu Leu Thr Phe Gly Ile Pro Ala Phe
            180                 185                 190

Lys Leu Glu Lys Glu Val Met Thr Arg Arg Arg Glu Ile Phe Thr Gly
        195                 200                 205

Met Gly Ile Glu Phe Lys Leu Asn Thr Glu Val Gly Arg Asp Val Gln
    210                 215                 220

Leu Asp Asp Leu Leu Ser Asp Tyr Asp Ala Val Phe Leu Gly Val Gly
225                 230                 235                 240

Thr Tyr Gln Ser Met Arg Gly Gly Leu Glu Asn Glu Asp Ala Asp Gly
                245                 250                 255

Val Tyr Ala Ala Leu Pro Phe Leu Ile Ala Asn Thr Lys Gln Leu Met
            260                 265                 270

Gly Phe Gly Glu Thr Arg Asp Glu Pro Phe Val Ser Met Glu Gly Lys
        275                 280                 285

Arg Val Val Val Leu Gly Gly Gly Asp Thr Ala Met Asp Cys Val Arg
    290                 295                 300

Thr Ser Val Arg Gln Gly Ala Lys His Val Thr Cys Ala Tyr Arg Arg
305                 310                 315                 320

Asp Glu Glu Asn Met Pro Gly Ser Arg Arg Glu Val Lys Asn Ala Arg
                325                 330                 335

Glu Glu Gly Val Glu Phe Lys Phe Asn Val Gln Pro Leu Gly Ile Glu
            340                 345                 350

Val Asn Gly Asn Gly Lys Val Ser Gly Val Lys Met Val Arg Thr Glu
        355                 360                 365

Met Gly Glu Pro Asp Ala Lys Gly Arg Arg Arg Ala Glu Ile Val Ala
    370                 375                 380

Gly Ser Glu His Ile Val Pro Ala Asp Ala Val Ile Met Ala Phe Gly
385                 390                 395                 400

Phe Arg Pro His Asn Met Glu Trp Leu Ala Lys His Ser Val Glu Leu
                405                 410                 415

Asp Ser Gln Gly Arg Ile Ile Ala Pro Glu Gly Ser Asp Asn Ala Phe
            420                 425                 430

Gln Thr Ser Asn Pro Lys Ile Phe Ala Gly Gly Asp Ile Val Arg Gly
        435                 440                 445

Ser Asp Leu Val Val Thr Ala Ile Ala Glu Gly Arg Lys Ala Ala Asp
    450                 455                 460

Gly Ile Met Asn Trp Leu Glu Val
465                 470
```

```
<210> SEQ ID NO 39
<211> LENGTH: 370
<212> TYPE: PRT
<213> ORGANISM: Saccharomyces cerevisiae (strain ATCC 204508 S288c)
      (Baker's yeast)
```

<400> SEQUENCE: 39

```
Met Ala Glu Ala Ser Ile Glu Lys Thr Gln Ile Leu Gln Lys Tyr Leu
1               5                   10                  15

Glu Leu Asp Gln Arg Gly Arg Ile Ile Ala Glu Tyr Val Trp Ile Asp
            20                  25                  30

Gly Thr Gly Asn Leu Arg Ser Lys Gly Arg Thr Leu Lys Lys Arg Ile
        35                  40                  45

Thr Ser Ile Asp Gln Leu Pro Glu Trp Asn Phe Asp Gly Ser Ser Thr
    50                  55                  60

Asn Gln Ala Pro Gly His Asp Ser Asp Ile Tyr Leu Lys Pro Val Ala
65                  70                  75                  80

Tyr Tyr Pro Asp Pro Phe Arg Arg Gly Asp Asn Ile Val Val Leu Ala
                85                  90                  95

Ala Cys Tyr Asn Asn Asp Gly Thr Pro Asn Lys Phe Asn His Arg His
            100                 105                 110

Glu Ala Ala Lys Leu Phe Ala Ala His Lys Asp Glu Glu Ile Trp Phe
        115                 120                 125

Gly Leu Glu Gln Glu Tyr Thr Leu Phe Asp Met Tyr Asp Asp Val Tyr
    130                 135                 140

Gly Trp Pro Lys Gly Gly Tyr Pro Ala Pro Gln Gly Pro Tyr Tyr Cys
145                 150                 155                 160

Gly Val Gly Ala Gly Lys Val Tyr Ala Arg Asp Met Ile Glu Ala His
                165                 170                 175

Tyr Arg Ala Cys Leu Tyr Ala Gly Leu Glu Ile Ser Gly Ile Asn Ala
            180                 185                 190

Glu Val Met Pro Ser Gln Trp Glu Phe Gln Val Gly Pro Cys Thr Gly
        195                 200                 205

Ile Asp Met Gly Asp Gln Leu Trp Met Ala Arg Tyr Phe Leu His Arg
    210                 215                 220

Val Ala Glu Glu Phe Gly Ile Lys Ile Ser Phe His Pro Lys Pro Leu
225                 230                 235                 240

Lys Gly Asp Trp Asn Gly Ala Gly Cys His Thr Asn Val Ser Thr Lys
                245                 250                 255

Glu Met Arg Gln Pro Gly Gly Met Lys Tyr Ile Glu Gln Ala Ile Glu
            260                 265                 270

Lys Leu Ser Lys Arg His Ala Glu His Ile Lys Leu Tyr Gly Ser Asp
        275                 280                 285

Asn Asp Met Arg Leu Thr Gly Arg His Glu Thr Ala Ser Met Thr Ala
    290                 295                 300

Phe Ser Ser Gly Val Ala Asn Arg Gly Ser Ser Ile Arg Ile Pro Arg
305                 310                 315                 320

Ser Val Ala Lys Glu Gly Tyr Gly Tyr Phe Glu Asp Arg Arg Pro Ala
                325                 330                 335

Ser Asn Ile Asp Pro Tyr Leu Val Thr Gly Ile Met Cys Glu Thr Val
            340                 345                 350

Cys Gly Ala Ile Asp Asn Ala Asp Met Thr Lys Glu Phe Glu Arg Glu
        355                 360                 365

Ser Ser
    370
```

<210> SEQ ID NO 40
<211> LENGTH: 1875
<212> TYPE: DNA
<213> ORGANISM: Artificial
<220> FEATURE:
<223> OTHER INFORMATION: Codon-optimized and/or mutated sequence

<400> SEQUENCE: 40

```
atgtccgagt ccctgtctaa agacctcaac ctcaatgcac tgttcattgg tgacaaggcc     60
gagaatggcc agatctacaa ggccctgctt aacgagcttg tcgatgagca cctcggctgg    120
agacagaact atatgcctca ggacatgccc attattactc cagaagagaa atcttctgca    180
tcctttgagc acaccgtgaa caagaccaag gacgtcctct ctgagatttc ggcccgaatg    240
cgaacacatt ctgtgccctg gcataatgct ggcagatact ggggacacat gaactctgag    300
actctcatgc catcccttct ggcttacaat tttgcaatgc tgtggaatgg aaacaatgtc    360
gcctacgagt cctccccagc tacctcccag atggaggagg aggtcggcat ggagtttgca    420
aagctgatgt cctataaaga cggttggggt cacattgttg ctgatggttc tctcgccaat    480
ctcgaaggcc tgtggtacgc tcgaaatatc aagagccttc ctctggctat gaaggaggtg    540
acccccgagc tcgttgccgg taagtctgat tgggagctca tgaacctctc cactgaagag    600
attatgaacc tcctcgactc tgtgcctgag aaaatcgacg agattaaggc ccattcggct    660
cgttccggca agcatctgga gaagcttggc aagtggcttg tgccacagac gaagcactat    720
tcctggctta aggctgccga tatcatcggt attggcctgg accaagtgat ccctgtgccc    780
gttgatcaca actaccggat ggacatcaat gagctcgaaa agattgttcg aggactggcc    840
gccgagaaga ccccaatcct cggagtcgtg ggtgtcgttg gttccaccga ggagggagct    900
attgatggta tcgacaagat tgtcgctctc cgacgagtcc tcgagaagga tggaatttac    960
ttttacctcc acgttgacgc tgcctacgga ggctacggcc gagctatctt cctcgacgaa   1020
gacaataact ttattccttt tgaggatctt aaggatgtcc actacaagta taacgtcttt   1080
accgagaaca aagattacat cctggaagag gttcatagcg cctacaaggc tattgaggaa   1140
gctgagtcgg tcaccattga cccacacaag atgggttacg tcccctacag cgccggaggc   1200
attgttatta aggacattag aatgcgagac gttatctcct acttcgctac ctacgtgttt   1260
gagaagggcg ctgacatccc cgctcttctc ggagcctaca tcctggaagg ctctaaggcc   1320
ggagccacgg ccgcttctgt ctgggccgcc caccatgttc tgcccctgaa cgtgactggc   1380
tacggaaagc ttatgggtgc ctccattgag ggagcacacc gtttctacaa cttcctcaac   1440
gacctgtctt tcaaggttgg cgacaaggag atcgaagttc accctctcac ttaccctgat   1500
ttcaatatgg ttgactacgt ctttaaggag aagggcaacg atgacctcgt tgccatgaat   1560
aagctcaacc acgatgtgta cgattactcg tcctacgtca agggaagcat ctacggtaac   1620
gagttcctga cttcccacac ggacttcgct atccctgact atggaaacag cccccttcag   1680
ttcgtgaacc agctgggatt ttctgacgag gaatggaacc gagcaggtaa agtcaccgtg   1740
ctgcgagctt cggtcatgac cccctacatg aacaaagaag agcacttcga ggagtacgca   1800
gagaaaatca aggctgccct gcaggagaag cttgagaaga tttacgccga tcagctcctg   1860
gcatccgagg ctaaa                                                    1875
```

<210> SEQ ID NO 41
<211> LENGTH: 522
<212> TYPE: DNA
<213> ORGANISM: Artificial
<220> FEATURE:
<223> OTHER INFORMATION: Codon-optimized and/or mutated sequence

<400> SEQUENCE: 41

```
atgactcaac ccttattctt gattggcccg aggggttgtg gtaagacaac cgttggtatg      60
gccctggctg attctcttaa caggaggttc gtcgataccg atcaatggtt gcaatcacaa     120
cttaatatga ctgtcgcaga gattgttgag agagaggagt gggcaggttt tagggctaga     180
gaaacggcgg cattggaggc tgtaacagct ccgtctaccg tgattgcaac aggagggggt     240
attattttaa cggaatttaa tagacacttt atgcaaaata atggaattgt tgtatacctt     300
tgtgctccgg ttagtgtttt ggtaaacaga ttacaagcgg ccccagaaga agatttgaga     360
cctactttga ccgggaagcc actaagcgaa gaagttcagg aagtcttaga agaaagagat     420
gccctttaca gagaagttgc ccacatcata atcgatgcca ctaacgaacc atctcaggtg     480
atatctgaaa tacgttctgc gttggcccag acgattaatt gc                        522
```

<210> SEQ ID NO 42
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 42

```
atgagcgagt caccaatgtt tgcagctaat ggtatgccga aggtcaacca gggcgccgag      60
gaagacgtaa ggattcttgg atatgatccc ttagcatcac cagctttatt acaagttcaa     120
attccagcta cgcctactag tttagaaacg gctaaaagag gtagaagaga agccattgat     180
attatcacag gaaaggacga tagggtcttg gttatagttg ggccttgttc tatccacgat     240
ttggaagcag cacaggaata tgccctaaga ttgaaaaagc taagtgatga attgaagggt     300
gatctgtcaa ttattatgcg tgcatacctg gaaaagccta gaacaaccgt tggttggaaa     360
ggcctaatca atgaccccga tgtcaataat acgtttaata ttaataaagg attacaatca     420
gcgaggcaat tgttcgtgaa cttgacaaac attggtttgc ccattggttc cgaaatgcta     480
gataccattt ctcctcaata cttagccgac ttggtctctt tcggtgcgat aggagctaga     540
actaccgaat ctcagctgca tagagagctt gcatctggtc tgagctttcc agttggtttt     600
aaaaatggca ctgatggtac gcttaatgtt gctgtcgatg cttgccaggc cgcagctcat     660
tcacaccatt tcatgggcgt taccaagcat ggagtagcag ctataactac aaccaaagga     720
aatgagcatt gctttgtaat tttaagaggt ggaaagaagg gcactaatta cgacgccaaa     780
tctgttgcag aggccaaagc ccaattgcct gcaggtagta acggactaat gattgattac     840
agtcatggaa attcaaacaa agatttcaga aaccaaccca aagtaaacga cgtggtttgt     900
gaacaaattg ctaatggtga aaacgctatc accggtgtta tgatagaatc taacattaat     960
gaaggcaacc aaggcattcc agctgaaggt aaagctggtt tgaaatacgg tgtttctata    1020
accgacgcct gcataggatg ggaaacaact gaggacgtat tacgtaaatt agccgccgct    1080
gtgagacaaa gaagggaggt taacaaaaag                                     1110
```

<210> SEQ ID NO 43
<211> LENGTH: 1875
<212> TYPE: DNA
<213> ORGANISM: Artificial
<220> FEATURE:
<223> OTHER INFORMATION: Codon-optimized and/or mutated sequence

<400> SEQUENCE: 43

```
atgtctgagt cacttagcaa agatttaaac ttaaatgctt tgtttattgg ggataaggct      60
gaaaatggtc aaatttacaa agccctttta aatgaacttg tcgatgagca tttgggttgg     120
```

agacaaaact acatgccaca ggatatgcca ataatcacac cagaggagaa atctagcgct 180
agctttgaac atacagtcaa taaaacgaag gatgtcttgt ccgaaattag cgctaggatg 240
agaactcata gtgtgccatg gcataatgca ggtagatatt ggggacacat gaactcagaa 300
accttgatgc ccagcttact tgcgtacaat tttgctatgt tgtggaacgg gaataacgtt 360
gcatatgaat cctcccccgc tacatctcaa atggaggagg aggtaggaat ggaatttgca 420
aagctgatgt cctataaaga tggctggggc catattgttg ctgatggtag tttagcaaac 480
ttggaaggtc tttggtacgc aaggaacatt aaaagcctgc cattggccat gaaggaagtg 540
actccagaac tggtagcggg taagtccgat tgggagctga tgaacttgtc tactgaggag 600
ataatgaact tgttagactc cgttccagaa aagatcgatg aaattaaggc acacagcgca 660
aggtccggga aacatctaga aaaactaggg aaatggttgg ttccccaaac aaaacattat 720
tcttggttga aggcggccga cattattggt attggactag atcaagttat acctgtcccg 780
gttgaccaca actatagaat ggatattaat gaattagaaa agatagtgag ggtttagca 840 gcggaaaaga ctccaatctt aggtgtagtg ggggtggtcg gatccaccga agaaggtgca 900
attgatggaa tcgacaagat cgtagcacta aggcgtgtct tggaaaagga cggtatatac 960
ttctacttgc atgtcgacgc tgcctatggg ggttatggcc gtgcaatttt tctggacgaa 1020
gacaataatt tcatcccgtt tgaagatctt aaagatgtgc attataaata taatgttttt 1080
accgagaata aagactacat cttagaagaa gtacactctg catataaagc catcgaagaa 1140
gcggagagtg tcactataga ccctcataag atgggctatg tgccatactc tgctggtggt 1200
atcgttatta aagatataag aatgcgtgac gtaattagtt acttcgctac ctatgtgttt 1260
gagaagggtg cagatatccc tgcactgctt ggcgcttaca ttttggaagg ttcaaaagct 1320
ggtgcgactg cagctagcgt gtgggctgca catcatgtct taccattaaa tgttactggc 1380
tatggaaagt tgatgggtgc atcaatagaa ggcgctcacc gtttctacaa ctttttaaac 1440
gacctatcat ttaaagttgg tgacaaggag attgaggttc accctctaac ataccccgat 1500
ttcaatatgg ttgactatgt ctttaaagag aagggcaacg acgatttagt ggcgatgaat 1560
aagctaaatc atgatgtcta tgactacagt tcctacgtga agggtagcat ttacggtaac 1620
gaatttttaa ctagccatac agacttcgct ataccggact atggtaattc tccgttgcaa 1680
ttcgttaatc aactagggtt ctctgatgag gaatggaata gagcgggtaa agttaccgta 1740
ctacgtgcaa gtgtcatgac cccttatatg aataaggaag aacactttga agaatacgcc 1800
gaaaaaatta aggcagcact tcaggaaaag cttgaaaaaa tttatgcgga tcaattgtta 1860
gcaagtgaag cgaag 1875

<210> SEQ ID NO 44
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 44
atgagcgagt ctcccatgtt tgcggcgaac ggcatgccga aagttaacca gggtgcagaa 60
gaggatgtgc gtattctcgg ctacgacccg ttggcgtctc cagccctgtt gcaagttcaa 120
atcccagcca ccccgacgtc tctcgagact gctaagcgcg gtcgccgtga agccatcgat 180
attatcacgg gaaaagacga tcgcgttttg gtcatcgtgg gcccatgctc tatccacgac 240

```
ctggaagcag cacaggagta cgccttgcgc ttgaagaagc tttccgacga actcaagggc    300

gacctttcta tcatcatgcg tgcttacttg gagaagcccc gaaccaccgt cggatggaag    360

ggcttgatta atgatcctga tgttaataac acgttcaata ttaataaggg cttgcagtcc    420

gctcgtcaac tgttcgttaa cctgaccaat atcggccttc cgattggctc tgagatgttg    480

gataccatct cccctcagta cctcgctgat ctcgtttcct ttggcgcgat cggtgctcgt    540

accaccgaat ctcagctgca tcgcgagctg gcgtccggcc tctccttccc tgtcggtttt    600

aaaaatggca cggatggtac cttgaatgtc gcggtggatg catgtcaggc tgcggctcat    660

tcacatcatt tcatgggagt gaccttgcac ggagttgccg ctatcaccac tacgaaggga    720

aacgagcact gctttgtgat ccttcgtggt ggcaaaaaag gcaccaacta tgacgcaaag    780

tcggtggctg aggccaaagc ccagttgcct gcaggcagca atggactcat gattgactat    840

tcccatggaa actcaaacaa agactttcgc aaccagccaa aagtcaatga cgtggtgtgc    900

gaacaaatcg ctaacggtga aaatgcaatc accggcgtga tgatcgaaag caatattaat    960

gagggcaacc aaggcatccc ggctgagggc aaagcgggcc tgaaatacgg tgttagcatc   1020

accgatgcat gtatcggctg ggaaacaacg gaagacgttc tccgaaagct cgctgcggca   1080

gttcgccagc gccgcgaagt taacaagaag                                    1110
```

<210> SEQ ID NO 45
<211> LENGTH: 1875
<212> TYPE: DNA
<213> ORGANISM: Artificial
<220> FEATURE:
<223> OTHER INFORMATION: Codon-optimized and/or mutated sequence

<400> SEQUENCE: 45

```
atgtccgaat ccctttccaa agacctgaac ctcaacgcat tgttcattgg cgacaaggcc     60

gagaacggtc agatttacaa ggctctgctc aatgagctcg tggacgaaca tctgggctgg    120

cgtcagaact acatgcccca ggacatgccc atcatcaccc ccgaagagaa atctagcgcg    180

tcattcgaac acacggtaaa caaaacaaaa gatgtgctgt ctgaaatctc ggcccgcatg    240

cgcacacatt ccgtgccctg gcataacgcc ggccgctact ggggccatat gaattcagaa    300

accctcatgc cctcactgtt ggcatataat ttcgcgatgc tgtggaacgg taacaacgtt    360

gcgtatgaaa gctctccagc aacctcccag atggaagaag aagttggcat ggagttcgcg    420

aagctcatgt cgtataaaga tggttggggc catatcgtag ccgatggttc tctggcgaat    480

ttggagggct tgtggtatgc gcgtaacatc aagtccttgc cactggcaat gaaagaggtt    540

acaccagagc tcgtggccgg caagtccgat tgggagctga tgaacctctc aacagaggaa    600

attatgaacc ttctggactc ggtgcccgaa aaaatcgacg agatcaaggc ccactccgcc    660

cgttcgggca agcacctgga gaagttgggc aaatggttgg tccctcagac caaacactat    720

tcctggttga aagccgcgga tattatcgga atcggtctgg atcaagttat ccctgttccg    780

gtagaccata actaccgaat ggatattaac gagctcgaga agattgtccg cggcctggcc    840

gccgaaaaga cacccatcct gggtgtcgtt ggcgtcgttg gttcgactga agagggcgcc    900

attgacggca ttgacaagat cgtggcgttg cgccgcgttc ttgaaaagga tggcatttat    960

ttctaccttc acgtggacgc ggcttacggc ggctacggcc gcgccatctt tcttgacgaa   1020

gataataatt tcatcccctt cgaggatctc aaggacgtcc actataagta caacgtattc   1080

accgagaaca aagactacat tttggaggag gttcattccg cttataaggc gattgaggaa   1140

gcggagtccg ttacgattga tccgcacaag atgggctatg tgccttacag cgcgggcggc   1200
```

```
atcgtgatca aggatatccg tatgcgtgat gtcatttcct attttgccac ctacgtgttc   1260

gagaagggag cagatatccc tgccctgctc ggagcgtaca tcctggaagg ctcaaaagca   1320

ggtgctactg ctgcctcagt ttgggccgca caccacgtcc tcccattgaa cgtgaccggc   1380

tacggaaaat tgatgggtgc ctccattgaa ggcgcccacc gtttctacaa ctttctgaat   1440

gacctgagct tcaaggtcgg tgataaggaa atcgaagttc atccgctgac ctaccccgat   1500

tttaacatgg tcgattacgt atttaaagaa aaaggaaacg acgatctcgt ggcaatgaac   1560

aagctgaacc acgatgtgta tgattacagc tcttatgtga agggatcgat ttacggtaat   1620

gaattcttga cctcccatac cgatttcgca atcccagatt acggaaattc tcctttgcag   1680

ttcgttaacc agctgggctt ttctgacgag gagtggaatc gcgcaggaaa ggtcaccgta   1740

ttgcgtgcct cagtgatgac cccatacatg aacaaggagg agcattttga ggagtacgcc   1800

gagaaaatta aagcagcact tcaggaaaag ttggagaaaa tctacgctga tcaacttctt   1860

gcgtcggagg ctaag                                                    1875
```

<210> SEQ ID NO 46
<211> LENGTH: 540
<212> TYPE: PRT
<213> ORGANISM: Escherichia coli (strain K12)

<400> SEQUENCE: 46

```
Met Arg Val Asn Asn Gly Leu Thr Pro Gln Glu Leu Glu Ala Tyr Gly
1               5                   10                  15

Ile Ser Asp Val His Asp Ile Val Tyr Asn Pro Ser Tyr Asp Leu Leu
            20                  25                  30

Tyr Gln Glu Glu Leu Asp Pro Ser Leu Thr Gly Tyr Glu Arg Gly Val
        35                  40                  45

Leu Thr Asn Leu Gly Ala Val Ala Val Asp Thr Gly Ile Phe Thr Gly
    50                  55                  60

Arg Ser Pro Lys Asp Lys Tyr Ile Val Arg Asp Asp Thr Thr Arg Asp
65                  70                  75                  80

Thr Phe Trp Trp Ala Asp Lys Gly Lys Gly Lys Asn Asp Asn Lys Pro
                85                  90                  95

Leu Ser Pro Glu Thr Trp Gln His Leu Lys Gly Leu Val Thr Arg Gln
            100                 105                 110

Leu Ser Gly Lys Arg Leu Phe Val Val Asp Ala Phe Cys Gly Ala Asn
        115                 120                 125

Pro Asp Thr Arg Leu Ser Val Arg Phe Ile Thr Glu Val Ala Trp Gln
    130                 135                 140

Ala His Phe Val Lys Asn Met Phe Ile Arg Pro Ser Asp Glu Glu Leu
145                 150                 155                 160

Ala Gly Phe Lys Pro Asp Phe Ile Val Met Asn Gly Ala Lys Cys Thr
                165                 170                 175

Asn Pro Gln Trp Lys Glu Gln Gly Leu Asn Ser Glu Asn Phe Val Ala
            180                 185                 190

Phe Asn Leu Thr Glu Arg Met Gln Leu Ile Gly Gly Thr Trp Tyr Gly
        195                 200                 205

Gly Glu Met Lys Lys Gly Met Phe Ser Met Met Asn Tyr Leu Leu Pro
    210                 215                 220

Leu Lys Gly Ile Ala Ser Met His Cys Ser Ala Asn Val Gly Glu Lys
225                 230                 235                 240

Gly Asp Val Ala Val Phe Phe Gly Leu Ser Gly Thr Gly Lys Thr Thr
```

```
                245                 250                 255

Leu Ser Thr Asp Pro Lys Arg Arg Leu Ile Gly Asp Asp Glu His Gly
            260                 265                 270

Trp Asp Asp Asp Gly Val Phe Asn Phe Glu Gly Gly Cys Tyr Ala Lys
        275                 280                 285

Thr Ile Lys Leu Ser Lys Glu Ala Glu Pro Glu Ile Tyr Asn Ala Ile
    290                 295                 300

Arg Arg Asp Ala Leu Leu Glu Asn Val Thr Val Arg Glu Asp Gly Thr
305                 310                 315                 320

Ile Asp Phe Asp Asp Gly Ser Lys Thr Glu Asn Thr Arg Val Ser Tyr
                325                 330                 335

Pro Ile Tyr His Ile Asp Asn Ile Val Lys Pro Val Ser Lys Ala Gly
            340                 345                 350

His Ala Thr Lys Val Ile Phe Leu Thr Ala Asp Ala Phe Gly Val Leu
        355                 360                 365

Pro Pro Val Ser Arg Leu Thr Ala Asp Gln Thr Gln Tyr His Phe Leu
    370                 375                 380

Ser Gly Phe Thr Ala Lys Leu Ala Gly Thr Glu Arg Gly Ile Thr Glu
385                 390                 395                 400

Pro Thr Pro Thr Phe Ser Ala Cys Phe Gly Ala Ala Phe Leu Ser Leu
                405                 410                 415

His Pro Thr Gln Tyr Ala Glu Val Leu Val Lys Arg Met Gln Ala Ala
            420                 425                 430

Gly Ala Gln Ala Tyr Leu Val Asn Thr Gly Trp Asn Gly Thr Gly Lys
        435                 440                 445

Arg Ile Ser Ile Lys Asp Thr Arg Ala Ile Ile Asp Ala Ile Leu Asn
    450                 455                 460

Gly Ser Leu Asp Asn Ala Glu Thr Phe Thr Leu Pro Met Phe Asn Leu
465                 470                 475                 480

Ala Ile Pro Thr Glu Leu Pro Gly Val Asp Thr Lys Ile Leu Asp Pro
                485                 490                 495

Arg Asn Thr Tyr Ala Ser Pro Glu Gln Trp Gln Glu Lys Ala Glu Thr
            500                 505                 510

Leu Ala Lys Leu Phe Ile Asp Asn Phe Asp Lys Tyr Thr Asp Thr Pro
        515                 520                 525

Ala Gly Ala Ala Leu Val Ala Ala Gly Pro Lys Leu
    530                 535                 540


<210> SEQ ID NO 47
<211> LENGTH: 373
<212> TYPE: PRT
<213> ORGANISM: Escherichia coli (strain K12)

<400> SEQUENCE: 47

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
            20                  25                  30

Val Gly Glu Val Lys Ser Arg Phe Gly Leu Pro Ile Tyr Val Pro Glu
        35                  40                  45

Arg Glu Ala Ser Ile Leu Ala Ser Arg Arg Ala Glu Ala Glu Ala Leu
    50                  55                  60

Gly Val Pro Pro Asp Leu Ile Glu Asp Val Leu Arg Arg Val Met Arg
65                  70                  75                  80
```

```
Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gly Gln Met Gly Arg
            100                 105                 110

Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
    130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
    210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
            260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
    290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
            340                 345                 350

Tyr Val Gln Arg Phe Gln Ser Glu Ser Arg Val Leu Leu Arg Gln Ala
        355                 360                 365

Asn Asp Asn Arg Gln
    370
```

<210> SEQ ID NO 48
<211> LENGTH: 173
<212> TYPE: PRT
<213> ORGANISM: Dickeya chrysanthemi (Pectobacterium chrysanthemi) (Erwinia chrysanthemi)

<400> SEQUENCE: 48

```
Met Thr Glu Pro Ile Phe Met Val Gly Ala Arg Gly Cys Gly Lys Thr
1               5                   10                  15

Thr Val Gly Arg Glu Leu Ala Arg Ala Leu Gly Tyr Glu Phe Val Asp
            20                  25                  30

Thr Asp Ile Phe Met Gln His Thr Ser Gly Met Thr Val Ala Asp Val
        35                  40                  45

Val Ala Ala Glu Gly Trp Pro Gly Phe Arg Arg Arg Glu Ser Glu Ala
    50                  55                  60

Leu Gln Ala Val Ala Thr Pro Asn Arg Val Val Ala Thr Gly Gly Gly
```

```
65                  70                  75                  80

Met Val Leu Leu Glu Gln Asn Arg Gln Phe Met Arg Ala His Gly Thr
                85                  90                  95

Val Val Tyr Leu Phe Ala Pro Ala Glu Glu Leu Ala Leu Arg Leu Gln
            100                 105                 110

Ala Ser Pro Gln Ala His Gln Arg Pro Thr Leu Thr Gly Arg Pro Ile
        115                 120                 125

Ala Glu Glu Met Glu Ala Val Leu Arg Glu Arg Glu Ala Leu Tyr Gln
    130                 135                 140

Asp Val Ala His Tyr Val Val Asp Ala Thr Gln Pro Pro Ala Ala Ile
145                 150                 155                 160

Val Ser Glu Leu Met Gln Thr Met Arg Leu Pro Ala Ala
                165                 170


<210> SEQ ID NO 49
<211> LENGTH: 334
<212> TYPE: PRT
<213> ORGANISM: Clostridium acetobutylicum (strain ATCC 824 DSM 792 JCM
      1419 LMG 5710 VKM B-1787)

<400> SEQUENCE: 49

Met Ala Lys Ile Ala Ile Asn Gly Phe Gly Arg Ile Gly Arg Leu Ala
1               5                   10                  15

Leu Arg Arg Ile Leu Glu Val Pro Gly Leu Glu Val Val Ala Ile Asn
            20                  25                  30

Asp Leu Thr Asp Ala Lys Met Leu Ala His Leu Phe Lys Tyr Asp Ser
        35                  40                  45

Ser Gln Gly Arg Phe Asn Gly Glu Ile Glu Val Lys Glu Gly Ala Phe
    50                  55                  60

Val Val Asn Gly Lys Glu Val Lys Val Phe Ala Glu Ala Asp Pro Glu
65                  70                  75                  80

Lys Leu Pro Trp Gly Asp Leu Gly Ile Asp Val Val Leu Glu Cys Thr
                85                  90                  95

Gly Phe Phe Thr Lys Lys Glu Lys Ala Glu Ala His Val Arg Ala Gly
            100                 105                 110

Ala Lys Lys Val Val Ile Ser Ala Pro Ala Gly Asn Asp Leu Lys Thr
        115                 120                 125

Ile Val Phe Asn Val Asn Asn Glu Asp Leu Asp Gly Thr Glu Thr Val
    130                 135                 140

Ile Ser Gly Ala Ser Cys Thr Thr Asn Cys Leu Ala Pro Met Ala Lys
145                 150                 155                 160

Val Leu Asn Asp Lys Phe Gly Ile Glu Lys Gly Phe Met Thr Thr Ile
                165                 170                 175

His Ala Phe Thr Asn Asp Gln Asn Thr Leu Asp Gly Pro His Arg Lys
            180                 185                 190

Gly Asp Leu Arg Arg Ala Arg Ala Ala Ala Val Ser Ile Ile Pro Asn
        195                 200                 205

Ser Thr Gly Ala Ala Lys Ala Ile Ser Gln Val Ile Pro Asp Leu Ala
    210                 215                 220

Gly Lys Leu Asp Gly Asn Ala Gln Arg Val Pro Val Pro Thr Gly Ser
225                 230                 235                 240

Ile Thr Glu Leu Val Ser Val Leu Lys Lys Lys Val Thr Val Glu Glu
                245                 250                 255

Ile Asn Ala Ala Met Lys Glu Ala Ala Asp Glu Ser Phe Gly Tyr Thr
            260                 265                 270
```

Glu Asp Pro Ile Val Ser Ala Asp Val Val Gly Ile Asn Tyr Gly Ser
        275                 280                 285

Leu Phe Asp Ala Thr Leu Thr Lys Ile Val Asp Val Asn Gly Ser Gln
    290                 295                 300

Leu Val Lys Thr Ala Ala Trp Tyr Asp Asn Glu Met Ser Tyr Thr Ser
305                 310                 315                 320

Gln Leu Val Arg Thr Leu Ala Tyr Phe Ala Lys Ile Ala Lys
                325                 330

<210> SEQ ID NO 50
<211> LENGTH: 396
<212> TYPE: PRT
<213> ORGANISM: Arabidopsis thaliana (Mouse-ear cress)

<400> SEQUENCE: 50

Met Ala Ser Val Thr Phe Ser Val Pro Lys Gly Phe Thr Glu Phe Ser
1               5                   10                  15

Gly Leu Arg Ser Ser Ser Ala Ser Leu Pro Phe Gly Lys Lys Leu Ser
            20                  25                  30

Ser Asp Glu Phe Val Ser Ile Val Ser Phe Gln Thr Ser Ala Met Gly
        35                  40                  45

Ser Ser Gly Gly Tyr Arg Lys Gly Val Thr Glu Ala Lys Leu Lys Val
    50                  55                  60

Ala Ile Asn Gly Phe Gly Arg Ile Gly Arg Asn Phe Leu Arg Cys Trp
65                  70                  75                  80

His Gly Arg Lys Asp Ser Pro Leu Asp Ile Ile Ala Ile Asn Asp Thr
                85                  90                  95

Gly Gly Val Lys Gln Ala Ser His Leu Leu Lys Tyr Asp Ser Thr Leu
            100                 105                 110

Gly Ile Phe Asp Ala Asp Val Lys Pro Ser Gly Glu Thr Ala Ile Ser
        115                 120                 125

Val Asp Gly Lys Ile Ile Gln Val Val Ser Asn Arg Asn Pro Ser Leu
    130                 135                 140

Leu Pro Trp Lys Glu Leu Gly Ile Asp Ile Val Ile Glu Gly Thr Gly
145                 150                 155                 160

Val Phe Val Asp Arg Glu Gly Ala Gly Lys His Ile Glu Ala Gly Ala
                165                 170                 175

Lys Lys Val Ile Ile Thr Ala Pro Gly Lys Gly Asp Ile Pro Thr Tyr
            180                 185                 190

Val Val Gly Val Asn Ala Asp Ala Tyr Ser His Asp Glu Pro Ile Ile
        195                 200                 205

Ser Asn Ala Ser Cys Thr Thr Asn Cys Leu Ala Pro Phe Val Lys Val
    210                 215                 220

Leu Asp Gln Lys Phe Gly Ile Ile Lys Gly Thr Met Thr Thr Thr His
225                 230                 235                 240

Ser Tyr Thr Gly Asp Gln Arg Leu Leu Asp Ala Ser His Arg Asp Leu
                245                 250                 255

Arg Arg Ala Arg Ala Ala Ala Leu Asn Ile Val Pro Thr Ser Thr Gly
            260                 265                 270

Ala Ala Lys Ala Val Ala Leu Val Leu Pro Asn Leu Lys Gly Lys Leu
        275                 280                 285

Asn Gly Ile Ala Leu Arg Val Pro Thr Pro Asn Val Ser Val Val Asp
    290                 295                 300

Leu Val Val Gln Val Ser Lys Lys Thr Phe Ala Glu Glu Val Asn Ala

```
305                 310                 315                 320

Ala Phe Arg Asp Ser Ala Glu Lys Glu Leu Lys Gly Ile Leu Asp Val
                325                 330                 335

Cys Asp Glu Pro Leu Val Ser Val Asp Phe Arg Cys Ser Asp Phe Ser
            340                 345                 350

Thr Thr Ile Asp Ser Ser Leu Thr Met Val Met Gly Asp Asp Met Val
        355                 360                 365

Lys Val Ile Ala Trp Tyr Asp Asn Glu Trp Gly Tyr Ser Gln Arg Val
    370                 375                 380

Val Asp Leu Ala Asp Ile Val Ala Asn Asn Trp Lys
385                 390                 395


<210> SEQ ID NO 51
<211> LENGTH: 374
<212> TYPE: PRT
<213> ORGANISM: Chlamydomonas reinhardtii (Chlamydomonas smithii)

<400> SEQUENCE: 51

Met Ala Ala Met Met Gln Lys Ser Ala Phe Thr Gly Ser Ala Val Ser
1               5                   10                  15

Ser Lys Ser Gly Val Arg Ala Lys Ala Ala Arg Ala Val Val Asp Val
            20                  25                  30

Arg Ala Glu Lys Lys Ile Arg Val Ala Ile Asn Gly Phe Gly Arg Ile
        35                  40                  45

Gly Arg Asn Phe Leu Arg Cys Trp His Gly Arg Gln Asn Thr Leu Leu
    50                  55                  60

Asp Val Val Ala Ile Asn Asp Ser Gly Gly Val Lys Gln Ala Ser His
65                  70                  75                  80

Leu Leu Lys Tyr Asp Ser Thr Leu Gly Thr Phe Ala Ala Asp Val Lys
                85                  90                  95

Ile Val Asp Asp Ser His Ile Ser Val Asp Gly Lys Gln Ile Lys Ile
            100                 105                 110

Val Ser Ser Arg Asp Pro Leu Gln Leu Pro Trp Lys Glu Met Asn Ile
        115                 120                 125

Asp Leu Val Ile Glu Gly Thr Gly Val Phe Ile Asp Lys Val Gly Ala
    130                 135                 140

Gly Lys His Ile Gln Ala Gly Ala Ser Lys Val Leu Ile Thr Ala Pro
145                 150                 155                 160

Ala Lys Asp Lys Asp Ile Pro Thr Phe Val Val Gly Val Asn Glu Gly
                165                 170                 175

Asp Tyr Lys His Glu Tyr Pro Ile Ile Ser Asn Ala Ser Cys Thr Thr
            180                 185                 190

Asn Cys Leu Ala Pro Phe Val Lys Val Leu Glu Gln Lys Phe Gly Ile
        195                 200                 205

Val Lys Gly Thr Met Thr Thr Thr His Ser Tyr Thr Gly Asp Gln Arg
    210                 215                 220

Leu Leu Asp Ala Ser His Arg Asp Leu Arg Arg Ala Arg Ala Ala Ala
225                 230                 235                 240

Leu Asn Ile Val Pro Thr Thr Thr Gly Ala Ala Lys Ala Val Ser Leu
                245                 250                 255

Val Leu Pro Ser Leu Lys Gly Lys Leu Asn Gly Ile Ala Leu Arg Val
            260                 265                 270

Pro Thr Pro Thr Val Ser Val Val Asp Leu Val Val Gln Val Glu Lys
        275                 280                 285
```

```
Lys Thr Phe Ala Glu Glu Val Asn Ala Ala Phe Arg Glu Ala Ala Asn
    290                 295                 300

Gly Pro Met Lys Gly Val Leu His Val Glu Asp Ala Pro Leu Val Ser
305                 310                 315                 320

Ile Asp Phe Lys Cys Thr Asp Gln Ser Thr Ser Ile Asp Ala Ser Leu
                325                 330                 335

Thr Met Val Met Gly Asp Asp Met Val Lys Val Val Ala Trp Tyr Asp
            340                 345                 350

Asn Glu Trp Gly Tyr Ser Gln Arg Val Val Asp Leu Ala Glu Val Thr
        355                 360                 365

Ala Lys Lys Trp Val Ala
    370


<210> SEQ ID NO 52
<211> LENGTH: 336
<212> TYPE: PRT
<213> ORGANISM: Staphylococcus epidermidis (strain ATCC 35984 RP62A)

<400> SEQUENCE: 52

Met Ala Ile Lys Val Ala Ile Asn Gly Phe Gly Arg Ile Gly Arg Leu
1               5                   10                  15

Ala Phe Arg Arg Ile Gln Asp Val Glu Gly Leu Glu Val Val Ala Val
            20                  25                  30

Asn Asp Leu Thr Asp Asp Asp Met Leu Ala His Leu Leu Lys Tyr Asp
        35                  40                  45

Thr Met Gln Gly Arg Phe Thr Gly Glu Val Glu Val Ile Glu Gly Gly
    50                  55                  60

Phe Arg Val Asn Gly Lys Glu Ile Lys Ser Phe Asp Glu Pro Asp Ala
65                  70                  75                  80

Gly Lys Leu Pro Trp Gly Asp Leu Asp Ile Asp Val Val Leu Glu Cys
                85                  90                  95

Thr Gly Phe Tyr Thr Asp Lys Glu Lys Ala Gln Ala His Ile Asp Ala
            100                 105                 110

Gly Ala Lys Lys Val Leu Ile Ser Ala Pro Ala Lys Gly Asp Val Lys
        115                 120                 125

Thr Ile Val Phe Asn Thr Asn His Asp Thr Leu Asp Gly Ser Glu Thr
    130                 135                 140

Val Val Ser Gly Ala Ser Cys Thr Thr Asn Ser Leu Ala Pro Val Ala
145                 150                 155                 160

Lys Val Leu Ser Asp Glu Phe Gly Leu Val Glu Gly Phe Met Thr Thr
                165                 170                 175

Ile His Ala Tyr Thr Gly Asp Gln Asn Thr Gln Asp Ala Pro His Arg
            180                 185                 190

Lys Gly Asp Lys Arg Arg Ala Arg Ala Ala Ala Glu Asn Ile Ile Pro
        195                 200                 205

Asn Ser Thr Gly Ala Ala Lys Ala Ile Gly Lys Val Ile Pro Glu Ile
    210                 215                 220

Asp Gly Lys Leu Asp Gly Gly Ala Gln Arg Val Pro Val Ala Thr Gly
225                 230                 235                 240

Ser Leu Thr Glu Leu Thr Val Val Leu Asp Lys Gln Asp Val Thr Val
                245                 250                 255

Asp Gln Val Asn Ser Ala Met Lys Gln Ala Ser Asp Glu Ser Phe Gly
            260                 265                 270

Tyr Thr Glu Asp Glu Ile Val Ser Ser Asp Ile Val Gly Met Thr Tyr
        275                 280                 285
```

```
Gly Ser Leu Phe Asp Ala Thr Gln Thr Arg Val Met Thr Val Gly Asp
    290                 295                 300

Arg Gln Leu Val Lys Val Ala Ala Trp Tyr Asp Asn Glu Met Ser Tyr
305                 310                 315                 320

Thr Ala Gln Leu Val Arg Thr Leu Ala His Leu Ala Glu Leu Ser Lys
                325                 330                 335


<210> SEQ ID NO 53
<211> LENGTH: 356
<212> TYPE: PRT
<213> ORGANISM: Escherichia coli (strain K12)

<400> SEQUENCE: 53

Met Gln Lys Asp Ala Leu Asn Lys Val His Ile Thr Asp Glu Gln Val
1               5                   10                  15

Leu Met Thr Pro Glu Gln Leu Lys Ala Ala Phe Pro Leu Ser Leu Gln
            20                  25                  30

Gln Glu Ala Gln Ile Ala Asp Ser Arg Lys Ser Ile Ser Asp Ile Ile
        35                  40                  45

Ala Gly Arg Asp Pro Arg Leu Leu Val Val Cys Gly Pro Cys Ser Ile
    50                  55                  60

His Asp Pro Glu Thr Ala Leu Glu Tyr Ala Arg Arg Phe Lys Ala Leu
65                  70                  75                  80

Ala Ala Glu Val Ser Asp Ser Leu Tyr Leu Val Met Arg Val Tyr Phe
                85                  90                  95

Glu Lys Pro Arg Thr Thr Val Gly Trp Lys Gly Leu Ile Asn Asp Pro
            100                 105                 110

His Met Asp Gly Ser Phe Asp Val Glu Ala Gly Leu Gln Ile Ala Arg
        115                 120                 125

Lys Leu Leu Leu Glu Leu Val Asn Met Gly Leu Pro Leu Ala Thr Glu
    130                 135                 140

Ala Leu Asp Pro Asn Ser Pro Gln Tyr Leu Gly Asp Leu Phe Ser Trp
145                 150                 155                 160

Ser Ala Ile Gly Ala Arg Thr Thr Glu Ser Gln Thr His Arg Glu Met
                165                 170                 175

Ala Ser Gly Leu Ser Met Pro Val Gly Phe Lys Asn Gly Thr Asp Gly
            180                 185                 190

Ser Leu Ala Thr Ala Ile Asn Ala Met Arg Ala Ala Ala Gln Pro His
        195                 200                 205

Arg Phe Val Gly Ile Asn Gln Ala Gly Gln Val Ala Leu Leu Gln Thr
    210                 215                 220

Gln Gly Asn Pro Asp Gly His Val Ile Leu Arg Gly Gly Lys Ala Pro
225                 230                 235                 240

Asn Tyr Ser Pro Ala Asp Val Ala Gln Cys Glu Lys Glu Met Glu Gln
                245                 250                 255

Ala Gly Leu Arg Pro Ser Leu Met Val Asp Cys Ser His Gly Asn Ser
            260                 265                 270

Asn Lys Asp Tyr Arg Arg Gln Pro Ala Val Ala Glu Ser Val Val Ala
        275                 280                 285

Gln Ile Lys Asp Gly Asn Arg Ser Ile Ile Gly Leu Met Ile Glu Ser
    290                 295                 300

Asn Ile His Glu Gly Asn Gln Ser Ser Glu Gln Pro Arg Ser Glu Met
305                 310                 315                 320

Lys Tyr Gly Val Ser Val Thr Asp Ala Cys Ile Ser Trp Glu Met Thr
```

```
                325                 330                 335

Asp Ala Leu Leu Arg Glu Ile His Gln Asp Leu Asn Gly Gln Leu Thr
            340                 345                 350

Ala Arg Val Ala
        355


<210> SEQ ID NO 54
<211> LENGTH: 449
<212> TYPE: PRT
<213> ORGANISM: Helicobacter pylori (strain J99 ATCC 700824)
      (Campylobacter pylori J99)

<400> SEQUENCE: 54

Met Ser Asn Thr Thr Trp Ser Pro Thr Ser Trp His Ser Phe Lys Ile
1               5                   10                  15

Glu Gln His Pro Thr Tyr Lys Asp Glu Gln Glu Leu Glu Arg Val Lys
            20                  25                  30

Lys Glu Leu Arg Ser Tyr Pro Pro Leu Val Phe Ala Gly Glu Ala Arg
        35                  40                  45

Asn Leu Gln Glu Arg Leu Ala Gln Val Ile Asp Asn Lys Ala Phe Leu
    50                  55                  60

Leu Gln Gly Gly Asp Cys Ala Glu Ser Phe Ser Gln Phe Ser Ala Asn
65                  70                  75                  80

Arg Ile Arg Asp Met Phe Lys Val Met Met Gln Met Ala Ile Val Leu
                85                  90                  95

Thr Phe Ala Gly Ser Ile Pro Ile Val Lys Val Gly Arg Ile Ala Gly
            100                 105                 110

Gln Phe Ala Lys Pro Arg Ser Asn Ala Thr Glu Ile Leu Asp Asp Glu
        115                 120                 125

Glu Val Leu Ser Tyr Arg Gly Asp Ile Ile Asn Gly Ile Ser Lys Lys
    130                 135                 140

Glu Arg Glu Pro Lys Pro Glu Arg Met Leu Lys Ala Tyr His Gln Ser
145                 150                 155                 160

Val Ala Thr Leu Asn Leu Ile Arg Ala Phe Ala Gln Gly Gly Leu Ala
                165                 170                 175

Asp Leu Glu Gln Val His Arg Phe Asn Leu Asp Phe Val Lys Asn Asn
            180                 185                 190

Asp Phe Gly Gln Lys Tyr Gln Gln Ile Ala Asp Arg Ile Thr Gln Ala
        195                 200                 205

Leu Gly Phe Met Arg Ala Cys Gly Val Glu Ile Glu Arg Thr Pro Ile
    210                 215                 220

Leu Arg Glu Val Glu Phe Tyr Thr Ser His Glu Ala Leu Leu Leu His
225                 230                 235                 240

Tyr Glu Glu Pro Leu Val Arg Lys Asp Ser Leu Thr Asn Gln Phe Tyr
                245                 250                 255

Asp Cys Ser Ala His Met Leu Trp Ile Gly Glu Arg Thr Arg Asp Pro
            260                 265                 270

Lys Gly Ala His Val Glu Phe Leu Arg Gly Val Cys Asn Pro Ile Gly
        275                 280                 285

Val Lys Ile Gly Pro Asn Ala Ser Val Ser Glu Val Leu Glu Leu Cys
    290                 295                 300

Asp Val Leu Asn Pro His Asn Leu Lys Gly Arg Leu Asn Leu Ile Val
305                 310                 315                 320

Arg Met Gly Ser Lys Ile Ile Lys Glu Arg Leu Pro Lys Leu Leu Gln
                325                 330                 335
```

```
Gly Val Leu Lys Glu Lys Arg His Ile Leu Trp Ser Ile Asp Pro Met
            340                 345                 350

His Gly Asn Thr Val Lys Thr Asn Leu Gly Val Lys Thr Arg Ala Phe
        355                 360                 365

Asp Ser Val Leu Asp Glu Val Lys Ser Phe Phe Glu Ile His Arg Ala
    370                 375                 380

Glu Gly Ser Leu Ala Ser Gly Val His Leu Glu Met Thr Gly Glu Asn
385                 390                 395                 400

Val Thr Glu Cys Ile Gly Gly Ser Gln Ala Ile Thr Glu Glu Gly Leu
                405                 410                 415

Ser Cys His Tyr Tyr Thr Gln Cys Asp Pro Arg Leu Asn Ala Thr Gln
            420                 425                 430

Ala Leu Glu Leu Ala Phe Leu Ile Ala Asp Met Leu Lys Lys Gln Arg
        435                 440                 445

Thr


<210> SEQ ID NO 55
<211> LENGTH: 276
<212> TYPE: PRT
<213> ORGANISM: Aeropyrum pernix (strain ATCC 700893 DSM 11879 JCM 9820
      NBRC 100138 K1)

<400> SEQUENCE: 55

Met Trp Arg Trp Leu Pro Val Ala Gly Phe Lys Gly Val Lys Leu Ala
1               5                   10                  15

Leu Lys Ser Glu Glu Arg Arg Glu Thr Val Val Glu Val Glu Gly Val
            20                  25                  30

Arg Ile Gly Gly Gly Ser Lys Ala Val Ile Ala Gly Pro Cys Ser Val
        35                  40                  45

Glu Ser Trp Glu Gln Val Arg Glu Ala Ala Leu Ala Val Lys Glu Ala
    50                  55                  60

Gly Ala His Met Leu Arg Gly Gly Ala Phe Lys Pro Arg Thr Ser Pro
65                  70                  75                  80

Tyr Ser Phe Gln Gly Leu Gly Leu Glu Gly Leu Lys Leu Leu Arg Arg
                85                  90                  95

Ala Gly Asp Glu Ala Gly Leu Pro Val Val Thr Glu Val Leu Asp Pro
            100                 105                 110

Arg His Val Glu Thr Val Ser Arg Tyr Ala Asp Met Leu Gln Ile Gly
        115                 120                 125

Ala Arg Asn Met Gln Asn Phe Pro Leu Leu Arg Glu Val Gly Arg Ser
    130                 135                 140

Gly Lys Pro Val Leu Leu Lys Arg Gly Phe Gly Asn Thr Val Glu Glu
145                 150                 155                 160

Leu Leu Ala Ala Ala Glu Tyr Ile Leu Leu Glu Gly Asn Trp Gln Val
                165                 170                 175

Val Leu Val Glu Arg Gly Ile Arg Thr Phe Glu Pro Ser Thr Arg Phe
            180                 185                 190

Thr Leu Asp Val Ala Ala Val Ala Val Leu Lys Glu Ala Thr His Leu
        195                 200                 205

Pro Val Ile Val Asp Pro Ser His Pro Ala Gly Arg Arg Ser Leu Val
    210                 215                 220

Pro Ala Leu Ala Lys Ala Gly Leu Ala Ala Gly Ala Asp Gly Leu Ile
225                 230                 235                 240

Val Glu Val His Pro Asn Pro Glu Glu Ala Leu Ser Asp Ala Lys Gln
```

```
                245                 250                 255

Gln Leu Thr Pro Gly Glu Phe Ala Arg Leu Met Gly Glu Leu Arg Trp
            260                 265                 270

His Arg Leu Leu
        275


<210> SEQ ID NO 56
<211> LENGTH: 350
<212> TYPE: PRT
<213> ORGANISM: Escherichia coli (strain K12)

<400> SEQUENCE: 56

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45

Gly Asn Asp Asp Arg Leu Leu Val Val Ile Gly Pro Cys Ser Ile His
    50                  55                  60

Asp Pro Val Ala Ala Lys Glu Tyr Ala Thr Arg Leu Leu Ala Leu Arg
65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
    130                 135                 140

Leu Asp Met Ile Thr Leu Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
    210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
    290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335
```

```
Leu Leu Arg Gln Leu Ala Asn Ala Val Lys Ala Arg Arg Gly
            340                 345                 350


<210> SEQ ID NO 57
<211> LENGTH: 1593
<212> TYPE: DNA
<213> ORGANISM: Artificial
<220> FEATURE:
<223> OTHER INFORMATION: Codon-optimized and/or mutated sequence

<400> SEQUENCE: 57

atgggctcac tgaacacaga ggacgtactt gaaaactcct cggcatttgg cgtgactaat      60

cctttagatc cggaggagtt tagacgtcag ggacacatga tcattgattt tctcgcggat     120

tattatcgcg acgtcgagaa gtatccggtt cggagtcaag tcgaaccggg atatcttaga     180

aaaagactgc ctgaaactgc gccatataat ccggagtcta tcgaaacaat tttacaagac     240

gtaacgacag agatcattcc gggcctgaca cactggcagt cacctaatta ttacgcgtac     300

tttccgagct cgggctcggt tgccggcttt ttgggtgaaa tgctgtcgac gggattcaat     360

gtcgtcggat ttaactggat gagttctcca gcggcgacag aacttgaatc tgttgttatg     420

gactggttcg gcaaaatgct taacttaccg gaaagcttcc tcttttcagg gagtggaggc     480

ggtgttcttc agggcacaag ttgcgaggct attttatgta cactgactgc agcgcgcgac     540

cggaaactca ataagatagg tagagaacat attggtagac tggtcgtata tggtagcgat     600

cagacacact gcgcgttgca aaaagcggca caggtagccg gcattaaccc gaaaaatttc     660

cgtgcaatca aaacctttaa agaaaactca tttggcctta gcgcggctac actgagagag     720

gttatcctgg aggacattga ggcgggactg attccacttt ttgtgtgtcc gacggtaggt     780

acaacaagtt ccactgcagt tgatccgatt tctccgattt gtgaagttgc aaaggaatat     840

gagatgtggg tccatgtcga tgccgcgtat gctggcagcg cgtgtatttg tcctgaattt     900

cgacatttta tagatggtgt ggaagaagcc gactcctttt ctcttaacgc acataagtgg     960

ttcttcacaa ctctcgattg ctgctgctta tgggttaagg atccttccgc actggtcaag    1020

gccttatcta cgaacccgga atatcttcgc aataaggcga ccgaatccag acaggttgta    1080

gattataaag actggcagat cgcgttatca agacgttttc ggtcattaaa gctgtggatg    1140

gtgctccgga gctatggtgt gacgaacctc cgcaactttc ttagaagcca cgtcaagatg    1200

gcgaaaactt tcgagggatt gatttgcatg gatggtcgct tcgagattac ggttcctcgc    1260

acatttgcga tggtttgctt tcgcctgctt ccaccgaaga cgataaaagt ctatgacaac    1320

ggtgtgcacc agaacggcaa tggtgttgtt ccgctgcgtg atgaaaacga aaatcttgtc    1380

ctggcgaaca aactgaatca agtgtatctg gagacagtca acgccacggg tagtgtatat    1440

atgacgcatg ctgttgtcgg tggcgtgtat atgattagat tcgctgttgg aagtacactt    1500

acggaagaac gccacgtcat ttatgcgtgg aaaatcctgc aagaacacgc tgatttaatt    1560

cttggcaaat tttctgaagc tgatttttcc tct                                 1593


<210> SEQ ID NO 58
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 58

atgtctgaaa gcccaatgtt tgctgccaat ggaatgccga aagtaaatca gggtgcagaa      60
```

```
gaggacgtcc ggattctggg atatgacccg cttgcatccc cggccctgtt gcaagttcaa    120

atcccagcga cgcctactag ccttgagact gccaagcgcg gccggagaga agcaattgac    180

ataattaccg gaaaggacga tagagtactg gtcattgtag gtccatgctc aatccatgat    240

ttggaggcgg ctcaggaata tgccctgcgg ttaaaaaagt tgtcggatga acttaaaggc    300

gatctgtcga ttattatgcg cgcgtattta gagaagccgc gcacaacagt aggctggaag    360

ggccttatta acgacccaga cgtaaacaac acatttaaca ttaataaagg attacaaagc    420

gctcgccaac tttttgttaa cctcacgaac atcggactcc cgataggaag tgaaatgctg    480

gatacaataa gcccacagta tcttgcagat cttgtctcgt ttggcgctat aggagcccgc    540

acgacggaat ctcaactgca ccgggaactt gccagtggac tgtcattccc ggtggggttt    600

aagaacggca cggatggtac cctgaatgta gcggtcgacg cgtgccaggc ggccgctcac    660

tctcatcatt tcatgggcgt cacactccat ggggtagccg caattacgac gacaaaagga    720

aacgaacact gcttcgtaat tttacgcgga ggtaagaaag gcacgaatta tgacgctaag    780

tcagtcgccg aggcgaaagc acagcttccg gcaggtagca acgggctgat gattgattac    840

tctcatggga attctaataa agatttcaga aaccaaccta aggtcaacga tgttgtatgc    900

gaacagatag ccaatggaga aaacgctatt acaggcgtga tgatagaatc taacattaac    960

gagggaaatc aggggatccc agccgaggga aaggcaggtc ttaagtatgg agtctccatc   1020

acagacgcat gcatagggtg ggaaacgacc gaagatgtcc ttcgcaagtt agcagcggca   1080

gttcgtcaac gccgtgaggt aaataaaaaa                                    1110
```

<210> SEQ ID NO 59
<211> LENGTH: 1593
<212> TYPE: DNA
<213> ORGANISM: Artificial
<220> FEATURE:
<223> OTHER INFORMATION: Codon-optimized and/or mutated sequence

<400> SEQUENCE: 59

```
atgggcagcc tgaacaccga agatgtcttg gaaaactcct ccgcgtttgg cgtgaccaac     60

cctctggacc cagaagagtt tcgccgtcaa ggacatatga tcatcgattt cctcgcagat    120

tactatcgcg acgttgagaa gtacccggtg cgatctcagg tcgaacctgg ttatctgcgc    180

aagcgtctcc ccgagaccgc cccctataat ccagaatcta ttgagaccat tctgcaggat    240

gttaccactg agatcatccc tggtttgacc cactggcagt ctccaaacta ctacgcttat    300

ttcccttcca gcggttccgt tgcaggtttc ctgggcgaaa tgctgtccac cggctttaac    360

gtggtgggct tcaactggat gtcttctcct gcggctacgg aattggaatc cgtcgtcatg    420

gactggttcg gcaaaatgct gaacctgcca gaatcgtttt tgttttccgg ctctggtggc    480

ggagttctgc aaggcaccag ctgcgaggct atcctctgta cactgacggc cgcgcgcgat    540

cgcaagctca ataaaatcgg ccgcgagcac attggccgtc tcgtagtata tggtagcgac    600

caaacccatt gcgcccttca aaaagcagcg caggtcgcgg gcatcaaccc caaaaacttc    660

cgcgcaatca agacttttaa agagaactcc ttcggtctca gcgctgctac cctgcgcgag    720

gtgattctcg aagatatcga agctggcctg attccactgt ttgtttgtcc taccgtgggc    780

accacttcca gcacggcagt agatccgatc tccccgattt gcgaggtagc taaggaatat    840

gagatgtggg tgcacgtcga tgccgcttat gctggttccg cttgcatctg cccagaattc    900

cgccacttta ttgatggtgt agaggaggcg gattcctttt cccttaatgc tcacaagtgg    960

ttcttcacga cactggattg ttgctgtttg tgggtaaaag atccgtcagc gttggttaaa   1020
```

```
gcgttgagca caaaccccga atatctgcgc aataaagcaa ccgagtcccg acaagttgtt   1080

gattataagg actggcagat cgccctctca cgtcgcttcc gctccctgaa gctttggatg   1140

gtgctccgct cctatggtgt cacaaatctg cgcaacttcc tccgctccca tgtaaaaatg   1200

gcgaaaacct tcgaaggact gatctgtatg gatggccgtt ttgagatcac cgtgccacgt   1260

acgttcgcga tggtgtgctt tcgccttctg cctccgaaaa ccattaaggt gtacgacaat   1320

ggtgttcacc agaatggcaa cggcgtcgtc ccattgcgag acgagaacga gaatttggtg   1380

ctggcaaaca agttgaatca ggtctacctg gaaaccgtca acgctacagg aagcgtctac   1440

atgactcacg cagttgttgg cggcgtctac atgatccgtt tcgcagtggg atcgacgctg   1500

acggaagagc gccacgtcat ttacgcgtgg aagatcctgc aagagcacgc ggatttgatc   1560

ttgggcaaat tctctgaggc tgatttctcc tcg                                 1593
```

<210> SEQ ID NO 60
<211> LENGTH: 1593
<212> TYPE: DNA
<213> ORGANISM: Artificial
<220> FEATURE:
<223> OTHER INFORMATION: Codon-optimized and/or mutated sequence

<400> SEQUENCE: 60

```
atgggctcct taaatacaga agatgtttta gagaatagct ctgcgtttgg cgttacaaat     60

cctttagatc cagaagaatt tagaagacaa ggtcacatga taattgactt tttggctgac    120

tattacagag acgtagaaaa atacccagtt aggtcccaag tggagcctgg ctatttgcgt    180

aaacgtttgc ctgaaacagc tccatataac cctgaatcta tagaaactat tcttcaggat    240

gtgaccactg aaataatccc aggcctaaca cattggcaat cacctaacta ttacgcgtat    300

ttccccagca gtggaagtgt tgcaggtttt ttaggtgaaa tgttatctac aggattcaat    360

gtcgtgggct tcaactggat gtcatcacca gctgctaccg aactagagtc cgtagtaatg    420

gactggtttg ggaaaatgtt aaatttacca gagtcattct tgttttcagg ttctggtggc    480

ggagttcttc aaggaacctc ttgtgaagct attttgtgta ccctaactgc cgccagagat    540

agaaagctga ataaaattgg tagagaacat ataggcagat tggtcgttta cgggtccgat    600

caaacacact gcgctctgca aaaggctgcg caggttgctg gcataaaccc gaaaaacttc    660

agggccatta agacgttcaa agaaaattcc tttggcttat cagcagctac cttgagggaa    720

gtcatattag aagacattga agcaggccta atccctttgt ttgtatgccc tacagtgggt    780

acaacgtctt ccacggctgt cgatccaatt tctcctatct gtgaagtagc gaaagaatac    840

gaaatgtggg ttcacgtcga cgcagcatat gctggatcag catgtatatg tccagaattt    900

agacacttta tagatggtgt agaagaagcc gattcatttt cattgaatgc acataagtgg    960

ttttttacaa cacttgattg ctgttgtttg tgggttaagg acccaagcgc attagttaaa   1020

gcattgtcca caaatcctga gtaccttagg aacaaagcta cagaaagcag gcaagttgtt   1080

gattacaagg attggcagat tgcattgtca aggagattta gaagtttaaa gttatggatg   1140

gtcctgaggt cctatggtgt tactaatttg agaaatttcc tgagatctca tgtaaagatg   1200

gccaagacct tcgaaggctt gatttgcatg gacgggagat ttgaaataac tgtgccgaga   1260

acctttgcga tggtctgttt tagattattg ccacccaaaa ccatcaaggt gtacgataac   1320

ggcgtgcatc aaaatggaaa tggagttgtg ccactgagag acgagaatga aaacttggtt   1380

ttggcaaata agctaaatca agtgtattta gaaaccgtaa atgccacagg ttcagtttat   1440
```

```
atgacccatg cagttgtagg tggtgtgtat atgatcagat ttgctgtcgg aagcactcta   1500

accgaagaaa ggcatgtaat ctacgcgtgg aaaattctgc aagaacatgc tgatcttatc   1560

ttggggaagt tttctgaggc tgacttttca tct                                1593
```

```
<210> SEQ ID NO 61
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 61

atgtcagaat caccgatgtt tgctgcaaat ggaatgccga aggttaacca gggtgcagaa     60

gaggatgtaa gaatattggg gtatgaccca ctggcatcac cagcattgtt gcaggttcaa    120

attccggcaa ctcctacgtc attagaaacg gcaaagagag gtagacgtga agctatagat    180

attataacag gcaaagacga ccgtgtgctg gtgattgtgg gtccctgctc cattcatgac    240

cttgaagcag cacaggagta tgctttgcgt ctgaagaaac tgtcagacga gcttaaaggt    300

gaccttagta tcattatgag agcctatttg gaaaagccta ggaccaccgt aggctggaaa    360

ggtttgatta atgatccaga tgtaaacaac acctttaata taaataaggg tctacagagt    420

gccagacaac ttttcgtaaa ccttaccaat atcggacttc cgattggctc cgagatgtta    480

gatacaatct caccacaata ccttgccgat cttgtctcat tcggtgctat cggtgctaga    540

actaccgagt ctcagttgca tagagaatta gcttccgggc tatcatttcc agtcggcttc    600

aagaacggta ctgacggcac attgaatgtt gctgtggatg catgtcaagc cgcagcccat    660

agtcaccatt tcatgggcgt tactcttcac ggggttgctg ctataacgac cactaagggg    720

aatgaacatt gctttgtaat cttaaggggt ggcaagaagg gaactaatta cgatgctaaa    780

tctgtagccg aggcgaaagc acagttacca gctgggtcaa acggcttaat gatagattac    840

agtcatggga attctaataa agactttaga aaccaaccaa aagtaaatga tgttgtatgc    900

gagcagattg ctaacggtga aaatgccatc acgggcgtga tgattgaatc caatataaat    960

gagggaaacc aaggcatacc tgccgaaggt aaagctggtc ttaagtacgg cgtttctatt   1020

acagacgcgt gcataggctg ggagacaaca gaagatgtgt tgagaaagct tgctgcggct   1080

gttagacaaa ggagggaagt aaataaaaag                                    1110
```

```
<210> SEQ ID NO 62
<211> LENGTH: 1593
<212> TYPE: DNA
<213> ORGANISM: Artificial
<220> FEATURE:
<223> OTHER INFORMATION: Codon-optimized and/or mutated sequence

<400> SEQUENCE: 62

atgggctcgc tcaacaccga ggatgtgctg gagaactcgt ctgcctttgg cgttaccaac     60

cctctggacc ctgaggagtt tcggagacaa ggccacatga ttatcgactt tctggctgac    120

tattacagag acgtggagaa gtaccctgtt cggtctcaag tggagccagg ataccttcgg    180

aagcgactgc ccgaaactgc tccctacaat cccgaatcca ttgagaccat tctgcaggac    240

gtgactacgg agatcattcc tggactgacc cactggcaaa gccctaacta ctacgcctac    300

ttcccttcta gcggctcggt cgcaggattt cttggtgaga tgctgtcgac cggttttaac    360

gttgttggct tcaactggat gtcctcccct gctgctacag aactggaatc ggtggttatg    420

gactggttcg gtaagatgct gaacctccct gagtcttttc tgttctccgg tagcggcggc    480
```

```
ggagtgctgc agggcacgtc ctgtgaagcc atcctgtgta ctctgaccgc tgcccgtgac    540
cgaaaactta acaaaattgg ccgagagcac attggccggc tggtcgtcta cggatctgac    600
cagacccact gcgctctcca gaaggcagct caggtggccg gcatcaaccc taaaaacttt    660
cgagcaatca agacctttaa ggagaactcg ttcggcctga gcgctgctac tcttagagag    720
gttattctcg aagacattga ggccggtctt attcccctct tcgtctgtcc caccgtcggc    780
actacgtctt ccacggctgt ggatccaatc tcccccatct gtgaggtcgc aaaggagtac    840
gagatgtggg tgcacgtcga cgcagcttac gccggctctg catgcatttg cccagagttc    900
cgtcacttca ttgacggagt tgaggaagcc gactccttca gcctcaacgc ccataaatgg    960
ttcttcacca ccctcgactg ttgttgtctc tgggtcaagg acccctctgc cctggtcaag   1020
gccctgtcga ccaaccccga gtacctgcgg aacaaggcta ccgagtctcg acaagttgtc   1080
gactacaagg actggcaaat cgccctgtcc cgacgattcc ggtctctgaa gctgtggatg   1140
gtgctgcgat cgtatggtgt taccaatctc cgaaatttcc tgcgatctca tgtcaagatg   1200
gcaaaaactt tcgagggtct gatctgtatg gacggaagat ttgagatcac tgttccccga   1260
acattcgcaa tggtttgttt ccgactgctg cctcccaaga ctattaaggt ttacgacaac   1320
ggagtgcatc aaaacggtaa cggtgtggtt cccctccggg acgagaacga aaacctggtc   1380
ctcgccaaca agcttaacca agtctacctc gagaccgtca acgctacagg ctctgtgtac   1440
atgactcatg ccgttgttgg tggagtgtac atgattagat ttgctgtcgg ctctaccctt   1500
actgaggaac gacatgtgat ttacgcctgg aaaattctgc aagagcacgc cgatctgatc   1560
ctgggtaagt tttccgaagc cgacttctcc tcg                                1593
```

```
<210> SEQ ID NO 63
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 63

atgtctgagt cccccatgtt cgccgcaaac ggcatgccta aggtcaacca gggtgccgag     60
gaggatgtcc gtatcctcgg ctatgaccct cttgcatccc ccgctcttct ccaggtccag    120
attccagcta ctcccaccag cctcgaaact gccaagagag gacgaagaga agctattgac    180
atcattactg gcaaggacga tcgagtcctt gtcattgttg gcccctgcag cattcacgac    240
ctggaggccg ctcaggaata cgctctgaga cttaagaagc tctctgatga actgaaggga    300
gacctttcca tcatcatgcg tgcctacctg gagaagcccc gaactaccgt cggttggaag    360
ggcctgatca acgacccaga tgtcaacaac acctttaaca tcaataaggg acttcagtcc    420
gctcgacagc tcttcgtcaa cctcacgaac attggtctgc caatcggctc cgaaatgctg    480
gacaccattt cgccccagta cctggctgac cttgtttcgt ttggtgctat cggagctcgg    540
accaccgagt cccagctgca tagagagctt gcttccggcc tgtccttccc tgtgggtttc    600
aagaatggta ccgatggaac cctgaacgtt gccgtcgatg cttgccaagc tgctgcccac    660
tcgcatcact tcatgggagt gaccctgcac ggtgtcgccg ctattactac cacaaagggc    720
aacgagcact gttttgtgat tctgcgaggt ggaaagaagg gcaccaacta cgacgccaag    780
tccgttgccg aggctaaggc tcagctgccc gctggttcca acggtctcat gattgactac    840
tcccatggaa acagcaacaa ggattttcga aaccagccta aagttaacga cgtggtttgc    900
```

```
gagcagatcg ccaacggaga aaatgctatt acgggagtga tgatcgagag caacattaac    960

gagggcaacc agggtatccc cgctgaaggt aaggccggac tgaagtacgg tgtttcgatc   1020

accgatgctt gcatcggctg ggaaaccact gaggacgtgc tgcgtaaact cgccgctgcc   1080

gttcgacagc gacgagaggt gaataagaag                                    1110


<210> SEQ ID NO 64
<211> LENGTH: 1875
<212> TYPE: DNA
<213> ORGANISM: Artificial
<220> FEATURE:
<223> OTHER INFORMATION: Codon-optimized and/or mutated sequence

<400> SEQUENCE: 64

atgtcagaat ctttaagcaa ggaccttaat ctgaatgcat tattcattgg agataaagcc     60

gagaatggac agatctataa agcattactc aacgaacttg tggatgaaca cttgggttgg    120

agacagaatt acatgcctca ggatatgcct attataaccc cggaagagaa aagctccgct    180

tcatttgagc atacagtcaa taaaacgaaa gacgtcttat cagaaattag cgcccggatg    240

cgaacacact cagtcccttg gcacaatgcg ggccggtact ggggacatat gaactctgaa    300

actctgatgc cgtcattgct ggcatacaat tttgcgatgt tgtggaacgg caataatgtt    360

gcatatgaat cgagcccggc cacctcgcaa atggaagaag aagtcggtat ggaatttgca    420

aaactgatga gttataaaga tggatggggc catattgtag ctgatggaag cttagctaat    480

ctggaagggt tatggtatgc tcgcaatatc aagtctcttc ctcttgcgat gaaggaggtc    540

actccggagc ttgtcgctgg caaatccgat tgggaactga tgaatctctc aacggaagag    600

atcatgaacc ttttagattc agtgccggag aaaatcgatg agattaaggc acactcagca    660

cgctccggaa aacatcttga gaagttggga aaatggcttg tgccacagac aaagcattat    720

tcatggctta aagcagctga tatcattgga attggcttag atcaggtcat tccagtaccg    780

gtggaccaca attatcgaat ggacattaat gagctcgaga aaattgtcag aggcttggca    840

gctgagaaaa caccgatcct cggagtagtg ggtgttgttg gaagtactga ggaaggggct    900

attgacggca ttgataaaat tgtagcgctt cgccgagtgc tggagaaaga cggtatttac    960

ttttacctgc acgtcgacgc ggcgtatgga ggctatggcc gcgcgatttt tcttgatgaa   1020

gataataatt ttattccgtt cgaggatctg aaggatgtcc attacaaata caatgtgttc   1080

actgaaaata aagactacat cctggaggag gtacattctg cttataaggc cattgaagaa   1140

gcagaatccg taaccataga tcctcataaa atgggctacg tgccgtatag cgcgggggc    1200

attgttatta aagacattag aatgcgggat gtgatctctt actttgctac gtatgttttt   1260

gaaaaagggg cggatattcc tgcgctcttg ggagcgtata ttctcgaagg gtcaaaggcg   1320

ggggccacag ctgcctcagt ctgggccgca catcacgttc ttccgttgaa cgttacaggg   1380

tacgggaagc ttatgggagc tagcattgaa ggggcccatc ggttttataa cttcttgaat   1440

gacctgtctt ttaaagtggg cgataaagag attgaagttc atccgttgac ctatccggat   1500

ttcaacatgg ttgattacgt cttcaaagaa aaaggcaatg atgacttagt tgctatgaac   1560

aagttaaacc atgacgttta cgactattcg agctacgtta aaggaagcat ttatggcaat   1620

gaatttctca catcgcacac agactttgcc ataccggatt atgggaatag tccattacag   1680

tttgtaaatc aactgggctt tagcgacgaa gagtggaaca gagcaggaaa agttacggta   1740

cttagagcgt cagtcatgac accgtacatg aacaaggagg aacattttga ggagtacgct   1800

gaaaaaatta aagctgccct ccaggagaaa ctggaaaaga tctatgcgga ccaattattg   1860
```

gcgtctgaag caaaa 1875

<210> SEQ ID NO 65
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 65
atgtcggaga gccctatgtt tgctgctaat ggaatgccga aggtgaatca gggagcagag 60
gaggatgtta gaattttagg ttatgaccct ttggcctcac ctgccctgtt gcaggtccag 120
attccagcca cgccaacatc attagaaaca gcgaaaagag gaagacggga ggctattgat 180
atcatcacag ggaaagatga tcgagtgtta gtgattgttg ggccatgctc aatccacgat 240
ctggaagcgg cacaagagta cgctctgcgc ttaaagaaac tgtcggatga attgaagggc 300
gatctgtcaa ttattatgcg tgcgtatctt gaaaaacctc gcactacagt cggctggaaa 360
gggctgatca acgacccgga cgtcaataat acgtttaata ttaataaagg actccaaagc 420
gcacgccagc tgttcgtgaa cttaacgaac atcggactgc ctattggatc ggaaatgctc 480
gatactatta gtccgcaata cctggctgat ctcgtatcct tcggagcgat aggcgcaaga 540
accactgaga gccaattaca tagagaactg gcctctggcc tttctttccc tgttggattc 600
aaaaatggca ctgacggtac tctgaatgta gccgtggacg cttgccaagc cgcagcgcac 660
tctcatcatt ttatgggagt aacaaagcac ggtgtggctg ctatcacgac aacgaaaggc 720
aatgagcatt gctttgtaat cctgagagga ggaaaaaagg gaaccaatta cgacgcaaaa 780
agcgtagcgg aagcgaaagc gcaacttccg gccgggagca atggacttat gattgattac 840
tctcatggaa acagtaataa agattttcgc aatcagccta aagttaatga tgtcgtgtgc 900
gaacaaattg ccaacgggga aaacgcaata acgggagtca tgattgagtc taacattaat 960
gaagggaatc agggaatccc ggctgagggc aaagctggtc ttaagtacgg cgtgagcatt 1020
actgatgcat gcattggctg ggaaacaaca gaagatgtgc ttcggaaact ggctgcggcc 1080
gtaagacaaa gacgtgaagt caacaagaaa 1110

<210> SEQ ID NO 66
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 66
atgagcgaat ctccaatgtt cgcagctaac ggtatgccga aggtgaacca gggagccgag 60
gaagatgttc gcatccttgg ctacgatcca ctggcatccc ccgctcttct gcaggtccag 120
atcccagcga cccctactag ccttgaaact gctaagcgcg gccgccgcga ggcgattgac 180
attatcaccg gaaaggatga tcgtgttctg gtaatcgttg gcccatgctc catccacgac 240
ttggaagccg cccaggagta tgccctccgt ttgaagaagc tgtcagatga acttaagggc 300
gatttgtcca tcatcatgcg tgcttacctt gaaaagcccc gcacgacggt gggctggaaa 360
ggattgatca acgatccaga cgtaaataac accttcaaca ttaacaaggg actgcaatct 420
gctcgccaac tgttcgtcaa cctcaccaac atcggcttgc ctatcggaag cgagatgctg 480
gatacaatct cccctcaata cctggctgat ctggtgagct tcggtgcaat tggtgcgcgt 540

```
accaccgagt cccagctcca ccgtgaactg gcgtccggcc ttagcttccc tgtgggattc    600

aagaacggta ccgacggcac cctcaacgtg gctgtggacg cctgccaggc cgctgcgcat    660

tcccatcact tcatgggcgt taccaagcat ggtgtggcgg ctatcaccac aaccaaaggc    720

aatgagcact gtttcgtgat cttgcgcggc ggtaagaagg gcaccaacta cgacgcaaaa    780

tctgttgccg aagcaaaggc ccaactcccc gctggttcca acggattgat gatcgattac    840

agccacggaa atagcaacaa ggattttcgt aaccaaccta aggttaatga cgtcgtgtgc    900

gaacagatcg ctaacggaga aaacgctatt accggcgtta tgatcgaaag caatattaac    960

gagggtaacc aaggcattcc tgccgaaggt aaggcgggcc tgaagtacgg agtgtcaatc   1020

accgatgcat gtatcggctg ggagaccacc gaagatgtcc tgcgcaagtt ggcagccgcg   1080

gtgcgtcagc gacgcgaagt taataagaag                                    1110
```

```
<210> SEQ ID NO 67
<211> LENGTH: 522
<212> TYPE: DNA
<213> ORGANISM: Artificial
<220> FEATURE:
<223> OTHER INFORMATION: Codon-optimized and/or mutated sequence

<400> SEQUENCE: 67

atgacccaac ccctgtttct tattggaccc cgaggttgcg gcaaaaccac cgtgggcatg     60

gccctggcag actcgctgaa tagacgattt gttgataccg atcagtggct gcagtcccag    120

ctgaacatga ctgtcgctga gatcgtcgaa cgagaggagt gggctggctt ccgggcccgt    180

gagaccgctg cccttgaggc agtgactgct ccctcgactg ttatcgccac cggtggaggt    240

atcattctta ctgagtttaa ccggcacttt atgcagaaca acggtatcgt ggtctacctc    300

tgtgcccctg tgtccgttct tgtgaaccga ctgcaagctg cccccgagga ggacctgcga    360

cccacgctga ctggtaagcc tctgtccgaa gaggtgcagg aggtgctgga ggagagagac    420

gccctctacc gagaggtcgc ccatatcatt atcgacgcca ccaacgaacc ctctcaggtc    480

atctccgaga tccgatctgc ccttgcccaa acaatcaact gc                       522
```

```
<210> SEQ ID NO 68
<211> LENGTH: 522
<212> TYPE: DNA
<213> ORGANISM: Artificial
<220> FEATURE:
<223> OTHER INFORMATION: Codon-optimized and/or mutated sequence

<400> SEQUENCE: 68

atgacccagc cactgtttct cattggcccg cgcggatgcg gtaaaaccac tgtaggaatg     60

gcacttgcag actcccttaa ccgtcgcttt gtcgatacag accagtggct tcagtcccaa    120

ctgaacatga ctgtcgccga gatcgtagag cgcgaggaat gggcgggttt ccgcgcacgt    180

gaaacagcgg cacttgaggc agtcaccgct ccttccacag tcatcgcaac gggtggaggc    240

atcatcctga ccgaattcaa tcgccacttt atgcaaaaca acggaattgt cgtctatttg    300

tgcgccccag tgtcagtgct ggtcaatcgc cttcaggccg ccccagaaga agacctccgc    360

ccgacactga ccggtaaacc tctttccgag gaagttcagg aggtcttgga ggaacgcgat    420

gccctttacc gcgaagtcgc acacattatc attgacgcca ccaacgaacc gagccaggtt    480

atttccgaaa tccgttccgc tctggcgcaa accatcaact gc                       522
```

```
<210> SEQ ID NO 69
<211> LENGTH: 1593
```

<212> TYPE: DNA
<213> ORGANISM: Artificial
<220> FEATURE:
<223> OTHER INFORMATION: Codon-optimized and/or mutated sequence

<400> SEQUENCE: 69

```
atgggttctc ttaatacaga agatgttttg gagaatagtt cagcatttgg tgtaactaat      60

ccccttgatc ctgaagaatt cagaagacaa ggacatatga tcatagattt tcttgctgac     120

tattatagag atgtggagaa atatccggtg agaagtcaag tggagcccgg ttatttaaga     180

aaaagactgc cagaaaccgc cccgtacaat ccagagtcca tcgagaccat attacaagat     240

gtaacaactg agattattcc aggtctaacc cattggcaaa gtcctaacta ttacgcctac     300

tttcctagct ccggtagcgt cgccggcttt cttggtgaaa tgttatccac cggtttcaat     360

gttgttggat tcaattggat gagttcacca gccgctactg aattagaatc cgtggttatg     420

gactggtttg gaaaaatgtt gaacctgccg gagtcatttc ttttctctgg aagtggtggt     480

ggcgtgttgc agggtactag ttgtgaagca attttatgca ctttgacggc agcaagagat     540

agaaagctta ataaaattgg tagagagcat atcggtagat tagtagtcta cggatcagac     600

cagactcatt gtgctttaca aaaggctgca caagtcgctg gcatcaatcc taagaatttc     660

agagcgatta agacgtttaa agaaaactcc tttggtttga gcgcagcaac tctaagagaa     720

gtgatcctag aggacatcga ggcagggttg ataccactgt ttgtttgccc tacagtgggg     780

accacttcta gcaccgccgt tgatcctata tctccgatct gtgaagtagc taaagaatac     840

gaaatgtggg tacacgtaga tgcagcttac gctgggtcag cctgtatttg cccagagttt     900

agacatttta ttgatggtgt cgaagaagcg gacagttttt ctcttaatgc tcataagtgg     960

tttttcacta ctttggactg ttgttgtttg tgggttaagg atccatctgc tctagttaaa    1020

gccctatcca ccaatccgga gtatttgaga aataaggcaa cagaatcaag acaagtcgta    1080

gattataaag actggcaaat agccctgtcc agaaggttca gatcattaaa gttatggatg    1140

gttctgagga gctatggcgt caccaatttg agaaattttt tgagaagcca cgtcaagatg    1200

gcaaagactt ttgaaggact gatctgtatg gatggtaggt ttgaaataac tgttcccagg    1260

acttttgcaa tggtttgttt tagattgctg cccccaaaaa caataaaagt atatgataac    1320

ggcgtgcatc aaaacggtaa cggggtagtt cctttgagag acgagaacga gaacctggtt    1380

ttagcgaata aactaaatca ggtttacctt gagactgtta acgctacggg atctgtatat    1440

atgacacatg ccgttgtagg tggcgtgtac atgatccgtt ttgctgtggg atccacccta    1500

acggaagaaa ggcatgtgat ctacgcttgg aaaatattac aagaacacgc cgacttgatt    1560

ttaggtaaat ttagtgaagc agacttttct tca                                 1593
```

<210> SEQ ID NO 70
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 70

```
atgtccgaat ctccaatgtt cgctgccaac ggcatgccga aggtgaacca gggagccgaa      60

gaagacgtgc gcatcctcgg ttatgatccg ctcgccagcc cggcactctt gcaagtgcag     120

attcccgcta cgccaacctc actcgagacc gcgaagcgcg gtcgccgcga agcaatcgac     180

atcattactg gtaaggacga tcgcgtgctc gtgatcgttg gcccgtgctc gattcacgac     240
```

```
ttggaagcgg ctcaagagta cgcgcttcgc ctcaagaaat tgagcgatga actgaaaggt    300

gatttgtcca tcattatgcg cgcgtacctt gaaaagccac gtacgactgt tggttggaag    360

ggtctgatca acgatcctga tgtcaacaac acctttaata ttaataaggg cctccagtcc    420

gcccgccaac ttttcgtgaa cctgaccaac attggccttc caattggctc agagatgctt    480

gacacgatct ctccacaata cctcgcagat ttggtcagct tcggcgcaat cggcgcgcgc    540

accaccgagt cccagctcca ccgcgaactg gcgagcggac tgagctttcc cgtcggcttc    600

aagaatggca cagatggcac cttgaacgtc gcggtggacg cgtgtcaagc cgccgcgcat    660

tcacaccact tcatgggagt gaccttgcac ggtgtagcgg ccatcactac cacgaagggt    720

aacgagcact gcttcgtgat cttgcgtgga ggtaagaagg gaactaatta cgacgccaag    780

tctgtggcgg aggctaaggc tcagttgcca gcgggatcca acggtttgat gatcgattat    840

agccacggca actccaacaa agactttcgt aatcaaccta aggtgaacga tgtagtctgc    900

gaacaaatcg cgaacggcga aaacgcgatc accggtgtga tgatcgaatc taatattaac    960

gaaggtaacc agggtattcc cgcggagggc aaggcaggtc tgaaatacgg agtcagcatt   1020

acggatgctt gcatcggatg ggagaccacc gaagatgttc tccgaaagtt ggcggcagcg   1080

gtgcgccagc gccgcgaagt gaataagaaa                                    1110
```

<210> SEQ ID NO 71
<211> LENGTH: 771
<212> TYPE: DNA
<213> ORGANISM: Artificial
<220> FEATURE:
<223> OTHER INFORMATION: Codon-optimized and/or mutated sequence

<400> SEQUENCE: 71

```
atggatttca caaaaccaga aactgtttta aatctacaaa atattagaga tgaattagtt     60

agaatggagg attcgatcat cttcaaattt attgagaggt cgcatttcgc cacatgtcct    120

tcagtttatg aggcaaacca tccaggttta gaaattccga attttaaagg atctttcttg    180

gattgggctc tttcaaatct tgaaattgcg cattctcgca tcagaagatt cgaatcacct    240

gatgaaactc ccttctttcc tgacaagatt cagaaatcat tcttaccgag cattaactac    300

ccacaaattt tggcgcctta tgccccagaa gttaattaca atgataaaat aaaaaaagtt    360

tatattgaaa agattatacc attaatttcg aaaagagatg gtgatgataa gaataacttc    420

ggttctgttg ccactagaga tatagaatgt ttgcaaagct tgagtaggag aatccacttt    480

ggcaagtttg ttgctgaagc caagttccaa tcggatatcc cgctatacac aaagctgatc    540

aaaagtaaag atgtcgaggg gataatgaag aatatcacca attctgccgt tgaagaaaag    600

attctagaaa gattaactaa gaaggctgaa gtctatggtg tggaccctac caacgagtca    660

ggtgaaagaa ggattactcc agaatatttg gtaaaaattt ttaaggaaat tgttatacct    720

atcactaagg aagttgaggt ggaatacttg ctaagaaggt tggaagagta a             771
```

<210> SEQ ID NO 72
<211> LENGTH: 786
<212> TYPE: DNA
<213> ORGANISM: Artificial
<220> FEATURE:
<223> OTHER INFORMATION: Codon-optimized and/or mutated sequence

<400> SEQUENCE: 72

```
atgaagtatt caaaggaata taaggaaaag acggtggtga agatcaacga cgtgaaattc     60

ggagaaggct tcaccatcat cgccggccca tgctcgatcg agtctcgcga ccagatcatg    120
```

```
aaggttgcgg agtttctggc tgaagtaggc atcaaggtgc ttcgcggcgg cgcttttaag    180

cctcgaacct ccccttactc cttccaggga tacggtgaga aggcgttgcg ctggatgcgt    240

gaagcagcgg atgagtatgg cctggtgacc gtcactgagg tcatggatac acgccatgtt    300

gagcttgtcg ccaaatatag cgatatcttg caaatcggcg cccgcaacag ccaaaacttt    360

gagctcctga aagaagtcgg taaagtggaa aatccagttc ttctgaaacg tggtatgggc    420

aacaccattc aagaacttct ctactctgcg gaatacatca tggcacaagg caatgaaaac    480

gttatcctgt gcgagcgagg catccgtaca ttcgaaactg caacgcgctt cactttggac    540

atctcggctg taccagtagt taaagaactt tcacacctcc caatcattgt ggacccaagc    600

cacccagccg gccgccgctc gctggtgatc ccactcgcca aagcagcgta tgcaattggt    660

gctgatggaa tcatggtgga agttcatccg gagcctgaaa aagctctttc cgactcgcaa    720

cagcaactca ccttcgacga ctttttgcag ctgctgaaag aactcgaagc actcggttgg    780

aaggga                                                              786
```

<210> SEQ ID NO 73
<211> LENGTH: 2376
<212> TYPE: DNA
<213> ORGANISM: Artificial
<220> FEATURE:
<223> OTHER INFORMATION: Codon-optimized and/or mutated sequence

<400> SEQUENCE: 73

```
atgtctaata atggctcatc acctctcgtc ttgtggtaca atcagctcgg tatgaacgat     60

gtcgaccgtg tgggaggaaa gaacgcctct ctgggtgaga tgattactaa tttgagcggt    120

atgggagttt ccgtgccaaa tggttttgct accacagccg acgcgttcaa ccaatttctc    180

gaccagagcg gcgttaacca gcgaatttac gagttgctgg acaaaaactga catcgatgac    240

gtcacccagc tggccaaggc aggcgcacag attcgccagt ggatcatcga taccccattt    300

cagcccgagc tcgagaacgc catccgcgag gcgtacgcac agctcagcgc ggacgacgaa    360

aacgcatcgt tcgctgtacg ttcgtcagca accgcggaag atatgccgga tgcgtctttt    420

gcaggtcagc aagagacgtt cctcaacgtg cagggcttcg atgccgttct tgtggcggta    480

aagcacgtgt tcgcgtccct tttcaacgac cgcgctatca gctaccgtgt tcaccagggc    540

tacgatcatc gtggagtggc tctgtcggca ggcgtacaac gcatggtccg cagcgacttg    600

gcttcttccg gcgttatgtt ctcaatcgac acggaatctg gctttgacca agttgttttc    660

attacctctg catggggtct tggcgaaatg gtcgtgcaag gcgcagtgaa ccccgatgaa    720

ttttatgtgc acaagccaac gctcgccgca aaccgtcccg ccattgtccg ccgtaccatg    780

ggctccaaaa agatccgtat ggtctatgcc ccaacgcaag aacatggcaa gcaggttaaa    840

atcgaagacg tgccacaaga acagcgtgat atcttctccc tgaccaacga ggaggtacag    900

gaactggcta agcaagctgt tcagatcgaa aagcactatg gtcgcccaat ggatatcgag    960

tgggctaagg atggccacac aggcaaattg ttcattgtcc aggcacgccc tgagactgtt   1020

cgctcccgtg gacaagtcat ggagcgctac accctgcaca gccagggaaa gattatcgct   1080

gaaggacgcg ccattggcca tcgcatcggc gccggccccg tgaaggttat tcacgacatc   1140

tccgagatga accgcatcga acctggcgac gtcctggtga ccgatatgac cgacccagat   1200

tgggagccta ttatgaagaa ggcttctgca atcgtaacca accgtggagg tcgcacctgt   1260

cacgctgcta ttatcgcacg cgagctgggt atccctgcag ttgtcggatg cggcgatgcc   1320
```

```
actgaacgaa tgaaagacgg agagaacgtg accgtgtctt gtgcagaagg agacactggc   1380

tacgtctacg cagagttgtt ggagttctcc gtgaaatctt cttcagtaga aaccatgcct   1440

gacttgcctc tgaaggtgat gatgaacgtg ggtaacccgg accgcgcgtt cgattttgcg   1500

tgcttgccga acgaaggtgt tggcttggct cgtctcgagt tcatcatcaa tcgcatgatc   1560

ggtgtgcacc cgcgcgcctt gctcgaattc gatgatcagg aacctcagtt gcagaacgaa   1620

atccgcgaaa tgatgaaggg tttcgactcc cctcgtgaat tttatgtcgg tcgtctcacc   1680

gaaggaatcg caacactcgg cgcggcgttc tatcccaagc gcgtcatcgt tcgactttcc   1740

gatttcaagt ccaacgagta cgccaatctg gtcggcggag agcgttacga gcccgacgaa   1800

gagaacccca tgcttggttt ccgcggtgca ggccgctatg tgtcggacag cttccgcgat   1860

tgtttcgctc tcgaatgtga agctgtcaag cgcgtgcgca acgacatggg ccttaccaac   1920

gtagaaatta tgatcccctt tgttcgcaca gtggatcagg ccaaagcggt tgtggaggaa   1980

ctcgctcgtc agggcctgaa acgcggtgaa aacggcctga agatcatcat gatgtgcgaa   2040

attccgtcca acgctctcct tgccgaacaa tttttggagt acttcgacgg cttctcgatt   2100

ggctccaacg acatgaccca actggccctg ggcctcgatc gcgattcggg cgtcgtcagc   2160

gaactcttcg acgaacgtaa tgacgccgtc aaggcattgt tgagcatggc cattcgcgcg   2220

gccaagaagc agggaaagta cgtgggcatt tgcggacagg gtccctcaga ccatgaggac   2280

tttgctgctt ggttgatgga agaaggtatt gattccttgt ctttgaaccc ggacaccgta   2340

gttcagacct ggctgtctct ggccgaactt aagaaa                             2376
```

<210> SEQ ID NO 74
<211> LENGTH: 801
<212> TYPE: DNA
<213> ORGANISM: Artificial
<220> FEATURE:
<223> OTHER INFORMATION: Codon-optimized and/or mutated sequence

<400> SEQUENCE: 74

```
atggatttta ccaagccaga aacagtgttg gaccttggca acattcgcca ggcacttatc     60

cgcatggagg acaccattgt ttttttcctg attgagcgtt cccagtttta cagcagccca    120

tccgtctaca ttaagaacaa gttccctatc ccgaacttcg acggctcatt ccttgattgg    180

agcctccaac agatggagcg tacccattct caaatccgcc gctacgaagc accagatgag    240

attccattct tcccagaggt gcttctggag agcttcctgc cccccatcaa ctatcctaat    300

atcttggcgt cctaccacaa agaggttaat cataatcaaa ccgtcctgaa cttctacgta    360

gaaaacatcg tccctcaagt cgcctgcgag attggtgagc aagaagaaaa catcggcagc    420

gtatcggtct gcgacatcga ttgtctccag tccctctccc gccgaattca cttcggaaag    480

ttcgtggcgg aggcaaaata ccaatctgac aagccaaagt acattaagtt gatcctggcc    540

aaggacgtta agggcatcga agattccatt actaactctg ctgtggaaga aaaaattctt    600

gaacgcttgc agaagaaggg acaatcctac ggaaccgacc caaccctgat gtattcccaa    660

aacccgcagt cgaaggttcg cccggaggtg attgcgcagc tctataaaga tcacgtcatt    720

ccgctgacga aaaaagttga ggtggactac ctcctgcgcc gattggaaga tgaagatgag    780

gctgttgtag caaaatacaa a                                              801
```

<210> SEQ ID NO 75
<211> LENGTH: 1620
<212> TYPE: DNA
<213> ORGANISM: Artificial
<220> FEATURE:
<223> OTHER INFORMATION: Codon-optimized and/or mutated sequence

<400> SEQUENCE: 75

```
atgcgtgtca acaacggttt gacccctcaa gaattggagg cgtacggtat ctctgatgtc     60
cacgacattg tgtacaatcc ctcttacgat cttctctacc aagaagaatt ggatccatcc    120
ctcaccggct acgagcgtgg cgtgcttact aatctgggcg ctgtcgccgt agataccggt    180
atctttactg gccgttctcc gaaagacaag tacattgtgc gagacgatac tacccgcgac    240
accttctggt gggctgataa gggtaaaggc aaaaacgaca acaaaccttt gtccccggaa    300
acctggcagc acctgaaagg actggtcacc cgtcagttgt caggtaagcg tcttttcgtc    360
gtggatgcct tctgcggcgc gaatccagac acccgcttgt ctgtacgctt cattaccgaa    420
gtcgcttggc aggcgcattt cgtgaagaat atgtttatcc gaccttccga cgaggaactg    480
gcgggcttca agccggactt catcgttatg aacggtgcca aatgtaccaa cccacaatgg    540
aaggaacagg gcctcaatag cgaaaacttt gtggctttca acttgaccga gcgcatgcaa    600
ctgatcggag gtacctggta cggtggagag atgaagaagg gtatgtttag catgatgaac    660
taccttctcc ctctcaaagg cattgcgtcc atgcattgct ctgcgaatgt cggcgaaaaa    720
ggagacgttg cggtgttttt tggattgtcg ggcaccggta agacgaccct cagcaccgat    780
ccaaaacgcc gtttgatcgg tgatgacgaa cacggatggg acgacgacgg tgtgttcaac    840
tttgagggcg gatgttacgc aaaaaccatt aagctttcca aagaagcaga gcctgagatc    900
tacaacgcaa ttcgccgcga cgctttgttg gaaaatgtga cagtacgcga agacggtacc    960
atcgactttg atgacggttc caagactgag aacactcgtg tgtcataccc tatttaccac   1020
attgataata tcgttaaacc agtgagcaag gcgggtcacg cgacaaaagt cattttcctg   1080
accgcagatg cgtttggtgt gttgccacca gtctcgcgct tgaccgctga ccaaacccaa   1140
tatcacttct tgtctggttt caccgctaag ctggcgggaa ctgagcgtgg catcaccgag   1200
ccgacgccaa cgttttcggc ctgcttcggc gccgcattcc tctcactcca cccaacccaa   1260
tatgccgaag tcttggttaa gcgcatgcaa gcggcgggtg cacaagctta cctggtaaac   1320
acgggctgga atggtaccgg caagcgtatt tcaattaagg acactcgagc gatcattgac   1380
gcgatcctta atggctcgct tgacaacgcc gagaccttca ccctcccgat gtttaacctc   1440
gcaatcccaa ccgaactgcc tggcgttgat actaaaatct tggacccccg aaacacgtac   1500
gcttcacctg agcaatggca ggagaaagcc gaaacacttg ccaagctgtt tatcgacaac   1560
ttcgacaaat ataccgatac ccctgctggc gccgcactgg tagcggcagg tcccaagctc   1620
```

<210> SEQ ID NO 76
<211> LENGTH: 1119
<212> TYPE: DNA
<213> ORGANISM: Artificial
<220> FEATURE:
<223> OTHER INFORMATION: Codon-optimized and/or mutated sequence

<400> SEQUENCE: 76

```
atggtagctg aactcaccgc tttgcgtgac cagatcgatg aagtggataa ggcactcttg     60
aacctgctcg cgaagcgcct cgagctcgtg gcagaggtgg gcgaggttaa atctcgtttt    120
ggcctcccga tctatgttcc tgaacgagag gcctccatcc tggccagccg tcgcgcagaa    180
gcggaggcac tcggagtgcc gcctgatctg atcgaggatg ttctgcgacg cgtaatgcga    240
gaaagctatt catccgagaa tgataaaggc tttaaaaccc tgtgtccttc cctgcgtcca    300
```

```
gtcgtgatcg tgggcggtgg cggccaaatg ggtcgtctct ttgaaaagat gttgacgctt    360

agcggctacc aagtgcgcat tctcgagcaa catgattggg accgtgccgc agacatcgtg    420

gccgatgcgg gtatggtcat tgtttcggtc cctatccatg tcaccgagca agtgattggc    480

aaactgccac cccttccaaa agactgtatt ctcgtggact tggcctcggt taaaaacggt    540

cctctccagg caatgctggt tgcacatgat ggcccagtct tgggcttgca cccaatgttc    600

ggcccagata gcggctcatt ggcaaagcag gtggttgttt ggtgcgatgg ccgaaaacca    660

gaggcatatc agtggttcct ggagcagatt caggtatggg gcgcccgtct gcatcgcatc    720

tcggctgttg aacatgatca gaacatggct ttcattcagg ctctccgaca cttcgcaacc    780

ttcgcttatg gtctgcacct ggcggaagag aacgttcagt tggagcagct gctggccttg    840

tccagcccca tttatcgctt ggagctggcc atggtgggcc gtctcttcgc acaggacccg    900

caactttacg ccgacatcat catgtcctca gagcgcaatc ttgcccttat caaacgctac    960

tacaaacgat tcggagaggc gatcgaactc ttggaacagg gcgacaaaca agccttcatc   1020

gattcttttc gcaaggtgga gcattggttt ggtgattatg ttcagcgttt tcagtccgaa   1080

tcgcgtgtac tcttgcgcca agccaacgac aaccgtcaa                          1119
```

<210> SEQ ID NO 77
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 77

```
atgtccgaat cacccatgtt cgcagccaac ggcatgccga aggtcaatca aggcgcggaa     60

gaagatgtcc gcattctcgg ctatgatcca cttgcatccc ctgcgctgct gcaagtacaa    120

attcctgcca ccccgacctc gctggaaact gccaagcgcg gtcgtcgcga ggcgatcgac    180

attattacag gtaaggatga ccgcgttctc gttattgtag gtccatgctc catccacgat    240

ctggaagccg cgcaggaata cgcactgcgt ctgaaaaaac tgtccgatga gctcaagggc    300

gacctttcga tcatcatgcg cgcatacctt gagaagcctc gcaccacggt cggctggaaa    360

ggcctgatca atgaccctga tgtgaataac acgttcaaca tcaacaaagg cttgcagtcc    420

gcgcgacaat tgttcgtgaa cctgaccaac atcggcctcc caattggtag cgaaatgttg    480

gacaccatca gccctcaata cttggcagat cttgtgtctt tcggagctat tggcgcacgc    540

accaccgagt cccaattgca ccgtgagctg gcatcaggtc tgagcttccc tgtgggtttc    600

aagaacggca ccgacggtac tctcaatgtg gcggtcgatg cttgtcaagc ggcggcccac    660

agccatcact ttatgggtgt tacattgcac ggtgtggctg ctattactac gacaaaagga    720

aacgaacact gcttcgtcat cctccgtggt ggtaagaagg gcaccaacta cgatgccaaa    780

tctgtggcag aagcaaaggc acaacttcct gcaggtagca acggcctcat gattgattac    840

tctcatggca actcgaacaa agactttcgc aaccaaccga aggtgaacga tgttgtttgc    900

gaacagattg caaacggcga gaatgccatc acgggtgtga tgatcgaatc taacattaat    960

gaaggaaacc aaggtattcc tgcagagggc aaggcgggct tgaaatacgg cgtatcaatc   1020

accgatgcct gtatcggctg ggaaaccacc gaagacgtgc ttcgaaagct tgccgcagcg   1080

gtgcgccagc gccgcgaagt taacaagaag                                    1110
```

<210> SEQ ID NO 78
<211> LENGTH: 522

<212> TYPE: DNA
<213> ORGANISM: Artificial
<220> FEATURE:
<223> OTHER INFORMATION: Codon-optimized and/or mutated sequence

<400> SEQUENCE: 78
atgacccagc cactgttcct gatcggccct cgcggttgcg gaaagaccac tgttggtatg 60
gcccttgcgg actcacttaa tcgccgtttc gtagacacag atcagtggct tcagagccag 120
cttaacatga cagtggcgga aatcgtggaa cgcgaagagt gggcaggttt tcgcgcccgc 180
gaaactgctg ccttggaagc agtgaccgca ccttcaactg tcattgccac tggcggcggc 240
atcatcctga cggagttcaa ccgccacttc atgcaaaata acggaatcgt agtatatctg 300
tgcgcccctg ttagcgtgct ggtcaaccgc ctgcaggcgg cgcctgagga agacctgcgt 360
cctaccctta ccggaaaacc actctccgag gaagtgcagg aagtgctcga ggaacgcgac 420
gcactctacc gcgaagtcgc ccatatcatt atcgatgcga ccaatgaacc atcacaggtg 480
atctccgaga ttcgctcagc tctggcccag acaattaact gc 522

<210> SEQ ID NO 79
<211> LENGTH: 519
<212> TYPE: DNA
<213> ORGANISM: Artificial
<220> FEATURE:
<223> OTHER INFORMATION: Codon-optimized and/or mutated sequence

<400> SEQUENCE: 79
atggcggaaa agcgtaacat ttttctggtg ggtccaatgg gagccggcaa gtctaccatt 60
ggtcgacagc tggctcaaca actgaacatg gagttctacg acagcgatca ggaaatcgaa 120
aaacgaaccg gagctgacgt tggctgggtg ttcgatttgg aaggcgagga gggttttcgt 180
gaccgcgagg agaaagtgat caacgagctg acagaaaagc aaggcatcgt cctcgccacc 240
ggcggcggtt ccgtgaagag ccgcgagact cgtaaccgac tgagcgcgcg aggcgttgtg 300
gtatatctcg aaaccaccat cgaaaagcag ctggcacgca cgcaacgcga caagaagcgc 360
cctctcctgc acgtcgaaac ccccaccgcgt gaggtcctgg aagcactggc gaacgagcgt 420
aacccgcttt acgaggagat cgccgacgta accatccgta ccgatgacca gagcgctaag 480
gttgtggcga accaaattat ccatatgttg gaatccaac 519

<210> SEQ ID NO 80
<211> LENGTH: 519
<212> TYPE: DNA
<213> ORGANISM: Artificial
<220> FEATURE:
<223> OTHER INFORMATION: Codon-optimized and/or mutated sequence

<400> SEQUENCE: 80
atgactgagc ccatctttat ggtcggtgct cgcggctgcg gaaaaacaac cgtaggccgc 60
gagctcgcac gtgcactggg ctacgaattt gtcgataccg atatctttat gcagcacacc 120
tcgggcatga ccgtggcaga tgtcgtggcc gccgaaggct ggccgggctt ccgccgtcgc 180
gagtccgagg cgctccaggc cgttgcaacc cccaaccgcg tagtggcgac cggcggaggt 240
atggtgctgc tcgagcagaa ccgccaattc atgcgtgctc acggcacggt ggtatatctg 300
ttcgcgcctg ctgaggaact cgcactgcgc ttgcaggcat ctccgcaggc acaccagcgc 360
ccgaccctga ccggccgccc catcgcggag gaaatggaag cggtcctgcg cgaacgcgaa 420
gctctctacc aggatgttgc ccactacgtt gtcgatgcaa cgcagccacc agcggccatc 480
gtgtcagaac tcatgcagac catgcgtctc cccgcggct 519

<210> SEQ ID NO 81
<211> LENGTH: 4764
<212> TYPE: DNA
<213> ORGANISM: Artificial
<220> FEATURE:
<223> OTHER INFORMATION: Codon-optimized and/or mutated sequence

<400> SEQUENCE: 81
atggtgcagc tggcaaaggt gccaatcctg ggcaacgata tcatccacgt gggctacaac 60
atccacgatc acctggtgga aaccatcatc aagcactgcc catcctccac ctacgtgatc 120
tgcaacgata ccaacctgtc caaggtgcca tactaccagc agctggtgct ggaattcaag 180
gcatccctgc cagaaggctc ccgtctgctg acctacgtgg tgaagccagg cgaaacctcc 240
aagtctcgtg aaaccaaggc acagctggaa gattacctgt tggtggaagg ctgcacccgt 300
gataccgtga tggtggcaat cggtggcggt gtgatcggcg atatgatcgg cttcgtggca 360
tccaccttca tgcgtggcgt gcgtgtggtg caggtcccaa cctccttgct ggcaatggtg 420
gattcctcca tcggtggcaa gaccgcaatc gataccccac tgggcaagaa cttcatcggt 480
gcattctggc agccaaagtt cgtgctggtc gatatcaagt ggctggaaac cctggcaaag 540
cgtgaattca tcaacggcat ggccgaagtg atcaagaccg cctgcatctg gaacgcagat 600
gagttcaccc gtctggaatc caacgcctcc ttgttcctga acgtggtcaa cggtgcaaag 660
aacgtgaagg tgaccaacca gctgaccaac gaaatcgatg aaatctccaa caccgatatc 720
gaagcaatgc tggatcacac ctacaagttg gtgttggaat ccatcaaggt gaaggctgaa 780
gtggtgtcct ccgatgaacg tgaatcctcc ttgcgtaacc tgctgaactt cggtcactcc 840
atcggccacg catacgaagc aatcttgacc ccacaggcac tgcacggcga atgcgtgtcc 900
atcggcatgg tgaaagaagc agaactgtcc cgttacttcg gcatcttgtc cccaactcag 960
gtggcacgtc tgtccaagat cctggtggca tacggcctgc cagtgtctcc agatgaaaag 1020
tggttcaaag aactgaccct gcacaagaaa accccattgg atatcctgct gaagaagatg 1080
tccatcgata agaagaacga aggctccaag aaaaaggtgg tgatccttga atccatcggt 1140
aagtgctacg gcgattccgc acagttcgtg tccgatgaag atctgcgttt catcctgacc 1200
gatgaaacct tggtgtaccc attcaaagat atcccagcag atcagcagaa ggtggtcatc 1260
ccaccaggtt ccaagtccat ctccaaccgt gcactgatcc tggcagcact tggcgaaggc 1320
cagtgcaaga tcaagaacct gctgcactcc gatgacacca agcacatgct gaccgcagtg 1380
cacgaactga agggtgcaac catctcctgg gaagataacg gcgaaaccgt ggtggtcgaa 1440
ggccacggtg gttccacctt gtccgcatgc gcagatccac tgtacttggg caacgcaggt 1500
actgcatccc gtttcttgac cagcttggca gccctggtga actccacctc ctctcagaag 1560
tacatcgtcc tgaccggcaa cgctcgtatg cagcagcgtc caatcgcacc actggtggac 1620
tccctgcgtg caaacggcac caagatcgaa tacctgaaca acgagggctc cctgccaatc 1680
aaggtctaca ccgattccgt gttcaaaggc ggtcgtatcg aactggcagc aaccgtgtcc 1740
tctcagtacg tgtcctccat cctgatgtgc gcaccatacg ccgaagaacc agtgaccttg 1800
gcactggttg gcggtaagcc aatctccaag ctgtacgtgg atatgaccat caagatgatg 1860
gaaaagttcg gcatcaacgt ggaaacctct accaccgaac catacaccta ctacatccca 1920
aagggccact acatcaaccc atccgaatac gtgatcgaat ccgatgcatc ctccgcaacc 1980
tatccactgg cattcgcagc aatgaccggc accaccgtga ccgtgccaaa catcggtttc 2040
gaatccttgc agggcgacgc acgtttcgca cgtgatgtgc tgaagccaat gggctgcaaa 2100
atcacccaga ccgcaacctc caccactgtg tctggcccac cagtcggcac cctgaagcca 2160
ctgaagcacg tggacatgga accaatgacc gatgcattcc tgaccgcatg cgtggtggca 2220
gcaatctccc acgattccga tccaaactcc gcaaacacca ccaccatcga aggtatcgca 2280
aaccagcgtg tgaaagaatg caaccgtatc ttggcaatgg caaccgaact ggctaagttc 2340
ggcgttaaga ccaccgagct gccagatggc atccaggtgc acggcctgaa ctccatcaaa 2400
gatctgaagg tcccatccga ttcctccggt ccagtgggcg tgtgcaccta cgacgatcac 2460
cgtgtggcaa tgtccttctc cttgttggct ggcatggtca actcccagaa cgaacgtgat 2520
gaagtggcaa acccagtgcg tatcctggaa cgtcactgca ccggcaagac ctggcctgga 2580
tggtgggacg tgttgcactc tgaactgggt gcaaagctgg atggcgcaga accattggaa 2640
tgcacctcca agaagaactc caaaaagtcc gtggtgatca tcggtatgcg tgccgcaggc 2700
aagaccacca tttccaagtg gtgcgcatcc gcattgggct ataagttggt ggatctggat 2760
gaactgttcg agcagcagca caacaaccag tccgtgaagc agttcgtggt ggaaaacggc 2820
tgggagaagt tccgtgaaga agaaacccgt atcttcaaag aagtgatcca gaactacggc 2880
gacgatggct acgtgttctc cactggcggt ggcatcgtgg aatccgcaga atcccgtaag 2940
gcactgaagg atttcgcgtc ctccggtggc tacgtcctgc acttgcaccg tgacatcgaa 3000
gaaaccatcg tgttcttgca gtccgatcca tctcgtccag catacgtgga agaaatccgt 3060
gaagtgtgga accgtcgtga aggttggtac aaagaatgct ccaacttctc cttcttcgca 3120
ccacactgct ccgcagaagc cgaattccag gcattgcgtc gttccttctc caagtacatt 3180
gcaaccatta ccggtgtgcg tgaaatcgaa atcccatccg gtcgttccgc attcgtgtgc 3240
ctgaccttcg acgatctgac cgaacagacc gaaaacttga cccctatctg ctacggctgc 3300
gaagctgtgg aagtgcgtgt cgatcacttg gcaaactact ccgctgattt cgtgtccaag 3360
cagctgtcca tcttgcgtaa ggcaaccgat tccattccaa tcatcttcac cgtgcgtacc 3420
atgaagcaag gcggtaactt cccagatgaa gaattcaaga ccctgcgtga actgtacgat 3480
atcgcactga agaacggcgt ggaattcctg gatttggaac tgaccttgcc aaccgatatc 3540
cagtacgagg tgatcaacaa gcgtggcaac accaaaatca tcggctccca ccacgatttc 3600
cagggcctgt actcctggga tgatgcagaa tgggaaaacc gtttcaacca ggccttgacc 3660
ttggatgtgg atgtggtgaa gttcgtgggc accgcagtga acttcgaaga taacctgcgt 3720
ttggaacact tccgtgacac ccacaagaac aagccattga tcgccgtgaa catgacctcc 3780
aagggctcca tctctcgtgt gttgaacaac gtgttgaccc cagtcacctc cgatctgctg 3840
cctaactccg cagcaccagg ccagttgacc gtggcacaga tcaacaaaat gtacacctcc 3900
atgggtggta tcgaaccaaa agaattgttc gtggtcggca agccaatcgg ccactctcgt 3960
tccccaatcc tgcacaacac cggctacgaa atcttgggcc tgccacacaa gttcgataag 4020
tttgaaaccg aatccgctca gctcgtgaaa gaaaagctgt tggatggcaa caaaaacttc 4080
ggtggcgcag cagtgaccat tccactgaag ttggatatca tgcagtacat ggatgaattg 4140
accgacgcag caaaggtgat cggtgctgtg aacaccgtga ttccattggg caacaagaag 4200
ttcaagggcg ataacaccga ttggttgggc atccgtaacg cattgattaa caacggcgtg 4260
ccagaatacg tgggccacac cgcaggcctg gtgattggcg ctggcggaac ctctcgtgca 4320
gcactgtacg cactgcactc cctgggttgc aagaaaatct tcatcatcaa ccgtaccacc 4380

```
tccaaactga aaccactgat cgagtccctg ccatccgagt tcaacatcat cggcatcgaa   4440

tccactaagt ccatcgaaga gatcaaagaa cacgtgggcg tcgcagtgtc ctgcgtgcca   4500

gcagataagc cactggatga tgaactgctg tccaagttgg aacgtttcct ggtgaaaggc   4560

gcacacgcag cattcgtgcc aaccttgctg gaagcagcat acaagccatc tgtcacccca   4620

gtgatgacca tctctcagga taagtaccag tggcacgtgg tgccaggctc tcagatgctg   4680

gtccaccagg gcgtcgccca gttcgaaaag tggaccggct tcaagggtcc attcaaggcc   4740

atcttcgatg ctgtgaccaa agag                                          4764
```

```
<210> SEQ ID NO 82
<211> LENGTH: 1356
<212> TYPE: DNA
<213> ORGANISM: Artificial
<220> FEATURE:
<223> OTHER INFORMATION: Codon-optimized and/or mutated sequence

<400> SEQUENCE: 82

atggtctccg aagacaaaat cgaacaatgg aaggctacca aagtaattgg cattattggt     60

ctgggagata tgggcctgtt gtatgcgaat aagttcaccg acgcaggttg gggcgtgatc    120

tgctgcgacc gtgaggaata ctacgatgaa cttaaggaaa aatacgcatc ggctaagttc    180

gagctcgtga aaaatggtca cctcgtctcg cgtcagtccg attacattat ctattcggtt    240

gaagcatcga acatctcgaa gatcgtggcc acttacggcc cctcgtccaa ggtcggtacc    300

atcgtgggtg gtcagacctc ctgcaaactg ccagagatcg aggcattcga aaagtacttg    360

cctaaggatt gcgatattat tacagttcac tctcttcatg gtccgaaggt taatacggag    420

ggtcagccac tggtcattat caaccaccgt tcgcaatacc ccgaatcctt tgagtttgtt    480

aacagcgtta tggcgtgcct taagtccaaa caggtctact tgacctacga ggaacacgac    540

aaaatcacag ctgacacaca ggccgtgact catgctgcat tcctctcgat gggcagcgct    600

tgggccaaga tcaaaattta cccttggacc ttgggcgtga acaaatggta tggtggcctc    660

gagaacgtga aagtcaacat ttccttgcgc atttattcta ataagtggca cgtttacgcg    720

ggcctcgcaa tcaccaaccc gtctgctcac caacaaattc tgcagtatgc cacatcagcc    780

accgaactct tttccctgat gatcgataat aaggagcaag agctgaccga ccgcctgctg    840

aaagcaaagc agttcgtatt tggaaaacat accggtctgc ttttgttgga cgatactatc    900

cttgagaagt actccctttc gaagtcctcc atcggcaact ctaataactg caagccagtg    960

ccaaactctc acctttcctt gctcgcaatc gtcgattcgt ggttccagct gggtatcgat   1020

ccatacgacc acatgatctg ctccactcca ctttttcgca tctttctcgg cgtgagcgag   1080

tacctctttc tcaagcccgg cttgctggag cagacgatcg acgcagcaat tcacgataaa   1140

tccttcatta aggatgattt ggagttcgtg atcagcgctc gtgagtggtc ctcggtggtg   1200

tcttttgcaa acttcgatat ctacaagaaa cagttccagt ccgtccaaaa gttctttgag   1260

ccgatgctcc ctgaagccaa ccttatcggc aacgagatga tcaaaaccat tttgtcccat   1320

tccagcgatc gatcggcggc tgaaaagcgc aacacg                             1356
```

```
<210> SEQ ID NO 83
<211> LENGTH: 4458
<212> TYPE: DNA
<213> ORGANISM: Artificial
<220> FEATURE:
<223> OTHER INFORMATION: Codon-optimized and/or mutated sequence

<400> SEQUENCE: 83
```

```
atgctgtacg acaagtccct ggagcgtgat aactgcggct ttggcctcat tgcccatatc     60
gaaggcgaac catcgcacaa ggtagtacga accgctatcc acgccttggc tcgaatgcag    120
caccgtggtg ctatcctcgc agacggaaag acgggtgacg gctgtggtct gttgctgcaa    180
aagccggatc gattcttccg cattgtggct caggaacgcg gctggcgcct ggcgaagaat    240
tacgccgttg gtatgctctt cttgaataag gacccagagc tggctgctgc tgcgcgtcgt    300
attgttgagg aggaactgca gcgcgagacc ctgtctatcg tgggctggcg cgatgtcccc    360
accaatgagg gcgttctcgg cgaaatcgca ctcagctcct tgccacgcat tgagcagatc    420
ttcgttaacg caccggcagg ttggcgtcct cgcgacatgg aacgccgttt gttcatcgca    480
cgtcgacgta ttgaaaaacg tctcgaagct gacaaagatt tctacgtgtg ctccctctcg    540
aacttggtaa acatttacaa gggcctgtgc atgcctacag atctgcctcg cttctacctg    600
gacctggctg acttgcgatt ggagtccgcg atctgccttt tccatcagcg tttttccacc    660
aataccgtcc cacgctggcc cctggcccag cctttccgct acctcgcgca taatggtgaa    720
atcaacacca tcacaggtaa ccgtcagtgg gcccgtgcgc gtacctacaa attccagact    780
ccactcatcc ctgacttgca cgacgcggca ccatttgtta atgaaacagg cagcgattcc    840
tcgtccatgg ataacatgct cgagctgctg ttggctggtg gcatggacat catccgcgca    900
atgcgccttc ttgtaccccc tgcttggcag aacaatcctg atatggatcc agaattgcgc    960
gccttcttcg atttcaattc aatgcatatg gagccttggg atggccctgc aggcattgtt   1020
atgagcgacg gtcgatttgc ggcatgcaat ctggatcgca atggtctccg cccagcgcgt   1080
tatgtcatta ctaaagataa gctgattact tgcgcctccg aagtcggaat ctgggactac   1140
cagccggatg aagtcgtaga aaaaggtcga gtgggaccag gtgaactcat ggttatcgac   1200
actcgttctg gacgaatcct gcactctgcc gaaacagatg atgacctgaa atcccgtcac   1260
ccctacaagg agtggatgga aaagaacgta cgccgtttgg tcccttttga agatctcccg   1320
gacgaggagg tgggcagccg cgagctcgat gatgatacgc tcgcttccta ccaaaaacag   1380
ttcaactact ccgcagaaga actcgatagc gtcatccgag ttctgggaga aaatggtcag   1440
gaagcggtcg gttccatggg agatgatacc ccttcgcag  tacttagctc ccagccccgt   1500
atcatctatg actattttcg ccagcaattc gcacaggtga caaacccacc aattgatcca   1560
ctgcgcgagg ctcacgtaat gtctctcgcg accagcatcg gtcgcgagat gaacgtcttt   1620
tgtgaggcag aaggccaggc tcaccgtctt tccttcaaga gcccaatcct cctgtactcg   1680
gattttaaac agttgactac catgaaggag gaacactacc gtgcggacac cttggatatc   1740
actttcgacg tgaccaagac cacactggaa gccaccgtga aagaactctg cgataaggct   1800
gaaaagatgg tccgctccgg caccgtgctt cttgttttgt cggaccgaaa cattgcaaag   1860
gatcgcctgc ctgtcccggc acctatggca gtcggagcca tccagacccg tcttgtggac   1920
caatcgctcc gctgcgacgc aaacatcatt gttgaaacag catcggcgcg cgacccacac   1980
cacttcgccg ttttgctggg attcggcgcc acggctattt acccgtattt ggcatatgaa   2040
accctgggcc gtctcgttga tacgcacgcc attgcgaagg attaccgcac tgtcatgctc   2100
aactaccgta atggtattaa caagggtctg tacaagatca tgtctaaaat gggaatcagc   2160
accatcgcga gctatcgatg ttccaagctc ttcgaagctg tgggcctgca tgatgatgtc   2220
gtcggactct gctttcaagg agcagttagc cgtatcggcg gagcatcttt tgaagatttc   2280
cagcaggacc tcctgaacct ctcaaagcgt gcttggctgg cacgcaaacc tatttcgcaa   2340
```

ggtggcctcc ttaaatacgt ccacggtggt gaataccatg cgtataatcc ggacgtggtt 2400
cgcacgctgc aacaagccgt ccagtccggc gaatactctg attatcaaga gtacgctaag 2460
cttgttaacg aacgtccagc caccaccttg cgcgacctgt tggcaattac gcccggagaa 2520
aacgctgtca acatcgccga tgttgaacca gcatcagaac tgtttaaacg attcgatact 2580
gcagcgatgt caattggtgc actgtcccca gaagcgcatg aagccttggc cgaggccatg 2640
aacagcatcg gaggtaatag caactcaggt gagggaggag aggacccagc acgctacggt 2700
accaacaagg tctcccgcat caagcaagtt gcatcgggcc gcttcggcgt gactccggca 2760
tatctggtga acgctgacgt gattcaaatc aaagtcgcac agggagccaa gccgggcgaa 2820
ggcggtcaac tgccaggcga taaggtaact ccctacatcg cgaaattgcg ctattcggtt 2880
cctggagtca ccctcatttc tccgccaccc caccacgata tctacagcat cgaggatttg 2940
gcccaattga tcttcgactt gaaacaggtc aacccgaagg ctatgatctc tgtaaaactg 3000
gtgtccgaac ctggtgtggg aaccatcgca accggtgtag caaaggccta cgccgacctg 3060
attaccattg ctggctacga tggcggcaca ggtgcttccc cgctctcgtc cgttaagtac 3120
gcgggttgtc catgggagct gggcttggta gaaacccaac aagcactggt tgcgaacggc 3180
ctccgtcaca agattcgctt gcaggttgat ggcggtctca agacgggtgt ggatatcatc 3240
aaagctgcca ttctgggagc cgaatccttc ggatttggaa ccggcccaat ggtggcgttg 3300
ggttgcaagt acctccgcat ctgtcacctt aataattgcg ctaccggtgt ggctacccag 3360
gatgacaagc tccgaaagaa ccactaccat ggcctcccct ttaaagtgac gaactacttc 3420
gagtttatcg cacgagagac acgcgagttg atggcccagc tcggcgtcac ccgcctggtg 3480
gatttgatcg gacgtaccga cttgctgaaa gagctggatg gcttcaccgc aaagcagcaa 3540
aagctggccc tgtcgaagct cctcgagacg gcagagcctc acccaggaaa agcgctctac 3600
tgtaccgaaa ataaccctcc tttcgataat ggcctgctta acgcacaatt gctgcagcag 3660
gccaaacctt tcgttgatga gcgccagtcg aagacgttct ggttcgatat ccgtaacacg 3720
gatcgctccg ttggcgcctc cttgtccgga tatattgccc aaacccacgg cgatcagggc 3780
ttggccgctg acccgatcaa ggcctatttc aacggtaccg ccggacagag cttcggcgtc 3840
tggaatgccg gaggtgttga gctctacttg actggagatg ctaacgatta cgtaggcaag 3900
ggtatggcgg gcggcttgat tgcgatccga ccccctgtcg gctccgcctt ccgaagccat 3960
gaagcatcta tcattggtaa cacctgtctt tatggcgcaa cgggaggtcg tctctacgct 4020
gccggtcgtg ccggagaacg cttcggagtc cgaaactccg gcgcgattac agttgttgag 4080
ggaatcggtg ataatggctg tgaatatatg accggcggca tcgtttgcat cttgggcaag 4140
accggagtga atttcggtgc tggcatgacc ggtggcttcg cctacgtctt ggacgagtcg 4200
ggcgatttcc gaaaacgtgt taacccagag ctcgtcgaag ttctgtctgt agatgcgctc 4260
gctatccatg aggaacactt gcgcggactc atcactgaac atgtccaaca taccggcagc 4320
cagcgcggcg aagagatctt ggccaactgg tcgaccttcg cgactaaatt tgcactcgtg 4380
aaacccaaat cttccgatgt gaaggctctc ttgggtcacc gtagccgttc tgcagctgaa 4440
ctgcgcgttc aagcgcag 4458

<210> SEQ ID NO 84
<211> LENGTH: 1539
<212> TYPE: DNA
<213> ORGANISM: Artificial
<220> FEATURE:
<223> OTHER INFORMATION: Codon-optimized and/or mutated sequence

<400> SEQUENCE: 84

```
atgactgcgg gctccgcccc acctgttgat tacacctccc tcaagaagaa cttccagcct      60
ttcctgtcgc gccgagtcga gaatcgctca ctcaagtcgt tttgggacgc gtcggatatc     120
tccgacgatg tgatcgagtt ggcgggcggt atgcctaatg aacgtttctt ccctattgag     180
tcaatggacc ttaaaatttc caaagtgccg ttcaacgata accctaagtg gcacaattca     240
ttcactaccg cccacctgga cttgggctca ccgtcggaat tgcccattgc ccgctctttc     300
cagtacgcag agacgaaagg ccttcctcca ctgttgcact ttgtaaagga tttcgtttca     360
cgcattaacc gtccagcttt ttccgatgag accgaatcca actgggatgt tattctgtct     420
ggcggtagca acgactctat gttcaaggtt ttcgagacca tctgtgacga gtccacgact     480
gtcatgattg aagagttcac ttttactcct gccatgtcca acgtagaagc gaccggtgcg     540
aaggtgatcc cgattaaaat gaaccttact tttgatcgcg aaagccaggg cattgatgtt     600
gagtacctca cccaactgct ggacaattgg tccaccggcc cgtacaagga tctgaacaaa     660
ccacgcgtcc tttataccat cgccactgga cagaacccga ctggtatgtc tgtgccacaa     720
tggaaacgcg aaaaaatcta ccaacttgcc caacgccacg acttcttgat tgtcgaagac     780
gatccatatg gctacctgta ctttccatcg tacaaccccc aagagccatt ggagaatccc     840
tatcattcat ccgatctcac cacggagcgc tacctgaacg acttcttgat gaaatcattc     900
ttgaccctcg ataccgacgc acgtgtgatc cgtttggaaa ccttttctaa aatttttgcc     960
cccggcctcc gcctgtcttt cattgtagcc aacaaattct tgctgcaaaa gattttggat    1020
ttggcggaca tcaccacccg cgcgcctagc ggtacttccc aagcaattgt gtactccacc    1080
attaaagcca tggccgaatc caatttgtcc tcaagccttt ctatgaaaga agcaatgttc    1140
gagggctgga ttcgctggat catgcaaatc gcatctaagt ataaccaccg caagaacttg    1200
actctgaaag cactctacga gacggaatct tatcaggccg gccaattcac cgttatggaa    1260
ccgtccgccg gtatgttcat cattatcaaa attaattggg gcaattttga tcgccctgat    1320
gatctcccgc aacaaatgga tatcttggac aagttcttgc ttaagaacgg agtgaaggtg    1380
gtcttgggct acaagatggc cgtctgcccc aattactcta agcagaactc cgactttttg    1440
cgcctcacca ttgcctatgc tcgcgatgat gatcagctga tcgaagcaag caagcgtatc    1500
ggctccggaa ttaaggagtt tttcgacaac tataagtcc                           1539
```

<210> SEQ ID NO 85
<211> LENGTH: 1362
<212> TYPE: DNA
<213> ORGANISM: Artificial
<220> FEATURE:
<223> OTHER INFORMATION: Codon-optimized and/or mutated sequence

<400> SEQUENCE: 85

```
atggacccat acatgatcca gatgtcctcg aaaggcaatc tgccatcaat ccttgatgtc      60
cacgttaacg taggtggtcg ctcatctgtc cccggcaaga tgaagggccg taaggcacgc     120
tggtccgtac gcccgagcga tatggcaaag aaaaccttta acccaatccg tgctatcgtt     180
gacaacatga aagtgaagcc taacccgaat aaaaccatga tttccctgtc gatcggagat     240
ccaactgtgt tcggcaacct cccaaccgat cccgaggtta ctcaggccat gaaagacgcg     300
ttggactcag gcaagtacaa tggatatgct ccttccatcg gatttttgtc tagccgcgaa     360
gagattgcat cttattacca ttgtccggaa gcccctcttg aggcaaagga tgtgattttg     420
```

```
acatccggtt gttctcaggc tatcgatctt tgtctcgcag tgctcgcgaa tcctggccaa    480

aacatccttg ttccacgtcc aggcttctcc ttgtataaaa cccttgccga atcaatggga    540

atcgaagtaa agctgtacaa cttgttgcca gagaaaagct gggaaatcga cctgaaacag    600

ctggaatacc ttattgatga aaagacagcc tgcctgatcg tgaataaccc atccaaccca    660

tgtggtagcg tgttctccaa gcgccatctc cagaagatcc tcgccgtggc tgcccgtcaa    720

tgcgttccaa tcctcgcaga cgagatctac ggcgacatgg ttttcagcga ttgtaagtac    780

gagccactgg cgacgttgtc aaccgatgtc ccgatcctga gctgtggagg tctggctaag    840

cgctggctgg taccaggttg gcgccttggc tggattctca ttcatgatcg ccgagacatt    900

ttcggaaatg agatccgcga cggtcttgtt aagctgtccc agcgcatctt gggtccttgt    960

acgattgtgc aaggtgcgct caaatctatc ctttgccgca ccccaggtga attctaccac   1020

aacactctct ctttcctgaa gtccaacgcg gatctttgct acggcgcgtt ggccgcaatc   1080

ccaggtttgc gccctgtccg accatccggc gccatgtacc tgatggtcgg tatcgaaatg   1140

gagcacttcc cagagttcga gaacgacgtt gaattcaccg agcgattggt ggctgaacag   1200

tccgttcact gcctcccagc aacctgcttt gaatacccaa acttcatccg tgtcgttatc   1260

accgtgccag aagtcatgat gctcgaagcg tgctcccgca tccaagagtt ctgtgagcag   1320

cactatcact gcgcagaggg ctcccaggaa gaatgtgata aa                       1362
```

<210> SEQ ID NO 86
<211> LENGTH: 2040
<212> TYPE: DNA
<213> ORGANISM: Artificial
<220> FEATURE:
<223> OTHER INFORMATION: Codon-optimized and/or mutated sequence

<400> SEQUENCE: 86

```
atgactcagt ttactgatat cgacaagctg gcagtttcta ccatccgcat cctggcggtc     60

gacaccgtct caaaggcaaa ctccggccac cctggtgcgc ctctgggtat ggctccagcg    120

gcccacgtcc tttggtcaca gatgcgaatg aatccaacga atcctgattg gatcaaccgc    180

gaccgcttcg ttctctccaa tggacacgca gttgctttgc tgtactcaat gcttcatctc    240

accggttacg atctgagcat tgaagatttg aagcaattcc gccagctggg ttcccgcacc    300

cccggtcacc ctgagttcga attgcccggc gttgaagtta cgaccggccc acttggacaa    360

ggtatttcca acgcagtcgg aatggctatg gcgcaggcga atctggcagc gacctacaac    420

aaaccgggtt ttacactctc cgacaattac acttacgttt tcctgggcga cggatgcctg    480

caagaaggca tctccagcga ggcgtcctcc ttggcgggcc acctcaaact gggtaacctg    540

attgcaatct atgacgataa caaaatcact attgacggcg ccacttccat ctctttcgac    600

gaggatgttg caaagcgcta cgaggcatac ggttgggaag tactgtacgt cgagaatgga    660

aacgaagatc tcgcaggcat cgcgaaagct atcgcccaag ccaagctgtc caaggataag    720

cccactctga ttaaaatgac gaccaccatt ggatacggct ccttgcacgc gggttcacac    780

tctgttcatg gtgctccttt gaaagccgat gatgttaagc aactcaaatc taagtttggc    840

ttcaatcctg ataagtcatt cgttgttcca caggaagtgt acgaccacta tcagaagacc    900

atcctcaaac ccggagttga agccaacaac aagtggaata agctcttcag cgaataccag    960

aagaagtttc ccgagctggg agcggaactt gcccgtcgtc tcagcggtca actgcctgcc   1020

aattgggaat ccaagctgcc cacgtacact gccaaggaca gcgccgttgc gacccgtaaa   1080

ctgtccgaaa ccgtcttgga ggacgtctac aaccaattgc ctgagctgat cggtggctcc   1140
```

gcggatctta caccgagcaa tttgacccgc tggaaggaag cgctcgattt tcagcctccc 1200
tcgtctggca gcggcaacta ctccggccgc tacatccgtt acggtatccg cgagcacgcc 1260
atgggcgcca tcatgaacgg aatcagcgca ttcggtgcca attacaagcc ttacggtggc 1320
acgttcctga atttcgtgag ctatgccgct ggtgcagttc gtttgtctgc actgtccggt 1380
cacccggtca tctgggtggc aactcacgac tctattggcg ttggagagga cggtccgacc 1440
catcaaccga tcgagactct ggcccacttc cgaagcctcc ccaacattca ggtctggcgc 1500
ccagccgacg gaaacgaggt ctctgcagcc tacaagaaca gccttgagtc caagcacacc 1560
cctagcatca tcgcgctctc tcgccagaat ctgccacagc tcgagggctc ctctatcgaa 1620
tccgcgtcca agggcggtta cgttttgcag gatgtggcaa atccggacat cattttggta 1680
gcaaccggct ccgaagtctc cctgtcagtg gaggccgcaa aaacactcgc ggcaaagaac 1740
atcaaggctc gagtggtctc gcttcccgat ttctttacct tcgataaaca gcccctggag 1800
taccgtttgt ctgtgttgcc agacaacgtg cccatcatgt cagtcgaggt actcgcaacc 1860
acgtgttggg gtaaatacgc gcaccagtcc ttcggcatcg atcgcttcgg agcgagcggc 1920
aaggcacccg aggtctttaa gtttttgga tttaccccag aaggagttgc agagcgtgcg 1980
caaaaaacca ttgcattcta taagggtgac aagctgatct cgccgctcaa gaaggcgttc 2040

<210> SEQ ID NO 87
<211> LENGTH: 1005
<212> TYPE: DNA
<213> ORGANISM: Artificial
<220> FEATURE:
<223> OTHER INFORMATION: Codon-optimized and/or mutated sequence

<400> SEQUENCE: 87
atgtccgaac cagcccaaaa aaagcaaaag gttgctaaca attccctgga gcaactgaag 60
gcctctggta ctgttgtagt ggctgatact ggtgatttcg gttccatcgc caagtttcag 120
cctcaggatt ccactacaaa cccctccttg atccttgccg ccgctaagca accaacctac 180
gccaagctca tcgacgtcgc agttgaatac ggcaagaaac acggtaagac tacggaggag 240
caagtcgaga acgcggtcga ccgcctgttg gtggagttcg gcaaggagat ccttaaaatc 300
gttcccggcc gcgtctccac cgaagtcgat gcccgattgt cctttgatac ccaagccacg 360
atcgaaaagg cccgtcacat cattaagctc tttgagcagg aaggcgtttc caaagaacga 420
gtcctcatta agattgcgtc aacctgggaa ggcatccaag cagccaaaga gcttgaggag 480
aaggacggta ttcattgtaa tctgacgctg ctcttttctt tcgttcaggc tgtagcttgt 540
gcagaggcgc aggttactct catctcccca ttcgtaggtc gaatcctgga ttggtacaaa 600
tcttcaaccg gcaaggatta caagggcgag gctgaccctg gcgtcatctc cgtcaaaaag 660
atctataact actacaagaa gtatggctat aagaccatcg tcatgggcgc ctctttccgt 720
tccaccgatg aaattaaaaa ccttgctggc gttgactatc tgacgatttc ccccgcactc 780
ctggacaaac tgatgaattc aaccgaaccc tttccccgtg tcttggatcc tgtctcggcg 840
aaaaaggaag ccggcgataa aatttcatac atctctgacg agtctaagtt ccgttttgat 900
ctgaatgaag acgctatggc aaccgaaaaa ctgtcagaag gcatccgtaa gttctccgcc 960
gacatcgtta cccttttga cctcattgaa aagaaagtga cagcc 1005

<210> SEQ ID NO 88
<211> LENGTH: 1002
<212> TYPE: DNA

<213> ORGANISM: Artificial
<220> FEATURE:
<223> OTHER INFORMATION: Codon-optimized and/or mutated sequence

<400> SEQUENCE: 88

```
atggcgaaaa tcgcaatcaa cggtttcggc cgaattggtc gcctggctct gcgccgcatc     60
ctcgaagttc cgggtttgga agttgtggca attaacgatc tgacggatgc taaaatgctt    120
gcgcatttgt ttaaatacga ctctagccag ggccgcttca atggagagat cgaagtgaaa    180
gaaggtgcct tcgtggttaa cggtaaagag gtgaaagtat tcgcagaagc cgacccggaa    240
aagttgcctt ggggcgattt gggcatcgac gtcgttctgg agtgcacggg tttctttacc    300
aagaaagaaa aggcagaagc ccacgtgcgt gcgggtgcta agaaggtcgt tatttcagcc    360
ccagcaggca acgacctcaa aaccatcgtg ttcaacgtaa ataacgaaga tctcgatggt    420
accgaaaccg tcatttcggg tgcctcttgc actactaact gtcttgctcc gatggcaaag    480
gttctcaacg acaaattcgg catcgagaag ggattcatga ctacgatcca cgccttcacg    540
aacgatcaga acactcttga cggacctcac cgtaagggtg atctccgtcg tgctcgtgcg    600
gcggcggttt cgatcattcc taatagcact ggcgccgcaa aggcaatttc gcaagtgatt    660
ccagacttgg ccggcaaact cgatggcaac gcgcagcgcg taccggtgcc caccggctcg    720
atcaccgaac tcgtgtccgt gctcaagaag aaggttacgg tggaagagat caatgcggct    780
atgaaggaag cagcagatga gtcgttcggc tatacagaag atcctatcgt tagcgcagac    840
gtggtgggca tcaactacgg atccttgttt gatgcaacct tgacgaagat tgttgatgta    900
aacggatccc agcttgtgaa aacggccgcg tggtacgata acgagatgag ctacacgtcg    960
caactcgtgc gtactctggc ctacttcgct aagatcgcga ag                      1002
```

<210> SEQ ID NO 89
<211> LENGTH: 1188
<212> TYPE: DNA
<213> ORGANISM: Artificial
<220> FEATURE:
<223> OTHER INFORMATION: Codon-optimized and/or mutated sequence

<400> SEQUENCE: 89

```
atggcatccg tgacgttctc tgtgcccaaa ggcttcaccg agttctcagg ccttcgaagc     60
tcctccgcat cgctgccctt tggtaaaaaa cttagctccg acgagttcgt atccattgtt    120
tcctttcaaa cgtccgcaat gggctcctct ggcggctatc gaaagggcgt gaccgaagct    180
aaactcaagg tcgcaattaa cggtttcggc cgtattggac gcaactttct tcgctgttgg    240
cacggccgca aggactctcc attggatatc atcgctatca acgacaccgg aggcgtgaag    300
caggcgtcac accttttgaa gtatgattcc acgctcggta ttttcgatgc agatgttaaa    360
ccttccggcg aaacggctat ttctgtggat ggaaagatca tccaggtcgt ctcaaatcgc    420
aacccgtccc tgcttccctg gaaggaactc ggaattgaca tcgtgatcga gggcaccggc    480
gtttttgtcg atcgtgaagg cgccggtaag cacattgagg caggcgccaa aaaggttatt    540
atcaccgcac ccggtaaggg cgacatccca acctacgtgg ttggtgttaa cgcagatgct    600
tatagccacg atgaaccaat catttcaaac gcatcatgca ctaccaactg tctcgctcca    660
ttcgttaaag ttcttgacca gaagttcggt atcatcaagg gtactatgac aacgacccac    720
tcctatacgg gtgatcagcg cctgctcgat gcctcccacc gcgaccttcg ccgcgcacgc    780
gcagctgccc tcaacattgt accgacctcc acgggagcgg caaaggcagt cgcattggtt    840
ctgccaaact tgaaaggtaa actcaacggt atcgctctgc gtgttcccac tccaaacgtc    900
```

```
tctgttgtgg acctggttgt acaggtttcc aagaagactt tcgccgaaga agtcaacgcc    960

gcttttcgcg attccgctga gaaagaattg aagggcattc tggacgtgtg tgacgaaccc   1020

ctggtgagcg tcgatttccg ctgttccgac ttctccacta ctattgattc ctcgctcact   1080

atggtgatgg gagatgacat ggttaaggtc atcgcgtggt atgacaacga gtggggttac   1140

tctcaacgcg ttgtcgatct cgcagatatc gttgccaata actggaaa                1188
```

```
<210> SEQ ID NO 90
<211> LENGTH: 1122
<212> TYPE: DNA
<213> ORGANISM: Artificial
<220> FEATURE:
<223> OTHER INFORMATION: Codon-optimized and/or mutated sequence

<400> SEQUENCE: 90

atggccgcca tgatgcagaa gtccgccttc actggctccg cagtttcatc caagtcagga     60

gtccgcgcaa aggccgcacg cgctgtggtc gacgtccgtg cggaaaaaaa gattcgtgtc    120

gccatcaatg gtttcggacg tatcggtcgc aacttcttgc gctgctggca cggccgccaa    180

aacaccctcc tggatgtagt cgctattaac gattccggtg gtgtcaagca ggcgtcccat    240

ctgcttaagt acgatagcac ccttggtacg ttcgccgcgg atgtcaagat cgtggatgat    300

tcccacattt ccgttgacgg caaacagatc aaaatcgtgt cctcgcgcga cccactccaa    360

ctgccgtgga aggagatgaa cattgacctg gttatcgagg gtaccggagt attcattgac    420

aaggttggag ccggtaaaca catccaggct ggcgcgagca aggtgctgat cactgcccca    480

gccaaggata aagacatccc aaccttcgtt gtgggcgtaa acgaaggaga ttataagcac    540

gaatacccta ttatcagcaa tgcttcctgc accactaact gtctggcgcc atttgtcaag    600

gtgcttgagc agaaattcgg catcgtgaag ggaactatga ctaccaccca tagctacacc    660

ggcgatcaac gcctcttgga cgcatcccac cgagatctgc gtcgcgcacg cgctgcggcc    720

cttaacatcg tccctaccac caccggcgct gcgaaggccg tgagccttgt gctgccgtcc    780

cttaaaggca aactgaatgg cattgcgctg cgcgttccaa ctcccaccgt ctccgtcgtg    840

gatttggtgg tgcaggtgga gaaaaagaca ttcgccgagg aggtcaatgc tgcgttccgc    900

gaagccgcaa acggccccat gaaaggcgta ctccatgttg aagacgctcc gcttgtatcc    960

attgacttca aatgcactga ccagagcacc tccattgatg cgtccctgac catggtcatg   1020

ggagacgaca tggtcaaagt ggttgcgtgg tacgataacg agtggggata ttcccaacgc   1080

gttgttgatc tggcagaggt cacggctaag aaatgggtcg ca                      1122
```

```
<210> SEQ ID NO 91
<211> LENGTH: 1008
<212> TYPE: DNA
<213> ORGANISM: Artificial
<220> FEATURE:
<223> OTHER INFORMATION: Codon-optimized and/or mutated sequence

<400> SEQUENCE: 91

atggccatta aggtggcgat caacggtttc ggtcgcattg gccgtcttgc gtttcgccgt     60

atccaggatg tggagggctt ggaggttgtg gccgtgaacg acctgaccga tgacgatatg    120

ctggcccacc ttctcaagta cgataccatg cagggacgct tcaccggaga agtggaggta    180

attgaaggtg gtttccgcgt gaatggaaag gagatcaaat cattcgatga accagatgca    240

ggaaagcttc catggggaga ccttgatatt gacgtggtgc tcgagtgcac cggtttctac    300
```

```
accgataagg agaaggcgca ggctcatatc gatgctggtg cgaagaaggt gctgatctca    360

gcaccagcaa agggtgacgt taagactatt gtcttcaaca ccaaccatga caccctggac    420

ggctcagaaa ccgtcgtcag cggagcatct tgtaccacaa acagcctggc gccggtggca    480

aaggttctct ccgatgaatt cggtctcgtc gagggcttca tgaccactat tcatgcatac    540

actggcgacc agaatacaca ggacgcgcca caccgaaagg gcgacaagcg acgagcacgc    600

gcagcagccg agaacatcat tcccaattcg acgggtgctg ccaaagctat cggcaaagtt    660

atcccagaga ttgatggcaa gctggatggc ggagcacaac gtgttccagt agcgacggga    720

tcacttacag aattgactgt ggttttggat aaacaagacg tgacggtgga ccaggtgaat    780

tctgctatga agcaggcgag cgacgaaagc ttcggctata ccgaagatga aatcgtctcc    840

tccgatatcg taggcatgac ctacggaagc ctgttcgacg cgacccagac ccgtgtcatg    900

acggtgggcg atcgccaact tgtgaaggtg gctgcctggt atgacaacga gatgtcctat    960

acggctcagt tggtccgcac cttggcacac ttggcggagc ttagcaag                1008
```

<210> SEQ ID NO 92
<211> LENGTH: 1248
<212> TYPE: DNA
<213> ORGANISM: Artificial
<220> FEATURE:
<223> OTHER INFORMATION: Codon-optimized and/or mutated sequence

<400> SEQUENCE: 92

```
atggctttcg ttgctccggt ttcttccgta ttctctacaa gctccaaatc cgctgtctgt     60

tccggccgct cttcgttcgc ccaattttcc ggcctgaaga aagtaaacaa taccgcacga    120

ctccagacgg cggagcaagg ctcggcattt ggaggcgtgt ctgatgcaaa cgatgcgttt    180

ttcaacgcag tgaacacaat gggagctcct gcacgaacaa gcaatgctcc gtccatgaag    240

gtccgagtgg ccatcaacgg cttcggccgc atcggccgca atttcatccg ctgttgggca    300

ggacgtaccg actcgaatat ggatgtcgtc tgcatcaatg atacctccgg cgtcaagacg    360

gccagccact tgctcaagta tgattcaatt ctcggcactt ttgacagcga cgtggtcgcc    420

ggagaggact ccattaccgt tgatggaaag accattaaag tcgtctcaaa ccgtaaccct    480

cttgaactgc cttggaaaga gatggaaatt gatatcgtgg ttgaggccac cggcgtgttc    540

gtcgatgccg tgggtgcagg aaagcacatc caggcgggtg ccaaaaaggt cttgattacc    600

gcacctggta aaggagaagg tgttggtacc ttcgttgtcg gcgttaatga tcatctctat    660

tcccacgata aattcgacat tgtcagcaac gcatcctgta caaccaattg catggcccca    720

tttatgaaag tgctggatga tgaattcggc gtggtgcgtg gcatgatgac tactactcat    780

tcgtacaccg gtgatcagcg tctgctcgat gcaggacacc gtgatctgcg tcgcgcgcgt    840

tctgccgccc tcaacatcgt tcccactacc accggtgctg cgaaagccgt cgcattggtt    900

gttccaactt tggctggtaa gcttaacggc atcgcgctcc gcgttcctac tccgaacgtt    960

tctgtgtgtg atgtggttat gcaggtcagc aagaaaactt tcaaggagga ggtcaatgga   1020

gctctcttga aagctgcgaa cggctcgatg aagggcatta tcaaatattc cgatgagccc   1080

cttgtgagct gtgattaccg tggaaccgac gaatcaacca tcatcgattc cagcctcact   1140

atggtgatgg gcgacgatat gcttaaggtg gtggcttggt acgacaacga atggggatac   1200

tcacaacgcg ttgtggatct cggcgaggtc atggcgagcc aatggaag                1248
```

<210> SEQ ID NO 93
<211> LENGTH: 1416

<212> TYPE: DNA
<213> ORGANISM: Artificial
<220> FEATURE:
<223> OTHER INFORMATION: Codon-optimized and/or mutated sequence

<400> SEQUENCE: 93
atgtcccaga acgtgtacca attcatcgac cttcagcgcg tcgatccacc gaagaaacct 60
ctcaagattc gcaagattga atttgtcgag atctacgagc ccttttccga gggtcaggcg 120
aaggcacagg ccgaccgctg cctctcctgc ggcaatccat actgcgaatg gaagtgtcca 180
gttcacaact acatcccaaa ttggcttaaa ctggcaaatg aaggacgcat cttcgaggct 240
gcggagctct cccaccagac caacacgctt ccagaagtat gcggacgtgt ttgccctcaa 300
gaccgtctct gcgaaggtag ctgcacgctt aacgatgaat tcggagccgt caccattggt 360
aatatcgagc gttacattaa cgacaaggcc ttcgaaatgg gatggcgccc ggacatgtcc 420
ggcgtgaagc aaaccggtaa gaaggtcgcg atcatcggcg cgggtccagc tggccttgct 480
tgcgccgatg tcctgacccg caacggtgtg aaagcagttg tattcgatcg ccatcccgaa 540
attggaggcc tgctcacttt tggcatcccc gcattcaaac tcgaaaaaga agtgatgacc 600
cgtcgtcgag agatttttac cggtatggga attgagttca agcttaacac tgaagtcgga 660
cgcgatgttc agctcgacga cctcctgtcc gactacgacg cagttttcct tggtgtcggt 720
acttaccagt caatgcgcgg tggtctggaa aatgaggatg cggacggtgt ttacgcagcg 780
cttccctttc ttattgctaa caccaagcag ctgatgggat ttggtgaaac tcgagatgaa 840
cctttcgttt caatggaagg aaagcgcgtt gtggttcttg gaggtggcga taccgccatg 900
gactgcgtgc gtacctccgt tcgacagggc gccaaacatg tcacctgtgc ataccgccgt 960
gacgaggaaa acatgcccgg ttcacgacgt gaggtgaaaa acgcccgcga agaaggtgtt 1020
gagttcaagt tcaacgtgca gccacttggt attgaggtga acggtaacgg aaaggtctcc 1080
ggagttaaga tggtgcgtac cgagatgggt gaaccagacg caaagggtcg tcgccgcgcc 1140
gagatcgtcg cgggatcgga gcatatcgtg ccagctgacg ctgtaatcat ggcatttggt 1200
ttccgcccac acaatatgga gtggctggcg aagcattccg tggagctcga tagccagggc 1260
cgtatcattg cacctgaggg ttcggacaat gcctttcaga cctccaaccc aaaaatcttc 1320
gctggcggcg acattgtgcg tggctcagat cttgttgtga ccgcaatcgc tgagggtcgt 1380
aaggcagctg acggtatcat gaattggctc gaagtc 1416

<210> SEQ ID NO 94
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 94
atggcagaag cctctattga gaaaacacag attctgcaga aatatcttga attggatcaa 60
cgtggtcgaa tcattgctga gtatgtttgg attgatggca ccggtaacct gcgctccaag 120
ggccgcaccc tcaagaagcg cattacatcc attgaccagt tgcccgaatg gaactttgat 180
ggctcaagca ccaaccaggc cccaggtcac gactctgata tctatctcaa gccagttgct 240
tattacccgg acccattccg ccgcggtgat aacatcgtcg tgttggctgc ttgctacaac 300
aacgatggaa ctcccaacaa attcaaccac cgacatgaag cagcgaagct gttcgccgcc 360
cacaaagacg aagaaatttg gttcggactt gaacaggaat acacgctgtt tgatatgtat 420

```
gatgatgtgt acggttggcc taagggaggc tacccagctc cacaaggtcc atactattgc    480

ggcgtcggcg cgggaaaggt gtacgctcgc gatatgatcg aagcacatta ccgcgcctgt    540

ttgtacgctg gccttgaaat ctccggtatc aacgcagaag tgatgccatc ccagtgggag    600

ttccaggtgg gtccgtgtac cggcattgac atgggagatc agctgtggat ggcccgctac    660

ttccttcatc gcgtcgcaga agaattcggt atcaaaatct ctttccatcc aaaacccttg    720

aaaggcgact ggaacggtgc gggttgtcat actaatgtat ccaccaagga gatgcgtcaa    780

ccgggaggca tgaagtacat cgagcaagct atcgaaaagc tcagcaaacg ccacgcggaa    840

cacattaaac tgtatggctc cgataacgac atgcgcctga ctggtcgcca tgagacggct    900

tccatgactg catttagctc cggtgtggcc aaccgtggct ccagcatccg aattcctcgt    960

agcgtggcaa aggaaggata tggttacttt gaggatcgac gcccagcatc caacatcgat   1020

ccttacctcg tcacaggcat tatgtgtgag accgtctgtg gagcaatcga caacgcagac   1080

atgaccaagg aatttgagcg tgagtcgtcg                                    1110
```

<210> SEQ ID NO 95
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 95

```
atgtctgaaa gcccgatgtt tgccgcgaat ggcatgccaa aggttaatca aggcgcagag     60

gaagatgttc gtatcctcgg ttacgatcca ctggcatcac ctgctctgct ccaagttcaa    120

attccggcga cccctacctc cttggagacc gcgaaacgcg gtcgccgcga ggcaatcgat    180

atcatcaccg gtaaagatga ccgcgtcctg gttattgtcg gcccatgctc catccacgac    240

ctggaagctg cgcaagaata tgccctccgt ctcaagaagc tgagcgacga actgaaagga    300

gacttgtcga ttatcatgcg cgcatacctg gagaagccac gtaccaccgt cggttggaaa    360

ggactgatca acgacccaga tgtcaataat acgttcaaca tcaataaagg actccagtcg    420

gctcgtcagt tgttcgtcaa cctcaccaac atcggtttgc caattggtag cgaaatgttg    480

gatactatca gcccaaagta ccttgccgac ctggtgtcgt tcggcgctat tggcgcccgt    540

actaccgaat cccaactcca ccgcgaactg gcctcaggcc tttctttccc tgttggcttc    600

aagaacggca ctgatggcac gttgaacgtt gcagtcgacg catgtcaggc agctgcccat    660

agccaccact ttatgggcgt tacaaaacac ggtgttgcgg ccatcaccac aacaaagggc    720

aacgaacact gctttgttat tttgcgcggc ggcaagaagg gtacaaacta cgatgcgaaa    780

tctgtggcag aagcaaaggc ccaactccct gcaggctcaa acggtctcat gatcgactac    840

tcccatggta actcgaataa agactttcgt aatcaaccca aagtcaacga cgtggtctgc    900

gagcagatcg ccaatggaga gaatgcaatc acaggtgtga tgatcgaatc aaatatcaat    960

gagggtaacc aaggaatccc agctgaaggt aaggcaggcc tcaaatacgg tgtgtccatt   1020

accgatgcat gtattggatg ggaaactacc gaggatgtgc tgcgcaagct cgcggccgca   1080

gttcgccagc gccgcgaggt gaacaaaaaa                                    1110
```

<210> SEQ ID NO 96
<211> LENGTH: 1050
<212> TYPE: DNA
<213> ORGANISM: Artificial
<220> FEATURE:
<223> OTHER INFORMATION: Codon-optimized and/or mutated sequence

<400> SEQUENCE: 96
atgaattatc aaaatgatga ccttcgtatc aaagaaatca aggagttgtt gcccccggta 60
gctttgcttg agaagtttcc cgcaaccgaa aatgctgcta ataccgttgc acacgcacgc 120
aaggctatcc ataagatttt gaagggcaac gacgatcgtc tgctcgtcgt catcggtcct 180
tgctcaattc acgacccggt tgctgccaaa gaatatgcca cccgtttgct ggcgctgcgc 240
gaggaactca aggacgaact ggagatcgtg atgcgagttt attttgaaaa accccgcact 300
accgtgggct ggaagggcct cattaatgac ccccacatgg ataactcgtt tcaaatcaac 360
gatggtcttc gcatcgcgcg caagctgctc ctggacatca atgattctgg tctgccagca 420
gccggcgaat tcctcaatat gatcaccccg caatacctgg ccgatctgat gtcgtggggt 480
gccatcggag cacgcacgac ggagtcacag gtacatcgcg agctggcatc cggtctgagc 540
tgcccagtcg gttttaaaaa cggcacggat ggcactatca aagtggcaat cgacgcaatc 600
aacgccgccg gagcacctca ctgttttttg agcgtaacta agtggggaca cagcgcgatt 660
gttaacacct ccggtaacgg cgactgtcac atcatcttgc gaggtggtaa agaaccaaac 720
tactcggcga aacacgtcgc agaagtcaag gagggtttga acaaagctgg cttgccggcc 780
caggtgatga ttgacttctc tcacgccaac agctcgaaac aatttaagaa gcaaatggat 840
gtctgcgcgg atgtctgcca acaaatcgca ggaggtgaaa aggcgattat tggtgtgatg 900
gttgagagcc acctggtgga aggcaaccaa tccctcgaga gcggtgagcc tctcgcctac 960
ggtaagtcca tcacggatgc gtgtattggc tgggaggaca cggatgcact cctccgtcag 1020
ctggcaaatg ccgttaaggc gcgtcgcggc 1050

<210> SEQ ID NO 97
<211> LENGTH: 1050
<212> TYPE: DNA
<213> ORGANISM: Artificial
<220> FEATURE:
<223> OTHER INFORMATION: Codon-optimized and/or mutated sequence

<400> SEQUENCE: 97
atgaactatc agaacgatga cctccgcatc aaggagatta aagagctgct ccctcctgtt 60
gcgctgttgg aaaagttccc agcgacggag aacgccgcga acaccgtcgc ccacgctcgc 120
aaagctattc acaagatttt gaagggcaac gatgaccgtc tcctggttgt cattggccca 180
tgttcgattc atgatcctgt ggcggccaag gaatacgcga cgcgtctgct tgccctgcgt 240
gaagagctta aggacgaact cgaaatcgtg atgcgcgtat atttcgagaa accacgcact 300
accgttggat ggaagggcct catcaatgat ccgcatatgg ataatagctt tcaaatcaat 360
gatggcttgc gcatcgctcg caagctcctc cttgatatta acgattccgg cctgccagct 420
gcgggtgaat tcttggatat gatcactctg caatacctgg cggacctgat gtcttggggc 480
gccatcggag cccgtaccac cgagtcccaa gtccatcgcg agctggcatc cggtctgtcc 540
tgcccggtcg gtttcaagaa cggaactgat ggtactatca aggtggccat cgacgctatt 600
aacgccgcag gagcgccgca ttgctttctc tcagtgacca agtggggtca ctccgccatc 660
gtcaatacat ctggcaatgg cgactgtcat atcatccttc gcggaggcaa agagcctaac 720
tattcggcta aacacgtggc agaagttaaa gaaggcctca acaaggccgg actgccagcc 780
caagttatga ttgatttttc acacgctaac tcctcaaaac agtttaagaa gcagatggac 840
gtttgcgcag atgtttgtca acaaatcgcg ggtggcgaaa aggcgatcat tggagttatg 900

```
gtggaaagcc acctggtgga aggcaaccaa tctctggagt ctggagaacc gcttgcatac     960

ggtaagagca ttaccgacgc atgcattggc tgggaagata cggacgcgct gctgcgacag    1020

ctcgcgaatg ctgttaaggc ccgacgcggt                                     1050


<210> SEQ ID NO 98
<211> LENGTH: 1068
<212> TYPE: DNA
<213> ORGANISM: Artificial
<220> FEATURE:
<223> OTHER INFORMATION: Codon-optimized and/or mutated sequence

<400> SEQUENCE: 98

atgcagaaag atgccctgaa caaagtgcac atcaccgatg agcaggtact tatgaccccg      60

gaacagctca aagcagcatt cccccttgagc cttcaacaag aagctcagat tgcagattcc    120

cgcaagtcga tttccgacat tattgccggt cgtgatccgc gactgctcgt ggtgtgcggc     180

ccatgctcca ttcacgatcc cgagaccgcc ctcgagtacg ctcgacgctt taaggccctt     240

gcggcagagg tatccgattc attgtatctg gtgatgcgcg tgtactttga aaagccgcgt     300

accaccgtgg gctggaaagg cttgatcaac gatccacaca tggatggctc attcgatgtt     360

gaagctggcc tgcaaatcgc ccgcaagctc ctgctggaat tggtgaacat gggtctgccc     420

ctcgcgactg aggccttgga tccaaactca ccacaatacc tgggtgacct cttttcctgg     480

tctgcgatcg gtgcacgcac caccgaatcc cagacccacc gcgagatggc gtctggactt     540

tctatgccag tgggcttcaa gaacggaact gacggttccc tggcaacagc gattaacgcg     600

atgcgcgcgg cggcacaacc gcatcgtttt gtgggcatca accaggcagg ccaggtagcc     660

ctgctgcaaa cccagggaaa tccggatggc cacgtcatcc tccgcggagg caaggctccg     720

aattactctc cagccgatgt tgcccaatgc gaaaaagaaa tggaacaagc cggtctgcgc     780

ccttcgttga tggtcgattg ctcccacggc aattccaaca aagactatcg tcgccagcca     840

gctgtcgcag aatccgttgt cgcacagatc aaagatggca atcgctccat cattggcctt     900

atgatcgaat ctaatatcca cgagggcaat caatcgtctg aacagccgcg ctccgaaatg     960

aaatatggcg tctccgtgac cgacgcgtgc atttcctggg agatgaccga tgcgctcctc    1020

cgcgaaatcc accaagatct taacggccaa cttactgctc gagtggcc                 1068


<210> SEQ ID NO 99
<211> LENGTH: 1347
<212> TYPE: DNA
<213> ORGANISM: Artificial
<220> FEATURE:
<223> OTHER INFORMATION: Codon-optimized and/or mutated sequence

<400> SEQUENCE: 99

atgtccaata ccacatggtc tcctacctca tggcactcct ttaaaattga acagcaccca      60

acctacaagg acgaacagga acttgaacgc gtgaagaaag aacttcgctc ctatcctcca     120

cttgtattcg ccggtgaggc gcgcaacctc caagaacgtc tcgcacaagt gattgacaac     180

aaggcattcc tcctccaggg tggcgattgt gccgagtcat ttcccagtt cagcgcgaat      240

cgcattcgcg atatgttcaa ggtcatgatg caaatggcga tcgttctgac cttcgctggt     300

tctatcccca tcgttaaggt gggccgaatc gcgggccaat ttgctaaacc tcgatcgaat     360

gccaccgaga ttctggacga cgaggaagtt ttgtcgtacc gcggcgatat tatcaatggc     420

atctcaaaga aggagcgcga accgaaacca gagcgcatgc tcaaggcgta ccatcaaagc     480

gtggcaacgc tgaacctgat ccgcgcattt gcacaaggtg gtctggccga ccttgaacag     540
```

```
gttcaccgct tcaacctgga tttcgtgaaa aacaacgatt tcggtcaaaa ataccaacaa    600

attgctgatc gcattactca ggcgctgggc ttcatgcgcg cttgcggcgt ggaaatcgaa    660

cgcactccta ttttgcgtga agtcgaattt tacacctctc acgaggcatt gcttctccac    720

tacgaagaac ctctggtacg caaggactcc ctcactaacc aattctacga ttgttccgcc    780

catatgcttt ggattggtga acgaacacgc gacccaaaag gcgctcacgt ggaattcttg    840

cgcggtgtat gtaaccctat tggtgtgaaa attggcccta atgcgagcgt gtccgaggtt    900

cttgagctgt gtgatgtgct caacccgcac aacttgaaag gccgtttgaa tctcatcgta    960

cgcatgggat ccaaaatcat caaagagcga cttccgaagc tgctgcaggg tgtactcaaa   1020

gagaaacgcc acattctgtg gtctattgat ccaatgcacg gaaacaccgt gaaaaccaac   1080

ctgggtgtga agacccgtgc tttcgactcc gtgcttgatg aagttaaatc attcttcgaa   1140

atccaccgtg cggagggttc cctggcatcc ggcgtccacc tcgagatgac gggtgaaaac   1200

gttacggaat gcattggcgg ctcgcaggcg atcaccgaag agggcctgag ctgccattac   1260

tatacgcagt gcgatccccg cctcaacgcg acccaagcat tggaacttgc ctttcttatc   1320

gctgacatgc tcaaaaaaca acgtacc                                       1347
```

```
<210> SEQ ID NO 100
<211> LENGTH: 828
<212> TYPE: DNA
<213> ORGANISM: Artificial
<220> FEATURE:
<223> OTHER INFORMATION: Codon-optimized and/or mutated sequence

<400> SEQUENCE: 100

atgtggcgtt ggctcccagt tgcgggattt aaaggtgtta aactcgccct gaagtcagag     60

gagcgtcgcg agaccgtcgt ggaggttgaa ggtgtgcgta ttggaggtgg ttctaaggca    120

gtaattgcag gtccttgttc tgttgaatcc tgggaacagg tgcgcgaagc cgcattggcg    180

gtcaaggaag ccggcgctca catgctgcgt ggcggcgcat tcaaaccacg tacctcgccc    240

tactccttcc agggtttggg tttggagggc ctgaagcttt tgcgccgcgc aggagatgag    300

gccggcctgc ccgttgtaac tgaggtattg gacccgcgcc acgtggagac agtttcccgt    360

tatgcggaca tgctgcagat cggtgcacgc aacatgcaga atttcccctt gctgcgtgaa    420

gttggtcgct ccggtaaacc agttcttttg aaacgcggct tcggcaatac tgtggaagaa    480

ctcctcgctg ctgctgaata tatcttgctc gaaggcaatt ggcaggttgt gctggtcgaa    540

cgaggaatcc gcaccttcga gccgtcaacc cgctttaccc tcgacgtagc tgcggtggcg    600

gtgttgaagg aagcaaccca tttgccagtg attgttgatc cctcgcaccc cgcgggacga    660

cgctctttgg ttcctgcgct ggctaaagcc ggcttggccg ctggcgccga tggtcttatc    720

gtcgaagtgc accctaatcc agaggaagct ttgagcgatg caaaacagca gttgaccccc    780

ggcgaattcg cgcgcttgat gggagaactg cgttggcatc gtttgctc                  828
```

```
<210> SEQ ID NO 101
<211> LENGTH: 1875
<212> TYPE: DNA
<213> ORGANISM: Artificial
<220> FEATURE:
<223> OTHER INFORMATION: Codon-optimized and/or mutated sequence

<400> SEQUENCE: 101

atgagcgagt ccctctccaa ggatcttaac ttgaatgcgc tgttcattgg cgataaagcc     60
```

```
gaaaacggtc agatctataa ggcgctgctt aacgaactcg tggatgagca cttgggatgg    120
cgccagaatt acatgcctca agacatgcca attattacac cggaggaaaa gtcttcagca    180
tccttcgaac acacggtgaa caagacaaag gacgtattga gcgagatctc cgcacgtatg    240
cgaactcatt ccgtcccttg gcacaatgcc ggtcgatatt ggggccacat gaactcggag    300
accctgatgc cttcccttct ggcctacaac ttcgccatgc tttggaacgg taataacgtg    360
gcttatgaat catcacctgc aacctcacag atggaggaag aggttggcat ggaattcgca    420
aagctcatga gctacaaaga tggctgggga cacatcgtgg cagacggttc cctggcaaac    480
cttgaaggct tgtggtacgc gcgtaacatc aaaagccttc ctttggccat gaaggaggtg    540
accccagaac tcgtggctgg caaatccgac tgggaactta tgaacctctc taccgaggag    600
atcatgaatc tgctggattc tgtcccagag aaaatcgatg aaattaaagc gcactcagcc    660
cgttcgggta agcacttgga gaaattgggt aagtggctgg ttcctcagac taagcactac    720
tcctggttga aggcagctga tatcatcggc atcggtcttg atcaagttat ccccgttccg    780
gtcgatcaca actatcgcat ggatattaat gagctcgaaa aaattgttcg tggccttgct    840
gctgaaaaga ctcctattct gggtgtggtc ggcgttgttg gttctaccga agaaggcgca    900
attgacggaa ttgacaagat cgtggctctt cgccgtgtgc tggaaaagga tggtatttac    960
ttctacctgc atgtcgacgc cgcttacggc ggatacggtc gcgccatttt tctcgatgag   1020
gacaacaatt ttatcccctt tgaagacctc aaagacgtcc actataagta caatgttttt   1080
accgagaaca aggactacat tcttgaggaa gtgcactcgg cgtacaaggc gattgaggaa   1140
gcagagtccg taactatcga ccctcacaag atgggctacg tcccttattc cgcaggaggc   1200
atcgttatca aagacattcg catgcgtgat gtaatctctt actttgcaac ctacgtattt   1260
gaaaagggcg ccgacatccc ggctctgctt ggtgcgtata tcctggaggg ttctaaggca   1320
ggcgcaactg ccgcgtccgt gtgggctgct catcatgtat tgccactgaa cgtcacgggt   1380
tacggtaaat tgatgggcgc ttccatcgaa ggcgcgcacc gcttctataa cttcctgaac   1440
gacttgtcct ttaaagtagg cgataaagag attgaagttc accccttgac ctacccggat   1500
tttaatatgg tcgactacgt cttcaaagaa aagggaaatg atgacctggt ggctatgaat   1560
aaactcaatc acgatgtcta cgattactct tcgtacgtaa aaggctccat ctacggcaat   1620
gaattcctca cctctcatac cgatttcgcc attccggatt acggaaattc ccctcttcag   1680
ttcgttaatc agttgggctt ctcggatgag gaatggaacc gagctggcaa ggtgaccgtt   1740
ctccgcgcat ccgtcatgac cccatacatg aataaggaag aacacttcga agaatacgct   1800
gagaaaatca aagcagccct ccaagaaaaa cttgaaaaga tctacgctga tcagctcctt   1860
gctagcgagg ctaaa                                                    1875
```

<210> SEQ ID NO 102
<211> LENGTH: 1530
<212> TYPE: DNA
<213> ORGANISM: Artificial
<220> FEATURE:
<223> OTHER INFORMATION: Codon-optimized and/or mutated sequence

<400> SEQUENCE: 102

```
atggacgcca ctaacatctc ggcctctgaa caagagaaaa ttctgggcaa tctctggaaa     60
gccgcgcaag gcccgggtga aggccacgtc ctgccgactg tggatcagct caaccgcgcc    120
cgcgcaagcc tttataattc cttgcctgag gagggcgtcg gctatcagtc ggttcagcgc    180
cacattctgg acgatatcgt cccagccttc aatggcggct ccatcaatcc aaactattac    240
```

```
ggctttgtga caggcggtgt aaccccagcg gctctgttcg cagatgcggt tgtgtccgca    300

tacgatcaga acgtccaagt tcatctgcag tcccactcaa tcgtcactga cgtcgagttc    360

aagaccttgg gcctcctgct ccagcttctc aagcttgacg tcccatcgtg gttgaacggc    420

acctttacta cgggcgccac cgcgtctaac atcattggct tggcatgtgg ccgagaattc    480

gtcatccaga aggcggctca gcgtaagggc tctccgatca aatccaccgc agatgctggt    540

cttcacgaag tcctgcaatc gattggagct tccggcatcc aggtcctgtc caccctcccg    600

cactcgtcac tggtcaaggc agccggagtc ctgggcatcg gtcgtatgaa cgttcgcgat    660

atctctactg aagctaaccc attggatatc gaccttaaga agctccagac ggagctctca    720

cgtgtcgatg tcgtgtcgat tgttgccatt agctgtggcg aggtcaactc cggacgtttc    780

gcatccgcgg gactgcatga attgcgtaag atccgccaac tctgcgaccg ccatggcgcc    840

tggctccacg ttgacggcgc tttcggaatc tttggccgct tggttggtga tgacacggaa    900

tttatggcta ttaaggaggg atgtgatggt attgagctgg cagactctat caccggagac    960

gcccacaaat tgctgaatgt tccgtacgac tgcggcttct tcttctgccg ccacgcctct   1020

attgcacgag aagtgtttca aaacgccaac gcagcttatt tggcttcagt tgacggccgc   1080

gattccttta ttccgtcccc actgaacatc ggaattgaga actctcgccg ctttcgcgct   1140

cttcctgtgt atgcgtcgtt gctggcctac ggtgaagtgg aataccgaaa gatgcttcat   1200

cgccagattc gcttggcccg tatgatctac ggctggatct tcgaccatcc gggatacacc   1260

gcactcccag aaaccacctc tcgtgaggaa ctgcttgatt tgacttacat ggttgtgctc   1320

ttccgtgcca aagatggcgg attgaaccga acgctcgaag ccaaaattaa cgcgacgtca   1380

cgaatgtttg tttctggcac ctcctgggcc gacgcaccgg cctgccgcat tgcaatctca   1440

aactggcgcg ttgatgaaaa gcgtgacttt gccctcgtca ccggtgtgtt ggagtccgcc   1500

ttgcgctcaa gcggtagcgc agtctcttgt                                    1530
```

<210> SEQ ID NO 103
<211> LENGTH: 1089
<212> TYPE: DNA
<213> ORGANISM: Artificial
<220> FEATURE:
<223> OTHER INFORMATION: Codon-optimized and/or mutated sequence

<400> SEQUENCE: 103

```
atgctgaata agggcttggc ggaagaagaa ttgttttcct ttctctctaa aaagcgtgag     60

gaagacctct gccactcaca cattctctcg tccatgtgta ccgtgcccca cccgattgcg    120

gttaaagcac acctcatgtt catggaaacc aacttgggcg acccaggcct tttcccgggc    180

accgcgtcac tggagcgcct gttgattgaa cgccttggtg acctgttcca ccaccgcgag    240

gcaggtggct acgctacctc cggtggaaca gaatctaata tccaagctct gcgaattgca    300

aaagcacaga aaaaagtgga caagcccaat gtggtgatcc ccgagacttc ccatttctcg    360

ttcaagaaag cttgtgatat tctgggtatt caaatgaaaa ctgtgcccgc tgatcgctct    420

atgcgcacgg atatctctga ggtctcagat gctatcgaca agaatactat cgccctcgtg    480

ggaattgccg gctccaccga gtatggtatg gtcgacgata tcggtgcact ggcgacaatc    540

gcagaagagg aggacctcta cctgcatgtc gatgccgcgt tcggaggcct ggtgatcccg    600

tttcttccaa atcctcccgc gtttgatttc gcgcttccag gcgtgtcgag cattgcggtg    660

gatcctcaca agatgggcat gtctactttg cctgctggcg ctctgctggt ccgcgagccg    720
```

```
cagatgctgg gcctgttgaa tatcgatacc ccgtacttga cggtgaagca ggagtataca    780

ctggcaggca cgcgcccggg tgcatccgtg gccggcgcac tggcagtctt ggactacatg    840

ggccgcgatg gaatggaggc ggtggtcgcg ggttgcatga aaaacacttc ccgcctcatc    900

cgaggtatgg agacacttgg atttcctcgt gcggtgacac cagatgtaaa tgtcgccacg    960

ttcatcacta accacccggc cccaaagaac tgggtcgtgt cccagactcg ccgcggacat   1020

atgcgaatta tttgcatgcc acatgtcaca gctgacatga ttgagcaatt cctgatcgac   1080

attggtgaa                                                           1089
```

<210> SEQ ID NO 104
<211> LENGTH: 1152
<212> TYPE: DNA
<213> ORGANISM: Artificial
<220> FEATURE:
<223> OTHER INFORMATION: Codon-optimized and/or mutated sequence

<400> SEQUENCE: 104

```
atgggaatgg atatttcatc acgcccagtg gagtgggcgt ctctctctga gattaccgct     60

agcgacgtct cattcgaggg cggcgctatc tttaattcga tctgcacgcg cccgcacccc    120

ctcgcagccc aggttatggc cgataacctt caccttaacg cgggagatgg ccgtttgttc    180

ccgtctgtcg cccgttgcga atccgaaatt acgaacttcc tgggcggcct gatgggcttg    240

ccccgcgccg tcggcatgtg cacatctggc gcaaccgaag caaacctcat tgctgtccac    300

tccgcgattg agaattggcg ccgcaaaggc ggacagggtc gcccacaagt tatcctgggt    360

cgtggtggtc acttctcctt cgacaaaatc tctgttctgt tgggcgtcga gttggtcctg    420

gcatggtcag atatcgacac tcttaaggtc gatccagaat ctgtgtcaga actgattagc    480

ccacgtactg cgctcatcgt tgccacagcg ggctcgagcg aaaccggtgc agtcgatgac    540

gtggagtggc tgagccgcgt ggcactgtct aagggtgtcc ccctgcacgt ggatgccgca    600

tccggtggct tgctgatccc cttcctccgc gatttgggtg gagctctccc tgatatcggt    660

tttcgtaatg acggtgtaac caccatcgcc atcgatccac ataagtttgg ctccgctcca    720

attccgtcag gccacctggt cgcacgcgaa tggacttgga tcgagggcct gcgcaccgag    780

tctcattatc agggaacggc ccgccacttg accttcctcg gtactcgctc cggaggctca    840

attctcgcaa cctatgcact gttcggccac cttggtgaaa aggattgcg cggcatggct     900

gaacagctca aggcgctccg ctcccacctg gtcgaccgtc tccgcaaggc tggagctacc    960

ttggcctacg tccctgaatt gatggtggtg gctctcaagg cggattctga tgcggtcaaa   1020

gtactggaac gccgcggcat ctttacctca tacgcgaaac gcttgggtta tctccgcatt   1080

gttgttcagc tgcatatgtc tgaaggccaa gtggacggct tggtcgatgc tctcctcatg   1140

gaaggaattg tt                                                       1152
```

<210> SEQ ID NO 105
<211> LENGTH: 1542
<212> TYPE: DNA
<213> ORGANISM: Artificial
<220> FEATURE:
<223> OTHER INFORMATION: Codon-optimized and/or mutated sequence

<400> SEQUENCE: 105

```
atgggatcta tcgacaacct taccgagaaa ttggcctccc aattccctat gaatacactt     60

gaaccagagg agtttcgccg ccaaggacac atgatgatcg acttcttggc cgattattac    120

cgtaaggttg aaaattaccc cgttcgctcg caagtttcgc ctggatatct gcgcgaaatc    180
```

```
cttcctgaat ccgcacccta caaccctgaa tcacttgaaa ccatcctgca ggacgtccaa    240

acaaaaatca ttccgggcat tacgcactgg cagtctccaa acttcttcgc ttattttcct    300

tcctctggca gcaccgcagg attcctgggc gagatgctgt caaccggctt caacgtagtg    360

ggatttaatt ggatggtatc tccagcggct acggaactgg aaaacgttgt caccgattgg    420

tttggaaaaa tgctccaact tccaaaatcc tttcttttct caggcggtgg aggcggtgtg    480

ctgcagggca ctacctgtga agcaattctg tgtactctgg ttgccgcccg cgacaagaac    540

ctccgccaac atggcatgga taacattgga aaacttgtcg tgtactgttc cgatcaaacg    600

cactccgccc tgcagaaggc tgccaaaatt gcgggtatcg atccgaaaaa ttttcgcgcg    660

attgaaacaa ccaagtcttc aaacttccag ttgtgcccaa aacgcctcga atccgcgatc    720

ctccatgatc tgcagaacgg tttgattcct ttgtacctgt gcgccaccgt gggaaccacc    780

agcagcacaa ccgttgaccc tctcccagca ctgaccgaag tggcgaaaaa gtatgatctg    840

tgggtgcacg ttgacgcggc atacgcgggt tcagcgtgca tctgccctga attccgacag    900

tacttggacg gtgtggagaa cgctgattcg ttcagcctga acgcccacaa gtggttcctg    960

accaccttgg actgctgttg cctctgggtc cgcaatcctt ccgcccttat caagtcgttg   1020

tccacttacc cggaattcct gaagaacaat gcatccgaga ccaataaggt cgtggattat   1080

aaagactggc agattatgct gtctcgccgt ttccgcgcac ttaagctttg gttcgtactg   1140

cgttcctacg gcgttggcca actgcgcgag tttatccgcg gtcacgttgg aatggcaaag   1200

tactttgaag gtctggtcaa catggacaag cgctttgagg tcgtagctcc tcgcctcttc   1260

agcatggtgt gtttccgcat taagccatcc gcaatgatcg gtaagaatga cgaagatgag   1320

gtgaacgaga tcaatcgcaa gcttctcgaa agcgtgaacg actcaggccg tatctacgtg   1380

tctcacactg tgctgggtgg tatctacgtg attcgctttg cgattggcgg tacccttacc   1440

gatatcaatc acgtgtctgc agcttggaaa gtactgcaag accacgcggg cgctctgctt   1500

gatgatacct tcacatccaa caaactcgtg gaggttctgt cc                      1542
```

<210> SEQ ID NO 106
<211> LENGTH: 1551
<212> TYPE: DNA
<213> ORGANISM: Artificial
<220> FEATURE:
<223> OTHER INFORMATION: Codon-optimized and/or mutated sequence

<400> SEQUENCE: 106

```
atggaacgaa accacctcaa agattctgtc ggcgtacagg tggacgatgg tcactcgaag     60

gagctctggg aaaccgcgct caatccacca cgtcgatctg tactgccacc ggccgcatcc    120

ctggctcaca gccgctcatc aattatcacg gaactgccac atgctggaca aggttacaca    180

caaaccaaag tgcatctgtt taatgatatc atcccaggct tgaacgattg tgccatcaac    240

gctaactatt acggtttcgt caccggtgga gtcaccccgg cagcactgtt ggcagacaat    300

gtcgtaagcg tttacgatca aaacgtttgc gttcacctgg ttgaccactc cgtagcaacg    360

gacgtcgatt acgcggccct gtgcctgttg aaagatctct tcggtcttaa gcgcgatgaa    420

tggccacacg gcatcttcac caccggcgct accgcgtcta accttgttgg actcgcgtgt    480

ggtcgagagt atgtgctccg caaagcggcc cagaagcgcg gcctgtcagg caatatcgca    540

tccggcaaca ttaccgactc ggtcggagaa tacggtatgc cagcagttct ggaggcagct    600

ggtttgaaag gtctccaagt tttgagcacc atgccacact cttccgtagg caaagtcgca    660
```

ggcatcctcg gcatcggtcg cgccaacgtt aaatctattg tttccaagac cggagaatcc 720
cacggccagc cactcgagtt cgacttcgaa ttgttcgaaa aagaattggc acgcgccggc 780
tttgcttcaa ttgtttccat cagctgcggt gaagtcaata ctggccgctt tgcaacaaag 840
ggtgtggatg agttccgccg tgtacgcgca ctgtgtgata aatataatgc gtggctccac 900
gtcgatgctg cgttcggcat gttcggtcgc gttttggacg attcccccga gtttgagact 960
attaagaaag gttccgaagg catcgaattg gctgattcga tcaccggtga tggtcacaaa 1020
ttgctgaacg tcccttacga ttgcggcttc ttcttctcac gccatggcga catcgctgaa 1080
gaggttttcc gcaatcccaa cgcggtttat ttgagctctt ccgcgggcga gcacatcccg 1140
actccgctga atattggcgt ggagaattct cgccgctttc gtgctctccc agtttattca 1200
accctcgtgg cttatggcaa ggatggctac cgcgctatgg tggaacgcca gattcgcctc 1260
gcacgcctga tcactggttg gttgcacgag catcctaagt acaccgtgct gggcggcggt 1320
gcatctaaag aagatttgat cgctgctact tatgtaatcg tgctttttcg tgcgaaggat 1380
gaagctctca atgcacgcct cgcatctgct attaatggta ccggaaagat gtttgtctct 1440
ggcaccaagt gggctggtga accagcctgc cgcgtagcta tcagcaactg gaaggtccaa 1500
gtggaacgtg acttcacctt ggtaaaggag gtcttggatg aggtctcgcg c 1551

<210> SEQ ID NO 107
<211> LENGTH: 1443
<212> TYPE: DNA
<213> ORGANISM: Artificial
<220> FEATURE:
<223> OTHER INFORMATION: Codon-optimized and/or mutated sequence

<400> SEQUENCE: 107
atgcccgact tggaaccgga tgaattccgc cgccaaggtc accagctggt ggattgggtt 60
gctcgatacc gaacctcact gccgtccctg cacgtccgcc cgaaggtggt gccaggaagc 120
gtaaaggccc aactgcctcg agagctgcca gaacagccat ctcaagcgct cggagatgat 180
ttgatcgctc tgttgaacga cgtagtcgtg ccatcctcac tccactggca gcatcccggc 240
ttcttcggct acttcccagc gaacgctagc cttctctccc tgctcggcga tattgcgtcc 300
ggcggcattg gcgcgcaggg aatgctgtgg tccactagcc ctgcaggtac cgagattgaa 360
caggtgctcc ttgacggctt ggccgatgca ctgggtctgg gtcgtgagtt caccttcgcg 420
ggtggtggag gcggctcgtt gcaggactct gcctccagcg cttcattggc ggcactcctc 480
gcggctctgc aacgcagcaa tcccgactgg cgcgaacacg gcgtcgatgg aacagaaact 540
gtttacgtga ctgctgagac tcattcgagc ctggctaagg ccgtgcgcgt tgcaggtctc 600
ggcgcgcgcg ctttgcgaat tgtgcccttt acacaaggaa ctttgtcgat gtcggccgat 660
gcgctcgcag atatgctggc aaaggatact gctgctggca aacgccctgt gatggtttgt 720
ccgaccgtag gcaccactgg caccggtgcc atcgatccgg ttcgagaagt agcactcgcc 780
gcgcgcacct atgaagcgtg ggttcacgtg gatgcggctt gggctggcgt cgcagccctt 840
tgcccggaat ttcgctggct tcttgacggt gtcaatctcg tggactcatt ttgcaccgac 900
gcgcacaagt ggttctacac cgcatttgac gccagcttca tgtgggttcg tgatgcacgc 960
gcgttgccaa ccgctctctc aattaccccg gagtacctgc gtaacgccgc gaccgaatcc 1020
ggagaagtca ttgattaccg tgactggcag gtccctcttg gccgccgcat gcgcgctctc 1080
aagatctggt ccgttgtaca tggcgcaggc ctcgaaggct tgcgtgagtc gattcgcggc 1140
cacgtggcca tggccaatag cctggcggga cgcattgaat ccgaaagcgg cttcgctctc 1200
gcaacccctc cgtcccttgc tctggtctgt ctgtacttgg tggaccaaga gggacgccct 1260
gacgatgctg ccaccaaggc ggcaatggaa gccgtcaacg cggaaggtca ctcattcttg 1320
actcatacca gcgtcaatgg acatttcgcc attcgcgtgg caatcggcgc taccaccacg 1380
ctccccgatc acatcgatac tctgtgggac tctttgtgta aagcggcgcg ccagtcaggc 1440
ggt 1443

<210> SEQ ID NO 108
<211> LENGTH: 1410
<212> TYPE: DNA
<213> ORGANISM: Artificial
<220> FEATURE:
<223> OTHER INFORMATION: Codon-optimized and/or mutated sequence

<400> SEQUENCE: 108
atgacgccgg aacagttccg ccagtatggt caccaactta tcgacttgat tgcggattac 60
cgccaaaccg tgggcgaacg accagtgatg gctcaggtgg aaccgggcta cctcaaagcc 120
gcgcttccgg cgaccgctcc gcagcagggc gaaccattcg ccgcgattct tgatgatgtc 180
aacaatcttg ttatgcctgg cctgagccac tggcaacacc ctgacttcta cggctacttc 240
ccatctaatg gtactctgtc atctgtgttg ggcgacttcc tgtccaccgg cctgggcgtg 300
cttggcttgt cgtggcaaag ctccccggca cttagcgaac tggaggaaac aaccctggat 360
tggttgcgac aactcctggg tctgtcagga cagtggtctg gtgtgattca ggacacagca 420
tctacatcca cgctcgtggc cctgatttct gcacgagagc gtgccaccga ctacgctctg 480
gtgcgcggcg gcctgcaggc tgagccaaag ccattgatcg tttatgtttc cgcgcatgct 540
cactccagcg tggataaagc ggcactcctg gcaggattcg gccgcgataa catccgcctg 600
atcccgacgg acgaacgcta cgccctccgt cccgaggctc tgcaagcggc aatcgagcag 660
gatctcgcgg cgggtaacca gccatgtgca gtggtcgcta ccaccggaac aaccactacg 720
accgccctgg atcccctccg ccctgttggc gaaatcgctc aggccaatgg actctggctc 780
cacgtcgata gcgccatggc aggatccgca atgatcctgc cggaatgtcg ctggatgtgg 840
gatggcatcg aactggctga ttctgttgta gttaacgccc acaagtggct gggagtcgcg 900
tttgactgct ccatttatta cgtgcgcgac ccacagcacc tgattcgagt gatgagcacc 960
aacccctctt acctccagtc cgccgtggat ggtgaggtga aaaacctgcg tgattggggc 1020
atcccgttgg gacgtcgctt ccgcgcgctg aaactttggt ttatgctccg ctcagaagga 1080
gtggacgctc ttcaggctcg cttgcgtcgt gacttggata acgcgcagtg gctcgcagga 1140
caggtggaag cagcggctga atgggaggtt ctggctccag tacagttgca gaccttgtgt 1200
attcgccacc gacctgccgg tcttgaagga gaagcgttgg acgcccacac aaaaggctgg 1260
gccgagcgtt tgaacgcatc tggtgcggca tacgtcacac cagccaccct tgacggacgt 1320
tggatggtgc gcgtgtctat cggagccctg cctactgaac gtggtgatgt gcagcgcctg 1380
tgggcacgac ttcaggacgt tatcaaagga 1410

<210> SEQ ID NO 109
<211> LENGTH: 1725
<212> TYPE: DNA
<213> ORGANISM: Artificial
<220> FEATURE:
<223> OTHER INFORMATION: Codon-optimized and/or mutated sequence

<400> SEQUENCE: 109

```
atgactggcc acatgacacc tgaacagttc cgccagcatg gtcatgaagt ggtcgattgg      60

attgcagatt actgggaacg aatcggttcg tttcccgtgc gtagccaggt ctctcccggc     120

gacgtgcgcg cttcactgcc acccaccgcg cccgagcaag gcgaaccatt ctctgcagtt     180

cttgccgacc tggaccgcgt ggtgctgccg ggcgttaccc actggcaaca tccaggtttt     240

ttcggttact tccccgcaaa cacatccggc cctccgtttt tgggagattt ggtatctgca     300

ggcctgggag ttcagggtat gtcgtgggtc acctcccctg cagcgactga actggagcaa     360

cacgtgatgg attggtttgc ggaccttctc ggccttccag aaagctttcg ctcgacgggt     420

tccggaggcg gagtggtgca agattcctct tctggtgcaa acttggtggc cctgttggcg     480

gcactccacc gcgcttccaa aggcgctact ctccgccatg gtgtccgccc cgaagatcat     540

acagtgtatg tctcggcaga gacacacagc tcgatggaga aggccgctcg catcgcagga     600

cttggaaccg acgctattcg cattgtggaa gtgggtcccg atctggcaat gaatccacgt     660

gcgcttgccc agcgcctcga gcgcgatgtg gctcgtggtt acacgcccgt gctggtttgt     720

gcaaccgtgg gcaccacgag caccactgca attgaccctc tggcggaact cggtcctatt     780

tgtcagcagc acggcgtttg gctgcatgtg gacgccgcgt atgcgggcgt gtccgcggtg     840

gcccctgaac ttcgcgcctt gcaagcagga gttgagtggg cagattccta tacgacagat     900

gcccacaagt ggctgctgac cggcttcgac gcaacgttgt tctgggtggc agaccgcgca     960

gctctcaccg gcgcgttgtc catccttcct gaatatctcc gcaacgccgc gaccgatact    1020

ggcgccgttg ttgattaccg cgattggcag attgaattgg gccgtcgatt ccgtgcgctt    1080

aaactctggt ttgttgtgcg ttggtacggt gcagagggct tgcgcgagca tgtccgctca    1140

cacgtcgccc tcgctcaaga actggctggc tgggcagatg ctgatgagcg ttttgatgtc    1200

gcggcccctc atcctttttc gctggtatgc ctgcgtcccc gttgggcccc cggcattgat    1260

gcagacgtcg caacgatgac gctcctggac cgcttgaacg acggtggcga ggtgtttctg    1320

actcatacaa ccgtggatgg cgcggctgtt ttgcgtgtcg cgattggcgc cccggccact    1380

acacgcgaac acgtcgagcg tgtgtgggcc ctcctcggag aggcacacga ttggttggct    1440

cgcgacttcg aggagcaggc ggccgaacgc cgcgctgcgg aactgcgcga acgagaagca    1500

gctgaggagc agctgcgcgc tcgacgcgag gcagaagctg ccgcggctgc cgctaccgaa    1560

gctccagtcg aaccagcggc ggaagagccg gaacagctcg tcgtgccacc tgtggaggtc    1620

ccagctgtcg aaaccccagc agcttgggat gaatcggcga ctcaggtggc cgcacagact    1680

gatctccacg cggatccagc accccaacca gctgatggac aaggc                    1725
```

<210> SEQ ID NO 110
<211> LENGTH: 1554
<212> TYPE: DNA
<213> ORGANISM: Artificial
<220> FEATURE:
<223> OTHER INFORMATION: Codon-optimized and/or mutated sequence

<400> SEQUENCE: 110

```
atgggttcac tgccagccaa caatttcgaa tccatgtcgc tgtgttccca aaatcccctt      60

gatccagatg agttccgacg ccagggtcac atgattatcg atttcttggc tgactattat     120

aagaacgttg aaaagtatcc agtccgtacc caagtcgacc ccggttactt gaaaaaacgc     180

cttccagaat cggctccata caatcccgag tctatcgaaa ccattcttga ggatgtgact     240

aatgatatca tcccaggact gactcactgg cagtccccca actatttcgc gtattttccg     300

tcgagcggct ccattgccgg atttcttgga gaaatgctgt caaccggctt caacgtggtt     360
```

```
ggtttcaact ggatgtcctc accagcagcc accgagcttg agagcatcgt catgaactgg    420
cttggccaga tgctcacctt gccaaagtcc tttctcttct cctccgatgg ttcctctggt    480
ggaggcggtg tcctccaggg cacgacctgc gaagcaatcc tttgtaccct gaccgccgcg    540
cgagataaga tgctcaacaa gattggacgt gaaaacatta acaagttggt agtctatgct    600
tcagatcaga cccttagcgc gcttcaaaaa gctgcgcaga ttgctggcat caaccccaag    660
aacttcttgg ccatcgcaac ctcaaaagct accaacttcg gactctctcc taactcgctt    720
cagagcacca tcctggctga tatcgagtca ggcttggttc ctttgttcct gtgtgccaca    780
gtgggtacta ccagctccac cgcagtggac ccaatcggcc cactgtgcgc cgttgctaag    840
ctccacggca tttgggtgca tatcgatgct gcgtacgccg gtagcgcatg catttgccct    900
gaatttcgcc atttcatcga tggagtggag gatgccgatt ctttctcact taacgcacac    960
aaatggttct ttaccactct cgattgttgt tgtctgtggg taaaggatag cgacagcttg   1020
gttaaggctc tctccacatc gcccgagtat ctgaagaata aggccacgga ttccaaacag   1080
gtcattgatt acaaggattg gcaaatcgct ctttcccgtc gcttccgcag catgaagctg   1140
tggctggtgc tgcgctccta cggaatcgcc aatctccgta cctttctgcg tagccacgtt   1200
aaaatggcca agcacttcca aggcctcatt ggaatggaca atcgctttga aattgttgta   1260
ccacgtactt ttgcaatggt atgcttccgc ctgaagcccg cagcaatctt tcgcaagaaa   1320
attgttgaag acgatcacat cgaagcgcag accaacgagg tgaatgcaaa gcttcttgag   1380
tccgtgaacg cctcaggaaa gatttacatg actcacgcgg tggtaggagg agtatatatg   1440
attcgcttcg ccgtgggtgc cactctgacc gaagaacgcc acgtgaccgg cgcatggaag   1500
gtggttcagg aacacacgga cgcaatcctg ggcgcgttgg gcgaggacgt ttgc         1554
```

<210> SEQ ID NO 111
<211> LENGTH: 1254
<212> TYPE: DNA
<213> ORGANISM: Artificial
<220> FEATURE:
<223> OTHER INFORMATION: Codon-optimized and/or mutated sequence

<400> SEQUENCE: 111

```
atgaagcaga ttcctgctaa gggtttggaa cgtgacgtca tcatgcagga gctgcgccaa     60
atgaagtctt tggactttga ttggcgcgcc ggtcgtgtgc cttcctacac ctatttcgtt    120
gatgacgaaa cccttgatgt gcaacgtgaa gcttacggag aatacattgc agagaacggc    180
ctgggtgccg gccgcgcgtt caaatcgctc gaactgatga cggacgatat taaaagcatg    240
gctatttccc tgtttaatgc cccggcagct gccggtgcat cgttcacctc tggcggcact    300
gaatccattt ttatggccgt aaagacagca cgagacctta cacgccaccg acgcggcgaa    360
cctgacggac gctataacat tgtggcctgc gaaaccgcac acccttgtct ggataaagcc    420
ggtcaattgc tgggagttga tattcgccgc accccgcaca ctgctgagtt ccgagcagat    480
ccagcactct tgcgaacttc gatcgatcaa aagaccatga tgctgtttgc atctgcacca    540
aactacccat tcggtacttt cgatcctatc tccaagattg gccgcttggc ccaggagcgc    600
gatttgcgtc tccacgttga tggctgctgg ggaggcttcc tgagcccatt cgctgagcgc    660
ctgggctacc ccatcccgga atgggatttt cgtgtaccag gagtttctag cctgtccgct    720
gatattcata aattcggtta cgccgctaag ggagcatctg ttgtcttgta ccgcgatgtc    780
gaagatcagg aacacgaacg cttttctttc tccggctggc ctcgtggcac ctacagcacc    840
```

```
ccgaccttcc tcggaaccaa ggccggcggc gcaatcgcct cggcatgggc tgtaatgcat     900

ttcctcggag ttgaaggcta cctgcgtgca gccaagctga ccatggatgc caccatgcaa     960

ttgattgaag gcctcaatgc cattccagat atctactgtc ttacgccaaa cggtgagtct    1020

aacctcatct ccttcgctac ttccgatccg aaacttgata tttacgcagt agcagaccgc    1080

ctcgaggagt gtggttggct gcgaggacgt atgcgcgaac ccaaggccat ccagcaggga    1140

gtgaatcctg cacacttggc tacagttacc gagtacctgg ccgaagtgcg caaggcaatc    1200

gatcatgtcc gcggtaacgt cgctgccccc gtggcctacg atgagcactc ctac          1254
```

<210> SEQ ID NO 112
<211> LENGTH: 1593
<212> TYPE: DNA
<213> ORGANISM: Artificial
<220> FEATURE:
<223> OTHER INFORMATION: Codon-optimized and/or mutated sequence

<400> SEQUENCE: 112

```
atgggttctc ttaatacaga agatgttttg gagaatagtt cagcatttgg tgtaactaat      60

ccccttgatc ctgaagaatt cagaagacaa ggacatatga tcatagattt tcttgctgac     120

tattatagag atgtggagaa atatccggtg agaagtcaag tggagcccgg ttatttaaga     180

aaaagactgc cagaaaccgc cccgtacaat ccagagtcca tcgagaccat attacaagat     240

gtaacaactg agattattcc aggtctaacc cattggcaaa gtcctaacta ttacgcctac     300

tttcctagct ccggtagcgt cgccggcttt cttggtgaaa tgttatccac cggtttcaat     360

gttgttggat tcaattggat gagttcacca gccgctactg aattagaatc cgtggttatg     420

gactggtttg gaaaaatgtt gaacctgccg gagtcatttc ttttctctgg aagtggtggt     480

ggcgtgttgc agggtactag ttgtgaagca attttatgca ctttgacggc agcaagagat     540

agaaagctta ataaaattgg tagagagcat atcggtagat tagtagtcta cggatcagac     600

cagactcatt gtgctttaca aaaggctgca caagtcgctg gcatcaatcc taagaatttc     660

agagcgatta agacgtttaa agaaaactcc tttggtttga gcgcagcaac tctaagagaa     720

gtgatcctag aggacatcga ggcagggttg ataccactgt ttgtttgccc tacagtgggg     780

accacttcta gcaccgccgt tgatcctata tctccgatct gtgaagtagc taaagaatac     840

gaaatgtggg tacacgtaga tgcagcttac gctgggtcag cctgtatttg cccagagttt     900

agacatttta ttgatggtgt cgaagaagcg gacagttttt ctcttaatgc tcataagtgg     960

tttttcacta ctttggactg ttgttgtttg tgggttaagg atccatctgc tctagttaaa    1020

gccctatcca ccaatccgga gtatttgaga aataaggcaa cagaatcaag acaagtcgta    1080

gattataaag actggcaaat agccctgtcc agaaggttca gatcattaaa gttatggatg    1140

gttctgagga gctatggcgt caccaatttg agaaattttt tgagaagcca cgtcaagatg    1200

gcaaagactt ttgaaggact gatctgtatg gatggtaggt ttgaaataac tgttcccagg    1260

acttttgcaa tggtttgttt tagattgctg cccccaaaaa caataaaagt atatgataac    1320

ggcgtgcatc aaaacggtaa cggggtagtt cctttgagag acgagaacga gaacctggtt    1380

ttagcgaata aactaaatca ggtttacctt gagactgtta acgctacggg atctgtatat    1440

atgacacatg ccgttgtagg tggcgtgtac atgatccgtt ttgctgtggg atccacccta    1500

acggaagaaa ggcatgtgat ctacgcttgg aaaatattac aagaacacgc cgacttgatt    1560

ttaggtaaat ttagtgaagc agacttttct tca                                 1593
```

<210> SEQ ID NO 113
<211> LENGTH: 1491
<212> TYPE: DNA
<213> ORGANISM: Artificial
<220> FEATURE:
<223> OTHER INFORMATION: Codon-optimized and/or mutated sequence

<400> SEQUENCE: 113

```
atggaaggag tgggaggtgg tggaggcggc gaggagtggc tgcgccccat ggatgccgag     60
cagctgcgtg agtgcggaca ccgaatggtt gacttcgttg ctgattacta caaatccatc    120
gaagcattcc cagtgctgag ccaggtccag cccggatacc ttaaggaagt tctcccggac    180
tcagcccctc gtcaacccga taccttggac agcctcttcg atgatattca gcagaagatc    240
atccccggtg tgacccattg gcaaagcccg aactacttcg cttattatcc cagcaactcg    300
tcgactgcag gttttctggg cgaaatgctg tccgcagcat tcaacatcgt cggctttttct    360
tggatcacga gcccggccgc aaccgaattg gaagttattg tcttggattg gttcgctaag    420
atgttgcagc ttccatccca gtttttgagc accgctctcg gcggcggcgt catccagggc    480
acggcatccg aagccgttct cgtggccctc ttggctgccc gtgatcgcgc gcttaaaaaa    540
cacggcaaac attccctgga aaagctcgtc gtgtatgcat ccgaccagac gcattccgcc    600
ctccagaagg cttgccaaat tgcaggtatt ttctccgaaa atgtccgtgt ggtcatcgcc    660
gattgtaaca agaactacgc ggtggccccc gaagctgtct ctgaggcact tagcatcgac    720
ttgtcgtccg gacttatccc ctttttcatt tgtgcaactg tgggcacaac ctcttcctcc    780
gccgttgatc cattgccaga gctcggtcag attgccaaga gcaatgacat gtggttccac    840
atcgacgcag cgtacgctgg ctccgcatgt atctgtccag aatatcgtca ccacctgaat    900
ggcgtggaag aggctgattc gttcaatatg aatgcccaca agtggtttct gactaacttt    960
gattgttccc tcttgtgggt taaagaccgt tcatttctga tccaatctct gtccaccaac   1020
cctgagttcc tgaaaaacaa ggccagccag gccaactccg tcgtggactt caaagactgg   1080
cagattcctc tgggtcgccg cttccgctct ttgaagttgt ggatggttct tcgactctat   1140
ggagtggata accttcaatc gtatatccgc aagcacatcc acctcgccga gcattttgaa   1200
cagctccttc tgtcagactc ccgctttgaa gttgtcaccc cacgaacctt cagccttgtc   1260
tgctttcgtc ttgtgccacc aacgtccgat cacgaaaatg gtcgcaagct taactacgat   1320
atgatggatg gcgttaacag ctccggtaag atctttttga gccacactgt attgtcgggc   1380
aaatttgtac tccgcttcgc agttggcgct ccattgactg aggaacgcca cgttgatgcg   1440
gcatggaagc tgctccgcga cgaagcgacc aaagttttgg gaaaaatggt c            1491
```

<210> SEQ ID NO 114
<211> LENGTH: 1188
<212> TYPE: DNA
<213> ORGANISM: Artificial
<220> FEATURE:
<223> OTHER INFORMATION: Codon-optimized and/or mutated sequence

<400> SEQUENCE: 114

```
atgagaaata tgcaagagaa aggtgtctcc gaaaaggaaa ttttagagga gttgaagaaa     60
tataggtcat tggacttaaa gtacgaggac ggtaacattt ttggtagtat gtgttctaac    120
gtattaccaa tcaccaggaa aattgtagat atctttcttg aaactaattt gggtgaccca    180
ggtttattca aaggtactaa gttattggaa gaaaaggctg ttgctttgtt gggttcttta    240
ttaaataaca aagatgccta tggccatatc gtttccggtg gtacagaagc taatttgatg    300
```

```
gcccttaggt gtattaaaaa tatctggagg gagaagagac gtaagggtct gtctaagaac     360

gagcacccca aaattatcgt tcctattaca gctcatttta gtttcgaaaa aggtagagaa     420

atgatggatc ttgaatacat ctatgctccc ataaaagaag actataccat tgacgaaaag     480

tttgttaagg atgctgtcga agattatgac gtcgacggca ttatcggtat tgcagggact     540

acagaattgg gtactattga taatatcgaa gagctatcta aaattgctaa agaaaataac     600

atatacatcc atgttgatgc ggcatttggt ggactggtta tcccttttt ggatgataaa     660

tacaaaaaaa aaggagtgaa ttataaattt gatttctcat taggtgtaga ttctataaca     720

atcgacccac ataagatggg ccattgtcct ataccttctg gtggcatcct atttaaggat     780

attggttata aacgttattt ggacgtcgat gccccatatt taactgagac cagacaagcc     840

accattttgg gtacgagagt tggattcgga ggcgcgtgta cttacgctgt tttaagatac     900

ttagggagag aaggtcagcg taaaatagtt aacgaatgta tggaaaatac cctatacctg     960

tacaaaaaat taaaagagaa taattttaaa ccagtgatcg aaccaattct taatatcgtc    1020

gctattgaag atgaggacta caaagaagtt tgtaaaaagt taagggacag ggcatatat    1080

gtcagcgtat gtaattgtgt aaaagcttta aggatagtag ttatgccaca catcaaaagg    1140

gagcatattg ataattttat tgagattttg aattccatca agagagat                1188
```

<210> SEQ ID NO 115
<211> LENGTH: 1110
<212> TYPE: DNA
<213> ORGANISM: Artificial
<220> FEATURE:
<223> OTHER INFORMATION: Codon-optimized and/or mutated sequence

<400> SEQUENCE: 115

```
atgtcggaaa gcccaatgtt cgccgccaac ggcatgccaa aagttaatca gggcgccgaa      60

gaggacgtcc gcattttggg ctatgatccc ctcgcctccc ccgcactcct gcaagtacag     120

attcccgcca ccccgacctc tttggaaacc gcgaagcgcg gccgccgaga agcgattgat     180

attatcaccg gcaaggatga ccgagtactc gttatcgtcg gtccctgctc gatccacgac     240

ctcgaagccg cgcaggagta tgcattgcga ttgaagaagc tgtctgatga gttgaagggt     300

gatctttcga ttattatgcg tgcgtacctg gaaaagcctc gcaccaccgt gggttggaag     360

ggattgatca atgatcctga cgtaaacaac accttcaaca tcaataaggg cctccaatct     420

gcccgccagc ttttcgttaa cctcactaac attggccttc ccatcggctc cgaaatgctc     480

gatacgatct cgccgaaata cctggccgat ttggtgtcct ttggtgcaat tggtgcccgt     540

accaccgaat cacaactgca ccgcgaattg gcaagcggat tgagcttccc cgtgggtttc     600

aaaaacggta ctgatggcac tcttaacgtg gccgtcgatg catgtcaagc cgccgcacac     660

tcccaccatt tcatgggtgt gactaaacac ggagtggcgg cgattactac caccaagggt     720

aatgagcact gcttcgtcat cctgcgtggc ggaaagaagg gtaccaacta cgacgcaaag     780

agcgtcgctg aggccaaggc ccaattgcca gcaggttcca atggccttat gatcgattat     840

tcccacggca attctaataa ggactttcgc aaccaaccga aggtgaatga tgtggtatgt     900

gagcagatcg cgaatggtga aaatgcgatc actggcgtga tgatcgaatc gaatattaat     960

gagggcaacc agggaattcc tgcggaggga aaggcgggtt tgaagtacgg cgtatctatt    1020

actgacgctt gcattggctg ggagaccacc gaggacgtgc tgcgcaagct tgcagcggcg    1080

gtccgccagc gtcgtgaagt taataaaaaa                                     1110
```

<210> SEQ ID NO 116
<211> LENGTH: 1050
<212> TYPE: DNA
<213> ORGANISM: Artificial
<220> FEATURE:
<223> OTHER INFORMATION: Codon-optimized and/or mutated sequence

<400> SEQUENCE: 116

```
atgaattacc agaacgacga ccttagaatt aaggaaataa aagagttgct acctcccgtc     60

gcgctgttgg aaaaattccc cgccacagaa aatgctgcta atacggtcgc acatgctaga    120

aaggctattc ataaaattct gaaaggtaat gatgatagat tattggttgt tattggtcca    180

tgttctatac acgaccccgt agccgcaaaa gaatatgcta ccagactttt agctttacgt    240

gaagagttga aagatgaact tgaaattgtc atgcgtgtgt acttcgaaaa accgagaacg    300

accgttggtt ggaagggctt aatcaacgac ccacatatgg acaactcttt ccagatcaat    360

gatggcctaa ggatcgcacg taaacttcta ttagatatta atgattcagg acttcccgct    420

gcaggagaat tccttaatat gattactcct cagtatctag ccgacttaat gtcctggggt    480

gccatcggtg cgagaacgac agaaagtcaa gttcacaggg aactggcctc cggtttgtcc    540

tgtccagttg gtttcaagaa cggtacagat ggtaccatca aagtcgcaat tgacgccata    600

aacgccgccg gagctccaca ctgctttttg agcgtcacta aatggggaca ctcagccata    660

gtcaacactt caggtaacgg tgattgtcat attattctta gaggtggcaa ggaacctaac    720

tactccgcca aacatgttgc tgaagttaaa gaaggtctta acaaggcggg tcttccggcc    780

caagtgatga tagattttag ccatgccaac agctctaagc aatttaaaaa acaaatggat    840

gtttgtgctg atgtttgtca acaaatcgcg ggtggggaga aagcgatcat tggtgtaatg    900

gtcgaaagcc acttggttga aggcaaccaa agtttagaat ctggagagcc cttagcgtat    960

ggaaaaagca tcacagatgc gtgtataggt tgggaagaca ctgacgcctt actaagacaa   1020

ctagctaatg cagttaaggc ccgtagaggg                                    1050
```

<210> SEQ ID NO 117
<211> LENGTH: 1050
<212> TYPE: DNA
<213> ORGANISM: Artificial
<220> FEATURE:
<223> OTHER INFORMATION: Codon-optimized and/or mutated sequence

<400> SEQUENCE: 117

```
atgaattacc agaacgatga tctccgcatc aaggaaatca aggagttgct cccaccggtg     60

gctctgttgg agaagtttcc agctactgag aatgctgcca acactgttgc tcacgctcgc    120

aaagcaatcc acaaaatcct caaaggcaat gatgaccgtc tgttggtcgt tatcggacca    180

tgctccattc atgaccccgt ggctgctaaa gaatacgcga cccgactctt ggctctgcgc    240

gaggagctca aggacgaact ggagattgtg atgcgcgtgt acttcgaaaa gccacgcacg    300

actgtgggat ggaaaggact gatcaacgac ccgcacatgg acaactcctt ccaaatcaac    360

gatggtcttc gcattgctcg caaacttctg ttggacatca acgattcagg actgcccgca    420

gcaggcgaat tccttaacat gatcacccct cagtacctgg ctgacctgat gtcctggggt    480

gcaatcggtg cgcgtacgac cgaatcccaa gttcatcgcg aactggcgtc aggtctctcc    540

tgcccggttg gcttcaaaaa cggaaccgac ggaacaatca aggtcgcaat tgacgccatc    600

aatgcggcag gcgccccgca ctgtttcttg tcggtcacca aatggggcca cagcgcgatc    660

gtcaatactt caggtaatgg tgattgccac atcatccttc gaggaggtaa ggagccgaac    720
```

```
tactccgcaa agcatgtcgc agaggtcaag gagggtctga acaaagctgg cctgcctgcg    780

caggttatga ttgatttctc tcacgcaaac agctcaaagc agttcaagaa gcagatggat    840

gtttgcgccg atgtgtgcca gcagattgcc ggaggcgaaa aggcaattat tggtgtaatg    900

gttgaatccc acctcgttga gggcaaccaa tccctcgaat ccggtgagcc gctggcctat    960

ggcaagtcca tcaccgatgc ctgtatcggt tgggaggaca ccgatgcact gcttcgccaa   1020

cttgctaacg ccgtgaaagc tcgtcgcggt                                    1050


<210> SEQ ID NO 118
<211> LENGTH: 1113
<212> TYPE: DNA
<213> ORGANISM: Saccharomyces cerevisiae CEN.PK2

<400> SEQUENCE: 118

atgagtgaat ctccaatgtt cgctgccaac ggcatgccaa aggtaaatca aggtgctgaa     60

gaagatgtca gaattttagg ttacgaccca ttagcttctc cagctctcct tcaagtgcaa    120

atcccagcca caccaacttc tttggaaact gccaagagag gtagaagaga agctatagat    180

attattaccg gtaaagacga cagagttctt gtcattgtcg gtccttgttc catccatgat    240

ctagaagccg ctcaagaata cgctttgaga ttaaagaaat tgtcagatga attaaaaggt    300

gatttatcca tcattatgag agcatacttg gagaagccaa gaacaaccgt cggctggaaa    360

ggtctaatta atgaccctga tgttaacaac actttcaaca tcaacaaggg tttgcaatcc    420

gctagacaat tgtttgtcaa cttgacaaat atcggtttgc caattggttc tgaaatgctt    480

gataccattt ctcctcaata cttggctgat ttggtctcct tcggtgccat tggtgccaga    540

accaccgaat ctcaactgca cagagaattg gcctccggtt tgtctttccc agttggtttc    600

aagaacggta ccgatggtac cttaaatgtt gctgtggatg cttgtcaagc cgctgctcat    660

tctcaccatt tcatgggtgt tactttgcat ggtgttgctg ctatcaccac tactaagggt    720

aacgaacact gcttcgttat tctaagaggt ggtaaaaagg gtaccaacta cgacgctaag    780

tccgttgcag aagctaaggc tcaattgcct gccggttcca acggtctaat gattgactac    840

tctcacggta actccaataa ggatttcaga aaccaaccaa aggtcaatga cgttgtttgt    900

gagcaaatcg ctaacggtga aaacgccatt accggtgtca tgattgaatc aaacatcaac    960

gaaggtaacc aaggcatccc agccgaaggt aaagccggct tgaaatatgg tgtttccatc   1020

actgatgctt gtataggttg ggaaactact gaagacgtct tgaggaaatt ggctgctgct   1080

gtcagacaaa gaagagaagt taacaagaaa tag                                1113


<210> SEQ ID NO 119
<211> LENGTH: 1110
<212> TYPE: DNA
<213> ORGANISM: Saccharomyces cerevisiae (strain ATCC 204508  S288c)
      (Baker's yeast)

<400> SEQUENCE: 119

atgttcatta aaaacgatca cgccggtgac aggaaacgct tggaagactg gagaatcaaa     60

ggttatgatc cattaacccc tccagatctg cttcaacatg aatttccaat ttcagccaaa    120

ggtgaggaaa acattatcaa ggcaagagac tccgtctgtg atattttgaa tggtaaagat    180

gatcgtttag ttatcgtgat cgggccatgt tccctacatg accccaaagc cgcttacgat    240

tacgctgaca gattggctaa aatttcagaa aagttgtcaa aagacttatt gattattatg    300

agagcgtatt tagaaaaacc aaggactacc gttggctgga aagggttgat taacgaccct    360
```

```
gatatgaata actcttttca aatcaataaa ggtctacgga tttcgagaga aatgttcata    420

agactggttg aaaaattacc cattgctggt gagatgttgg ataccatttc tccgcagttt    480

ttgagtgatt gtttctcctt gggtgccatc ggtgctagaa ctactgaatc ccaactgcac    540

agagaattag catccggtct atctttccct attggattta agaacggtac tgatggtggt    600

ttgcaagtcg ccatcgacgc tatgagagcc gctgcacatg atcattactt cctttctgtc    660

acaaagccag gtgtcactgc tatcgtgggc actgaaggta acaaggatac cttcctgatc    720

ttgagaggtg gtaagaacgg tactaacttt gacaaagaaa gtgttcaaaa tactaagaaa    780

caattagaaa aggccggttt gactgacgat tcacagaaaa gaatcatgat cgattgttca    840

cacgggaaca gtaataaaga tttcaagaac caaccgaagg ttgccaaatg catttatgac    900

caactgacgg aaggtgaaaa tagtctttgt ggtgttatga ttgagtccaa cataaatgaa    960

ggtagacaag atattcctaa agaaggtggc agagagggat tgaagtatgg ttgttctgta   1020

acggatgctt gtattggttg ggagaccacc gaacaggtat tggagctatt ggccgaaggt   1080

gttagaaaca gaagaaaagc cttgaagaaa                                    1110
```

<210> SEQ ID NO 120
<211> LENGTH: 1110
<212> TYPE: DNA
<213> ORGANISM: Saccharomyces cerevisiae (strain ATCC 204508 S288c) (Baker's yeast)

<400> SEQUENCE: 120

```
atgagtgaat ctccaatgtt cgctgccaac ggcatgccaa aggtaaatca aggtgctgaa     60

gaagatgtca gaattttagg ttacgaccca ttagcttctc cagctctcct tcaagtgcaa    120

atcccagcca caccaacttc tttggaaact gccaagagag gtagaagaga agctatagat    180

attattaccg gtaaagacga cagagttctt gtcattgtcg gtccttgttc catccatgat    240

ctagaagccg ctcaagaata cgctttgaga ttaaagaaat tgtcagatga attaaaaggt    300

gatttatcca tcattatgag agcatacttg gagaagccaa gaacaaccgt cggctggaaa    360

ggtctaatta atgaccctga tgttaacaac actttcaaca tcaacaaggg tttgcaatcc    420

gctagacaat tgtttgtcaa cttgacaaat atcggtttgc caattggttc tgaaatgctt    480

gataccattt ctcctcaata cttggctgat ttggtctcct tcggtgccat tggtgccaga    540

accaccgaat ctcaactgca cagagaattg gcctccggtt tgtctttccc agttggtttc    600

aagaacggta ccgatggtac cttaaatgtt gctgtggatg cttgtcaagc cgctgctcat    660

tctcaccatt tcatgggtgt tactaagcat ggtgttgctg ctatcaccac tactaagggt    720

aacgaacact gcttcgttat tctaagaggt ggtaaaaagg gtaccaacta cgacgctaag    780

tccgttgcag aagctaaggc tcaattgcct gccggttcca acggtctaat gattgactac    840

tctcacggta actccaataa ggatttcaga aaccaaccaa aggtcaatga cgttgtttgt    900

gagcaaatcg ctaacggtga aaacgccatt accggtgtca tgattgaatc aaacatcaac    960

gaaggtaacc aaggcatccc agccgaaggt aaagccggct tgaaatatgg tgtttccatc   1020

actgatgctt gtataggttg ggaaactact gaagacgtct tgaggaaatt ggctgctgct   1080

gtcagacaaa gaagagaagt taacaagaaa                                    1110
```

<210> SEQ ID NO 121
<211> LENGTH: 1500
<212> TYPE: DNA
<213> ORGANISM: Saccharomyces cerevisiae (strain ATCC 204508 S288c) (Baker's yeast)

<400> SEQUENCE: 121

```
atgactttac ctgaatcaag agacttttct tacttgtttt cggatgaaac caatgctcgt     60
aaaccatccc cattgaaaac ctgcatccat cttttccaag atcctaacat tatcttttttg   120
ggtggtggcc tgccattaaa agattatttc ccatgggata atctatctgt agattcaccc   180
aagcctcctt ttccccaggg tattggagct ccaattgacg agcagaattg cataaaatac   240
accgtcaaca aagattacgc tgataaaagt gccaatcctt ccaacgatat tcctttgtca   300
agagctttgc aatacgggtt cagcgctggt caacctgaac tgttaaactt cattagagat   360
cataccaaga ttatccacga tttgaagtat aaggattggg acgttttagc cactgcaggt   420
aacacaaatg cctgggaatc tactttaaga gtcttttgta accgaggtga tgtcatctta   480
gttgaggcac attctttttc ctcttcattg gcttctgcag aggctcaagg tgtcattacc   540
ttccccgtgc caattgacgc tgatggtatc attcctgaaa aattagctaa agtcatggaa   600
aactggacac ctggtgctcc taaaccaaag ttgttataca ctattccaac gggccaaaat   660
ccaactggta cttccattgc agaccataga aaggaggcaa tttacaagat cgctcaaaag   720
tacgacttcc taattgtgga agatgaacct tattatttct tacaaatgaa tccctacatc   780
aaagacttga aggaaagaga gaaggcacaa agttctccaa agcaggacca tgacgaattt   840
ttgaagtctt tggcaaacac tttcctttcc ttggatacag aaggccgtgt tattagaatg   900
gattcctttt caaaagtttt ggccccaggg acaagattgg gttggattac tggttcatcc   960
aaaatcttga agccttactt gagtttgcat gaaatgacga ttcaagcccc agcaggtttt  1020
acacaagttt tggtcaacgc tacgctatcc aggtggggtc aaaagggtta cttggactgg  1080
ttgcttggcc tgcgtcatga atacactttg aaacgtgact gtgccatcga tgccctttac  1140
aagtatctac cacaatctga tgctttcgtg atcaatcctc caattgcagg tatgtttttc  1200
accgtgaaca ttgacgcatc tgtccaccct gagtttaaaa caaaatacaa ctcagaccct  1260
taccagctag aacagagtct ttaccacaaa gtggttgaac gcggtgtttt agtggttccc  1320
ggttcttggt tcaagagtga gggtgagacg gaacctcctc aacccgctga atctaaagaa  1380
gtcagtaatc caaacataat tttcttcaga ggtacctatg cagctgtctc tcctgagaaa  1440
ctgactgaag gtctgaagag attaggtgat actttatacg aagaatttgg tatttccaaa  1500
```

<210> SEQ ID NO 122
<211> LENGTH: 1539
<212> TYPE: DNA
<213> ORGANISM: Saccharomyces cerevisiae (strain ATCC 204508 S288c) (Baker's yeast)

<400> SEQUENCE: 122

```
atgactgctg gttctgcccc ccctgttgat tacacttcct taaagaagaa cttccaaccg     60
tttctctcca gaagagtaga aaatagatct ctgaaaagct tttgggatgc ttctgatatc   120
tcagatgacg tcattgagct agctggtgga atgccaaacg agagattttt tcctatcgaa   180
tctatggatt tgaaaatatc aaaagttcct tttaatgata acccaaaatg gcataattcg   240
tttaccacgg cgcatttgga cttgggatcc cccagtgagc tacccattgc acgttctttc   300
caatatgcag aaaccaaggg tttacccccct ctcttacatt ttgttaaaga ttttgtgtcc   360
agaattaatc gcccagcctt ttccgatgag acggagtcta actgggatgt catcctttct   420
ggcgggtcca acgattcaat gtttaaggtt tttgaaacaa tttgcgacga atcgaccact   480
gtgatgattg aagagtttac tttcaccccg gctatgtcca atgtggaggc tacaggagca   540
```

-continued

```
aaagtcatcc ccatcaagat gaacctgacc ttcgacagag agtcccaggg tattgatgtc    600

gaatatctaa cgcagttgct cgataattgg tcaactggac catacaaaga cttaaacaag    660

ccaagggtcc tatataccat tgcaacgggc caaaatccta ccgggatgtc tgtcccccag    720

tggaaaagag agaaaattta ccagttggcc caaagacacg atttcctcat tgttgaagat    780

gatccctacg gttatctgta ctttccttcc tataatccgc aagagccatt agaaaaccct    840

taccattcta gcgacctgac tactgaacgg tatttgaatg attttttaat gaaatcattc    900

ttgactttgg atacagatgc ccgtgtcatc cgtttggaga ctttttctaa aatttttgct    960

cctggattaa ggttatcctt catcgttgct aataaattcc ttttgcaaaa aatcttggat   1020

ttggccgaca ttactacaag ggcccccagt ggtacctcac aagctattgt ttattctaca   1080

ataaaggcaa tggctgagtc caacttatcg tcctctcttt ctatgaaaga agcaatgttt   1140

gagggttgga taagatggat aatgcagatt gcttctaaat acaatcatag gaaaaatctt   1200

actttgaaag ccttatacga aacagaatct taccaagctg gtcagtttac cgttatggaa   1260

ccctccgcgg gtatgttcat cattattaaa atcaattggg ggaatttcga tagacctgac   1320

gatttgccgc aacagatgga tattttagat aagttcttgc tgaagaatgg tgttaaagta   1380

gtgcttggtt ataaaatggc tgtttgccca aattattcaa agcagaattc agattttcta   1440

agactcacca tcgcctatgc aagggatgat gatcagttga ttgaagcttc caaaagaatc   1500

ggtagtggca taaaagaatt ttttgacaac tataaaagt                          1539
```